(12) United States Patent
Hazlehurst et al.

(10) Patent No.: US 10,059,740 B2
(45) Date of Patent: Aug. 28, 2018

(54) INTEGRIN INTERACTION INHIBITORS FOR THE TREATMENT OF CANCER

(71) Applicants: H. LEE MOFFITT CANCER CENTER AND RESEARCH INSTITUTE, INC., Tampa, FL (US); UNIVERSITY OF SOUTH FLORIDA, Tampa, FL (US)

(72) Inventors: Lori Hazlehurst, Morgantown, WV (US); Mark McLaughlin, Tampa, FL (US); Priyesh Jain, Seattle, WA (US); William S. Dalton, Temple Terrace, FL (US)

(73) Assignees: H. LEE MOFFITT CANCER CENTER AND RESEARCH INSTITUTE, INC., Tampa, FL (US); UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 15/165,687

(22) Filed: May 26, 2016

(65) Prior Publication Data

US 2016/0257712 A1  Sep. 8, 2016

Related U.S. Application Data

(60) Division of application No. 14/465,106, filed on Aug. 21, 2014, which is a continuation of application No. 13/636,010, filed as application No. PCT/US2011/000512 on Mar. 21, 2011, now Pat. No. 8,853,149.

(60) Provisional application No. 61/315,730, filed on Mar. 19, 2010.

(51) Int. Cl.
| | |
|---|---|
| A61K 38/00 | (2006.01) |
| C07K 7/06 | (2006.01) |
| A61K 38/08 | (2006.01) |
| A61K 45/06 | (2006.01) |

(52) U.S. Cl.
CPC ............... *C07K 7/06* (2013.01); *A61K 38/08* (2013.01); *A61K 45/06* (2013.01); *A61K 38/00* (2013.01)

(58) Field of Classification Search
CPC .......... A61K 38/00; A61K 38/08; C07K 7/06; C07K 7/56
See application file for complete search history.

(56) References Cited

U.S. PATENT DOCUMENTS

| | | | |
|---|---|---|---|
| 5,595,756 A * | 1/1997 | Bally | A61K 9/1272 264/4.1 |
| 5,767,071 A | 6/1998 | Palladino et al. | |
| 5,770,565 A | 6/1998 | Cheng et al. | |
| 5,780,426 A | 7/1998 | Palladino et al. | |
| 5,817,750 A | 10/1998 | Ruoslahti et al. | |
| 5,821,329 A | 10/1998 | Lobl et al. | |
| 5,932,217 A | 8/1999 | Tuomanen et al. | |
| 5,955,572 A | 9/1999 | Ruoslahti et al. | |
| 6,034,056 A | 3/2000 | Dutta | |
| 6,034,057 A | 3/2000 | Dutta | |
| 6,096,707 A | 8/2000 | Heino et al. | |
| 6,107,275 A | 8/2000 | Harbeson et al. | |
| 6,235,711 B1 | 5/2001 | Dutta | |
| 6,713,604 B1 | 3/2004 | Kogan et al. | |
| 6,849,712 B1 | 2/2005 | McCarthy et al. | |
| 6,933,314 B2 | 8/2005 | Artis et al. | |
| 7,632,814 B2 | 12/2009 | Hazlehurst et al. | |
| 8,227,434 B1 | 7/2012 | Dalton et al. | |
| 2003/0125243 A1 | 7/2003 | Liu et al. | |
| 2004/0096906 A1 | 5/2004 | Lam et al. | |
| 2004/0126379 A1 | 7/2004 | Adolf et al. | |
| 2006/0019900 A1 | 1/2006 | Lam et al. | |
| 2006/0041105 A1 | 2/2006 | Jiang et al. | |
| 2007/0048325 A1 | 3/2007 | Van Epps et al. | |
| 2008/0108552 A1 | 5/2008 | Hazlehurst et al. | |
| 2009/0104116 A1 | 4/2009 | Zischinsky et al. | |
| 2009/0169570 A1 | 7/2009 | Daelken et al. | |
| 2009/0247549 A1 | 10/2009 | Frankel et al. | |
| 2010/0104510 A1 | 4/2010 | Rader et al. | |
| 2013/0171074 A1 | 7/2013 | Barbas et al. | |
| 2014/0080762 A1 | 3/2014 | Hazlehurst et al. | |
| 2014/0322227 A1 | 10/2014 | Hazlehurst et al. | |
| 2016/0229892 A1 | 8/2016 | Hazlehurst et al. | |

FOREIGN PATENT DOCUMENTS

| | | |
|---|---|---|
| WO | WO-2001/062776 | 8/2001 |
| WO | WO-2005/045430 | 5/2005 |
| WO | WO-2007/098575 | 9/2007 |

(Continued)

OTHER PUBLICATIONS

Cellular and Molecular Basis of Cancer-Merck Manual, pp. 1-5, Nov. 7, 2012.*

(Continued)

*Primary Examiner* — Hasan S Ahmed
*Assistant Examiner* — Kaipeen E Yang
(74) *Attorney, Agent, or Firm* — Saliwanchik, Lloyd & Eisenschenk

(57) ABSTRACT

Integrin interaction inhibitors using a beta-turn promoter are described herein. These peptides are useful in treating cancer, such as multiple myeloma, by administering a therapeutically effective amount of the integrin interaction inhibitor. Data show that integrin interaction inhibitors act synergistically or additively interact with anti-proliferative agents such as doxorubicin, SAHA, arsenic trioxide, and etoposide.

16 Claims, 53 Drawing Sheets

Specification includes a Sequence Listing.

(56) References Cited

FOREIGN PATENT DOCUMENTS

| WO | WO-2008/031064 | 3/2008 |
|---|---|---|
| WO | WO-2012/129335 | 9/2012 |
| WO | WO-2013/170066 | 11/2013 |
| WO | WO-2015/048477 | 4/2015 |

OTHER PUBLICATIONS

Sporn et al., Carcinogenesis, 2000, 21, pp. 525-530.*
Hait, Nature Reviews/Drug Discovery, 2010, 9, pp. 253-254.*
Gravanis et al., Chin. Clin. Oncol., 2014, 3, pp. 1-5.*
Cancer Drug Design and Discovery Neidle, Stephen, ed., Elsevier/ Academic Press, 2008.*
Jin L and Harrison SC, "Crystal structure of human calcineurin complexed with cyclosporin A and human cyclophilin" *PNAS*, 2002, 99(21):13522-13526.
Kim J-H et al., "Combined Use of Tamoxifen, Cyclosporin A, and Verapamil for Modulating Mutidrug Resistance in Human Hepatocellular Carcinoma Cell Lines" *Yonsei Medical Journal*, 1993, 34(1):35-44.
Bertrand RD et al., "Unusual behavior of Hexafluorobenzene and Benzene in the Aromatic Nuclear Magnetic Resonance Shift Effect" *Journal of the American Chemical Society*, 1970, 92(9):2702-9.
Chorev M and Goodman, M, "A Dozen Years of Retro-Inverso peptidomimetics" *American Chemical Society*, 1993, 26(5):266-73.
Crimmins MT and Zuercher, WJ, "Solid-Phase Synthesis of Carbocyclic Nucleosides" *Organic letters*, 2000, 2(8):1065-7.
Deroock IB et al., "Synthetic Peptides Inhibit Adhesion of Human Tumor Cells to Extracellular Matrix Proteins" *Cancer Research*, 2001, 61(8) :3308-3313.
Dressman BA et al., "Solid Phase Synthesis of Hydantoins Using a Carbamate Linker and a Novel Cyclization/Cleavage Step" *Tetrahedron Letters*, 1996, 37(7):937-40.
Favre M et al. ,"Structural Mimicry of Canonical Conformations in Antibody Hypervariable Loops Using Cyclic Peptides Containing a Heterochiral Diproline Template" *Journal of the American Chemical Society*, 1999, 121(12):2679-2685.
Ficht S et al., "Solid-Phase Synthesis of Peptide and Glycopeptide Thioesters through Side-Chain-Anchoring Strategies" *Chemistry-A European Journal*, 2008, 14(12):3620-3629.
Fletcher MD and Campbell MM, "Partially Modified Retro-Inverso Peptides: Development, Synthesis and Conformational Behavior" *Chemical Reviews (Washington, D. C.)*, 1998, 98(2):763-795.
His S et al., "Solid phase synthesis of amides by the Beckmann rearrangement of ketoxime carbonates" *Tetrahedron Letters*, 2003, 44(47):8581-8584.
Hughes RM and Waters ML, "Influence of N-Methylation on a Cation-pi Interaction Produces a Remarkably Stable beta-Hairpin Peptide" *Journal of the American Chemical Society*, 2005, 127(18):6518-6519.
Hutchinson EG et al., "Determinants of strand register in antiparallel beta-sheets of proteins" *Protein Science*, 1998, 7(11):2287-2300.
Kuwahara M et al., "Hybridization between Oxy-Peptide Nucleic Acids and DNAs: Dependence of Hybrid Stabilities on the Chain-Lengths, Types of Base Pairs, and the Chain Directions" *Journal of the American Chemical Society*, 2001, 123(20): 4653-4658.
Kuwahara M et al.,"Synthesis of delta-Amino Acids with an Ether Linkage in the Main Chain and Nucleobases on the Side Chain as Monomer Units for Oxy-peptide Nucleic Acids" *Tetrahedron*, 1999, 55(33):10067-10078.
Meester WJN et al., "Synthesis of Homoallylic Amines via N-Acyliminium Ion Reactions on Solid Support" *Tetrahedron Letters*, 1999, 40(8):1601-1604.
Nair RR et al., "HYD1—induced increase in ROS leads to autophagy and necrotic cell death in multiple myeloma cells" *Molecular Cancer Therapeutics*. 2009, 8(8):2441-51.
Nair DT et al., "Mimicry of Native Peptide Antigens by the Corresponding Retro-Inverso Analogs is Dependent on Their Intrinsic Structure and Interaction Propensities" *The Journal of Immunology*, 2003, 170(3):1362-1373.

Park KH and Cox, LJ, "Solid-phase synthesis of 1,2,4-triazolidine-3,5-diones" *Tetrahedron Letters*, 2002, 43(21):3899-3901.
Pennington ME et al., "The use of a combinatorial library method to isolate human tumor cell adhesion peptides" *Molecular Diversity*, 1996, 2(1/2):19-28.
Rabinowitz M et al., "Solid-Phase/ Solution-Phase Combinatorial Synthesis of Neuroimmunophilin Ligands" *Bioorganic & Medicinal Chemistry Letters*. 2000, 10(10):1007-1010.
Sroka T et al., "The Minimum Element of a Synthetic Peptide Required to Block Prostate Tumor Cell Migration" *Cancer Biological Therapies*, 2006, 5(11):1556-62.
Sroka T et al., "Synthetic D-amino acid peptide inhibits tumor cell motility on laminin-5" *Carcinogenesis*, 2006, 27(9):1748-57.
Taylor EM et al., "Retro-Inverso Prosaptide Peptides Retain Bioactivity, Are Stable in Vivo, and Are Blood-Brain Barrier Permeable" *The Journal of Pharmacological and Experimental Therapeutics*, 2000, 295(1):190-194.
Thomson SA et al., "Fmoc Mediated Synthesis of Peptide Nucleic Acids" *Tetrahedron*, 1995, 51(22):6179-94.
Wang C-C and Li W-R, "Traceless Solid-Phase Synthesis of Substituted Benzimidazolones" *Journal of Combinatorial Chemistry* 2004, 6(6):899-902.
Wang P. and Miranda LP, "Fmoc-Protein Synthesis: Preparation of Peptide Thioesters Using a Side-Chain Anchoring Strategy" *International Journal of Peptide Research and Therapeutics*, 2005, 11(2):117-123.
Wishart DS et al., "Relationship Between Nuclear Magnetic Resonance Chemical Shift and Protein Secondary Structure" *Journal of Molecular Biology*, 1991, 222(2):311-33.
Wishart DS et al., "The Chemical Shift Index: A Fast and Simple Method for the Assignment of Protein Secondary Structure Through NMR Spectroscopy" Biochemistry, 1992, 31(6):1647-51.
Yamamoto Y et al., "NMR study of *Galeorhinus japonicus* myoglobin: Proton-NMR study of molecular structure of the heme cavity" *European Journal of Biochemistry*, 1991, 198(2):299-306.
Zhou P et al., "Geometric characteristics of hydrogen bonds involving sulfur atoms in proteins" Proteins, 2009, 76:151-163.
Shibata K et al., "G-CSF receptor-binding cyclic peptides designed with artificial amino-acid links" *Biochemical and Biophysical Research Communications*, 2006, 341(2):483-488.
Abe M et al., "Vicious cycle between myeloma cell binding to bone marrow stromal cells via VLA-4-V CAM-1 adhesion and macrophage inflammatory protein-Iα and MIP-Iβ production" *Journal of Bone and Mineral Metabolism*, 2009, 27(1):16-23.
Abram CL and Lowell CA, "The ins and outs of leukocyte integrin signaling" *Annual Review of Immunology*, 2009, 27:339-362.
Anderson KC et al., "Multiple Myeloma: New Insights and Therapeutic Approaches" *Hematology*, 2000, 147-165.
Aoudjit F, and Vuori K. Integrin signaling inhibits paclitaxel-induced apoptosis in breast cancer cells. *Oncogene*. 2001; 20:4995-5004.
Astier A et al. The related adhesion focal tyrosine kinase differentially phosphorylates p130Cas and the Cas-like protein, p105HEF1. *J Biol Chem* . 1997;272:19719-19724.
Azab AK et al., "CXCR4 inhibitor AMD3100 disrupts the interaction of multiple myeloma cells with the bone marrow microenvironment and enhances their sensitivity to therapy" *Blood*, 2009, 113(18):4341-4351.
Baker DE, "Natalizumab: Overview of Its Pharmacology and Safety" *Reviews in Gastroenterological Disorders*, 2007, 7(1):38-46.
Banerjee D et al., "Novel aspects of resistance to drugs targeted to dihydrofolate reductase and thymidylate synthase" *Biochimica et Biophysica Acta*, 2002, 1587:164-173.
Bednarczykjl et al., "Post-translational Processing of the Leukocyte Integrin α4β1" *Journal of Biological Chemistry*, 1992, 267(35):25274-25281.
Bissell MJ and Radisky D, "Putting tumours in context" *Nature Review/Cancer*, 2001, 1(1):46-54.
Chen Q, et al. Integrin-mediated activation of MEK and mitogen-activated protein kinase is independent of Ras [corrected]. J Biol Chem. 1996;271:18122-18127.

(56) References Cited

OTHER PUBLICATIONS

Cox D et al. "Integrins as therapeutic targets: lessons and opportunities" *Nature Rev. Drug Disc.*, 2010, 9:804-820.
Dalton WS. "The tumor microenvironment: focus on myeloma" *Cancer Treat Rev.*, 2003, 29(Suppl 1):11-19.
Damiano JS et al. Cell adhesion mediated drug resistance (CAM-DR): role of integrins and resistance to apoptosis in human myeloma cell lines. *Blood*. 1999;93:1658-1667.
Damiano JS et al. Cell adhesion-mediated drug resistance (CAM-DR) protects the K562 chronic myelogenous leukemia cell line from apoptosis induced by BCR/ABL inhibition, cytotoxic drugs, and gamma-irradiation. *Leukemia* . 2001;15:1232-1239.
De Bruyn et al., "The small GTPase Rap1 is Required for Mn2+-and Antibody-induced LFA-1- and VLA-4-mediated Cell Adhesion" *Journal of Biological Chemistry*, 2002, 277(33):29468-29476.
Epstein J and Yaccoby S, "Consequences of interactions between the bone marrow stroma and myeloma" *The Hematology Journal*, 2003, 4(5):310-314.
Gatenby RA et al., "Adaptive Therapy" *Cancer Research*, 2009, 69(11):4894-4903.
Gebhard, A. et al. "MTI-101 (Cyclized HYD1) Binds a CD44 Containing Complex and Induces Necrotic Cell Death in Multiple Myeloma" *Mol. Cancer Ther.*, 2013, 12(11):2446-2458.
Gebhard A et al. "Validation of CD44 as a binding partner of the novel peptide HYD1 in multiple myeloma" presented at Moffitt Cancer Symposium in Tampa, FL on May 10, 2012, poster and abstract (Abstract No. B-68).
Gottesman MM and Ling V, "The molecular basis of multidrug resistance in cancer: The early years of P-glycoprotein research" *FEBS Letters*, 2006, 580(4):998-1009.
Gutman D et al., "Acquisition of a Multidrug Resistant Phenotype with a Proteasome Inhibitor in Multiple Myeloma" *Leukemia*, 2009, 23(11):2181-2183.
Hannigan GE et al. Regulation of cell adhesion and anchorage-dependent growth by a new beta 1-integrin-linked protein kinase. *Nature*. 1996; 379:91-96.
Hazlehurst L et al. "Comparison of aza-anthracenedione-induced DNA damage and cytotoxicity in experimental tumor cells" *Biochem Pharmacol.*, 1995, 50(7):1087-1094.
Hazlehurst L and Dalton WS "Mechanisms associated with cell adhesion mediated drug resistance (CAM-DR) in hematopoietic malignancies" *Cancer Metastasis Rev.*, 2001, 20:43-50.
Hazlehurst LA et al. Cell adhesion to fibronectin (CAM-DR) influences acquired mitoxantrone resistance in U937 cells. *Cancer Res.* 2006; 66:2338-2345.
Hazlehurst LA et al. Genotypic and phenotypic comparisons of de novo and acquired melphalan resistance in an isogenic multiple myeloma cell line model. *Cancer* Res. 2003; 63:7900-7906.
Hazlehurst LA et al. Reduction in drug-induced DNA double-strand breaks associated with beta1 integrin-mediated adhesion correlates with drug resistance in U937 cells. *Blood*. 2001;98:1897-1903.
Hazlehurst LA et al. β1 integrin adhesion increases Bim protein degradation and confers drug resistance in leukemia cells *British Journal Haematology*. 2006, 136:269-275.
Hazlehurst LA et al., "Multiple Mechanisms Confer Drug Resistance to Mitoxantrone in the Human 8226 Myeloma Cell Line" *Cancer Research*, 1999, 59(5):1021-1028.
Hazlehurst LA et al., "Role of the tumor microenvironment in mediating de novo resistance to drugs and physiological mediators of cell death" *Oncogene*, 2003, 22(47):7396-7402.
Hazlehurst LA, Targeting beta1 Integrins in Multiple Myeloma. Presentation at *Advancing Myeloma Therapy: Translating Laboratory Concepts Into Clinical Reality Symposium held in conjunction with the XI$^{th}$ International Myeloma Symposium*. 2007, Jun. 25.
Hofer, T. et al. "An engineered selenocysteine defines a unique class of antibody derivatives" PNAS, 2008, 105(34):12451-12456.
Hofer, T. et al. "Molecularly Defined Antibody Conjugation through a Selenocysteine Interface" *Biochemistry* , 2009, 48:12047-12057.
Li ZW, Dalton WS, "Tumor microenvironment and drug resistance in hematologic malignancies" *Blood Rev.* 2006, 20(6):333-342.

Li, X. et al., "Antibody conjugation via one and two C-terminal selenocysteines" *Methods*, 2014, 65:133-138.
Jain P. et al. "Cyclic β-hairpin peptidomimetics targeting protein-protein interactions" presented at Moffitt Cancer Symposium in Tampa, FL on May 10, 2012, poster and abstract (Abstract No. B-171).
Jemal A et al., "Cancer Statistics, 2010"*CA: A Cancer Journal for Clinicians*, 2010, 60(5):277-300.
Khleif SN et al., "AACRFDA-NCI Cancer Biomarkers Collaborative Consensus Report: Advancing the Use of Biomarkers in Cancer Drug Development" *Clinical Cancer Research*, 2010, 16(13):3299-3318.
King WG et al. Phosphatidylinositol 3-kinase is required for integrin-stimulated AKT and Raf-1/mitogen-activated protein kinase pathway activation. Mol Cell Biol. 1997;17:4406-4418.
Kyle RA and Rajkumar SV, "Multiple Myeloma" *New England Journal of Medicine*, 2004, 351(18):1860-1873.
Luo BH et al., "Structural basis of integrin regulation and signaling" *Annual Review of Immunology*, 2007, 25:619-647.
Lwin T et al. Cell adhesion induces p27Kip1-associated cell-cycle arrest through down-regulation of the SCFSkp2 ubiquitin ligase pathway in mantle cell and other non-Hodgkin's B-cell lymphomas. Blood. 2007, 110:1631-1638.
Mahon FX, et al., "Selection and Characterization of BCRABL positive cell lines with differential sensitivity to the tyrosine kinase inhibitor STI571: diverse mechanisms of resistance" *Blood*, 2000, 96(3):1070-1079.
Matsunago T et al., "Interaction between leukemic-cell VLA-4 and stromal fibronectin is a decisive factor for minimal residual disease of acute myelogenous leukemia" *Nature Medicine*, 2003, 9(9):1158-1165.
Mcmillin DW et al., "Tumor cell-specific bioluminescence platform to identify stroma-induced changes to anticancer drug activity" *Nature Medicine*, 2010, 16(4):483-489.
Morgan SE et al., "Differences in mutant p53 protein stability and functional activity in teniposide-sensitive and-resistant human leukemic CEM cells" *Oncogene*, 2000, 19(43):5010-5019.
Mori Y et al., "Anti-α4 integrin antibody suppresses the development of multiple myeloma and associated osteoclastic osteolysis" *Blood*, 2004, 104(7):2149-2154.
Morin PJ, "Drug resistance and the microenvironment: nature and nurture" *Drug Resistance Updates*, 2003, 6(4):169-172.
Murray P "cHYD1 solution phase synthesis optimization and the development of a novel human growth hormone antagonist and agonist" Graduate School Theses and Dissertations, University of South Florida, Apr. 4, 2012.
Nair RR et al., "The bone marrow microenvironment as a sanctuary for minimal residual disease in CML" *Biochemical Pharmacology*, 2010, 80(5):602-612.
Nefedova Y et al. Bone marrow stromal-derived soluble factors and direct cell contact contribute to de novo drug resistance of myeloma cells by distinct mechanisms. *Leukemia*. 2003;17:1175-1182.
Nefedova Y et al., "Inhibition of Notch signaling induces apoptosis of myeloma cells and enhances sensitivity to chemotherapy" *Blood*, 2008, 111(4):2220-2229.
Olson DL et al., "Anti-α4 integrin monoclonal antibody inhibits multiple myeloma growth in a murine model" *Molecular Cancer Therapeutics*, 2005, 4(1):91-99.
Palioura, S. et al. "The human SepSecS-tRNASec complex reveals the mechanism of selenocysteine formation" *Science*, 2009, 325(5938):321-325.
Rader, C. "Chemically programmed antibodies" *Trends Biotechnol.*, 2014, 32:186-197.
Robey RW et al., "ABCG2: determining its relevance in clinical drug resistance" *Cancer and Metastasis Reviews*, 2007, 26(1):39-57.
Roopenian, D.C. and Akilesh, S. "FcRn: The neonatal Fc receptor comes of age" *Nat Rev Immunol.*, 2007, 7:715-725.
Schaller MD and Parsons JT. pp125FAK-dependent tyrosine phosphorylation of paxillin creates a high-affinity binding site for Crk. *Mol Cell Biol* . 1995;15:2635-2645.

(56) References Cited

OTHER PUBLICATIONS

Schlaepfer DD et al. Integrin-mediated signal transduction linked to Ras pathway by GRB2 binding to focal adhesion kinase. *Nature.* 1994;372:786-791.

Sethi T et al. Extracellular matrix proteins protect small cell lung cancer cells against apoptosis: a mechanism for small cell lung cancer growth and drug resistance in vivo. *Nat Med.* 1999;5:662-668.

Teixido J et al., "Functional and Structural Analysis of VLA-4 Integrin α4 Subunit Cleavage" *Journal of Biological Chemistry*, 1992, 267(3):1786-1791.

Tian E et al., "The Role of the Wnt-Signaling Antagonist DKKI in the Development of Osteolytic Lesions in Multiple Myeloma" *New England Journal of Medicine*, 2003, 349(26):2483-2494.

Tolentino JH et al. "HM-27 targets AML cells via cell death by necrosis" presented at Moffitt Cancer Symposium in Tampa, FL on May 10, 2012, Abstract No. B-159).

Van Riet I et al. Expression of cytoadhesion molecules (CD56, CD54, CD18 and CD29) by myeloma plasma cells. Br J Haematol. 1991;79:421-427.

Yaccoby S et al. Primary myeloma cells growing in SCID-hu mice: a model for studying the biology and treatment of myeloma and its manifestations. *Blood.* 1998;92:2908-2913.

Yaccoby S et al., "Cancer and the Microenvironment: Myeloma—Osteoclast Interactions as a Model" *Cancer Research*, 2004, 64(6):2016-2023.

Zhu K et al. Farnesyltransferase inhibitor R115777 (Zarnestra, Tipifarnib) synergizes with paclitaxel to induce apoptosis and mitotic arrest and to inhibit tumor growth of multiple myeloma cells. *Blood.* 2005;105:4759-4766.

\* cited by examiner (a) BrCH$_2$CO$_2$$^t$Bu, THF (b) FmocNOSu, DIEA, DCM (c) MeSO$_2$Cl, DIEA, THF
(d) 1,4-Dioxane, 4M HCl (a) 20% Trifluoroethanol in DCM, rt (b) HATU, DIEA, DMF (c) 95%TFA, Et$_3$SiH, H$_2$O (a) 20% Piperidine/2%DBU in DMF, rt (b) Pd(PPh$_3$)$_4$ in CHCl$_3$-AcOH-NMM (37:2:1)

(c)HCTU, DIEA, DMF (d) 95%TFA, Et$_3$SiH, H$_2$O (a) BrCH$_2$CO$_2$tBu, THF, 85% (b) FmocNOSu, DIEA, DCM, 90% (c) MeSO$_2$Cl, DIEA, THF, 88%
(d) 1,4-Dioxane, 4M HCl, quant.

(a) NaOH, toluene, BrCH$_2$CO$_2$t-bu, TBAI, 77% (b) TFA/DCM (4:1) quant. (c) FmocOSu, DIEA, DCM, 79% (d) TFA/DCM, Triethylsilane, quant.

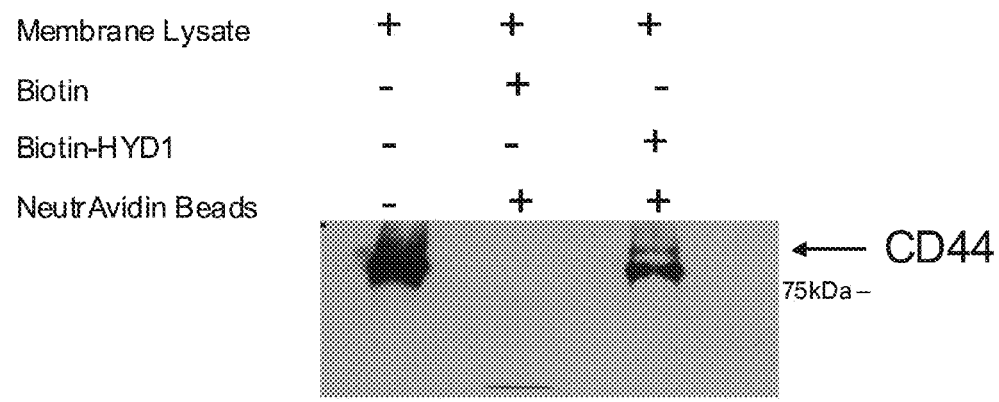
FIG. 44
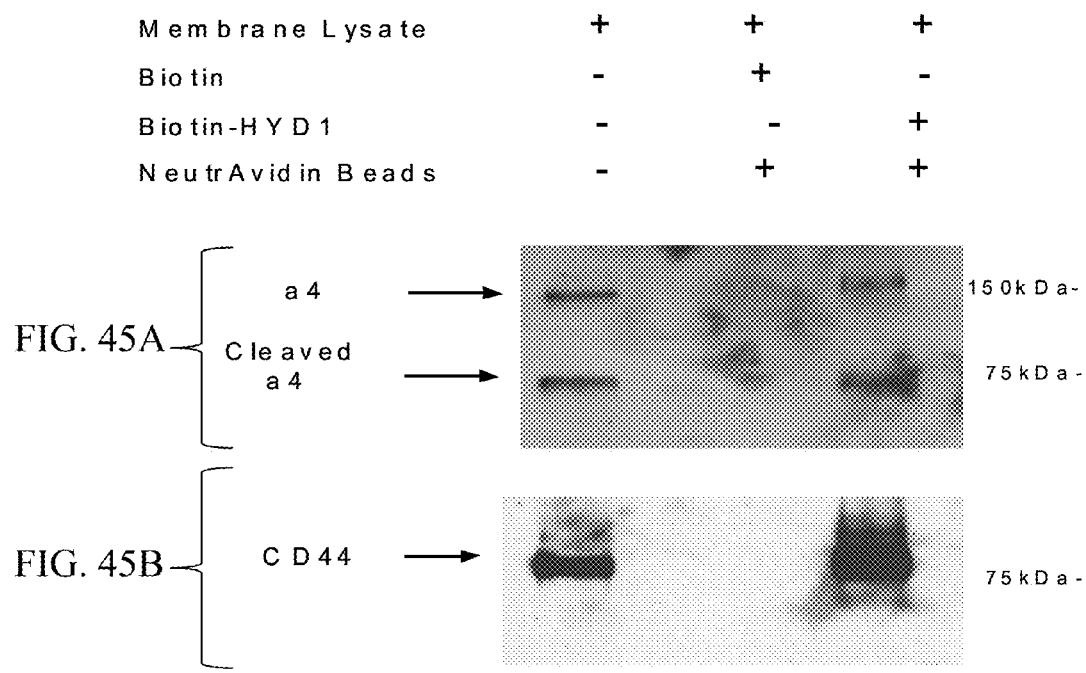
FIG. 45A
FIG. 45B

SEQUENCE LISTING

```
<160> NUMBER OF SEQ ID NOS: 282

<210> SEQ ID NO 1
<211> LENGTH: 10
<212> TYPE: PRT
<213> ORGANISM: Artificial Sequence
<220> FEATURE:
<223> OTHER INFORMATION: cyclic peptide amino acid sequence

<400> SEQUENCE: 1

Lys Leu Lys Leu Lys Met Val Val Ser Trp
1               5                   10

<210> SEQ ID NO 2
<211> LENGTH: 10
<212> TYPE: PRT
<213> ORGANISM: Artificial Sequence
<220> FEATURE:
<223> OTHER INFORMATION: cyclic peptide amino acid sequence

<400> SEQUENCE: 2

Lys Leu Lys Leu Lys Met Val Val Ser Trp
1               5                   10

<210> SEQ ID NO 3
<211> LENGTH: 10
<212> TYPE: PRT
<213> ORGANISM: Artificial Sequence
<220> FEATURE:
<223> OTHER INFORMATION: cyclic peptide amino acid sequence

<400> SEQUENCE: 3

Lys Leu Lys Leu Lys Met Val Val Ser Ala
1               5                   10

<210> SEQ ID NO 4
<211> LENGTH: 10
<212> TYPE: PRT
<213> ORGANISM: Artificial Sequence
<220> FEATURE:
<223> OTHER INFORMATION: cyclic peptide amino acid sequence

<400> SEQUENCE: 4

Lys Leu Lys Leu Lys Met Val Val Ala Trp
1               5                   10

<210> SEQ ID NO 5
<211> LENGTH: 10
<212> TYPE: PRT
<213> ORGANISM: Artificial Sequence
<220> FEATURE:
<223> OTHER INFORMATION: cyclic peptide amino acid sequence

<400> SEQUENCE: 5
```

```
Lys Leu Lys Leu Lys Met Val Ala Ser Trp
1               5                   10

<210> SEQ ID NO 6
<211> LENGTH: 10
<212> TYPE: PRT
<213> ORGANISM: Artificial Sequence
<220> FEATURE:
<223> OTHER INFORMATION: cyclic peptide amino acid sequence

<400> SEQUENCE: 6

Lys Leu Lys Leu Lys Met Ala Val Ser Trp
1               5                   10

<210> SEQ ID NO 7
<211> LENGTH: 10
<212> TYPE: PRT
<213> ORGANISM: Artificial Sequence
<220> FEATURE:
<223> OTHER INFORMATION: cyclic peptide amino acid sequence

<400> SEQUENCE: 7

Lys Leu Lys Leu Lys Ala Val Val Ser Trp
1               5                   10

<210> SEQ ID NO 8
<211> LENGTH: 10
<212> TYPE: PRT
<213> ORGANISM: Artificial Sequence
<220> FEATURE:
<223> OTHER INFORMATION: cyclic peptide amino acid sequence
<220> FEATURE:
<221> NAME/KEY: MISC_FEATURE
<222> LOCATION: (6)..(6)
<223> OTHER INFORMATION: Norleucine

<400> SEQUENCE: 8

Lys Leu Lys Leu Lys Xaa Val Val Ser Trp
1               5                   10

<210> SEQ ID NO 9
<211> LENGTH: 10
<212> TYPE: PRT
<213> ORGANISM: Artificial Sequence
<220> FEATURE:
<223> OTHER INFORMATION: cyclic peptide amino acid sequence
<220> FEATURE:
<221> NAME/KEY: MISC_FEATURE
<222> LOCATION: (6)..(6)
<223> OTHER INFORMATION: Norleucine

<400> SEQUENCE: 9

Lys Leu Lys Leu Lys Xaa Val Val Tyr Trp
1               5                   10

<210> SEQ ID NO 10
<211> LENGTH: 10
<212> TYPE: PRT
<213> ORGANISM: Artificial Sequence
<220> FEATURE:
<223> OTHER INFORMATION: cyclic peptide amino acid sequence

<400> SEQUENCE: 10

Lys Leu Lys Leu Lys Trp Ser Val Val Met
1               5                   10

<210> SEQ ID NO 11
```

```
<211> LENGTH: 10
<212> TYPE: PRT
<213> ORGANISM: Artificial Sequence
<220> FEATURE:
<223> OTHER INFORMATION: cyclic peptide amino acid sequence
<220> FEATURE:
<221> NAME/KEY: MISC_FEATURE
<222> LOCATION: (10)..(10)
<223> OTHER INFORMATION: Norleucine

<400> SEQUENCE: 11

Lys Leu Lys Leu Lys Trp Ala Val Val Xaa
1               5                   10

<210> SEQ ID NO 12
<211> LENGTH: 10
<212> TYPE: PRT
<213> ORGANISM: Artificial Sequence
<220> FEATURE:
<223> OTHER INFORMATION: cyclic peptide amino acid sequence

<400> SEQUENCE: 12

Lys Leu Lys Leu Lys Trp Ala Val Val Ala
1               5                   10

<210> SEQ ID NO 13
<211> LENGTH: 10
<212> TYPE: PRT
<213> ORGANISM: Artificial Sequence
<220> FEATURE:
<223> OTHER INFORMATION: cyclic peptide amino acid sequence
<220> FEATURE:
<221> NAME/KEY: MISC_FEATURE
<222> LOCATION: (10)..(10)
<223> OTHER INFORMATION: Norleucine

<400> SEQUENCE: 13

Lys Leu Lys Leu Lys Trp Ala Val Ala Xaa
1               5                   10

<210> SEQ ID NO 14
<211> LENGTH: 10
<212> TYPE: PRT
<213> ORGANISM: Artificial Sequence
<220> FEATURE:
<223> OTHER INFORMATION: cyclic peptide amino acid sequence
<220> FEATURE:
<221> NAME/KEY: MISC_FEATURE
<222> LOCATION: (10)..(10)
<223> OTHER INFORMATION: Norleucine

<400> SEQUENCE: 14

Lys Leu Lys Leu Lys Trp Ala Ala Val Xaa
1               5                   10

<210> SEQ ID NO 15
<211> LENGTH: 10
<212> TYPE: PRT
<213> ORGANISM: Artificial Sequence
<220> FEATURE:
<223> OTHER INFORMATION: cyclic peptide amino acid sequence
<220> FEATURE:
<221> NAME/KEY: MISC_FEATURE
<222> LOCATION: (10)..(10)
<223> OTHER INFORMATION: Norleucine

<400> SEQUENCE: 15

Lys Leu Lys Leu Lys Ala Ala Val Val Xaa
1               5                   10
```

```
<210> SEQ ID NO 16
<211> LENGTH: 10
<212> TYPE: PRT
<213> ORGANISM: Artificial Sequence
<220> FEATURE:
<223> OTHER INFORMATION: cyclic peptide amino acid sequence
<220> FEATURE:
<221> NAME/KEY: MISC_FEATURE
<222> LOCATION: (6)..(6)
<223> OTHER INFORMATION: Norleucine

<400> SEQUENCE: 16

Lys Leu Lys Leu Lys Xaa Val Val Ala Trp
1               5                   10

<210> SEQ ID NO 17
<211> LENGTH: 10
<212> TYPE: PRT
<213> ORGANISM: Artificial Sequence
<220> FEATURE:
<223> OTHER INFORMATION: cyclic peptide amino acid sequence
<220> FEATURE:
<221> NAME/KEY: MISC_FEATURE
<222> LOCATION: (6)..(6)
<223> OTHER INFORMATION: Norleucine

<400> SEQUENCE: 17

Lys Leu Lys Gln Lys Xaa Val Val Ala Trp
1               5                   10

<210> SEQ ID NO 18
<211> LENGTH: 10
<212> TYPE: PRT
<213> ORGANISM: Artificial Sequence
<220> FEATURE:
<223> OTHER INFORMATION: cyclic peptide amino acid sequence
<220> FEATURE:
<221> NAME/KEY: MISC_FEATURE
<222> LOCATION: (6)..(6)
<223> OTHER INFORMATION: Norleucine

<400> SEQUENCE: 18

Gln Leu Lys Leu Lys Xaa Val Val Ala Trp
1               5                   10

<210> SEQ ID NO 19
<211> LENGTH: 10
<212> TYPE: PRT
<213> ORGANISM: Artificial Sequence
<220> FEATURE:
<223> OTHER INFORMATION: cyclic peptide amino acid sequence
<220> FEATURE:
<221> NAME/KEY: MISC_FEATURE
<222> LOCATION: (6)..(6)
<223> OTHER INFORMATION: Norleucine

<400> SEQUENCE: 19

Lys Leu Lys Leu Gln Xaa Val Val Ala Trp
1               5                   10

<210> SEQ ID NO 20
<211> LENGTH: 10
<212> TYPE: PRT
<213> ORGANISM: Artificial Sequence
<220> FEATURE:
<223> OTHER INFORMATION: cyclic peptide amino acid sequence
<220> FEATURE:
<221> NAME/KEY: MISC_FEATURE
<222> LOCATION: (6)..(6)
<223> OTHER INFORMATION: Norleucine
```

<400> SEQUENCE: 20

Lys Gln Lys Leu Lys Xaa Val Val Ala Trp
1               5                   10

<210> SEQ ID NO 21
<211> LENGTH: 10
<212> TYPE: PRT
<213> ORGANISM: Artificial Sequence
<220> FEATURE:
<223> OTHER INFORMATION: cyclic peptide amino acid sequence
<220> FEATURE:
<221> NAME/KEY: MISC_FEATURE
<222> LOCATION: (6)..(6)
<223> OTHER INFORMATION: Norleucine

<400> SEQUENCE: 21

Lys Leu Lys Gln Lys Xaa Val Val Ala Trp
1               5                   10

<210> SEQ ID NO 22
<211> LENGTH: 10
<212> TYPE: PRT
<213> ORGANISM: Artificial Sequence
<220> FEATURE:
<223> OTHER INFORMATION: cyclic peptide amino acid sequence
<220> FEATURE:
<221> NAME/KEY: MISC_FEATURE
<222> LOCATION: (10)..(10)
<223> OTHER INFORMATION: Norleucine

<400> SEQUENCE: 22

Lys Leu Lys Leu Lys Trp Ala Val Val Xaa
1               5                   10

<210> SEQ ID NO 23
<211> LENGTH: 10
<212> TYPE: PRT
<213> ORGANISM: Artificial Sequence
<220> FEATURE:
<223> OTHER INFORMATION: cyclic peptide amino acid sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Norleucine

<400> SEQUENCE: 23

Lys Xaa Lys Xaa Lys Trp Ala Val Val Xaa
1               5                   10

<210> SEQ ID NO 24
<211> LENGTH: 10
<212> TYPE: PRT
<213> ORGANISM: Artificial Sequence
<220> FEATURE:
<223> OTHER INFORMATION: cyclic peptide amino acid sequence
<220> FEATURE:
<221> NAME/KEY: MISC_FEATURE
<222> LOCATION: (6)..(6)
<223> OTHER INFORMATION: Norleucine

<400> SEQUENCE: 24

```
Lys Leu Lys Leu Lys Xaa Val Leu Ala Trp
1               5                   10

<210> SEQ ID NO 25
<211> LENGTH: 10
<212> TYPE: PRT
<213> ORGANISM: Artificial Sequence
<220> FEATURE:
<223> OTHER INFORMATION: cyclic peptide amino acid sequence
<220> FEATURE:
<221> NAME/KEY: MISC_FEATURE
<222> LOCATION: (6)..(6)
<223> OTHER INFORMATION: Norleucine

<400> SEQUENCE: 25

Lys Leu Lys Leu Lys Xaa Val Ile Ala Trp
1               5                   10

<210> SEQ ID NO 26
<211> LENGTH: 10
<212> TYPE: PRT
<213> ORGANISM: Artificial Sequence
<220> FEATURE:
<223> OTHER INFORMATION: cyclic peptide amino acid sequence
<220> FEATURE:
<221> NAME/KEY: MISC_FEATURE
<222> LOCATION: (6)..(6)
<223> OTHER INFORMATION: Norleucine

<400> SEQUENCE: 26

Lys Leu Lys Leu Lys Xaa Val Phe Ala Trp
1               5                   10

<210> SEQ ID NO 27
<211> LENGTH: 5
<212> TYPE: PRT
<213> ORGANISM: Artificial sequence
<220> FEATURE:
<223> OTHER INFORMATION: amino acid non-recognition sequence

<400> SEQUENCE: 27

Lys Leu Lys Leu Lys
1               5

<210> SEQ ID NO 28
<211> LENGTH: 5
<212> TYPE: PRT
<213> ORGANISM: Artificial sequence
<220> FEATURE:
<223> OTHER INFORMATION: amino acid non-recognition sequence

<400> SEQUENCE: 28

Lys Leu Gln Leu Lys
1               5

<210> SEQ ID NO 29
<211> LENGTH: 5
<212> TYPE: PRT
<213> ORGANISM: Artificial sequence
<220> FEATURE:
<223> OTHER INFORMATION: amino acid non-recognition sequence

<400> SEQUENCE: 29

Gln Leu Lys Leu Lys
1               5

<210> SEQ ID NO 30
<211> LENGTH: 5
```

```
<212> TYPE: PRT
<213> ORGANISM: Artificial sequence
<220> FEATURE:
<223> OTHER INFORMATION: amino acid non-recognition sequence

<400> SEQUENCE: 30

Lys Gln Lys Leu Lys
1               5

<210> SEQ ID NO 31
<211> LENGTH: 5
<212> TYPE: PRT
<213> ORGANISM: Artificial sequence
<220> FEATURE:
<223> OTHER INFORMATION: amino acid non-recognition sequence
<220> FEATURE:
<221> NAME/KEY: MISC_FEATURE
<222> LOCATION: (2)..(2)
<223> OTHER INFORMATION: sarcosine
<220> FEATURE:
<221> NAME/KEY: MISC_FEATURE
<222> LOCATION: (4)..(4)
<223> OTHER INFORMATION: sarcosine

<400> SEQUENCE: 31

Lys Xaa Lys Xaa Lys
1               5

<210> SEQ ID NO 32
<211> LENGTH: 5
<212> TYPE: PRT
<213> ORGANISM: Artificial sequence
<220> FEATURE:
<223> OTHER INFORMATION: amino acid non-recognition sequence

<400> SEQUENCE: 32

Glu Leu Lys Leu Lys
1               5

<210> SEQ ID NO 33
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 33

Met Val Val Ser Trp
1               5

<210> SEQ ID NO 34
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 34

Met Val Val Ser Ala
1               5

<210> SEQ ID NO 35
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 35
```

```
Met Val Val Ala Trp
1               5

<210> SEQ ID NO 36
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 36

Met Val Ala Ser Trp
1               5

<210> SEQ ID NO 37
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 37

Met Ala Val Ser Trp
1               5

<210> SEQ ID NO 38
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 38

Ala Val Val Ser Trp
1               5

<210> SEQ ID NO 39
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (1)..(1)
<223> OTHER INFORMATION: norleucine

<400> SEQUENCE: 39

Xaa Val Val Ser Trp
1               5

<210> SEQ ID NO 40
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (1)..(1)
<223> OTHER INFORMATION: norleucine

<400> SEQUENCE: 40

Xaa Val Val Tyr Trp
1               5

<210> SEQ ID NO 41
```

```
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (1)..(1)
<223> OTHER INFORMATION: norleucine

<400> SEQUENCE: 41

Xaa Val Val Ala Trp
1               5

<210> SEQ ID NO 42
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 42

Ala Val Val Ala Trp
1               5

<210> SEQ ID NO 43
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (1)..(1)
<223> OTHER INFORMATION: norleucine

<400> SEQUENCE: 43

Xaa Ala Val Ala Trp
1               5

<210> SEQ ID NO 44
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (1)..(1)
<223> OTHER INFORMATION: norleucine

<400> SEQUENCE: 44

Xaa Val Ala Ala Trp
1               5

<210> SEQ ID NO 45
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (1)..(1)
<223> OTHER INFORMATION: norleucine

<400> SEQUENCE: 45

Xaa Val Leu Ala Trp
1               5
```

<210> SEQ ID NO 46
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (1)..(1)
<223> OTHER INFORMATION: norleucine

<400> SEQUENCE: 46

Xaa Val Ile Ala Trp
1               5

<210> SEQ ID NO 47
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (1)..(1)
<223> OTHER INFORMATION: norleucine

<400> SEQUENCE: 47

Xaa Val Phe Ala Trp
1               5

<210> SEQ ID NO 48
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 48

Trp Ser Val Val Trp
1               5

<210> SEQ ID NO 49
<211> LENGTH: 10
<212> TYPE: PRT
<213> ORGANISM: Artificial sequence
<220> FEATURE:
<223> OTHER INFORMATION: cyclic peptide amino acid sequence
<220> FEATURE:
<221> NAME/KEY: MISC_FEATURE
<222> LOCATION: (6)..(6)
<223> OTHER INFORMATION: norleucine

<400> SEQUENCE: 49

Lys Leu Gln Leu Lys Xaa Val Val Ala Trp
1               5                   10

<210> SEQ ID NO 50
<211> LENGTH: 5
<212> TYPE: PRT
<213> ORGANISM: Artificial sequence
<220> FEATURE:
<223> OTHER INFORMATION: recognition amino acid sequence

<400> SEQUENCE: 50

Trp Ala Val Ala Trp
1               5

<210> SEQ ID NO 51

```
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 51

Trp Ala Val Ala Ala
1               5

<210> SEQ ID NO 52
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 52

Trp Ala Val Ala Met
1               5

<210> SEQ ID NO 53
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 53

Trp Ala Val Ala Xaa
1               5

<210> SEQ ID NO 54
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 54

Trp Ala Val Val Xaa
1               5

<210> SEQ ID NO 55
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 55

Trp Ala Val Ser Xaa
1               5

<210> SEQ ID NO 56
<211> LENGTH: 5
<212> TYPE: PRT
```

```
<213> ORGANISM: Artificial sequence
<220> FEATURE:
<223> OTHER INFORMATION: amino acid recognition sequence

<400> SEQUENCE: 56

Trp Ala Ala Ala Trp
1               5

<210> SEQ ID NO 57
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 57

Trp Ala Ala Ala Ala
1               5

<210> SEQ ID NO 58
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 58

Trp Ala Ala Ala Met
1               5

<210> SEQ ID NO 59
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 59

Trp Ala Ala Ala Xaa
1               5

<210> SEQ ID NO 60
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 60

Trp Ala Ala Val Trp
1               5

<210> SEQ ID NO 61
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 61

Trp Ala Ala Val Ala
1               5
```

```
<210> SEQ ID NO 62
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 62

Trp Ala Ala Val Met
1               5

<210> SEQ ID NO 63
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 63

Trp Ala Ala Val Xaa
1               5

<210> SEQ ID NO 64
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 64

Trp Ala Ala Ser Xaa
1               5

<210> SEQ ID NO 65
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 65

Trp Val Val Ala Trp
1               5

<210> SEQ ID NO 66
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 66

Trp Val Val Ala Ala
1               5

<210> SEQ ID NO 67
<211> LENGTH: 5
<212> TYPE: PRT
<213> ORGANISM: Artificial sequence
<220> FEATURE:
<223> OTHER INFORMATION: amino acid recognition sequence
```

<400> SEQUENCE: 67

Trp Val Val Ala Met
1               5

<210> SEQ ID NO 68
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 68

Trp Val Val Ala Xaa
1               5

<210> SEQ ID NO 69
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 69

Trp Val Val Val Trp
1               5

<210> SEQ ID NO 70
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 70

Trp Val Val Val Ala
1               5

<210> SEQ ID NO 71
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 71

Trp Val Val Val Met
1               5

<210> SEQ ID NO 72
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 72

Trp Val Val Val Xaa
1               5

<210> SEQ ID NO 73
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 73

Trp Val Val Ser Xaa
1               5

<210> SEQ ID NO 74
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 74

Trp Val Ala Ala Xaa
1               5

<210> SEQ ID NO 75
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 75

Trp Val Ala Val Trp
1               5

<210> SEQ ID NO 76
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 76

Trp Val Ala Val Ala
1               5

<210> SEQ ID NO 77
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 77

Trp Val Ala Val Met
1               5

<210> SEQ ID NO 78
<211> LENGTH: 5
<212> TYPE: PRT
<213> ORGANISM: Artificial sequence
<220> FEATURE:

```
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 78

Trp Val Ala Val Xaa
1               5

<210> SEQ ID NO 79
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 79

Trp Val Ala Ser Xaa
1               5

<210> SEQ ID NO 80
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 80

Trp Ser Val Ala Trp
1               5

<210> SEQ ID NO 81
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 81

Trp Ser Val Ala Ala
1               5

<210> SEQ ID NO 82
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 82

Trp Ser Val Ala Met
1               5

<210> SEQ ID NO 83
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine
```

<400> SEQUENCE: 83

Trp Ser Val Ala Xaa
1               5

<210> SEQ ID NO 84
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 84

Trp Ser Val Val Ala
1               5

<210> SEQ ID NO 85
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 85

Trp Ser Val Val Met
1               5

<210> SEQ ID NO 86
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 86

Trp Ser Val Val Xaa
1               5

<210> SEQ ID NO 87
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 87

Trp Ser Val Ser Trp
1               5

<210> SEQ ID NO 88
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 88

Trp Ser Val Ser Ala
1               5

<210> SEQ ID NO 89
<211> LENGTH: 5
<212> TYPE: PRT
<213> ORGANISM: Artificial sequence

```
<220> FEATURE:
<223> OTHER INFORMATION: amino acid recognition sequence

<400> SEQUENCE: 89

Trp Ser Val Ser Met
1               5

<210> SEQ ID NO 90
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 90

Trp Ser Val Ser Xaa
1               5

<210> SEQ ID NO 91
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 91

Trp Ser Ala Ala Trp
1               5

<210> SEQ ID NO 92
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 92

Trp Ser Ala Ala Ala
1               5

<210> SEQ ID NO 93
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 93

Trp Ser Ala Ala Met
1               5

<210> SEQ ID NO 94
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 94

Trp Ser Ala Ala Xaa
```

```
1               5
```

<210> SEQ ID NO 95
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 95

```
Trp Ser Ala Val Trp
1               5
```

<210> SEQ ID NO 96
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 96

```
Trp Ser Ala Val Ala
1               5
```

<210> SEQ ID NO 97
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 97

```
Trp Ser Ala Val Met
1               5
```

<210> SEQ ID NO 98
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 98

```
Trp Ser Ala Val Xaa
1               5
```

<210> SEQ ID NO 99
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 99

```
Trp Ser Ala Ser Trp
1               5
```

<210> SEQ ID NO 100
<211> LENGTH: 5
<212> TYPE: PRT
<213> ORGANISM: Artificial sequence
<220> FEATURE:
<223> OTHER INFORMATION: amino acid recognition sequence

```
<400> SEQUENCE: 100

Trp Ser Ala Ser Ala
1               5

<210> SEQ ID NO 101
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 101

Trp Ser Ala Ser Met
1               5

<210> SEQ ID NO 102
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 102

Trp Ser Ala Ser Xaa
1               5

<210> SEQ ID NO 103
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 103

Trp Tyr Val Ala Trp
1               5

<210> SEQ ID NO 104
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 104

Trp Tyr Val Ala Ala
1               5

<210> SEQ ID NO 105
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 105

Trp Tyr Val Ala Met
1               5

<210> SEQ ID NO 106
<211> LENGTH: 5
<212> TYPE: PRT
<213> ORGANISM: Artificial sequence
```

```
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 106

Trp Tyr Val Ala Xaa
1               5

<210> SEQ ID NO 107
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 107

Trp Tyr Val Val Trp
1               5

<210> SEQ ID NO 108
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 108

Trp Tyr Val Val Ala
1               5

<210> SEQ ID NO 109
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 109

Trp Tyr Val Val Met
1               5

<210> SEQ ID NO 110
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 110

Trp Tyr Val Val Xaa
1               5

<210> SEQ ID NO 111
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 111

Trp Tyr Val Ser Trp
```

```
1               5

<210> SEQ ID NO 112
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 112

Trp Tyr Val Ser Ala
1               5

<210> SEQ ID NO 113
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 113

Trp Tyr Val Ser Met
1               5

<210> SEQ ID NO 114
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 114

Trp Tyr Val Ser Xaa
1               5

<210> SEQ ID NO 115
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 115

Trp Tyr Ala Ala Trp
1               5

<210> SEQ ID NO 116
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 116

Trp Tyr Ala Ala Ala
1               5

<210> SEQ ID NO 117
<211> LENGTH: 5
<212> TYPE: PRT
<213> ORGANISM: Artificial sequence
<220> FEATURE:
<223> OTHER INFORMATION: amino acid recognition sequence
```

```
<400> SEQUENCE: 117

Trp Tyr Ala Ala Met
1               5

<210> SEQ ID NO 118
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 118

Trp Tyr Ala Ala Xaa
1               5

<210> SEQ ID NO 119
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 119

Trp Tyr Ala Val Trp
1               5

<210> SEQ ID NO 120
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 120

Trp Tyr Ala Val Ala
1               5

<210> SEQ ID NO 121
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 121

Trp Tyr Ala Val Met
1               5

<210> SEQ ID NO 122
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 122

Trp Tyr Ala Val Xaa
1               5
```

```
<210> SEQ ID NO 123
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 123

Trp Tyr Ala Ser Trp
1               5

<210> SEQ ID NO 124
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 124

Trp Tyr Ala Ser Ala
1               5

<210> SEQ ID NO 125
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 125

Trp Tyr Ala Ser Met
1               5

<210> SEQ ID NO 126
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 126

Trp Tyr Ala Ser Xaa
1               5

<210> SEQ ID NO 127
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 127

Ala Ala Val Ala Ala
1               5

<210> SEQ ID NO 128
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 128

Ala Ala Val Ala Met
```

```
1               5

<210> SEQ ID NO 129
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 129

Ala Ala Val Ala Xaa
1               5

<210> SEQ ID NO 130
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 130

Ala Ala Val Val Xaa
1               5

<210> SEQ ID NO 131
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 131

Ala Ala Val Ser Xaa
1               5

<210> SEQ ID NO 132
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 132

Ala Ala Ala Ala Ala
1               5

<210> SEQ ID NO 133
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 133

Ala Ala Ala Ala Met
1               5
```

```
<210> SEQ ID NO 134
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 134

Ala Ala Ala Ala Xaa
1               5

<210> SEQ ID NO 135
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 135

Ala Ala Ala Val Trp
1               5

<210> SEQ ID NO 136
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 136

Ala Ala Ala Val Ala
1               5

<210> SEQ ID NO 137
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 137

Ala Ala Ala Val Met
1               5

<210> SEQ ID NO 138
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 138

Ala Ala Ala Val Xaa
1               5

<210> SEQ ID NO 139
<211> LENGTH: 5
<212> TYPE: PRT
<213> ORGANISM: Artificial sequence
<220> FEATURE:
```

```
<223> OTHER INFORMATION: amino acid recognition sequence

<400> SEQUENCE: 139

Ala Ala Ala Ser Met
1               5

<210> SEQ ID NO 140
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 140

Ala Ala Ala Ser Xaa
1               5

<210> SEQ ID NO 141
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 141

Ala Val Val Ala Trp
1               5

<210> SEQ ID NO 142
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 142

Ala Val Val Ala Ala
1               5

<210> SEQ ID NO 143
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 143

Ala Val Val Ala Met
1               5

<210> SEQ ID NO 144
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 144

Ala Val Val Ala Xaa
1               5
```

```
<210> SEQ ID NO 145
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 145

Ala Val Val Val Ala
1               5

<210> SEQ ID NO 146
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 146

Ala Val Val Val Met
1               5

<210> SEQ ID NO 147
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 147

Ala Val Val Val Xaa
1               5

<210> SEQ ID NO 148
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 148

Ala Val Val Ser Xaa
1               5

<210> SEQ ID NO 149
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 149

Ala Val Ala Ala Met
1               5

<210> SEQ ID NO 150
<211> LENGTH: 5
<212> TYPE: PRT
<213> ORGANISM: Artificial sequence
```

```
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 150

Ala Val Ala Ala Xaa
1               5

<210> SEQ ID NO 151
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 151

Ala Val Ala Val Ala
1               5

<210> SEQ ID NO 152
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 152

Ala Val Ala Val Met
1               5

<210> SEQ ID NO 153
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 153

Ala Val Ala Val Xaa
1               5

<210> SEQ ID NO 154
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 154

Ala Val Ala Ser Xaa
1               5

<210> SEQ ID NO 155
<211> LENGTH: 5
<212> TYPE: PRT
<213> ORGANISM: Artificial sequence
<220> FEATURE:
<223> OTHER INFORMATION: amino acid recognition sequence
```

```
<400> SEQUENCE: 155

Ala Ser Val Ala Trp
1               5

<210> SEQ ID NO 156
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 156

Ala Ser Val Ala Ala
1               5

<210> SEQ ID NO 157
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 157

Ala Ser Val Ala Met
1               5

<210> SEQ ID NO 158
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 158

Ala Ser Val Ala Xaa
1               5

<210> SEQ ID NO 159
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 159

Ala Ser Val Val Trp
1               5

<210> SEQ ID NO 160
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 160

Ala Ser Val Val Ala
1               5

<210> SEQ ID NO 161
<211> LENGTH: 5
<212> TYPE: PRT
```

```
<213> ORGANISM: Artificial sequence
<220> FEATURE:
<223> OTHER INFORMATION: amino acid recognition sequence

<400> SEQUENCE: 161

Ala Ser Val Val Met
1               5

<210> SEQ ID NO 162
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 162

Ala Ser Val Val Xaa
1               5

<210> SEQ ID NO 163
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 163

Ala Ser Val Ser Ala
1               5

<210> SEQ ID NO 164
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 164

Ala Ser Val Ser Met
1               5

<210> SEQ ID NO 165
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 165

Ala Ser Val Ser Xaa
1               5

<210> SEQ ID NO 166
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 166
```

```
Ala Ser Ala Ala Trp
1               5

<210> SEQ ID NO 167
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 167

Ala Ser Ala Ala Ala
1               5

<210> SEQ ID NO 168
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 168

Ala Ser Ala Ala Met
1               5

<210> SEQ ID NO 169
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 169

Ala Ser Ala Ala Xaa
1               5

<210> SEQ ID NO 170
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 170

Ala Ser Ala Val Trp
1               5

<210> SEQ ID NO 171
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 171

Ala Ser Ala Val Ala
1               5

<210> SEQ ID NO 172
<211> LENGTH: 5
<212> TYPE: PRT
<213> ORGANISM: Artificial sequence
<220> FEATURE:
<223> OTHER INFORMATION: amino acid recognition sequence
```

```
<400> SEQUENCE: 172

Ala Ser Ala Val Met
1               5

<210> SEQ ID NO 173
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 173

Ala Ser Ala Val Xaa
1               5

<210> SEQ ID NO 174
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 174

Ala Ser Ala Ser Ala
1               5

<210> SEQ ID NO 175
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 175

Ala Ser Ala Ser Met
1               5

<210> SEQ ID NO 176
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 176

Ala Ser Ala Ser Xaa
1               5

<210> SEQ ID NO 177
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 177

Ala Tyr Val Ala Trp
1               5
```

<210> SEQ ID NO 178
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 178

Ala Tyr Val Ala Ala
1               5

<210> SEQ ID NO 179
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 179

Ala Tyr Val Ala Met
1               5

<210> SEQ ID NO 180
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 180

Ala Tyr Val Ala Xaa
1               5

<210> SEQ ID NO 181
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 181

Ala Tyr Val Val Trp
1               5

<210> SEQ ID NO 182
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 182

Ala Tyr Val Val Ala
1               5

<210> SEQ ID NO 183
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 183

```
Ala Tyr Val Val Met
1               5

<210> SEQ ID NO 184
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 184

Ala Tyr Val Val Xaa
1               5

<210> SEQ ID NO 185
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 185

Ala Tyr Val Ser Trp
1               5

<210> SEQ ID NO 186
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 186

Ala Tyr Val Ser Ala
1               5

<210> SEQ ID NO 187
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 187

Ala Tyr Val Ser Met
1               5

<210> SEQ ID NO 188
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 188

Ala Tyr Val Ser Xaa
1               5

<210> SEQ ID NO 189
<211> LENGTH: 5
```

```
<212> TYPE: PRT
<213> ORGANISM: Artificial sequence
<220> FEATURE:
<223> OTHER INFORMATION: amino acid recognition sequence

<400> SEQUENCE: 189

Ala Tyr Ala Ala Trp
1               5

<210> SEQ ID NO 190
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 190

Ala Tyr Ala Ala Ala
1               5

<210> SEQ ID NO 191
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 191

Ala Tyr Ala Ala Met
1               5

<210> SEQ ID NO 192
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 192

Ala Tyr Ala Ala Xaa
1               5

<210> SEQ ID NO 193
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 193

Ala Tyr Ala Val Trp
1               5

<210> SEQ ID NO 194
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 194

Ala Tyr Ala Val Ala
1               5
```

```
<210> SEQ ID NO 195
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 195

Ala Tyr Ala Val Met
1               5

<210> SEQ ID NO 196
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 196

Ala Tyr Ala Val Xaa
1               5

<210> SEQ ID NO 197
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 197

Ala Tyr Ala Ser Trp
1               5

<210> SEQ ID NO 198
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 198

Ala Tyr Ala Ser Ala
1               5

<210> SEQ ID NO 199
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 199

Ala Tyr Ala Ser Met
1               5

<210> SEQ ID NO 200
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
```

<223> OTHER INFORMATION: norleucine

<400> SEQUENCE: 200

Ala Tyr Ala Ser Xaa
1               5

<210> SEQ ID NO 201
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 201

Met Ala Val Ala Ala
1               5

<210> SEQ ID NO 202
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 202

Met Ala Val Ala Met
1               5

<210> SEQ ID NO 203
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 203

Met Ala Val Ala Xaa
1               5

<210> SEQ ID NO 204
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 204

Met Ala Val Val Xaa
1               5

<210> SEQ ID NO 205
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

```
<400> SEQUENCE: 205

Met Ala Val Ser Xaa
1               5

<210> SEQ ID NO 206
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 206

Met Ala Ala Ala Ala
1               5

<210> SEQ ID NO 207
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 207

Met Ala Ala Ala Met
1               5

<210> SEQ ID NO 208
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 208

Met Ala Ala Ala Xaa
1               5

<210> SEQ ID NO 209
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 209

Met Ala Ala Val Trp
1               5

<210> SEQ ID NO 210
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 210

Met Ala Ala Val Ala
1               5

<210> SEQ ID NO 211
<211> LENGTH: 5
<212> TYPE: PRT
<213> ORGANISM: Artificial sequence
```

```
<220> FEATURE:
<223> OTHER INFORMATION: amino acid recognition sequence

<400> SEQUENCE: 211

Met Ala Ala Val Met
1               5

<210> SEQ ID NO 212
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 212

Met Ala Ala Val Xaa
1               5

<210> SEQ ID NO 213
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 213

Met Ala Ala Ser Xaa
1               5

<210> SEQ ID NO 214
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 214

Met Val Val Ala Trp
1               5

<210> SEQ ID NO 215
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 215

Met Val Val Ala Ala
1               5

<210> SEQ ID NO 216
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 216

Met Val Val Ala Met
```

```
1               5

<210> SEQ ID NO 217
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 217

Met Val Val Ala Xaa
1               5

<210> SEQ ID NO 218
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 218

Met Val Val Val Met
1               5

<210> SEQ ID NO 219
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 219

Met Val Val Val Xaa
1               5

<210> SEQ ID NO 220
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 220

Met Val Val Ser Xaa
1               5

<210> SEQ ID NO 221
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 221

Met Val Ala Ala Met
1               5
```

```
<210> SEQ ID NO 222
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 222

Met Val Ala Ala Xaa
1               5

<210> SEQ ID NO 223
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 223

Met Val Ala Val Met
1               5

<210> SEQ ID NO 224
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 224

Met Val Ala Val Xaa
1               5

<210> SEQ ID NO 225
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 225

Met Val Ala Ser Xaa
1               5

<210> SEQ ID NO 226
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 226

Met Ser Val Ala Trp
1               5

<210> SEQ ID NO 227
```

```
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 227

Met Ser Val Ala Ala
1               5

<210> SEQ ID NO 228
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 228

Met Ser Val Ala Met
1               5

<210> SEQ ID NO 229
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 229

Met Ser Val Ala Xaa
1               5

<210> SEQ ID NO 230
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 230

Met Ser Val Val Trp
1               5

<210> SEQ ID NO 231
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 231

Met Ser Val Val Ala
1               5

<210> SEQ ID NO 232
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 232

Met Ser Val Val Met
1               5
```

```
<210> SEQ ID NO 233
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 233

Met Ser Val Val Xaa
1               5

<210> SEQ ID NO 234
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 234

Met Ser Val Ser Met
1               5

<210> SEQ ID NO 235
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 235

Met Ser Val Ser Xaa
1               5

<210> SEQ ID NO 236
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 236

Met Ser Ala Ala Trp
1               5

<210> SEQ ID NO 237
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 237

Met Ser Ala Ala Ala
1               5

<210> SEQ ID NO 238
<211> LENGTH: 5
<212> TYPE: PRT
<213> ORGANISM: Artificial sequence
```

-continued

```
<220> FEATURE:
<223> OTHER INFORMATION: amino acid recognition sequence

<400> SEQUENCE: 238

Met Ser Ala Ala Met
1               5

<210> SEQ ID NO 239
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 239

Met Ser Ala Ala Xaa
1               5

<210> SEQ ID NO 240
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 240

Met Ser Ala Val Trp
1               5

<210> SEQ ID NO 241
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 241

Met Ser Ala Val Ala
1               5

<210> SEQ ID NO 242
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 242

Met Ser Ala Val Met
1               5

<210> SEQ ID NO 243
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 243

Met Ser Ala Val Xaa
```

```
1               5

<210> SEQ ID NO 244
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 244

Met Ser Ala Ser Met
1               5

<210> SEQ ID NO 245
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 245

Met Ser Ala Ser Xaa
1               5

<210> SEQ ID NO 246
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 246

Met Tyr Val Ala Trp
1               5

<210> SEQ ID NO 247
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 247

Met Tyr Val Ala Ala
1               5

<210> SEQ ID NO 248
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 248

Met Tyr Val Ala Met
1               5

<210> SEQ ID NO 249
<211> LENGTH: 5
<212> TYPE: PRT
<213> ORGANISM: Artificial sequence
<220> FEATURE:
<223> OTHER INFORMATION: amino acid recognition sequence
<220> FEATURE:
```

```
<221> NAME/KEY: MISC_FEATURE
<222> LOCATION: (5)..(5)
<223> OTHER INFORMATION: norleucine

<400> SEQUENCE: 249

Met Tyr Val Ala Xaa
1               5

<210> SEQ ID NO 250
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 250

Met Tyr Val Val Trp
1               5

<210> SEQ ID NO 251
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 251

Met Tyr Val Val Ala
1               5

<210> SEQ ID NO 252
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 252

Met Tyr Val Val Met
1               5

<210> SEQ ID NO 253
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 253

Met Tyr Val Val Xaa
1               5

<210> SEQ ID NO 254
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 254

Met Tyr Val Ser Trp
1               5
```

-continued

```
<210> SEQ ID NO 255
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 255

Met Tyr Val Ser Ala
1               5

<210> SEQ ID NO 256
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 256

Met Tyr Val Ser Met
1               5

<210> SEQ ID NO 257
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 257

Met Tyr Val Ser Xaa
1               5

<210> SEQ ID NO 258
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 258

Met Tyr Ala Ala Trp
1               5

<210> SEQ ID NO 259
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 259

Met Tyr Ala Ala Ala
1               5

<210> SEQ ID NO 260
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 260

Met Tyr Ala Ala Met
```

```
1               5
```

<210> SEQ ID NO 261
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 261

```
Met Tyr Ala Ala Xaa
1               5
```

<210> SEQ ID NO 262
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 262

```
Met Tyr Ala Val Trp
1               5
```

<210> SEQ ID NO 263
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 263

```
Met Tyr Ala Val Ala
1               5
```

<210> SEQ ID NO 264
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 264

```
Met Tyr Ala Val Met
1               5
```

<210> SEQ ID NO 265
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 265

```
Met Tyr Ala Val Xaa
1               5
```

<210> SEQ ID NO 266
<211> LENGTH: 5
<212> TYPE: PRT

```
<213> ORGANISM: Artificial sequence
<220> FEATURE:
<223> OTHER INFORMATION: amino acid recognition sequence

<400> SEQUENCE: 266

Met Tyr Ala Ser Trp
1               5

<210> SEQ ID NO 267
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 267

Met Tyr Ala Ser Ala
1               5

<210> SEQ ID NO 268
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 268

Met Tyr Ala Ser Met
1               5

<210> SEQ ID NO 269
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: norleucine

<400> SEQUENCE: 269

Met Tyr Ala Ser Xaa
1               5

<210> SEQ ID NO 270
<211> LENGTH: 10
<212> TYPE: PRT
<213> ORGANISM: Artificial sequence
<220> FEATURE:
<223> OTHER INFORMATION: cyclic peptide amino acid sequence

<400> SEQUENCE: 270

Lys Leu Lys Leu Lys Ala Ser Val Val Met
1               5                   10

<210> SEQ ID NO 271
<211> LENGTH: 10
<212> TYPE: PRT
<213> ORGANISM: Artificial sequence
<220> FEATURE:
<223> OTHER INFORMATION: cyclic peptide amino acid sequence

<400> SEQUENCE: 271

Lys Leu Lys Leu Lys Trp Ala Val Val Met
1               5                   10
```

```
<210> SEQ ID NO 272
<211> LENGTH: 10
<212> TYPE: PRT
<213> ORGANISM: Artificial sequence
<220> FEATURE:
<223> OTHER INFORMATION: cyclic peptide amino acid sequence

<400> SEQUENCE: 272

Lys Leu Lys Leu Lys Trp Ser Ala Val Met
1               5                   10

<210> SEQ ID NO 273
<211> LENGTH: 10
<212> TYPE: PRT
<213> ORGANISM: Artificial sequence
<220> FEATURE:
<223> OTHER INFORMATION: cyclic peptide amino acid sequence

<400> SEQUENCE: 273

Lys Leu Lys Leu Lys Trp Ser Val Ala Met
1               5                   10

<210> SEQ ID NO 274
<211> LENGTH: 10
<212> TYPE: PRT
<213> ORGANISM: Artificial sequence
<220> FEATURE:
<223> OTHER INFORMATION: cyclic peptide amino acid sequence

<400> SEQUENCE: 274

Lys Leu Lys Leu Lys Trp Ser Val Val Ala
1               5                   10

<210> SEQ ID NO 275
<211> LENGTH: 10
<212> TYPE: PRT
<213> ORGANISM: Artificial sequence
<220> FEATURE:
<223> OTHER INFORMATION: cyclic peptide amino acid sequence
<220> FEATURE:
<221> NAME/KEY: MISC_FEATURE
<222> LOCATION: (10)..(10)
<223> OTHER INFORMATION: norleucine

<400> SEQUENCE: 275

Lys Leu Lys Leu Lys Trp Ser Val Val Xaa
1               5                   10

<210> SEQ ID NO 276
<211> LENGTH: 10
<212> TYPE: PRT
<213> ORGANISM: Artificial sequence
<220> FEATURE:
<223> OTHER INFORMATION: cyclic peptide amino acid sequence
<220> FEATURE:
<221> NAME/KEY: MISC_FEATURE
<222> LOCATION: (10)..(10)
<223> OTHER INFORMATION: norleucine

<400> SEQUENCE: 276

Lys Leu Lys Leu Lys Trp Tyr Val Val Xaa
1               5                   10

<210> SEQ ID NO 277
<211> LENGTH: 10
<212> TYPE: PRT
<213> ORGANISM: Artificial sequence
<220> FEATURE:
<223> OTHER INFORMATION: cyclic peptide amino acid sequence
```

```
<400> SEQUENCE: 277

Lys Leu Lys Leu Lys Trp Ser Val Val Trp
1               5                   10

<210> SEQ ID NO 278
<211> LENGTH: 10
<212> TYPE: PRT
<213> ORGANISM: Artificial sequence
<220> FEATURE:
<223> OTHER INFORMATION: D-amino acid peptide (HYD1)

<400> SEQUENCE: 278

Lys Ile Lys Met Val Ile Ser Trp Lys Gly
1               5                   10

<210> SEQ ID NO 279
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 279

Met Val Ile Ser Trp
1               5

<210> SEQ ID NO 280
<211> LENGTH: 9
<212> TYPE: PRT
<213> ORGANISM: Artificial sequence
<220> FEATURE:
<223> OTHER INFORMATION: cyclic peptide amino acid sequence

<400> SEQUENCE: 280

Lys Met Val Ile Tyr Trp Lys Ala Gly
1               5

<210> SEQ ID NO 281
<211> LENGTH: 5
<212> TYPE: PRT
<213> ORGANISM: Artificial sequence
<220> FEATURE:
<223> OTHER INFORMATION: amino acid non-recognition sequence

<400> SEQUENCE: 281

Lys Leu Lys Leu Gln
1               5

<210> SEQ ID NO 282
<211> LENGTH: 5
<212> TYPE: PRT
<213> ORGANISM: Artificial sequence
<220> FEATURE:
<223> OTHER INFORMATION: amino acid non-recognition sequence

<400> SEQUENCE: 282

Lys Leu Lys Gln Lys
1               5
```

INTEGRIN INTERACTION INHIBITORS FOR THE TREATMENT OF CANCER

CROSS-REFERENCE TO RELATED APPLICATIONS

The present application is a divisional of U.S. application Ser. No. 14/465,106, filed Aug. 21, 2014, which is a continuation of U.S. application Ser. No. 13/636,010, filed Nov. 20, 2012, which is the National Stage of International Application Number PCT/US2011/000512, filed Mar. 21, 2011, which claims the benefit of U.S. Provisional Application Ser. No. 61/315,730, filed Mar. 19, 2010, each of which is hereby incorporated by reference herein in its entirety, including any figures, tables, nucleic acid sequences, amino acid sequences, and drawings.

The Sequence Listing for this application is labeled "2HR4695.TXT" which was created on May 25, 2016 and is 57 KB. The entire contents of the sequence listing is incorporated herein by reference in its entirety.

GOVERNMENT SUPPORT

This invention was made with government support under Grant No. CA122065, awarded by the National Institutes of Health (NIH). The government has certain rights in the invention.

BACKGROUND OF THE INVENTION

This invention relates to treatment of malignancies with peptides. Specifically, the invention provides contacting cancer cells, tumors, or pre-tumorigenic masses with integrin interaction inhibitor proteins to effect treatment.

Multiple myeloma (MM) is a cancer of the plasma cell, which primarily develops in the elderly population. The progression of the tumor is well understood, and it can be diagnosed by the presence of multiple myeloma cells in the bone marrow and monitored by the amount of antibody secretion from the clonal population of plasma cells. A premalignant condition known as monoclonal gammopathy of undetermined significance (MGUS) develops at a certain rates in the US population: 3% at age 50, 5% at age 70, and 7% by age 85; approximately 1% of MGUS patients progress to multiple myeloma on an annual basis (Kyle R A, et. al, Prevalence of monoclonal gammopathy of undetermined significance. *N. Engl. J. Med.* 354, 1362-1369 (2006)). The molecular causes for progression from MGUS to MM are unknown. After the onset of the cancer, multiple myeloma patients suffer from several symptoms, including calcium dysregulation, renal failure, anemia, and bone lesions. A diagnosis of multiple myeloma is established using blood and urine tests. For advanced stage patients, complete skeletal surveys are also used to examine the damage caused by multiple myeloma in the bone marrow. Staging with serum calcium, creatinine, hemoglobin, and most importantly, the concentration of the "monoclonal serum protein" was established in 1975 by Durie and Salmon (Durie B G, Salmon S E, A clinical staging system for multiple myeloma. Correlation of measured myeloma cell mass with presenting clinical features, response to treatment, and survival. *Cancer* 36, 842-854 (1975)). The International Staging System determined in 2005 uses those markers as well as serum albumin and β-2-microglobulin (Greipp P R, et. al, International staging system for multiple myeloma. *J. Clin. Oncol.* 23, 3412-3420 (2005)). The survival statistics indicate the importance of early detection and proper staging, and show the devastating impact of multiple myeloma. Stage I patients have median survival times of 62 months, stage II 45 months, and stage III patient median survival is reduced to 29 months.

Despite the highly specific and easily detectable biomarkers, many challenges still exist for MM treatment. Several different treatment regimens are under investigation; these strategies have been the subject of numerous recent reviews (Fonseca R, Stewart A K, Targeted therapeutics for multiple myeloma: the arrival of a risk-stratified approach. *Mol. Cancer Ther.* 6, 802-810 (2007); Chanan-Khan A A, Lee K, Pegylated liposomal doxorubicin and immunomodulatory drug combinations in multiple myeloma: rationale and clinical experience. *Clin. Lymph. Myel.* 7, S163-S169 (2007); Thomas S, Alexanian R. Current treatment strategies for multiple myeloma. *Clin. Lymph. Myel.* 7, S139-S144 (2007); Falco P, et al., Melphalan and its role in the management of patients with multiple myeloma. *Expert. Rev. Anticancer Ther.* 7, 945-957(2007)). Novel therapeutic strategies include proteasome inhibition with agents like bortezomib (Voorhees P M, Orlowski R Z, Emerging data on the use of anthracyclines in combination with Bortezomib in multiple myeloma. *Clin. Lymph. Myel.* 7, S156-S162 (2007); Manochakian R, et al., Clinical Impact of Bortezomib in frontline regimens for patients with multiple myeloma. *The Oncologist* 12, 978-990 (2007)) and a combination of cancer cell targeting and immune modulation with thalidomide derivatives like Lenalidomide (Singhal S, Mehta J. Lenalidomide in myeloma. *Curr. Treatment Options in Oncology* 8, 154-163 (2007)). While each of these agents can have some success against multiple myeloma cells, proteasome inhibitors are the only molecularly guided therapy to date: treatment is more effective for patients with myelomas that secrete high levels of monoclonal antibodies (Meister S, et al., Extensive immunoglobulin production sensitizes myeloma cells for proteasome inhibition. *Cancer Res.* 67, 1783-1792 (2007)). The use of the other agents is directed by the expected tolerance for side effects rather than molecular targeting.

Regardless, these agents improve the patient outcome when compared to the current standard of care (Ma M H, et al., The proteasome inhibitor PS-341 markedly enhances sensitivity of multiple myeloma tumor cells to chemotherapeutic agents. *Clin, Cancer Res.* 9, 1136-1144 (2003)), and drug combination strategies are currently in clinical trials (Srikanth M, Davies F E, Morgan G J, An update on drug combinations for treatment of myeloma. *Expert Opn. Investig. Drugs* 17, 1-12 (2008); Richardson P G, et al., The emerging role of novel therapies for the treatment of relapsed myeloma. *J. Natl. Comp. Cancer Network* 5, 149-162 (2007); Merchionne F, et al., New therapies in multiple myeloma. *Clin. Exp. Med.* 7, 83-97 (2007)). Proteomic research may contribute to guidance of existing and emerging therapies. Identification of novel targets including c-Jun and the Fanconi anemia pathway (Chen Q, et al., The FA/BRCA pathway is involved in Melphalan-induced DNA interstrand cross-link repair and accounts for Melphalan resistance in multiple myeloma cells. *Blood* 106, 698-705 (2005)) also offers opportunities to examine protein expression, binding partners, and post-translational modification.

Initial treatment is positive, as MM responds to standard chemotherapy treatment. However, relapse of the tumor usually occurs due to unsuccessful elimination of minimal residual disease (MRD). Recurrence of disease is associated with emergence of multi drug resistance (MDR) of tumor cells to standard cytotoxic agents (Hazlehurst, L. A., Alsina, M., Dalton, W. S. *Cancer Research,* 63, 7900-7906 (2003);

Daminao, J. S., Cress, A. E., Hazlehurst, L. A., Shtil, A. A., Dalton, W. S. *Blood*, 93(5), 1658-1667 (1999)). MRD is typically found in the bone marrow compartment, suggesting that this particular microenvironment may provide tumor cell survival signals. Multiple myeloma cells adhere to bone marrow, an environment that is rich in extracellular matrices via cell surface receptors.

The emergence of drug-resistant cells is an obstacle to treatment of diseases. The bone marrow microenvironment is critical for progression of multiple myeloma and likely contributes to drug resistance; (Li Z W, Dalton W S, Tumor microenvironment and drug resistance in hematologic malignancies. *Blood Rev.* 20(6), 333-342 (2006); Hazlehurst L A, et al., Role of the tumor microenvironment in mediating de novo resistance to drugs and physiological mediators of cell death. *Oncogene* 22, 7396-7402 (2003); Dalton W S. The tumor microenvironment: focus on myeloma. *Cancer Treat Rev.* 29 Suppl 1, 11-19(2003)) this knowledge has led to preclinical models examining multiple myeloma in the context of the bone marrow microenvironment. Plausible targets in the bone marrow microenvironment include cytokine signaling, e.g. IL-6, (Chauhan D, et al., Interleukin-6 inhibits Fas-induced apoptosis and stress-activated protein kinase activation in multiple myeloma cells. *Blood* 89, 227-234 (1997); Urashima M, et al., Interleukin-6 overcomes p21WAF1 upregulation and G1 growth arrest induced by dexamethasone and interferon-gamma in multiple myeloma cells. *Blood* 90, 279-289 (1997)) and integrin mediated drug resistance (Damiano J S, et al., Cell adhesion mediated drug resistance (CAM-DR): role of integrins and resistance to apoptosis in human myeloma cell lines. *Blood* 93, 1658-1667 (1999)).

In some situations, leukemias have gained resistance through cellular adhesion to extracellular matrix through 1 integrin. (Hazlehurst, et al. *Oncogene*. 2000; 19:4319-4327; Hazlehurst, et al. *Cancer Res.* 2003; 63:7900-7906; Hazlehurst, et al. *Blood.* 2001; 98:1897-1903; Hazlehurst, et al. *Cancer Res.* 2006; 66:2338-2345; Hazlehurst, et al. *Cancer Metastasis Rev.* 2001; 20:43-50; Hazlehurst, et al. *Cancer Res.* 1999; 59: 1021-1028; Hazlehurst, et al. *Biochem Pharmacol.* 1995; 50:1087-1094; Hazlehurst, et al. 55 *Oncogene.* 2003; 22:7396-7402). Hazlehurst et. al. have shown that adhesion of leukemia and multiple myeloma cell lines to extracellular matrix component, fibronectin (FN) via integrin influences cell survival and inhibits drug-induced apoptosis (Hazlehurst, L. A., Damiano, J. S., Buyuksalml., Pledger, W. J., Dalton, W. S. *Oncogene*, 38, 4319-4327 (2000)). Studies have found these findings extend to the clininical setting, where cell adhesion induced drug resistance (CAMDR) phenotype is operative in clinical samples taken from primary multiple myeloma (Hazlehurst L A, et al. *Cancer Res.* 2003; 63:7900-7906).

BRIEF SUMMARY OF THE INVENTION

The present invention provides novel designs for integrin interaction inhibitors, compositions comprising these integrin interaction inhibitors, methods of producing these integrin interaction inhibitors, and methods of use. In preferred embodiments, the integrin interaction inhibitors comprise a cyclic compound comprising a recognition sequence and a non-recognition sequence, wherein the recognition sequence comprises at least four amino acids, wherein the non-recognition sequence comprises at least four amino acids, and wherein the recognition sequence is joined to the non-recognition sequence by a first linker and a second linker.

One aspect of the invention concerns a method of treating a proliferation disorder such as cancer in a human or animal subject, comprising administering an effective amount of at least one integrin interaction inhibitor of the invention to the subject. In some embodiments, the proliferation disorder is cancer. In some embodiments, the proliferation disorder is cancer and the cancer cells are in suspension, e.g., part of a circulating tumor cell (CTC) population, and the integrin interaction inhibitors kill the CTC. In some embodiments, the integrin interaction inhibitor of the invention prevent or delay onset of metastasis of the cancer cells (e.g., to the bone). In some embodiments, the disorder is mediated by cells that exhibit the cell adhesion induced drug resistance (CAM-DR) phenotype.

Another aspect of the invention concerns a method of suppressing the growth of malignant cells, comprising contacting the cells in vitro or in vivo with an effective amount of at least one integrin interaction inhibitor of the invention. In some embodiments, the malignant cells exhibit the CAM-DR phenotype.

Another aspect of the invention concerns a method of inducing cell death in malignant cells, comprising contacting the cells in vitro or in vivo with an effective amount of at least one integrin interaction inhibitor of the invention. In some embodiments, the malignant cells are in suspension, e.g., part of a circulating tumor cell (CTC) population, and the peptides kill the CTC. In some embodiments of the in vivo method, the integrin interaction inhibitors of the invention prevent or delay onset of metastasis (e.g., to the bone). In some embodiments, the malignant cells exhibit the CAM-DR phenotype. Without being bound by theory, it is proposed that the integrin interaction inhibitors of the invention induce cell death by cell surface binding and activation of a non-caspase dependent cell death mechanism involving autophagy.

Another aspect of the invention concerns a method of inhibiting (e.g., reducing, interfering with, or disrupting) β1 integrin mediated adhesion, comprising contacting cells in vitro or in vivo with an effective amount of at least one integrin interaction inhibitor of the invention.

Another aspect of the invention concerns a method for increasing the efficacy of chemotherapy or radiation therapy in a subject, comprising administering at least one integrin interaction inhibitor to the subject. Preferably, the method further comprises administering the chemotherapy and/or radiation treatment to the subject before, during, or after administration of the integrin interaction inhibitor, wherein the effectiveness of the treatment is increased.

In another aspect, the invention pertains to an adhesion trap comprising a substrate (surface) with integrin interaction inhibitor immobilized to the surface, and a method of removing circulating tumor cells (CTC) from blood by contacting a subject's blood with the immobilized integrin interaction inhibitor.

Another aspect of the invention concerns a method of identifying modulators of integrin interaction inhibitor binding (a screen for molecules that displace integrin interaction inhibitor binding), the method comprising providing a candidate agent (such as a chemical compound, antibody, nucleic acid, peptide, or other substance); and determining whether the candidate agent inhibits (e.g., disrupts, prevents, or interferes with), the ability of an integrin interaction inhibitor of the invention to bind to β1 integrin on a cancer cell surface and/or inhibit β1 integrin mediated adhesion, in vitro or in vivo (e.g., in an animal model). Optionally, the integrin interaction inhibitor is labeled with a detectable moiety (e.g., fluorescently) to facilitate the determining step.

The determining step can be carried out by contacting the candidate agent with the cells in the presence of the integrin interaction inhibitor. Optionally, the integrin interaction inhibitor may be immobilized on a surface or in suspension.

In another aspect, the invention concerns a method for detecting circulating tumor cells (CTC). Thus, the invention includes an in vitro screening assay for detecting CTC in a biological sample from a subject (such as peripheral blood), comprising obtaining a biological sample from a subject; and determining whether the integrin interaction inhibitor of the invention binds to cells (β1 integrin on the cell surface) in the sample. Preferably, the integrin interaction inhibitor is labeled with a detectable moiety (e.g., fluorescently) to facilitate the determining step. The integrin interaction inhibitor binding can be carried out using flow cytometry analysis or in tandem with CTC detection machines, for example. Optionally, the integrin interaction inhibitor may be immobilized on a surface, or in suspension. In other embodiments, the integrin interaction inhibitors of the invention can be tested for potency by determining their ability to prevent or interfere with the binding of labeled ligand to target cells. In this case, the ligand is labeled and incubated in the presence of the test cells and unlabelled integrin interaction inhibitor.

Another aspect of the invention concerns an in vitro screening test for the presence of malignant cells in a mammalian tissue, the test including: obtaining a sample containing viable cells of the tissue; culturing the sample under conditions promoting growth of the viable cells contained therein; treating the cultured sample with an integrin interaction inhibitor of the invention; and analyzing the treated sample by a method effective to determine percent of cell death as an indicator of presence of malignant cells in the sample.

The invention also concerns a composition comprising an integrin interaction inhibitor and one or more anti-cancer agents (e.g., chemotherapeutic agents). In some embodiments, the anti-cancer agent is selected from among suberoylanilide hydroxamic acid (SAHA) or other histone deacetylase inhibitor, arsenic trioxide, doxorubicin or other anthracycline DNA intercalating agent, and etoposide or other topoisomerase II inhibitor. The composition is useful for inhibiting the growth of cancer cells (for example, myeloma cells) in vitro or in vivo, when administered thereto.

The invention also concerns a composition comprising a HYD1 peptide and one or more anti-cancer agents (e.g., chemotherapeutic agents). In some embodiments, the anti-cancer agent is selected from among suberoylanilide hydroxamic acid (SAHA) or other histone deacetylase inhibitor, arsenic trioxide, doxorubicin or other anthracycline DNA intercalating agent, and etoposide or other topoisomerase II inhibitor. The composition is useful for inhibiting the growth of cancer cells (for example, myeloma cells) in vitro or in vivo, when administered thereto. In some embodiments, the HYD1 peptide comprises the all D-amino acid peptide KIKMVISWKG (HYD1) (SEQ ID NO:278).

As used herein, unless specified, "a HYD1 peptide" is inclusive of the d-amino acid peptide having the sequence: KIKMVISWKG (HYD1) (SEQ ID NO:278), as well as other HYD1-related peptides (which includes d-amino acid containing peptides and non-d-amino acid containing peptides) disclosed in U.S. Pat. No. 7,632,814 (Hazelhurst et al., "HYD1 Peptides as Anti-Cancer Agents"), which is incorporated herein by reference in its entirety. As used herein, reference to c-HYD1, C-HYD1 refers to a cyclized or cyclic peptidomimetic of the invention.

The invention also concerns methods for treating a malignancy in a subject, comprising administering a HYD1 peptide and one or more anti-cancer agents selected from suberoylanilide hydroxamic acid (SAHA) or other histone deacetylase inhibitor, arsenic trioxide, doxorubicin or other anthracycline DNA intercalating agent, and etoposide or other topoisomerase II inhibitor. The HYD1 peptide may be administered before, during, or after the one or more of the aforementioned agents. In some embodiments, the malignancy is multiple myeloma or another hematologic malignancy. In some embodiments, the HYD1 peptide comprises the all D-amino acid peptide KIKMVISWKG (HYD1) (SEQ ID NO:278).

The invention also concerns a method of suppressing the growth of malignant cells, comprising contacting the cells in vitro or in vivo with an effective amount of a HYD1 peptide, and at least one other anti-cancer agent. In some embodiments, the malignant cells are cells of a multiple myeloma or another hematologic malignancy. In some embodiments, the HYD1 peptide comprises the all D-amino acid peptide KIKMVISWKG (HYD1) (SEQ ID NO:278).

BRIEF DESCRIPTION OF THE DRAWINGS

For a fuller understanding of the invention, reference should be made to the following detailed description, taken in connection with the accompanying drawings, in which:

FIG. 14A: Labeled positions on the methylsulfonamido aminoethyl glycine turn. Newman projection of the β-turn viewed down the δ-γ bond: FIG. 14B: N-Ms pointing down and away from the β-sheet; FIG. 14C: N-Ms pointing into the center of the β-sheet.

FIG. 17A: same-strand NOEs; FIG. 17B: cross-strand NOEs. (Black=strong, Green=Medium, Red=Weak).

FIG. 18A: same-strand NOEs; FIG. 18B: cross-strand NOEs. (Black=strong, Green=Medium, Red=Weak).

FIG. 33A: Intra-residue NOEs; FIG. 33B: Same-strand NOEs; FIG. 33C: Cross-strand NOEs.

FIG. 34A: Intra-residue NOEs; FIG. 34B: Same-strand NOEs; FIG. 34C: Cross-strand NOEs.

FIG. 35A: Intra-residue NOEs; FIG. 35B: Same-strand NOEs; FIG. 35C: Cross-strand NOEs.

FIG. 36A: Intra-residue NOEs; FIG. 36B: Same-strand NOEs; FIG. 36C: Cross-strand NOEs.

FIG. 37A: Intra-residue NOEs; FIG. 37B: Same-strand NOEs; FIG. 37C: Cross-strand NOEs.

FIG. 44. Biotin-HYD1 interacts with CD44 in H929 cells. Thirty micrograms of membrane extract was incubated with either biotin or biotin-HYD1 bound NeutrAvidin beads. The first lane is 30 μg of membrane extract only. CD44 was detected by western blot analysis using a pan-CD44 antibody.

FIGS. 45A-45B. Biotin-HYD1 interacts with α4 integrin (FIG. 45A) and CD44 (FIG. 45B). Biotin-HYD1 or biotin was immobilized to NeutraAvidin beads prior to incubation with 150 μg of membrane extract. The blot was initially probed for α4 integrin and subsequently stripped and reprobed with CD44 antibody.

Figure 46:
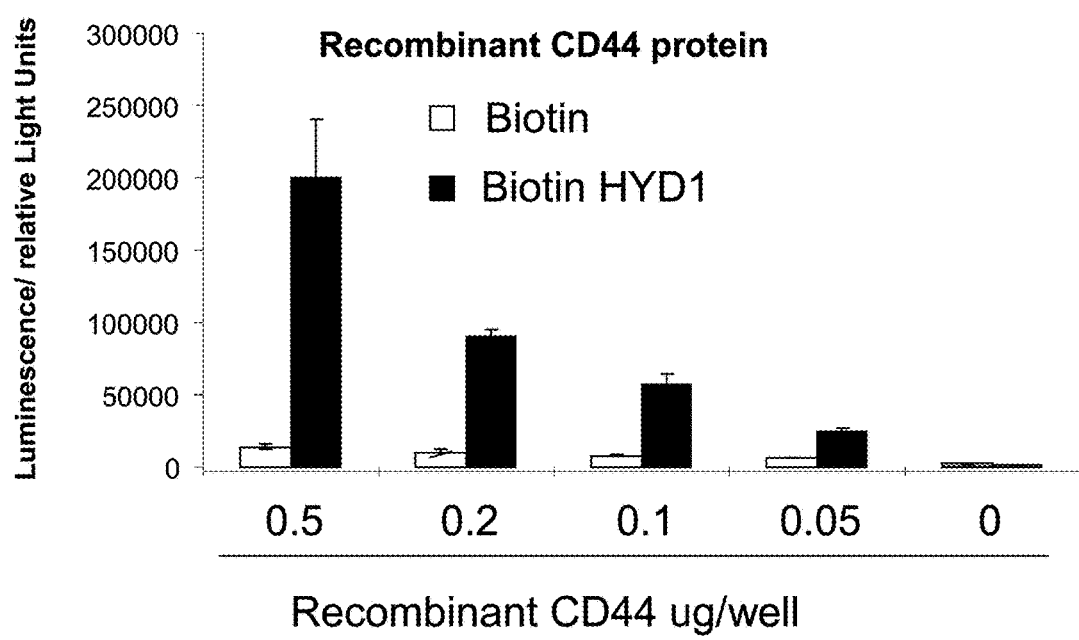

FIG. 46. Biotin-HYD1 binds recombinant CD44 in a direct ELISA. A primary CD44 antibody and HRP conjugated secondary antibody and chemiluminescence detection was used to quantify rCD44 binding to immobilized biotin-HYD1.

DETAILED DISCLOSURE OF THE INVENTION

Figure 1:
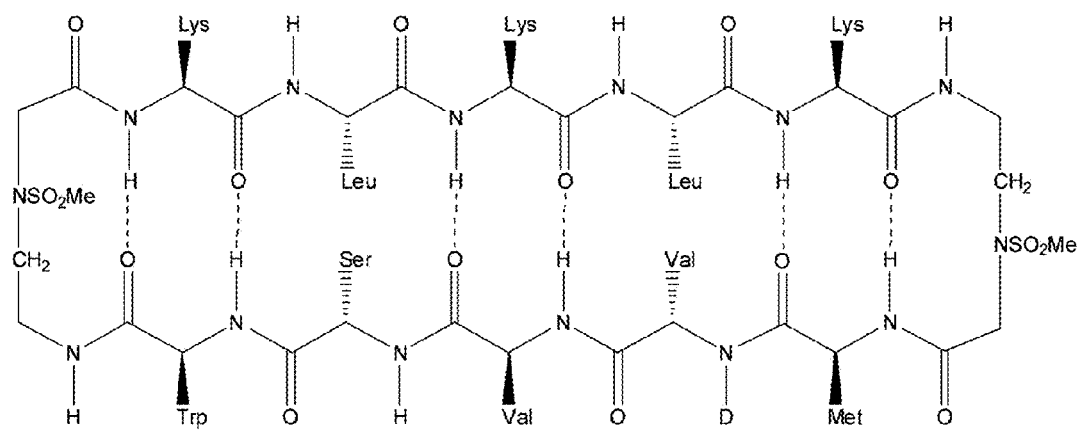
FIG. 1 is a diagram of the cyclic III peptide (SEQ ID NO:10).
Figure 2:
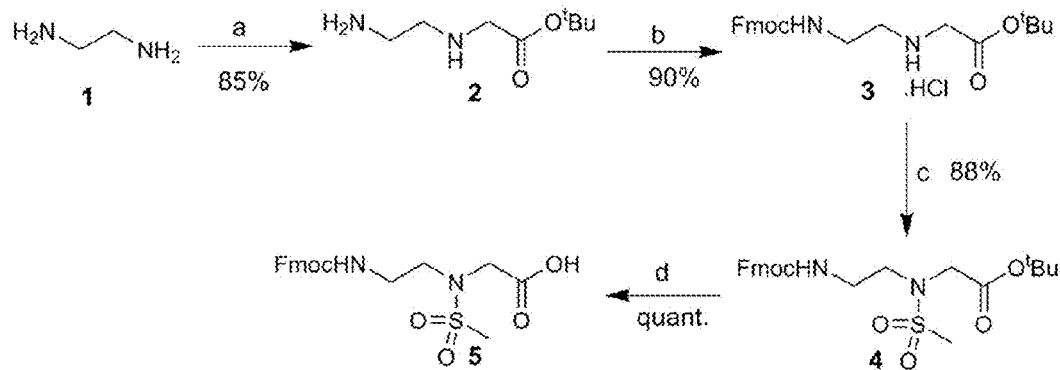
FIG. 2 is a diagram of the synthesis scheme for generation of the β-hairpin turn promoter for cyclic III peptides/integrin interaction inhibitors.

The present invention concerns integrin interaction inhibitors (also referred to interchangeably herein as "compounds of the invention" and "peptides of the invention"), compounds comprising such inhibitors, and methods of using such inhibitors. Integrin interaction inhibitors, such as those shown in FIG. 1, were generated. Generation of the β-hairpin turn promoter is seen in FIG. 2. In some embodiments, the integrin interaction inhibitor is a cyclic peptide disclosed herein.

Since the inventors determined that HYD1 induced an underutilized therapeutic strategy of inducing cell death in tumor cells (programmed necrosis) and binds to a novel target in MM (CD44), it was decided to pursue strategies which would increase the therapeutic potential of this novel agent. To this end, the inventors sought to determine whether cyclization of the peptide was a viable strategy for increasing the potency and in vivo efficacy of the peptide. Scanning the sequence of the peptide, it became evident that if a secondary structure was important for binding, that a beta sheet or beta-turn conformation was the most likely candidate. To this end, the inventors initially performed N- and C-terminus truncation studies and identified MVISW (SEQ ID NO:279) as the likely core region of D-HYD1 required for biological activity. Using this information and the finding that V for I replacement gave a more active D-HYD1 analog, the inventors developed a cyclized version of D-HYD1 that is designed to display the core bioactive sequence (MV-VSW) (SEQ ID NO:33) in an extended or beta-sheet-like conformation. Side chain-side chain or N- to C-terminus cyclization of linear peptides, to constrain the number of conformations available to the linear peptide, is a well known strategy that increases the affinity of the cyclized peptide for its target when the constraint stabilizes the bound conformation of the peptide. The cyclic beta-hairpin further constrains the recognition portion of the cyclic peptide specifically into an extended or beta-sheet-like conformation.

Figure 39:
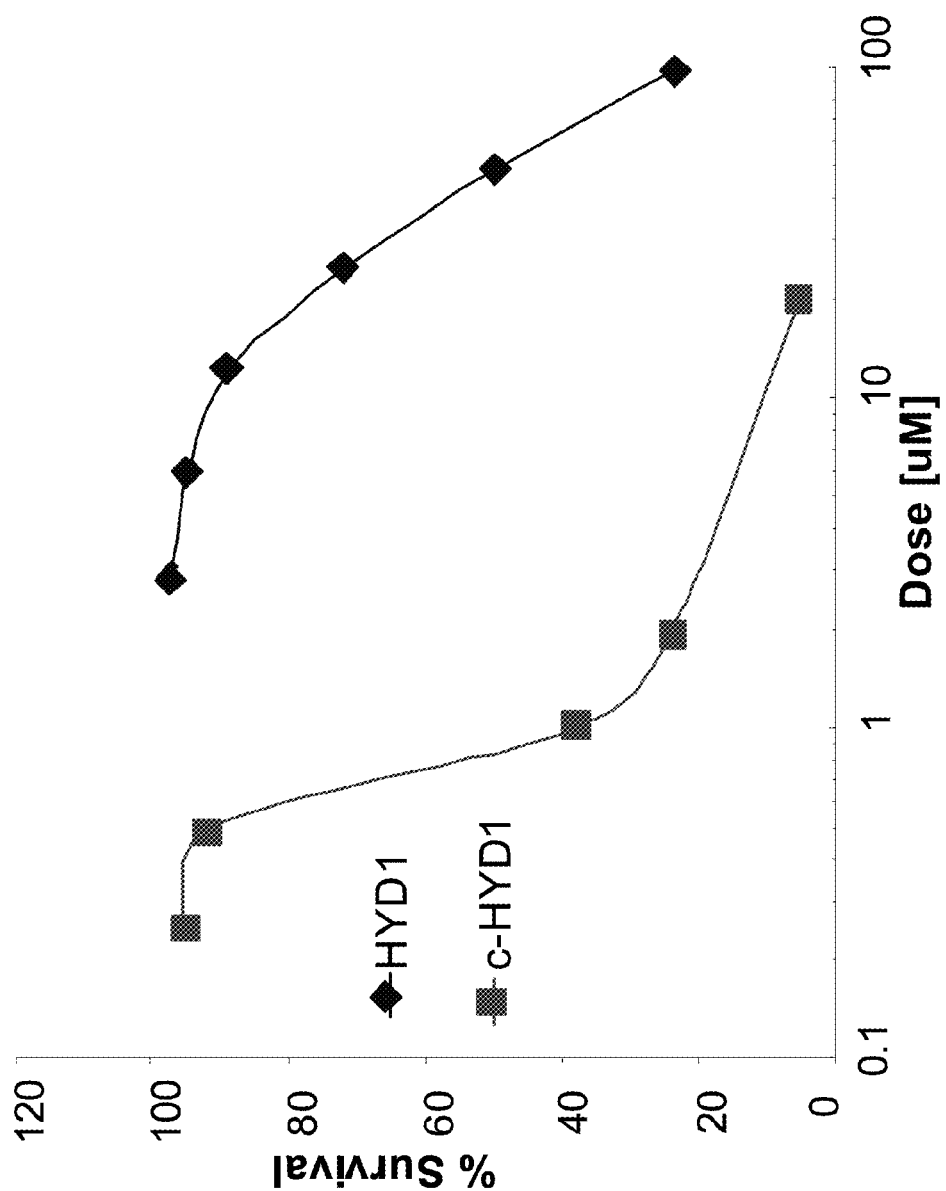
FIG. 39 is a graph showing that cyclized HYD1 (represented as C-HYD1 or c-HYD1) is 30-fold more potent compared to the parent linear HYD1 peptide. H929 cells were treated for 24 hours with varying concentrations of peptide. Cell death was measured by Topro-3 staining and FACS analysis. The IC$_{50}$ values were obtained from linear regression analysis and an average value was obtained from 3 independent experiments. In H929 cells, the mean IC$_{50}$ value for HYD1 was 33 µM, while the IC$_{50}$ value for c-HYD1 is 1.2 µM.
Figure 40:
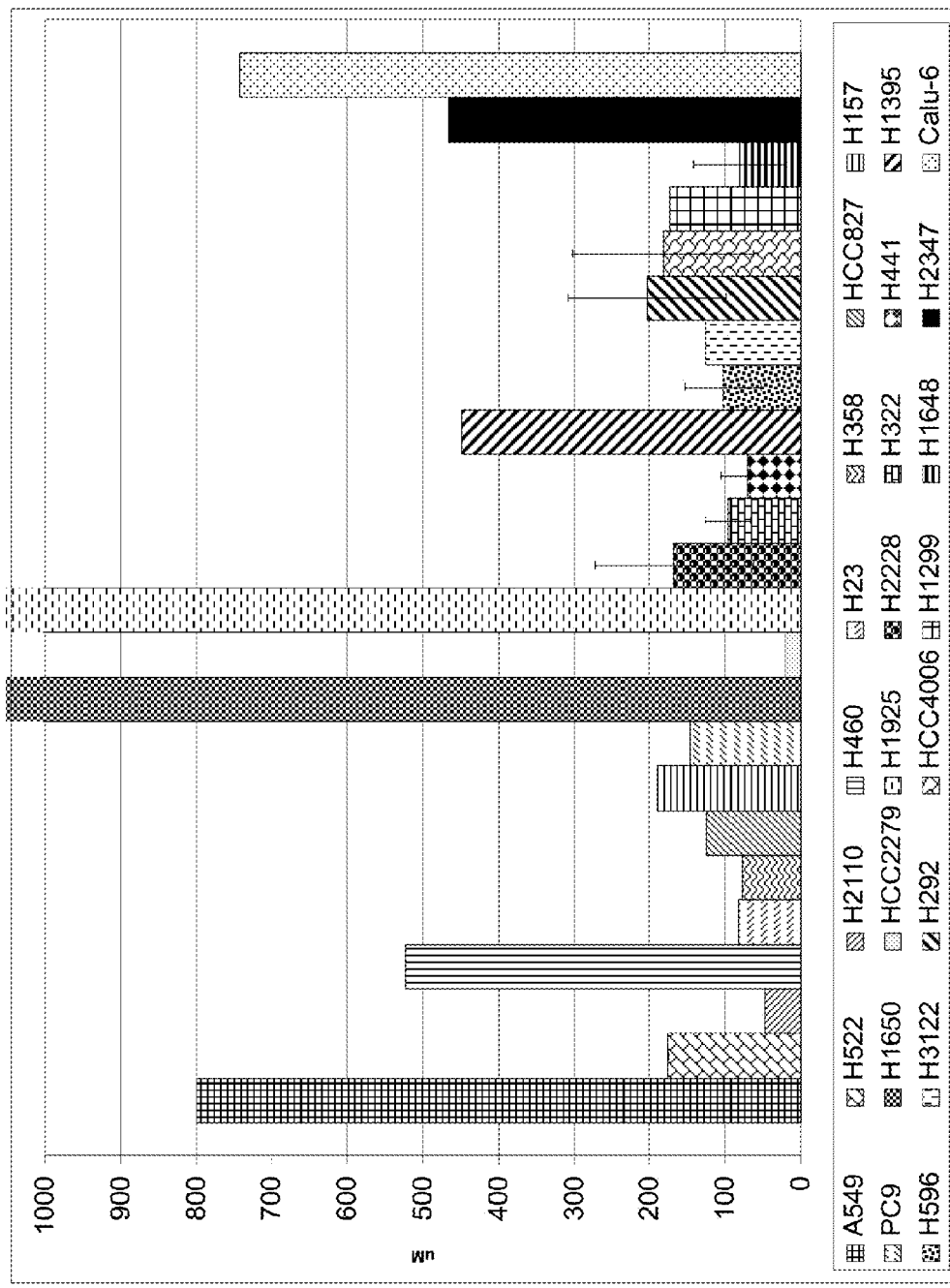
FIG. 40 is a graph showing IC-50 levels of 24 lung cancer (LC) cell lines treated with cyclized HYD1. The activity of c-HYD1 was screened using a high-throughput CellTiter-Blue cell viability assay. Cell viability was assessed by the ability of the remaining viable cells to bioreduce resazurin to resorufin. Resazurin is dark blue in color and has little intrinsic fluorescence until it is reduced to resorufin (579 nm Ex/584 nm Em). The change in fluorescence was measured with a Synergy 4 microplate reader (Bio-Tek Instruments, Inc.). The fluorescence data was transferred to a spreadsheet program to calculate the percent viability relative to the four replicate cell wells that did not receive drug. IC50s were determined as the concentration of drug required for 50% reduction in growth/viability. Shown is the mean IC50 value for each lung cancer cell line tested. Experiments were repeated 2-3 times.
Figure 41:
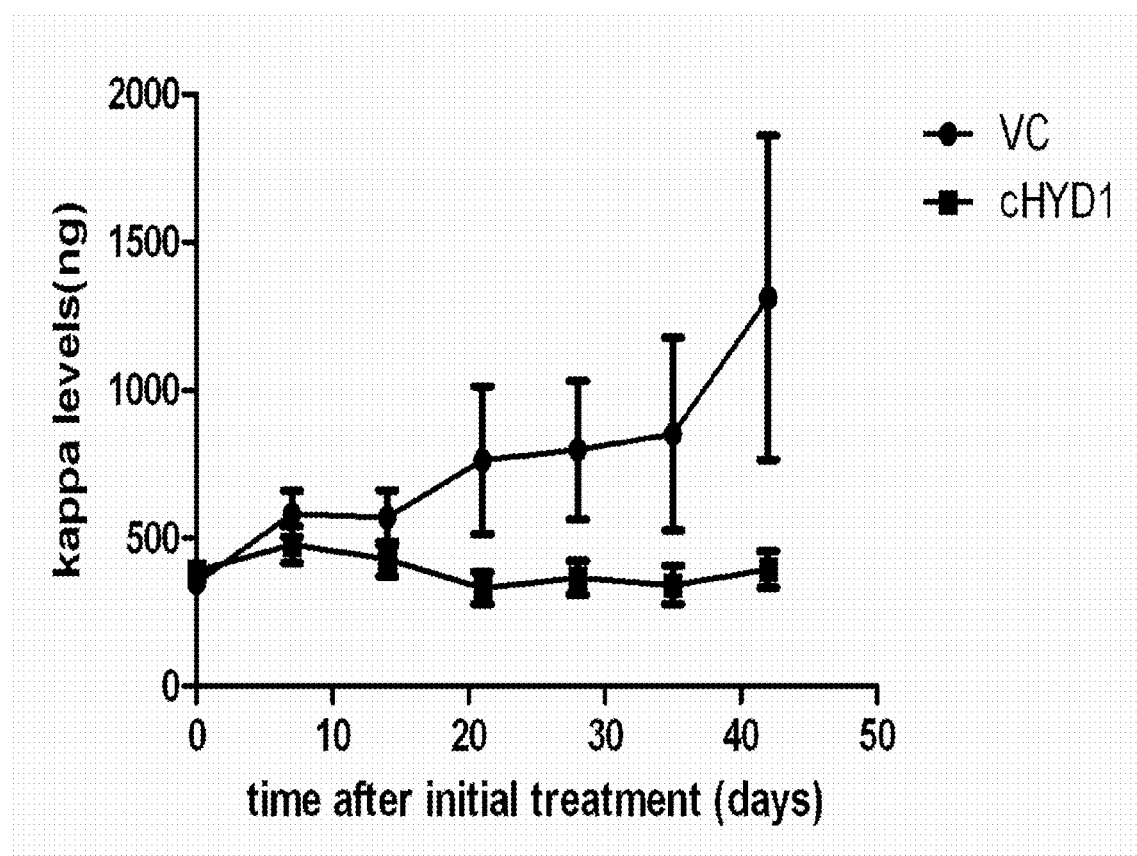
FIG. 41 is a graph showing that cyclized HYD1 (represented as C-HYD1 or c-HYD1) treatment significantly reduces tumor growth (p<0.05 ANOVA) in a MM SCID-Hu in vivo model. Briefly, 50,000 H929 myeloma cells were engrafted into the bone implant for 10 days prior to initiation of peptide treatment. Following tumor engraftment mice were randomized (0 time point) and injected with 8 mg/kg c-HYD1 or vehicle control (VC) daily (I.P. injections) for 14 days and every other day from day 14-28 at which time treatment stopped. Tumor burden was measured by circulating Kappa levels by ELISA weekly. N=10 mice for vehicle control (VC) and 9 mice for c-HYD1 treated.
Figure 42:
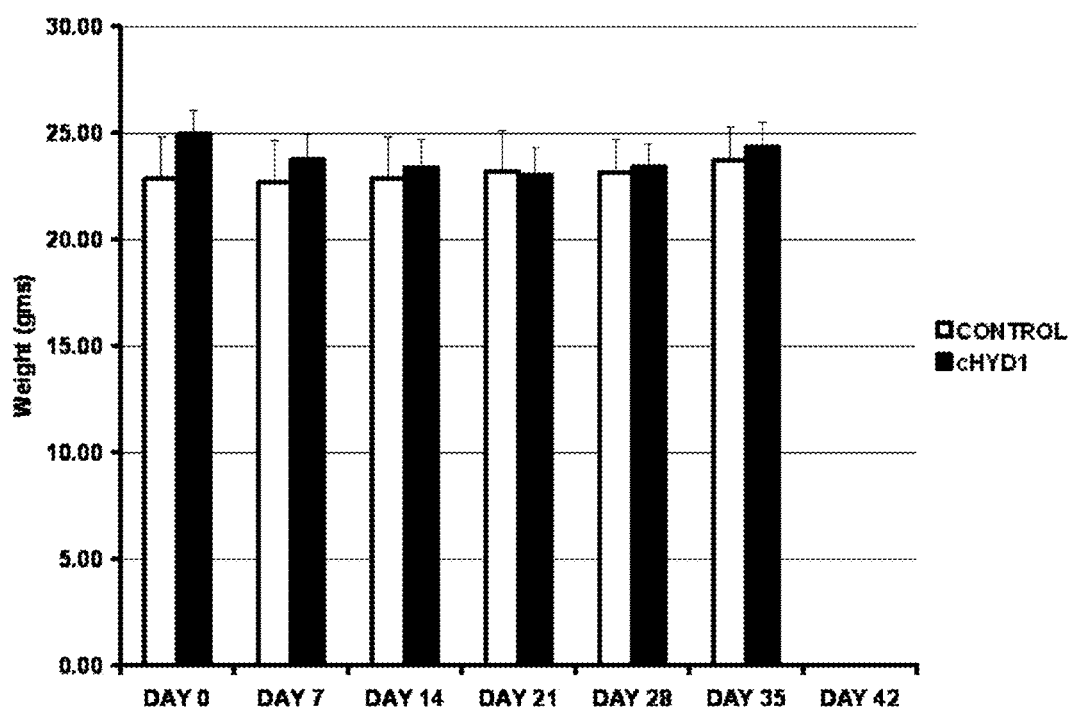
FIG. 42 is a graph showing the effect of cyclized HYD1 (c-HYD1) injection on the weight of mice. No weight loss or any overt signs of toxicity were observed.

The inventors first made the all D-amino acid analog of the linear D-HYD1 and found that the cyclized D-HYD1 (c-D-HYD1) was about twice as active as linear D-HYD1. Surprisingly, the inverso (L-HYD1) cyclic compound was 2 fold more potent compared to the cyclic D-HYD1 variant. The inventors have modified the MVVSW (SEQ ID NO:33) recognition strand and found replacing the S for an A makes the compound approximately 10 fold more potent (MV-VAW) (SEQ ID NO:35) and replacing the methionine for nor-Leucine (NorLeuVVSW) (SEQ ID NO:39) made the compound 15 fold more potent. Finally, the combination of those modifications (NorLeuVVAW) (SEQ ID NO:41) was 30-fold more potent than HYD1. Going forward herein, the most potent cyclic analog is referred to as c-HYD1. The $IC_{50}$ value of c-HYD1 in H929 cells is 1.2+/−0.02 uM while the $IC_{50}$ value of the linear HYD1 is 33 uM in H929 cells (see FIG. 39).

As used herein, the terms "treatment" and "treating", and grammatical variations thereof, include therapy and prophylaxis. When used as a therapy, the integrin interaction inhibitors of the invention, by themselves or in conjunction with other agents, alleviate or reduce one or more symptoms associated with a proliferation disorder (e.g., cancer). Thus, the treatment methods may or may not be curative in nature. When used as a prophylactic treatment, the integrin interaction inhibitors of the invention, by themselves or in conjunction with other agents, delay the onset of (and may prevent) one or more symptoms associated with a proliferation disorder (e.g., cancer), or may prevent the genesis of the condition.

In one aspect, the method of the invention is a method for treating a proliferation disorder, such as cancer, comprising administering an effective amount of an integrin interaction inhibitor of the invention to a subject in need thereof.

In another aspect, the method of the invention is a method for inhibiting the growth of cancer cells in vitro or in vivo, comprising administering an effective amount of an integrin interaction inhibitor of the invention to the cancer cells.

In another aspect, the subject invention provides pharmaceutical compositions comprising at least one integrin interaction inhibitor of the invention; and a pharmaceutically acceptable carrier.

By inhibiting the growth of cells proliferating in an aberrant manner, the methods, integrin interaction inhibitors, and compositions of the present invention can be used to treat a number of cell proliferation disorders, such as cancers, including, but not limited to, leukemias and lymphomas, such as acute lymphocytic leukemia, acute non-lymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms' Tumor, bone tumors, and soft-tissue sarcomas, common solid tumors of adults such as lung cancer, colon and rectum cancer, breast cancer, prostate cancer, urinary cancers, uterine cancers, bladder cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer. The methods of the subject invention can be carried out in vivo or in vitro, to inhibit the growth of cells (e.g., cancer cells) in humans and non-human mammals. Treatment for a proliferation disorder can proceed by the integrin interaction inhibitor's anti-proliferative activity, or by other mechanisms. Without being bound by theory, in some embodiments, the proliferation disorder is one on which the integrin interaction inhibitor(s) acts by binding to β1 integrin, and/or inhibits β1 integrin signaling, and/or β1 integrin mediated adhesion.

Without being bound by theory, integrin interaction inhibitors of the invention having the capability to modulate (e.g., reduce or eliminate) β1 integrin signaling in vitro and/or in vivo, or to inhibit the growth of cancer cells in vitro and/or in vivo by inhibition of β1 integrin signaling or a different mechanism, would be considered to have the desired biological activity in accordance with the subject invention. For therapeutic applications, without being bound by theory, integrin interaction inhibitors of the subject invention can have the capability to inhibit β1 integrin signaling or β1 integrin mediated adhesion, or to inhibit the growth of cancer cells in vitro and/or in vivo by inhibition of β1 integrin signaling or β1 integrin mediated adhesion or a different mechanism. Treatment for a proliferation disorder can proceed by the integrin interaction inhibitor's antiproliferative activity, regardless of underlying mechanism.

In some embodiments, the proliferation disorder to be treated is a cancer producing a tumor characterized by β1 integrin signaling or β1 integrin mediated adhesion. Examples of susceptible cancer types include, but are not limited to, cancer of the breast, pancreas, prostate, melanoma, myeloma, and lung. In some embodiments, the proliferation disorder to be treated is a cancer producing a tumor characterized by the CAM-DR phenotype. In some embodiments, the proliferation disorder to be treated is a cancer that exhibits elevated levels of the cleaved form of α4 integrin. In some embodiments, the treatment methods further include determining whether the proliferation disorder exhibits the aforementioned characteristics (β1 integrin signaling or β1 integrin mediated adhesion; CAM-DR phenotype; elevated α4 integrin level) prior to administration of the one or more integrin interaction inhibitors.

In some embodiments, the proliferation disorder to be treated is characterized by a proliferation of T-cells such as autoimmune disease, e.g., type 1 diabetes, lupus and multiple sclerosis, and pathological states such as graft rejection induced by the presentation of a foreign antigen such as a graft in response to a disease condition (e.g., kidney failure). Other non-malignant diseases characterized by proliferation of cells include cirrhosis of the liver and restenosis.

The methods of the present invention can be advantageously combined with at least one additional treatment method, including but not limited to, chemotherapy, radiation therapy, or any other therapy known to those of skill in the art for the treatment and management of proliferation disorders such as cancer.

While integrin interaction inhibitors of the invention can be administered to cells in vitro and in vivo as isolated agents, it is preferred to administer these integrin interaction inhibitors as part of a pharmaceutical composition. The subject invention thus further provides compositions comprising an integrin interaction inhibitor of the invention in association with at least one pharmaceutically acceptable carrier. The pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

The integrin interaction inhibitors of the invention can be formulated according to known methods for preparing pharmaceutically useful compositions. Formulations are described in a number of sources which are well known and readily available to those skilled in the art. For example, *Remington's Pharmaceutical Science* (Martin, E. W., 1995, Easton Pa., Mack Publishing Company, 19$^{th}$ ed.) describes formulations which can be used in connection with the subject invention. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts of compounds may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

As used herein, the term "analogs" refers to compounds which are substantially the same as another compound but which may have been modified by, for example, adding side groups, oxidation or reduction of the parent structure. Analogs of the integrin interaction inhibitors, and other agents disclosed herein, can be readily prepared using commonly known standard reactions. These standard reactions include, but are not limited to, hydrogenation, alkylation, acetylation, and acidification reactions. Chemical modifications can be accomplished by those skilled in the art by protecting all functional groups present in the molecule and deprotecting them after carrying out the desired reactions using standard procedures known in the scientific literature (Greene, T. W. and Wuts, P. G. M. "Protective Groups in Organic Synthesis" John Wiley & Sons, Inc. New York. 3rd Ed. pg. 819, 1999; Honda, T. et al. *Bioorg. Med. Chem. Lett.,* 1997, 7:1623-1628; Honda, T. et al. *Bioorg. Med. Chem. Lett.,* 1998, 8:2711-2714; Konoike, T. et al. *J. Org. Chem.,* 1997, 62:960-966; Honda, T. et al. J. Med. Chem., 2000, 43:4233-4246; each of which are hereby incorporated herein by reference in their entirety). Analogs, fragments, and variants of the integrin interaction inhibitors exhibiting the desired biological activity (such as induction of cell death, cytotoxicity, cytostaticity, induction of cell cycle arrest, etc.) can be identified or confirmed using cellular assays or other in vitro or in vivo assays. For example, assays that detect β1 integrin signaling, β1 integrin mediated adhesion, ERK activation, $G_2$/M cell cycle arrest, and/or reduction of tumor growth may be utilized. Examples of assays to assess β1 integrin signaling, β1 integrin adhesion, and ERK activation are described in Gilcrease, M. S., *Cancer Letters,* 2007, 247(1): 1-25; Larsen M. et al., *Current Opinion in Cell Biology,* 2006, 18(5):463-471; Luo B. H. and T. A. Springer, *Current Opinion in Cell Biology,* 2006, 18(5):579-586.

The integrin interaction inhibitors of the invention are useful for various non-therapeutic and therapeutic purposes. The integrin interaction inhibitors may be used for reducing aberrant cell growth in animals and humans. Because of such anti-proliferative properties of the integrin interaction inhibitors, they are useful in reducing unwanted cell growth in a wide variety of settings including in vitro and in vivo. In addition to their use in treatment methods, the integrin interaction inhibitors of the invention are useful as agents for investigating the role of α4 and β1 integrin signaling and/or α4 and β1 integrin mediated adhesion in cellular metabolism, and controlling α4 and/or β1 integrin mediated malignant or non-malignant cell growth in vitro or in vivo. They are also useful as standards and for teaching demonstrations.

Therapeutic application of the integrin interaction inhibitors and compositions comprising them can be accomplished by any suitable therapeutic method and technique presently or prospectively known to those skilled in the art. Further, the integrin interaction inhibitors of the invention can be used as starting materials or intermediates for the preparation of other useful compounds and compositions.

Integrin interaction inhibitors of the invention may be locally administered at one or more anatomical sites, such as sites of unwanted cell growth (such as a tumor site, e.g., injected or topically applied to the tumor), optionally in combination with a pharmaceutically acceptable carrier such as an inert diluent. Integrin interaction inhibitors of the invention may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the integrin interaction inhibitors may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the integrin interaction inhibitors may be incorporated into sustained-release preparations and devices.

The active agent (e.g., integrin interaction inhibitors of the invention) may also be administered intravenously or intraperitoneally by infusion or injection. Solutions of the active agent can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the integrin interaction inhibitors of the invention which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating the integrin interaction inhibitors of the invention in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the integrin interaction inhibitors may be applied in pure-form, i.e., when they are liquids. However, it will generally be desirable to administer them topically to the skin as compositions, in combination with a dermatologically acceptable carrier, which may be a solid or a liquid.

The integrin interaction inhibitors of the subject invention can be applied topically to a subject's skin to reduce the size (and may include complete removal) of malignant or benign growths. The integrin interaction inhibitors of the invention can be applied directly to the growth. Preferably, the integrin interaction inhibitor is applied to the growth in a formulation such as an ointment, cream, lotion, solution, tincture, or the like. Drug delivery systems for delivery of pharmacological substances to dermal lesions can also be used, such as that described in U.S. Pat. No. 5,167,649 (Zook).

Useful solid carriers include finely divided solids such as talc, clay, microcrystalline cellulose, silica, alumina and the like. Useful liquid carriers include water, alcohols or glycols or water-alcohol/glycol blends, in which the peptide can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the peptides to the skin are disclosed in Jacquet et al. (U.S. Pat. No. 4,608,392), Geria (U.S. Pat. No. 4,992,478), Smith et al. (U.S. Pat. No. 4,559,157) and Woltzman (U.S. Pat. No. 4,820,508).

Useful dosages of the pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Accordingly, the present invention includes a pharmaceutical composition comprising an integrin interaction inhibitor of the invention in combination with a pharmaceutically acceptable carrier. Pharmaceutical compositions adapted for oral, topical or parenteral administration, comprising an amount of an integrin interaction inhibitor of the invention constitute a preferred embodiment of the invention. The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition. Advantageously, in some embodiments, administration of the integrin interaction inhibitors does not induce weight loss or overt signs of toxicity in the subject.

Depending upon the disorder or disease condition to be treated, a suitable dose(s) may be that amount that will reduce proliferation or growth of the target cell(s), or induce cell death. In the context of cancer, a suitable dose(s) is that which will result in a concentration of the active agent (one or more integrin interaction inhibitors of the invention) in cancer tissue, such as a malignant tumor, which is known to achieve the desired response. The preferred dosage is the amount which results in maximum inhibition of cancer cell growth, without unmanageable side effects. Administration of an integrin interaction inhibitor of the invention can be continuous or at distinct intervals, as can be determined by a person of ordinary skill in the art.

To provide for the administration of such dosages for the desired therapeutic treatment, in some embodiments, pharmaceutical compositions of the invention can comprise between about 0.1% and 45%, and especially, 1 and 15%, by weight of the total of one or more of the compounds of the invention based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Mammalian species which benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient", "subject", and "individual" are used interchangeably and are intended to include such human and non-human species. Likewise, in vitro methods of the present invention can be carried out on cells of such human and non-human species.

Patients in need of treatment using the methods of the present invention can be identified using standard techniques known to those in the medical or veterinary professions, as appropriate.

The terms "cancer" and "malignancy" are used herein interchangeably to refer to or describe the physiological condition in mammals that is typically characterized by unregulated cell growth. The cancer may be multi-drug resistant (MDR) or drug-sensitive. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer. In some embodiments, the cancer is multiple myeloma or another hematologic malignancy.

In some embodiments, the cancer or malignancy is one that expresses CD44. In some embodiments, the methods of the invention further comprise obtaining a sample of the cancer cells and determining whether the cells express CD44 prior to administration of a peptide of the invention. Optionally, the methods may further comprise administering the peptide if the cancer sample expresses CD44.

Other non-limiting examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas. Examples of cancer types that may potentially be treated using the integrin interaction inhibitors of the present invention are also listed in Table 1.

TABLE 1

Examples of Cancer Types

| | |
|---|---|
| Acute Lymphoblastic Leukemia, Adult | Hairy Cell Leukemia |
| Acute Lymphoblastic Leukemia, | Head and Neck Cancer |

TABLE 1-continued

Examples of Cancer Types

Childhood
Acute Myeloid Leukemia, Adult
Acute Myeloid Leukemia, Childhood
Adrenocortical Carcinoma
Adrenocortical Carcinoma, Childhood
AIDS-Related Cancers
AIDS-Related Lymphoma
Anal Cancer
Astrocytoma, Childhood Cerebellar
Astrocytoma, Childhood Cerebral
Basal Cell Carcinoma
Bile Duct Cancer, Extrahepatic
Bladder Cancer
Bladder Cancer, Childhood
Bone Cancer, Osteosarcoma/Malignant Fibrous Histiocytoma
Brain Stem Glioma, Childhood
Brain Tumor, Adult
Brain Tumor, Brain Stem Glioma, Childhood
Brain Tumor, Cerebellar Astrocytoma, Childhood
Brain Tumor, Cerebral Astrocytoma/Malignant Glioma, Childhood
Brain Tumor, Ependymoma, Childhood
Brain Tumor, Medulloblastoma, Childhood
Brain Tumor, Supratentorial Primitive Neuroectodermal Tumors, Childhood
Brain Tumor, Visual Pathway and Hypothalamic Glioma, Childhood
Brain Tumor, Childhood
Breast Cancer
Breast Cancer, Childhood
Breast Cancer, Male
Bronchial Adenomas/Carcinoids, Childhood
Burkitt's Lymphoma
Carcinoid Tumor, Childhood
Carcinoid Tumor, Gastrointestinal
Carcinoma of Unknown Primary
Central Nervous System Lymphoma, Primary
Cerebellar Astrocytoma, Childhood
Cerebral Astrocytoma/Malignant Glioma, Childhood
Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see Mycosis Fungoides and Sézary Syndrome
Endometrial Cancer
Ependymoma, Childhood
Esophageal Cancer
Esophageal Cancer, Childhood
Ewing's Family of Tumors
Extracranial Germ Cell Tumor, Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid Tumor
Germ Cell Tumor, Extracranial, Childhood
Germ Cell Tumor, Extragonadal
Germ Cell Tumor, Ovarian
Gestational Trophoblastic Tumor
Glioma, Adult
Hepatocellular (Liver) Cancer, Adult (Primary)
Hepatocellular (Liver) Cancer, Childhood (Primary)
Hodgkin's Lymphoma, Adult
Hodgkin's Lymphoma, Childhood
Hodgkin's Lymphoma During Pregnancy
Hypopharyngeal Cancer
Hypothalamic and Visual Pathway Glioma, Childhood
Intraocular Melanoma
Islet Cell Carcinoma (Endocrine Pancreas)
Kaposi's Sarcoma
Kidney (Renal Cell) Cancer
Kidney Cancer, Childhood
Laryngeal Cancer
Laryngeal Cancer, Childhood
Leukemia, Acute Lymphoblastic, Adult
Leukemia, Acute Lymphoblastic, Childhood
Leukemia, Acute Myeloid, Adult
Leukemia, Acute Myeloid, Childhood
Leukemia, Chronic Lymphocytic
Leukemia, Chronic Myelogenous
Leukemia, Hairy Cell
Lip and Oral Cavity Cancer
Liver Cancer, Adult (Primary)
Liver Cancer, Childhood (Primary)
Lung Cancer, Non-Small Cell
Lung Cancer, Small Cell
Lymphoma, AIDS-Related
Lymphoma, Burkitt's
Lymphoma, Cutaneous T-Cell, see Mycosis Fungoides and Sézary Syndrome
Lymphoma, Hodgkin's, Adult
Lymphoma, Hodgkin's, Childhood
Lymphoma, Hodgkin's During Pregnancy
Lymphoma, Non-Hodgkin's, Adult
Lymphoma, Non-Hodgkin's, Childhood
Lymphoma, Non-Hodgkin's During Pregnancy
Lymphoma, Primary Central Nervous System
Macroglobulinemia, Waldenström's
Malignant Fibrous Histiocytoma of Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with Occult Primary
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer
Nasopharyngeal Cancer, Childhood
Neuroblastoma
Non-Hodgkin's Lymphoma, Adult
Non-Hodgkin's Lymphoma, Childhood
Non-Hodgkin's Lymphoma During Pregnancy
Non-Small Cell Lung Cancer
Oral Cancer, Childhood
Oral Cavity Cancer, Lip and
Oropharyngeal Cancer
Osteosarcoma/Malignant Fibrous Histiocytoma of Bone
Ovarian Cancer, Childhood
Ovarian Epithelial Cancer TABLE 1-continued Examples of Cancer Types

| | |
|---|---|
| Glioma, Childhood Brain Stem | Ovarian Germ Cell Tumor |
| Glioma, Childhood Cerebral Astrocytoma | Ovarian Low Malignant Potential Tumor |
| | Pancreatic Cancer |
| Glioma, Childhood Visual Pathway and Hypothalamic | Pancreatic Cancer, Childhood |
| | Pancreatic Cancer, Islet Cell |
| Skin Cancer (Melanoma) | Paranasal Sinus and Nasal Cavity Cancer |
| Skin Carcinoma, Merkel Cell | Parathyroid Cancer |
| Small Cell Lung Cancer | Penile Cancer |
| Small Intestine Cancer | Pheochromocytoma |
| Soft Tissue Sarcoma, Adult | Pineoblastoma and Supratentorial Primitive Neuroectodermal Tumors, Childhood |
| Soft Tissue Sarcoma, Childhood | |
| Squamous Cell Carcinoma, see Skin Cancer (non-Melanoma) | Pituitary Tumor |
| | Plasma Cell Neoplasm/Multiple Myeloma |
| Squamous Neck Cancer with Occult Primary, Metastatic | Pleuropulmonary Blastoma |
| | Pregnancy and Breast Cancer |
| Stomach (Gastric) Cancer | Pregnancy and Hodgkin's Lymphoma |
| Stomach (Gastric) Cancer, Childhood | Pregnancy and Non-Hodgkin's Lymphoma |
| Supratentorial Primitive Neuroectodermal Tumors, Childhood | Primary Central Nervous System Lymphoma |
| | Prostate Cancer |
| T-Cell Lymphoma, Cutaneous, see Mycosis Fungoides and Sézary Syndrome | Rectal Cancer |
| | Renal Cell (Kidney) Cancer |
| | Renal Cell (Kidney) Cancer, Childhood |
| Testicular Cancer | Renal Pelvis and Ureter, Transitional Cell Cancer |
| Thymoma, Childhood | |
| Thymoma and Thymic Carcinoma | Retinoblastoma |
| Thyroid Cancer | Rhabdomyosarcoma, Childhood |
| Thyroid Cancer, Childhood | Salivary Gland Cancer |
| Transitional Cell Cancer of the Renal Pelvis and Ureter | Salivary Gland Cancer, Childhood |
| | Sarcoma, Ewing's Family of Tumors |
| Trophoblastic Tumor, Gestational | Sarcoma, Kaposi's |
| Unknown Primary Site, Carcinoma of, Adult | Sarcoma, Soft Tissue, Adult |
| | Sarcoma, Soft Tissue, Childhood |
| Unknown Primary Site, Cancer of, Childhood | Sarcoma, Uterine |
| | Sezary Syndrome |
| Unusual Cancers of Childhood | Skin Cancer (non-Melanoma) |
| Ureter and Renal Pelvis, Transitional Cell Cancer | Skin Cancer, Childhood |
| Urethral Cancer | |
| Uterine Cancer, Endometrial | |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

As used herein, the term "tumor" refers to all neoplastic cell growth and proliferation, whether malignant or benign, and all pre-cancerous and cancerous cells and tissues. For example, a particular cancer may be characterized by a solid mass tumor or non-solid tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography) or magnetic resonance imaging (MRI), or by needle aspirations. The use of these latter techniques is more common in early detection. Molecular and phenotypic analysis of cancer cells within a tissue can usually be used to confirm if the cancer is endogenous to the tissue or if the lesion is due to metastasis from another site. The treatment methods of the invention can be utilized for early, middle, or late stage disease, and acute or chronic disease. In some embodiments, the tumor is characterized as one exhibiting the CAM-DR phenotype.

According to the method of the subject invention, an integrin interaction inhibitor of the invention can be administered to a patient by itself, or co-administered with one or more other agents such as another integrin interaction inhibitor, or a different agent or agents. Co-administration can be carried out simultaneously (in the same or separate formulations) or consecutively. Furthermore, according to the method of the subject invention, integrin interaction inhibitors of the invention can be administered to a patient as adjuvant therapy. For example, integrin interaction inhibitors of the invention can be administered to a patient in conjunction with chemotherapy.

Thus, the integrin interaction inhibitors of the invention, whether administered separately, or as a pharmaceutical composition, can include various other components as additives. Examples of acceptable components or adjuncts which can be employed in relevant circumstances include antioxidants, free radical scavenging agents, peptides, growth factors, antibiotics, bacteriostatic agents, immunosuppressives, anticoagulants, buffering agents, anti-inflammatory agents, anti-angiogenics, anti-pyretics, time-release binders, anesthetics, steroids, and corticosteroids. Such components can provide additional therapeutic benefit, act to affect the therapeutic action of the compounds of the invention, or act towards preventing any potential side effects which may be posed as a result of administration of the compounds. The integrin interaction inhibitors of the subject invention can be conjugated to a therapeutic agent, as well.

Additional agents that can be co-administered to target cells in vitro or in vivo, such as in a patient, in the same or as a separate formulation, include those that modify a given biological response, such as immunomodulators. For example, proteins such as tumor necrosis factor (TNF), interferon (such as alpha-interferon and beta-interferon), nerve growth factor (NGF), platelet derived growth factor (PDGF), and tissue plasminogen activator can be administered. Biological response modifiers, such as lymphokines, interleukins (such as interleukin-1 (IL-1), interleukin-2 (IL-2), and interleukin-6 (IL-6)), granulocyte macrophage colony stimulating factor (GM-CSF), granulocyte colony stimulating factor (G-CSF), or other growth factors can be administered. In one embodiment, the methods and compositions of the invention incorporate one or more agents selected from the group consisting of anti-cancer agents, cytotoxic agents, chemotherapeutic agents, anti-signaling agents, and anti-angiogenic agents.

In some embodiments of the methods of the invention, at least one additional anti-cancer agent (e.g., a chemotherapeutic agent) is administered with the integrin interaction inhibitor or HYD1 peptide. In some embodiments, the anti-cancer agent is selected from among suberoylanilide hydroxamic acid (SAHA) or other histone deacetylase inhibitor, arsenic trioxide, doxorubicin or other anthracycline DNA intercalating agent, and etoposide or other topoisomerase II inhibitor.

Integrin interaction inhibitors as described herein may include residues of L-amino acids, D-amino acids, or any combination thereof. In some embodiments, all amino acids of the peptide are D-amino acids. Amino acids may be from natural or non-natural sources. The 20 L-amino acids commonly found in proteins are identified herein by the conventional one-letter abbreviations known in the art, and the corresponding D-amino acids are generally designated by a lower case one letter symbol. Integrin interaction inhibitors may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylamino), with or without any of a wide variety of side chain modifications and/or substitutions (e.g., methylation, benzylation, t-butylation, tosylation, alkoxycarbonylamino, and the like). Such modifications and derivatives of an amino acid sequence, and others known to those of skill in the art, are herein termed "variants". Some derivatives include amino acids having an N-acetyl group (such that the amino group that represents the N-terminus of the linear peptide is acetylated) and/or a C-terminal amide group (i.e., the carboxy terminus of the linear peptide is amidated). Residues other than common amino acids that may be present include, but are not limited to, penicillamine, tetramethylene cysteine, pentamethylene cysteine, mercaptopropionic acid, pentamethylene-mercaptopropionic acid, 2-mercaptobenzene, 2-mercaptoaniline, 2-mercaptoproline, ornithine, diaminobutyric acid, aminoadipic acid, m-aminomethylbenzoic acid, and diaminopropionic acid.

Functional fragments according to the subject invention can comprise a contiguous span of at least 4 consecutive amino acids of a recognition sequence (also referred to as the recognition portion) and/or a non-recognition sequence (also referred to as the non-recognition portion) of the integrin interaction inhibitors disclosed herein. Peptides fragments according to the subject invention can be any integer in length from at least 4 consecutive amino acids to 1 amino acid less than a full length peptide (e.g., 1 amino acid less than the full length peptide). Thus, in some embodiments, functional fragments may be 4, 5, 6, 7, 8, or 9 amino acids in length (e.g., a span of 4, 5, 6, 7, 8, or 9 consecutive amino acids).

Each fragment of the subject invention can also be described in terms of its N-terminal and C-terminal positions. For example, combinations of N-terminal to C-terminal fragments of 6 contiguous amino acids to 1 amino acid less than the full length peptide of are included in the present invention. Thus, a 6 consecutive amino acid fragment could occupy positions selected from the group consisting of 1-6, 2-7, 3-8, 4-9, 5-10, etc. It is noted that all ranges used to describe any embodiment of the present invention are inclusive unless specifically set forth otherwise and that fragments of a given peptide can be any integer in length, provided that the length of the peptide fragment is at least one amino acid shorter than the full-length peptide from which the fragment is derived.

Fragments, as described herein, can be obtained by cleaving the peptides of the invention with a proteolytic enzyme (such as trypsin, chymotrypsin, or collagenase) or with a chemical reagent, such as cyanogen bromide (CNBr). Alternatively, peptide fragments can be generated in a highly acidic environment, for example at pH 2.5. Such peptide fragments may be equally well prepared by chemical synthesis or using hosts transformed with an expression vector according to the invention.

In certain preferred embodiments, fragments of the peptides disclosed herein retain at least one property or activity of the full-length peptide from which the fragments are derived. Thus, functional fragments of the invention may have one or more of the following properties or biological activities: 1) specifically bind to antibodies specific for the full-length peptide from which the fragment was derived (such as HYD1); 2) specifically bind β1 integrin; 3) inhibit β1 integrin mediated cell adhesion; 4) induce ERK signaling; 5) cause apoptosis in target cells (e.g., malignant cells), by one or more mechanisms of action. Examples of assays to assess β1 integrin signaling, β1 integrin adhesion, and ERK activation are described in Gilcrease, M. S., *Cancer Letters,* 2007, 247(1):1-25; Larsen M. et al., *Current Opinion in Cell Biology,* 2006, 18(5):463-471; Luo B. H. and T. A. Springer, *Current Opinion in Cell Biology,* 2006, 18(5): 579-586.

Ligands that may find use with the integrin interaction inhibitors of the present invention can include but not be limited to sugars, lectins, antigens, intercalators, chelators, biotin, digoxygenin and combinations thereof. The particular choice of a dye as a labeling agent or cell uptake facilitator may depend upon physical characteristics such as absorption maxima, emission maxima, quantum yields, chemical stability and solvent solubility. A large number of fluorescent and chemiluminescent compounds have been shown to be useful for labeling proteins and nucleic acids. Examples of compounds that may be used as the dye portion can include but not be limited to xanthene, anthracene, cyanine, porphyrin and coumarin dyes. Examples of xanthene dyes that may be coupled to the peptides of the present invention can include but not be limited to fluorescein, 6-carboxyfluorescein (6-FAM), 5-carboxyfluorescein (5-Fam), 5- or 6-carboxy-4,7,2',7'-tetrachlorofluorescein (TET), 5- or 6-carboxy-4'5'2'4'5'7' hexachlorofluorescein (HEX), 5' or 6'-carboxy-4',5'-dichloro-2',7'-dimethoxyfluorescein (JOE), 5-carboxy-2',4',5',7'-tetrachlorofluorescein (ZOE) rhodol, rhodamine, tetramethylrhodamine (TAMRA), 4,7-dichlorotetramethyl rhodamine (DTAMRA), rhodamine X (ROX) and Texas Red. Examples of cyanine dyes that may find use with the peptides of the present invention can include but not be limited to Cy 3, Cy 3.5, Cy 5, Cy 5.5, Cy 7 and Cy 7.5. Other dyes that may find use with the peptides of the present invention can include but not be limited to energy transfer dyes, composite dyes and other aromatic compounds that give fluorescent signals. Chemiluminescent compounds that may be used with the peptides of the present invention can include but not be limited to dioxetane and acridinium esters. It should also be understood that ligands and dyes are not mutually exclusive groups. For instance, fluorescein is a well known example of a moiety that has been used as a fluorescent label and also as an antigen for labeled antibodies.

The integrin interaction inhibitors of the invention may be monomeric or multimeric (e.g., dimers, trimers, tetramers and higher multimers). Accordingly, the present invention relates to monomers and multimers of the integrin interaction inhibitors of the invention, their preparation, and compositions containing them. Multimeric integrin interaction inhibitors of the subject invention can be derived from the same peptide sequence ("homomultimers") or derived from different sequences disclosed herein ("heteromultimers"). A homomultimer may contain peptides having identical or different amino acid sequences; however these sequences are derived from the same original peptide. A heteromultimer refers to a multimeric peptide containing one or more heterologous peptides (i.e., peptides of different proteins) in addition to the peptides of the invention. Thus, a heteromultimer, in the context of the subject invention can refer to a multimeric peptide that contains any combination of peptides of the invention. Alternatively, a heteromultimeric peptide may comprise any peptide of the invention fused to a peptide or other element that forms a hydrophobic, hydrophilic, ionic and/or covalent association.

Multimeric peptides, as set forth herein, may be formed by hydrophobic, hydrophilic, ionic and/or covalent associations and/or may be indirectly linked, by for example, liposome formation. Thus, in one embodiment, multimers of the invention, such as, for example, homodimers or homotrimers, are formed when peptides of the invention contact one another in solution. In another embodiment, heteromultimers of the invention, such as, for example, heterotrimers or heterotetramers, are formed when peptides of the invention contact antibodies to the peptides of the invention (including antibodies to the heterologous polypeptide sequence in a fusion protein of the invention) in solution. In other embodiments, multimers of the invention are formed by covalent associations with and/or between the peptides of the invention. Examples include those peptide linkers described in U.S. Pat. No. 5,073,627 (hereby incorporated by reference).

Multimeric peptides can also be generated using chemical techniques known in the art. For example, peptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimeric peptides can be generated by introducing disulfide bonds between the cysteine residues located within the sequence of the peptides that are being used to construct the multimeric polypeptide (see, e.g., U.S. Pat. No. 5,478,925, which is herein incorporated by reference in its entirety).

Further, peptides of the invention may be modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, other techniques known in the art may be applied to generate liposomes containing the peptides components desired to be contained in the multimer of the invention (see, e.g., U.S. Pat. No. 5,478,925, which is herein incorporated by reference in its entirety).

The peptides expressly provided herein, as well as the fragments thereof, may further comprise linker elements that facilitate the attachment of the fragments to other molecules, amino acids, or polypeptide sequences. The linkers can also be used to attach the peptides, or fragments thereof, to solid support matrices for use in affinity purification protocols. Non-limiting examples of "linkers" suitable for the practice of the invention include chemical linkers (such as those sold by Pierce, Rockford, Ill.), or peptides that allow for the connection combinations of peptides (see, for example, linkers such as those disclosed in U.S. Pat. Nos. 6,121,424, 5,843,464, 5,750,352, and 5,990,275, hereby incorporated by reference in their entirety).

In other embodiments, the linker element can be an amino acid sequence (a peptide linker). In some embodiments, the peptide linker has one or more of the following characteristics: a) it allows for the free rotation of the peptides that it links (relative to each other); b) it is resistant or susceptible to digestion (cleavage) by proteases; and c) it does not interact with the peptides it joins together. In various embodiments, a multimeric construct according to the subject invention includes a peptide linker and the peptide linker is 5 to 60 amino acids in length. More preferably, the peptide linker is 10 to 30, amino acids in length; even more preferably, the peptide linker is 10 to 20 amino acids in length. In some embodiments, the peptide linker is 17 amino acids in length.

Multimeric constructs of the subject invention can also comprise a series of repeating elements, optionally interspersed with other elements. As would be appreciated by one skilled in the art, the order in which the repeating elements occur in the multimeric polypeptide is not critical and any arrangement of the repeating elements as set forth herein can be provided by the subject invention. Thus, a "multimeric construct" according to the subject invention can provide a multimeric peptide comprising a series of peptides, or peptide fragments, that are, optionally, joined together by linker elements (either chemical linker elements or amino acid linker elements).

A "variant" or "variant peptide" (or peptide variant) is to be understood to designate peptides exhibiting, in relation to the peptides disclosed herein, certain modifications. These modifications can include a deletion, addition, or substitution of at least one amino acid (e.g., one, two, three or more amino acids), a truncation, an extension, a chimeric fusion (fusion protein), a mutation, or polypeptides exhibiting post-translational modifications. These modifications can occur anywhere in the peptide, e.g., one or both ends and/or in the middle. Among these homologous variant peptides, are those comprising amino acid sequences exhibiting between at least (or at least about) 20.00% to 99.99% (inclusive) identity to the full length, native, or naturally occurring polypeptide are another aspect of the invention. The aforementioned range of percent identity is to be taken as including, and providing written description and support for, any fractional percentage, in intervals of 0.01%, between 20.00% and, up to, including 99.99%. These percentages are purely statistical and differences between two polypeptide sequences can be distributed randomly and over the entire sequence length. Thus, variant peptides can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the peptide sequences of the instant invention. In a preferred embodiment, a variant or modified peptide exhibits at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity to the reference peptide. The percent identity is calculated with reference to the full-length polypeptide or the length of the fragment of a particular SEQ ID NO: that is identified. Preferably, the variant peptides retain at least one of the biological activities associated with the reference peptide (for example, the ability to: 1) specifically bind to antibodies specific for the full-length peptide from which the fragment was derived (such as HYD1); 2) specifically bind β1 integrin; 3) to inhibit β1 integrin mediated cell adhesion; 4) to induce ERK signaling; 5) cause apoptosis in target cells (e.g., malignant cells), regardless of mechanism of action (e.g., caspase-dependent and/or caspase independent)). Examples of assays to assess β1 integrin signaling, β1 integrin adhesion, and ERK activation are described in Gilcrease, M. S., *Cancer Letters,* 2007, 247(1): 1-25; Larsen M. et al., *Current Opinion in Cell Biology,* 2006, 18(5):463-471; Luo B. H. and T. A. Springer, *Current Opinion in Cell Biology,* 2006, 18(5):579-586.

For example, one or more amino acid residues within the sequence can be substituted by another amino acid of a similar polarity which acts as a functional equivalent, resulting in a silent alteration. In one aspect of the present invention, conservative substitutions for an amino acid within the sequence may be selected from other members of the class to which the amino acid belongs (see Table 2). Conservative substitutions also include substitutions by amino acids having chemically modified side chains that do not eliminate the biological function of the resulting variant.

TABLE 2

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Fusion proteins according to the subject invention comprise one or more heterologous peptide sequences (e.g., tags that facilitate purification of the peptides of the invention (see, for example, U.S. Pat. No. 6,342,362, hereby incorporated by reference in its entirety; Altendorf et al. [1999-WWW, 2000] "Structure and Function of the $F_o$ Complex of the ATP Synthase from *Escherichia Coli,*" J. of Experimental Biology 203:19-28, The Co. of Biologists, Ltd., G.B.; Baneyx [1999] "Recombinant Protein Expression in *Escherichia coli,*" Biotechnology 10:411-21, Elsevier Science Ltd.; Eihauer et al. [2001] "The FLAG™ Peptide, a Versatile Fusion Tag for the Purification of Recombinant Proteins," *J. Biochem Biophys Methods* 49:455-65; Jones et al. [1995] *J. Chromatography* 707:3-22; Jones et al. [1995] "Current Trends in Molecular Recognition and Bioseparation," *J. of Chromatography A.* 707:3-22, Elsevier Science B.V.; Margolin [2000] "Green Fluorescent Protein as a Reporter for Macromolecular Localization in Bacterial Cells," *Methods* 20:62-72, Academic Press; Puig et al. [2001] "The Tandem Affinity Purification (TAP) Method: A General Procedure of Protein Complex Purification," *Methods* 24:218-29, Academic Press; Sassenfeld [1990] "Engineering Proteins for Purification," TibTech 8:88-93; Sheibani [1999] "Prokaryotic Gene Fusion Expression Systems and Their Use in Structural and Functional Studies of Proteins," *Prep. Biochem. & Biotechnol.* 29(1):77-90, Marcel Dekker, Inc.; Skerra et al. "Applications of a Peptide Ligand for Streptavidin: the Strep-tag", *Biomolecular Engineering* 16:79-86, Elsevier Science, B.V.; Smith [1998] "Cookbook for Eukaryotic Protein Expression: Yeast, Insect, and Plant Expression Systems," *The* Scientist 12(22):20; Smyth et al. [2000] "Eukaryotic Expression and Purification of Recombinant Extracellular Matrix Proteins Carrying the Strep II Tag", *Methods in Molecular Biology,* 139:49-57; Unger [1997] "Show Me the Money: Prokaryotic Expression Vectors and Purification Systems," *The Scientist* 11(17): 20, each of which is hereby incorporated by reference in their entireties), or commercially available tags from vendors such as such as STRATAGENE (La Jolla, Calif.), NOVAGEN (Madison, Wis.), QIAGEN, Inc., (Valencia, Calif.), or InVitrogen (San Diego, Calif.).

In other embodiments, peptides of the subject invention can be fused to heterologous polypeptide sequences that have adjuvant activity (a polypeptide adjuvant). Non-limiting examples of such polypeptides include heat shock proteins (hsp) (see, for example, U.S. Pat. No. 6,524,825, the disclosure of which is hereby incorporated by reference in its entirety).

Peptides as described herein may be synthesized by methods well known in the art, including recombinant DNA methods and chemical synthesis. Chemical synthesis may generally be performed using standard solution phase or solid phase peptide synthesis techniques, in which a peptide linkage occurs through the direct condensation of the amino group of one amino acid with the carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1-4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.,* 1963, 85:2149, which involves assembling a linear peptide chain on a resin support using protected amino acids. Solid phase peptide synthesis typically utilizes either the Boc or Fmoc strategy, which are well known in the art.

Those of ordinary skill in the art will recognize that, in solid phase synthesis, deprotection and coupling reactions must go to completion and the side-chain blocking groups must be stable throughout the synthesis. In addition, solid phase synthesis is generally most suitable when peptides are to be made on a small scale.

Acetylation of the N-terminal can be accomplished by reacting the final peptide with acetic anhydride before cleavage from the resin. C-amidation is accomplished using an appropriate resin such as methylbenzhydrylamine resin using the Boc technology.

The peptides disclosed here in may be modified by attachment of a second molecule that confers a desired property upon the peptide, such as increased half-life in the body, for example, pegylation. Such modifications also fall within the scope of the term "variant" as used herein.

Covalent attachment of a molecule or solid support may generally be achieved by first reacting the support material with a bifunctional reagent that will also react with a functional group, such as a hydroxyl, thiol, carboxyl, ketone or amino group, on the modulating agent. A preferred method of generating a linkage is via amino groups using glutaraldehyde. A peptide may be linked to cellulose via ester linkages. Similarly, amide linkages may be suitable for linkage to other molecules such as keyhole limpet hemocyanin or other support materials.

Although integrin interaction inhibitors as described herein may preferentially bind to specific tissues or cells, and thus may be sufficient to target a desired site in vivo, it may be beneficial for certain applications to include an additional targeting agent. Accordingly, a targeting agent may also, or alternatively, be linked to an integrin interaction inhibitor to facilitate targeting to one or more specific tissues. As used herein, a "targeting agent," may be any substance (such as a compound or cell) that, when linked to a integrin interaction inhibitor, enhances the transport of the inhibitor to a target tissue, thereby increasing the local concentration of the inhibitor. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site.

For certain embodiments, it may be beneficial to also, or alternatively, link a drug to an integrin interaction inhibitor. As used herein, the term "drug" refers to any bioactive agent intended for administration to a human or non-human mammal to prevent or treat a disease or other undesirable condition. Drugs include hormones, growth factors, proteins, peptides and other compounds. The use of certain specific drugs within the context of the present invention is discussed below.

Within certain aspects of the present invention, one or more integrin interaction inhibitors as described herein may be present within a pharmaceutical composition. A pharmaceutical composition comprises one or more integrin interaction inhibitors in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. A integrin interaction inhibitor may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration. For certain topical applications, formulation as a cream or lotion, using well known components, is preferred.

Various techniques may be utilized to facilitate delivery of the integrin interaction inhibitors of the invention to the target cells in vitro (including ex vivo) and in vivo (Cellular Drug Delivery: Principles and Practice, edited by Lu, D. R. and Oie, S., Human Press, Totowa, N.J., 2004). Optionally, it may be desirable to facilitate delivery of the integrin interaction inhibitors of the invention through the outer cell membrane. Various protein carrier molecules may be coupled to the integrin interaction inhibitors of the invention to assist penetration through biological membranes. For example, small regions (e.g., 9-16 amino acids) of proteins called protein transduction domains (PTDs) cell penetrating peptides (CPP) possess the ability to traverse biological membranes through protein transduction (Barnett, E. M. et al., *Invest. Opthalmol. Vis. Sci.,* 2006, 47:2589-2595; Schwarze S. R. et al., *Science,* 1999, 285(5433):1569-1572; Wadia, J. S. and Dowdy, S. F., *Advanced Drug Delivery Reviews,* 2005, 57(4): 579-596; Wadia, J. S. and Dowdy, S. F., *Curr. Opin. Biotechnol.,* 2002, 13(1)52-56; Ho A. et al., *Cancer Research,* 2001, 61:474-477; Futaki et al., *J. Biol. Chem.,* 2001, February, 276(8):5836-5840; Cao G. et al., *J. Neurosci.,* 2002, 22(13):5423-5431; Becker-Hapk, M. et al., *Methods,* 2001, 24:247-256; Snyder, E. L. and Dowdy, S. F., *Curr. Opin. Mol. Ther.,* 2001, 3:147-152; Lewin, M. et al., *Nat. Biotechnol.,* 2000, 18:410-414; Tung, C. H. et al., *Bioorg. Med. Chem.,* 2002, 10:3609-3614; Richard, J. P., et al., *J. Biol. Chem.,* Oct. 30, 2002, epub ahead of print). Transduction can occur in a receptor- and transporter-independent fashion that appears to target the lipid bilayer directly. Proteins (peptides) and compounds that are linked to PTDs (e.g., covalently) have the capability to traverse outer cell membranes. Preferably, the delivery peptide is a trans-activating transcriptional activator (TAT) peptide or an Antennapedia (ANT) peptide, or a derivative of either. PTDs can be linked to the peptides of the subject invention for transport across the cell membrane. One well characterized PTD is the human immunodeficient virus (HIV)-1 Tat peptide (see, for example, U.S. Pat. Nos. 5,804,604; 5,747,641; 5,674,980; 5,670,617; and 5,652,122). Peptides such as the homeodomain of *Drosophila* antennapedia (ANTP) and arginine-rich peptides display similar properties can be employed. VP22, a tegument protein from Herpes simplex virus type 1 (HSV-1), also has the ability to transport proteins across a cell membrane, and may be coupled to the integrin interaction inhibitors of the invention.

Definitions

As used herein, the terms "administering" or "administer" are defined as the introduction of a substance into cells in vitro or into the body of an individual in vivo by any route (for example, oral, nasal, ocular, rectal, vaginal and parenteral routes). Integrin interaction inhibitors may be administered individually or in combination with other agents via any route of administration, including but not limited to subcutaneous (SQ), intramuscular (IM), intravenous (IV), intraperitoneal (IP), intradermal (ID), via the nasal, ocular or oral mucosa (IN), or orally. For example, the integrin interaction inhibitors can be administered by direct injection into or on a tumor, or systemically (e.g., into the circulatory system), to kill circulating tumor cells (CTC).

In the context of the instant invention, the terms "oligopeptide", "polypeptide", "peptide" and "protein" can be used interchangeably; however, it should be understood that the invention does not relate to the peptides in natural form, that is to say that they are not in their natural environment but that the peptide may have been isolated or obtained by purification from natural sources or obtained from host cells prepared by genetic manipulation (e.g., the peptides, or fragments thereof, are recombinantly produced by host cells, or by chemical synthesis). Integrin interaction inhibitors containing peptides according to the instant invention may also contain non-natural amino acids, as will be described below. The terms "oligopeptide", "polypeptide", "peptide" and "protein" are also used, in the instant specification, to designate a series of residues of any length, typically L-amino acids, connected one to the other, typically by peptide bonds between the α-amino and carboxyl groups of adjacent amino acids. Linker elements can be joined to the peptides of the subject invention, for example, through peptide bonds or via chemical bonds (e.g., heterobifunctional chemical linker elements) as set forth below. Additionally, the terms "amino acid(s)" and "residue(s)" can be used interchangeably.

As used herein, the terms "treat" or "treatment" refer to both therapeutic treatment and prophylactic or preventative measures, wherein the object is to prevent or slow down (lessen) an undesired physiological change or disorder, such as the development or spread of cancer or other proliferation disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. For example, treatment with an integrin interaction inhibitor of the invention may include reduction of undesirable cell proliferation, and/or induction of apoptosis and cytotoxicity. "Treatment" can also mean prolonging survival as compared to expected survival if not receiving treatment. Those in need of treatment include those already with the condition or disorder as well as those prone to have the condition or disorder or those in which the condition or disorder is to be prevented or onset delayed. Optionally, the patient may be identified (e.g., diagnosed) as one suffering from the disease or condition (e.g., proliferation disorder) prior to administration of the integrin interaction inhibitor of the invention.

As used herein, the term "(therapeutically) effective amount" refers to an amount of the integrin interaction inhibitor of the invention or other agent (e.g., a drug) effective to treat a disease or disorder in a mammal. In the case of cancer or other proliferation disorder, the therapeutically effective amount of the agent may reduce (i.e., slow to some extent and preferably stop) unwanted cellular proliferation; reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; reduce β1 integrin signaling in the target cells, and/or relieve, to some extent, one or more of the symptoms associated with the cancer. To the extent the administered integrin interaction inhibitor prevents growth of and/or kills existing cancer cells, it may be cytostatic and/or cytotoxic. For cancer therapy, efficacy can, for example, be measured by assessing the time to disease progression (TTP) and/or determining the response rate (RR).

As used herein, the term "growth inhibitory amount" of the integrin interaction inhibitor of the invention refers to an amount which inhibits growth or proliferation of a target cell, such as a tumor cell, either in vitro or in vivo, irrespective of the mechanism by which cell growth is inhibited (e.g., by cytostatic properties, cytotoxic properties, etc.). In a preferred embodiment, the growth inhibitory amount inhibits (i.e., slows to some extent and preferably stops) proliferation or growth of the target cell in vivo or in cell culture by greater than about 20%, preferably greater than about 50%, most preferably greater than about 75% (e.g., from about 75% to about 100%).

The terms "cell" and "cells" are used interchangeably herein and are intended to include either a single cell or a plurality of cells, in vitro or in vivo, unless otherwise specified.

As used herein, the term "anti-cancer agent" refers to a substance or treatment (e.g., radiation therapy) that inhibits the function of cancer cells, inhibits their formation, and/or causes their destruction in vitro or in vivo. Examples include, but are not limited to, cytotoxic agents (e.g., 5-fluorouracil, TAXOL), chemotherapeutic agents, and anti-signaling agents (e.g., the PI3K inhibitor LY). In one embodiment, the anti-cancer agent administered before, during, after administration of the peptide or encoding polynucleotide of the invention is melphalen. Anti-cancer agents include but are not limited to the chemotherapeutic agents listed Table 3.

As used herein, the term "cytotoxic agent" refers to a substance that inhibits or prevents the function of cells and/or causes destruction of cells in vitro and/or in vivo. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, toxins such as small molecule toxins or enzymatically active toxins of bacterial, fungal, plant or animal origin, and antibodies, including fragments and/or variants thereof.

As used herein, the term "chemotherapeutic agent" is a chemical compound useful in the treatment of cancer, such as, for example, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON, GTx, Memphis, Tenn.), and anti-androgens such as flutamide, nilutamide, bicalutamide, leuprolide, and goserelin, etc. Examples of chemotherapeutic agents that may be used in conjunction with the compounds of the invention are listed in Table 3. In a preferred embodiment, the chemotherapeutic agent is one or more anthracyclines. Anthracyclines are a family of chemotherapy drugs that are also antibiotics. The anthracyclines act to prevent cell division by disrupting the structure of the DNA and terminate its function by: (1) intercalating into the base pairs in the DNA minor grooves; and (2) causing free radical damage of the ribose in the DNA. The anthracyclines are frequently used in leukemia therapy. Examples of anthracyclines include daunorubicin (CERUBIDINE), doxorubicin (ADRIAMYCIN, RUBEX), epirubicin (ELLENCE, PHARMORUBICIN), and idarubicin (IDAMYCIN).

TABLE 3

Examples of Chemotherapeutic Agents

| | |
|---|---|
| 13-cis-Retinoic Acid | MYLOCEL product |
| 2-Amino-6-Mercaptopurine | LETROZOLE product |
| 2-Cladribine (2-CDA) | NEOSAR product |
| 2-Chlorodeoxyadenosine | NEULASTA product |
| 5-fluorouracil (5-FU) | NEUMEGA product |
| | NEUPOGEN product |
| | NILANDRON product |
| 6-Thioguanine (6-TG) | NILUTAMIDE product |
| 6-Mercaptopurine (6-MP) | Nitrogen Mustard |
| | NOVALDEX product |
| ACCUTANE | NOVANTRONE product |
| ACTINOMYCIN-D | OCTREOTIDE product |
| ADRIAMYCIN | OCTREOTIDE ACETATE product |
| ADRUCIL | ONCOSPAR product |
| AGRYLIN | ONCOVIN product |
| ALA-CORT | ONTAK product |
| ALDESLEUKIN | ONXAL product |
| ALEMTUZUMAB | OPREVELKIN product |
| ALITRETINOIN | ORAPRED product |
| ALKABAN-AQ | ORASONE product |
| ALKERAN | OXALIPLATIN product |
| All-transretinoic acid | PACLITAXEL product |
| Alpha interferon | PAMIDRONATE product |
| ALTRETAMINE | PANRETIN product |
| AMETHOPTERIN | PARAPLATIN product |
| AMIFOSTINE | PEDIAPRED product |
| AMINOGLUTETHIMIDE | Interferon Alfa-2b (PEG Interferon) |
| ANAGRELIDE | PEGASPARGASE product |
| ANANDRON | PEGFILGRASTIM product |
| ANASTROZOLE | PEG-INTRON product |
| ARABINOSYLCYTOSINE | PEG-L-asparaginase |
| arabinosylcytosine (Ara-C) | Phenylalanine Mustard |
| ARANESP | PLATINOL product |
| AREDIA | PLATINOL-AQ product |
| ARIMIDEX | PREDNISOLONE product |
| AROMASIN | PREDNISONE product |
| Arsenic trioxide | PRELONE product |
| ASPARAGINASE | PROCARBAZINE product |
| All-trans retinoic acid | PROCRIT product |
| AVASTIN | PROLEUKIN product |
| Bacillus-Calmette-Guerin | PROLIFEPROSPAN 20 WITH CARMUSTINE IMPLANT product |
| chloroethylnitrosourea (BCNU) | PURINETHOL product |
| BEVACIZUMAB | RALOXIFENE product |
| BEXAROTENE | RHEUMATREX product |
| BICALUTAMIDE | RITUXAN product |
| BiCNU | RITUXIMAB product |
| BLENOXANE | ROVERON-A (interferon alfa-2a) product |
| BLEOMYCIN | RUBEX product |
| BORTEZOMIB | RUBIDOMYCIN HYDROCHLORIDE product |
| BUSULFAN | SANDOSTATIN product |
| BUSULFEX | SANDOSTATIN LAR product |
| Cetuximab (C225) | SARGRAMOSTIM product |
| CALCIUM LEUCOVORIN | SOLU-CORTEF product |
| CAMPATH | SOLU-MEDROL product |
| CAMPTOSAR | Imatinib Mesylate (STI-571) |
| Camptothecin-11 (CPT-11) | STREPTOZOCIN product |
| CAPECITABINE | TAMOXIFEN product |
| CARAC | TARGRETIN product |
| CARBOPLATIN | TAXOL product |
| CARMUSTINE | TAXOTERE product |
| CARMUSTINE WAFER | TEMODAR product |
| CASODEX | TEMOZOLOMIDE product |
| Lomustine (CCNU) | TENIPOSIDE product |
| diamminedinedichloroplatinum (CDDP) | Thiotepa (TESPA) |
| CeeNU | THALIDOMIDE product |
| CERUBIDINE | THALOMID product |
| CETUXIMAB | THERACYS product |
| CHLORAMBUCIL | THIOGUANINE product |
| CISPLATIN | THIOGUANINE TABLOID product |
| CITROVORUM FACTOR | THIOPHOSPHOAMIDE product |
| CLADRIBINE | THIOPLEX product |
| CORTISONE | THIOTEPA product |
| COSMEGEN | TICE product |
| | TOPOSAR product |
| Cyclophosphamide | TOPOTECAN product |
| CYTADREN | TOREMIFENE product |
| CYTARABINE | TRASTUZUMAB product |
| CYTARABINE LIPOSOMAL | TRETINOIN product |
| CYTOSAR-U | TREXALL product |
| CYTOXAN | TRISENOX product |
| DACARBAZINE | Thiotepa (TSPA) |
| DACTINOMYCIN | |
| DARBEPOETIN ALFA | VELBAN product |
| DAUNOMYCIN | VELCADE product |
| Daunorubicin | VEPESID product |
| DAUNORUBICIN HYDROCHLORIDE | VESANOID product |
| DAUNORUBICIN LIPOSOMAL | VIADUR product |
| DAUNOXOME | Vinblastine (VLB) |
| DECADRON | Vinblastine Sulfate |
| DELTA-CORTEF | VINCASAR PFS product |
| DELTASONE | Vincristine (VCR) |
| DENILEUKIN DIFTITOX | VINORELBINE product |
| DEPOCYT | VINORELBINE TARTRATE product |
| DEXAMETHASONE | |
| DEXAMETHASONE ACETATE | |
| DEXAMETHASONE SODIUM PHOSPHATE | VUMON product |
| DEXASONE | XELODA product |
| DEXRAZOXANE | ZANOSAR product |
| Mitoxantrone (DHAD) | ZEVALIN product |
| Dacarbazine (DIC or DTIC) | ZINECARD product |
| DIODEX | ZOLADEX product |
| DOCETAXEL | ZOLEDRONIC ACID product |
| DOXIL | ZOMETA product |
| DOXORUBICIN | GLIADEL WAFER product |
| DOXORUBICIN LIPOSOMAL | GLIVEC product |
| DROXIA | Granulocyte-macrophage colony-stimulating factor (GM-CSF) |
| | GOSERELIN product |
| DTIC-Dome | granulocyte - colony stimulating factor |
| DURALONE | Granulocyte macrophage colony stimulating factor |
| EFUDEX | HALOTESTIN product |
| ELIGARD | HERCEPTIN product |
| ELLENCE | HEXADROL product |
| ELOXATIN | HEXALEN product |
| ELSPAR | Hexamethylmelamine |
| EMCYT | Hexamethylmelamine (HMM) |
| EPIRUBICIN | HYCAMTIN product |
| EPOETIN ALFA | HYDREA product |
| ERBITUX | HYDROCORT ACETATE product |
| ERWINIA L-ASPARAGINASE | HYDROCORTISONE product |
| ESTRAMUSTINE | HYDROCORTISONE SODIUM PHOSPHATE product |
| ETHYOL | HYDROCORTISONE SODIUM SUCCINATE product |
| ETOPOPHOS | HYDROCORTONE PHOSPHATE product |
| Etoposide (VP-16) | HYDROXYUREA product |
| Etoposide phosphate | IBRITUMOMAB product |
| EULEXIN | IBRITUMOMAB TIUXETAN product |
| EVISTA | IDAMYCIN product |
| EXEMESTANE | IDARUBICIN product |
| FARESTON | IFEX product |
| FASLODEX | |
| FEMARA | IFOSFAMIDE product |
| FILGRASTIM | |
| FLOXURIDINE | |
| FLUDARA | IMATINIB MESYLATE product |
| FLUDARABINE | IMIDAZOLE CARBOXAMIDE product |
| FLUOROPLEX | Interferon alfa (IFN-alpha) |
| FLUOROURACIL | Interferon Alfa-2b (PEG conjugate) |
| FLUOROURACIL (cream) | Interleukin - 2 (IL-2) |
| FLUOXYMESTERONE | Interleukin-11 (IL-11) |
| FLUTAMIDE | Intron A (interferon alfa-2b) |
| Folinic Acid | LEUCOVORIN product |
| Floxuridine (FUDR) | LEUKERAN product |
| FULVESTRANT | LEUKINE product |
| Granulocyte-colony stimulating factor (G-CSF) | LEUPROLIDE product |

TABLE 3-continued

Examples of Chemotherapeutic Agents

| | |
|---|---|
| GEFITINIB | Leurocristine (LCR) product |
| GEMCITABINE | LEUSTATIN product |
| GEMTUZUMAB OZOGAMICIN | Liposomal cytarabine (Liposomal Ara-C) |
| GEMZAR | Liquid Pred |
| GLEEVEC | LOMUSTINE product |
| LUPRON | |
| LUPRON DEPOT | L-SARCOLYSIN product |
| MATULANE | METICORTEN product |
| MAXIDEX | Mitomycin (MTC) |
| MECHLORETHAMINE | Mitomycin-C |
| MECHLORETHAMINE HYDROCHLORINE product | MITOXANTRONE product |
| MEDRALONE | M-PREDNISOL product |
| MEDROL | |
| MEGACE | |
| MEGESTROL | MUSTARGEN product |
| MEGESTROL ACETATE | MUSTINE product |
| Melphalan (L-PAM) | MUTAMYCIN product |
| MERCAPTOPURINE | MYLERAN product |
| MESNA | IRESSA product |
| MESNEX | IRINOTECAN product |
| Methotrexate (MTX) | ISOTRETINOIN product |
| Methotrexate Sodium | KIDROLASE product |
| Methylprednisolone | LANACORT product |
| | L-asparaginase |

As used herein, the term "tumor" refers to all neoplastic cell growth and proliferation, whether malignant or benign, and all pre-cancerous and cancerous cells and tissues. For example, a particular cancer may be characterized by a solid tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture, or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site. The peptides of the invention are capable of inducing apoptosis in tumor cells and reducing tumor cell growth. The peptides of the invention (or nucleic acids encoding them) can be administered locally at the site of a tumor (e.g., by direct injection) or remotely. The peptides of the invention can induce cell death in circulating tumor cells (CTC) in a subject, e.g., by administering the peptides or encoding nucleic acids intravenously. Furthermore, the peptides of the invention can prevent or reduce onset of metastasis to other tissues, e.g., to the bone.

As used herein, the term "signaling" and "signaling transduction" represents the biochemical process involving transmission of extracellular stimuli, via cell surface receptors through a specific and sequential series of molecules, to genes in the nucleus resulting in specific cellular responses to the stimuli.

As used herein, the term "pharmaceutically acceptable salt or prodrug" is intended to describe any pharmaceutically acceptable form (such as an ester, phosphate ester, salt of an ester or a related group) of an integrin interaction inhibitor of the invention or other agent, which, upon administration to a subject, provides the mature or base compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The terms "link" or "join" refers to any method known in the art for functionally connecting peptides, including, without limitation, recombinant fusion, covalent bonding, disulfide bonding, ionic bonding, hydrogen bonding, and electrostatic bonding.

The terms "comprising", "consisting of" and "consisting essentially of" are defined according to their standard meaning. The terms may be substituted for one another throughout the instant application in order to attach the specific meaning associated with each term.

The terms "isolated" or "biologically pure" refer to material that is substantially or essentially free from components which normally accompany the material as it is found in its native state. Thus, isolated peptides or integrin interaction inhibitors in accordance with the invention preferably do not contain materials normally associated with the peptides in their in situ environment.

As used in this specification, the singular forms "a", "an", and "the" include plural reference unless the context clearly dictates otherwise. Thus, for example, a reference to "a compound" includes more than one such compound. Reference to "an integrin interaction inhibitor" includes more than one such inhibitor. A reference to "a peptide" includes more than one such peptide, and so forth.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. Eds. (1991) IRL Press)), each of which are incorporated herein by reference in their entirety.

Experimental controls are considered fundamental in experiments designed in accordance with the scientific method. It is routine in the art to use experimental controls in scientific experiments to prevent factors other than those being studied from affecting the outcome.

Materials and Methods

Reagents. Organic and inorganic reagents (ACS grade) were obtained from commercial sources and used without further purification, unless otherwise noted. Fmoc-protected amino acids and the coupling agent HCTU were obtained from Protein Technologies, Calbiochem-Novabiochem, or Chem-impex International. 2-Chlorotrityl chloride resin was purchased from Anaspec Inc. All linear peptides were synthesized on the Symphony peptide synthesizer, Protein Technologies Instruments. Solvents for peptide synthesis and reverse-phase HPLC were obtained from Applied Biosystems. Other chemicals used were obtained from Aldrich and were of the highest purity commercially available. Thin layer chromatography (TLC) was performed on glass plates (Whatman) coated with 0.25 mm thickness of silica gel 60 Å (#70-230 mesh). High resolution mass spectra were obtained on an Agilent LC-MSD-TOF.

Circular Dichroism Measurement. Circular dichroism experiments were carried out at room temperature on the Aviv (Model #210) spectropolarimeter flushed with nitrogen. The samples were prepared as stock solutions in sodium acetate buffer and diluted to the desired concentration for measurements. Each spectra was collected from 250 nm to 184 nm using a 0.1 cm path length cylindrical quartz cell. Each spectrum was recorded as an average of three scans taken at a spectral bandwidth of 1 nm. All spectra were corrected for buffer contributions and presented in units of molar ellipticity.

NMR Spectroscopy. All deuterated reagents and solvents were purchased from Cambridge Isotopes. All 1D $^1$H and $^{13}$C NMR spectra were recorded on a Bruker 250 MHz or a Varian INOVA 400 MHz spectrometer in $CDCl_3$ unless otherwise specified and chemical shifts are reported in ppm (δ) relative to internal standard tetramethylsilane (TMS). 2D NMR samples were prepared by dissolving 1-2 mg peptide in 100 μL $D_2O$ and then adjusting the pD to 4.0 (uncorrected) with either 50 mM NaOAc-$d_3$ or 50 mM AcOH-$d_4$ to yield a final concentration between 3-7 mM. Chemical shifts are reported in parts per million (ppm) relative to 0.5 mM DSS. NMR experiments were run and processed on a three-channel Varian Inova 500 MHz instrument at 298.1 K using a 3-mm I.D. RT probe equipped with Z-axis PFGs running VnmrJ 2.2D. Spectra were then analyzed using ACD labs NMR Manager version 11.0. 1D NMR spectra were collected using 32K data points, between 16 and 64 scans were collected using a 0.5 s delay and 1 s presaturation. 2D TOCSY and NOESY experiments were run with a 5000 Hz window in both dimensions. TOCSY experiments were run with a mixing time of 60 ms, a 0.5 s relaxation delay followed by 1 s of presaturation and 512 increments in the $f_1$ dimension with 32 transients per increment (collecting 4096 data points per transient in the $f_2$ dimension). Zero-filling was then applied using 4096 points for each dimension. NOESY experiments were performed using a 500 ms mixing time, 1 s of presaturation and 512 increments of 32 transients each (collecting 4096 data points per transient in the $f_2$). Zero-filling was then applied using 4096 points for each dimension. Presaturation was used to suppress the water resonance both during the relaxation delay and during the mixing time. All spectra were analyzed using standard window functions (Gaussian without shifting). Assignments were made by using standard methods as described by Wüthrich[1].

Constrained Conformation Search with MacroModel. Structures were created with Maestro 8.5[2] for peptides 1 and 5. Minimizations of the structures were performed with MacroModel 9.8[3]. The OPLS 2005[4] force field was used with implicit water and a constant dielectric constant of 1.0 while using the Truncated Newtonian Conjugate Gradient algorithm with a threshold of 0.01 kJ/mol. A Mixed Monte Carlo Multiple Minimum (MCMM)/Low-Mode Conformational Search (LMCS) method was employed with NOEsy data, which were introduced as flat-bottom energetic restraint wells to yield a constrained potential energy. Torsion angles were similarly restrained for all peptide bonds. A 200 kJ/mol energy window of structures were kept during the conformation search where only structures in the lower 100 kJ/mol were outputted. Redundant conformations were eliminated and 20 lowest energy structures were kept for analysis.

Cyclic Peptide Synthesis & Purification.

a. Cyclic III peptide with D-Pro-L-Pro and N-(2-aminoethyl)-N-methylsulfonamido glycine linker.

2-Chlorotrityl chloride resin was treated with Fmoc-Pro-OH and then immediately Fmoc-deprotected using 20% piperidine/2% DBU in DMF. Fmoc quantification of resin indicated a loading of 0.19 mmol/g of resin. For a 25 μmol synthesis, 132 mg of resin was charged to the peptide reaction vessel on a Protein Technologies Symphony Peptide Synthesizer. For each coupling step, 5 equivalents of Fmoc-amino acid and 7.5 equivalents of HCTU are dissolved in 0.4 M NMM in DMF to equal 20 equivalents of NMM, which is added to the reactor. Each coupling reaction was carried out for 10 mins followed by NMP washes. Fmoc deprotection was done using 20% piperidine/2% DBU in DMF for (2×2.5 mins). The amino acids used for peptide synthesis were coupled in the following order: Fmoc-D-Pro-OH, Fmoc-Lys(Boc)-OH, Fmoc-Leu-OH, Fmoc-Lys(Boc)-OH, Fmoc-Leu-OH, Fmoc-Lys(Boc)-OH, Fmoc-NHCH$_2$CH$_2$N(O$_2$SCH$_3$)CH$_2$COOH, Fmoc-Trp(Boc)-OH, Fmoc-Ser(t-Bu)-OH, Fmoc-Val-OH, Fmoc-Val-OH, and Fmoc-Met-OH. After synthesis of the protected linear HYD1, the resin was transferred to a manual peptide synthesis vessel and treated with 5 mL of a cleavage solution of 20% trifluoroethanol in DCM for 2 hours. The resin was filtered and washed with 5 mL of cleavage solution. This cleavage cycle was repeated twice. The combined organic filtrates were concentrated to give crude protected linear III peptide. The crude III peptide was dissolved in 15 mL of 1% v/v DIEA in DMF and treated with 4 equivalents of HCTU for one hour. After one hour, the reaction mixture was concentrated to give crude protected cyclized III peptidomimetic. The crude peptidomimetic was then treated with a 10 mL solution of 87.5% TFA/5% H$_2$O/5% phenol/2.5% triethylsilane for 30 mins. The reaction mixture was concentrated and the thick viscous liquid was triturated twice with 10 mL of cold diethyl ether. The reaction contents were centrifuged to give crude cyclic III peptidomimetic. The crude peptidomimetic was dissolved in a solution of 0.1% TFA in H$_2$O and freeze-dried to give a white fluffy powder. All cyclic III peptides and peptidomimetics were purified using semi-preparative reverse phase HPLC (5 μM particle size C$_{18}$ AAPPTEC spirit column, 25×2.12 cm) with eluents: A=0.1% HCO$_2$H in H$_2$O, B=0.1% HCO$_2$H in H$_3$CCN. The purification was carried out using a gradient of 5-50% B Buffer over 40 min with a flow rate 20 mL/minute using 222 nm UV detection. All peaks with retention times expected for peptides were collected and lyophilized. The purified peptides were analyzed using similar analytical HPLC conditions and found to have >95% purity and were structurally characterized using a Bruker Autoflex MALDI-TOF instrument with α-cyano hydroxyl cinnamic acid (CHCA) as matrix. We have also characterized the secondary structure of selected cyclic III peptidomimetics and they show concentration independent CD spectra in pH 7.0 sodium acetate buffer at concentrations of 200 μM indicative of beta-sheet-like conformations with a minima around 200 nm for cyclic III and a maxima around 190 nm as expected. This supports the assertion of cyclic beta-hairpin-like structure.

b. Cyclic III peptides with two N-(2-aminoethyl)-N-methylsulfonamidoglycine linkers.

2-Chlorotrityl chloride resin was treated with Fmoc-Met-OH and then immediately Fmoc-deprotected using 20% piperidine/2% DBU in DMF. Fmoc quantification of resin indicated a loading of 0.24 mmol/g of resin. For a 25 µmol synthesis, 104 mg of resin was charged to the peptide reaction vessel on a Protein Technologies Symphony Peptide Synthesizer. Everything else was the same as above except the amino acids were coupled in the following order: Fmoc-NHCH$_2$CH$_2$N(O$_2$SCH$_3$)CH$_2$COOH, Fmoc-Lys(Boc)-OH, Fmoc-Leu-OH, Fmoc-Lys(Boc)-OH, Fmoc-Leu-OH, Fmoc-Lys(Boc)-OH, Fmoc-NHCH$_2$CH$_2$N(O$_2$SCH$_3$)CH$_2$COOH, Fmoc-Trp(Boc)-OH, Fmoc-Ser(t-Bu)-OH, Fmoc-Val-OH, and Fmoc-Val-OH. We saw no evidence of Met C-terminal racemization from the C-terminal peptide cyclization step, which can be detected by the appearance of diastereomeric peptide side products in the HPLC analysis.

c. Cyclic III Peptide Analogs Prepared by on Resin Cyclization Using Lysine Side Chain Anchoring Strategy p-Nitrophenyl Wang Resin (0.69 mmol/g, 0.25 g) was swollen in dichloromethane for 15 minutes. N$^\alpha$-Fmoc-Lys-OAllyl. TFA (4 equiv.) solution in DCM containing DIEA (8 equiv.) was added to the resin in peptide reaction vessel for 3 hours. The process is repeated twice to ensure maximum loading of the fmoc amino acid on the resin. N$^\alpha$-Fmoc-Lys-OAllyl. TFA salt was prepared by deprotection of N$^\alpha$-Fmoc-Lys(Boc)-OAllyl using 95% TFA in DCM at 0° C. Fmoc quantification of resin indicated a loading of 0.59 mmol/g of resin. The linear protected peptide was then synthesized using standard Fmoc solid phase strategy on a Protein Technologies Symphony Peptide Synthesizer. For a 25 µmol synthesis, 42 mg of resin was charged to the peptide reaction vessel. For each coupling step, 5 equivalents of Fmoc-amino acid and 7.5 equivalents of HCTU are dissolved in 0.4 M NMM in DMF to equal 20 equivalents of NMM, which is added to the reactor. Each coupling reaction was carried out for 10 mins followed by NMP washes. Fmoc deprotection was done using 20% piperidine/2% DBU in DMF for (2×2.5 mins). The amino acids used for peptide synthesis were coupled in the following order: Fmoc-Leu-OH, Fmoc-Lys(Boc)-OH, Fmoc-Leu-OH, Fmoc-Lys(Boc)-OH, Linker T$_3$, Fmoc-Trp(Boc)-OH, Fmoc-Ala-OH, Fmoc-Val-OH, Fmoc-Val-OH, Fmoc-Nle-OH and Linker T$_1$. After synthesis of the protected linear cyclic III peptide, the resin was transferred to a manual peptide synthesis vessel. The Fmoc group from last amino acid was cleaved by 20% piperidine/2% DBU in DMF. The C-terminal allyl group was then removed using Pd(PPh$_3$)$_4$ dissolved in CHCl$_3$—AcOH-NMM (37:2:1) for two hours. The allyl cleavage procedure was repeated again to ensure complete cleavage. The resulting side chain anchored peptide acid resin was then washed with DCM, NMP, MeOH, DCM and dried. After allyl deprotection, on resin cyclization of linear peptide was carried out by treating peptide side chain anchored peptide acid resin with 4 equivalents of HCTU in 4 ml DMF and 8 equivalents of DIEA for one hour.

After on the resin, the peptide was deprotected from the resin using cleavage cocktail of TFA/Triethylsilane/H$_2$O (95:2.5:5) solution at room temperature for 30 minutes. The reaction mixture was concentrated and the thick viscous liquid was triturated twice with 10 mL of cold diethyl ether. The reaction contents were centrifuged to give crude cyclic III peptidomimetic. The crude peptidomimetic was dissolved in a solution of 0.1% TFA in H$_2$O and freeze-dried to give a white fluffy powder. All cyclic III peptides and peptidomimetics were purified using semi-preparative reverse phase HPLC (5 µM particle size C$_{18}$ AAPPTEC spirit column, 25×2.12 cm) with eluents: A=0.1% HCO$_2$H in H$_2$O, B=0.1% HCO$_2$H in H$_3$CCN. The purification was carried out using a gradient of 5-50% B Buffer over 40 min with a flow rate 20 mL/minute using 222 nm UV detection. All peaks with retention times expected for peptides were collected and lyophilized. The purified peptides were analyzed using similar analytical HPLC conditions and found to have >95% purity and were structurally characterized using a Bruker Autoflex MALDI-TOF instrument with α-cyano hydroxyl cinnamic acid (CHCA) as matrix.

d. Cyclic III Peptide Analogs Prepared by on Resin Cyclization Using Glutamic Acid Side Chain Anchoring Strategy Fmoc protected Rink amide Resin (0.62 mmol/g, 0.25 g) was swollen in dichloromethane for 15 minutes. The Fmoc group was removed using 20% piperidine/2% DBU in DMF. N$^\alpha$-Fmoc-Glu(OH)—O$^\alpha$Allyl (4 equiv.), HCTU (4 equiv.) in DMF along with DIEA (8 equiv.) was added to the resin in peptide reaction vessel for 2 hours. The process is repeated twice to ensure maximum loading of the fmoc amino acid on the resin. Fmoc quantification of resin indicated a loading of 0.53 mmol/g of resin. The linear protected peptide was then synthesized using standard Fmoc solid phase strategy on a Protein Technologies Symphony Peptide Synthesizer. For a 25 µmol synthesis, 47 mg of resin was charged to the peptide reaction vessel. For each coupling step, 5 equivalents of Fmoc-amino acid and 7.5 equivalents of HCTU are dissolved in 0.4 M NMM in DMF to equal 20 equivalents of NMM, which is added to the reactor. Each coupling reaction was carried out for 10 mins followed by NMP washes. Fmoc deprotection was done using 20% piperidine/2% DBU in DMF for (2×2.5 mins). The amino acids used for peptide synthesis were coupled in the following order: Fmoc-Leu-OH, Fmoc-Lys(Boc)-OH, Fmoc-Leu-OH, Fmoc-Lys(Boc)-OH, Linker T$_3$, Fmoc-Trp(Boc)-OH, Fmoc-Ala-OH, Fmoc-Val-OH, Fmoc-Val-OH, Fmoc-Nle-OH and Linker T$_1$. After synthesis of the protected linear cyclic III peptide, the resin was transferred to a manual peptide synthesis vessel. The Fmoc group from last amino acid was cleaved by 20% piperidine/2% DBU in DMF. The C-terminal allyl group was then removed using Pd(PPh$_3$)$_4$ dissolved in CHCl$_3$—AcOH-NMM (37:2:1) for two hours. The allyl cleavage procedure was repeated again to ensure complete cleavage. The resulting side chain anchored peptide acid resin was then washed with DCM, NMP, MeOH, DCM and dried. After allyl deprotection, on resin cyclization of linear peptide was carried out by treating peptide side chain anchored peptide acid resin with 4 equivalents of HCTU in 4 ml DMF and 8 equivalents of DIEA for one hour. After on resin, the peptide was deprotected from the resin using cleavage cocktail of TFA/Triethylsilane/H$_2$O (95:2.5:5) solution at room temperature for 30 minutes. The reaction mixture was concentrated and the thick viscous liquid was triturated twice with 10 mL of cold diethyl ether. The reaction contents were centrifuged to give crude cyclic III peptidomimetic. The crude peptidomimetic was dissolved in a solution of 0.1% TFA in H$_2$O and freeze-dried to give a white fluffy powder. All cyclic III peptides and peptidomimetics were purified using semi-preparative reverse phase HPLC (5 µM particle size C$_{18}$ AAPPTEC spirit column, 25×2.12 cm) with eluents: A=0.1% HCO$_2$H in H$_2$O, B=0.1% HCO$_2$H in H$_3$CCN. The purification was carried out using a gradient of 5-50% B Buffer over 40 min with a flow rate 20 mL/minute using 222 nm UV detection. All peaks with retention times expected for peptides were collected and lyophilized. The purified peptides were analyzed using similar analytical HPLC conditions and found to have >95% purity and were structurally characterized using a Bruker Autoflex MALDI-TOF instrument with α-cyano hydroxyl cinnamic acid (CHCA) as matrix.

Figure 20A:
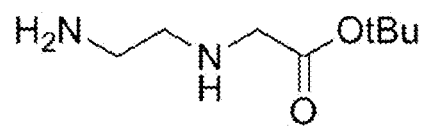
FIGS. 20A-20H show the N-(2-aminoethyl)-N-methyl sulfonamidoglycine linker tert-Butyl N-(2-aminoethyl) glycine 2 (FIG. 20A); tert-Butyl N-[2-(N-9-fluorenylmethoxycarbonyl)aminoethyl]glycinate hydrochloride 3 (FIG. 20B); tert-Butyl N-[2-(N-9-fluorenylmethoxycarbonyl)aminoethyl N-methylsulfonamido glycinate 4 (FIG. 20C); 2-(N-(2-(((9H-fluoren-9-yl)methoxy)carbonylamino)ethyl)methylsulfonamido)acetic acid 5 (FIG. 20D); 1-tert-butyl 2-((2-tert-butoxy-2-oxoethoxy)methyl)pyrrolidine-1-carboxylate 7 (FIG. 20E); 1-tert-butyl 2-(pyrrolidin-2-ylmethoxy) acetate 8 (FIG. 20F); 1-(9H-fluoren-9-yl)methyl 2-((2-tert-butoxy-2-oxoethoxy)methyl)pyrrolidine-1-carboxylate 9 (FIG. 20G); and 1-2-((1-(((9H-fluoren-9-yl)methoxy)carbonyl)pyrrolidin-2-yl)methoxy)acetic acid 10 (FIG. 20H).
Figure 20B:
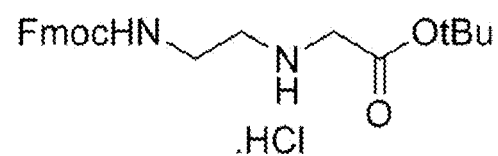
Figure 20C:
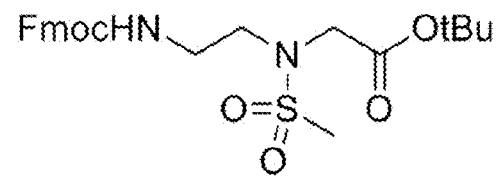

Synthesis of N-(2-aminoethyl)-N-methyl sulfonamidoglycine linker.

tert-Butyl N-(2-aminoethyl) glycine 2 (FIG. 20A). A solution of tert-butyl bromoacetate (27.6 mL, 0.18 mol) in 150 mL DCM was added dropwise to a solution of ethylenediamine (100 mL, 1.5 mol) in 700 mL DCM at 0° C. for a period of 30 mins. The reaction mixture was allowed to warm to room temperature and stirred for 15 hours. The reaction mixture was then washed with (2×150 mL) water. The aqueous layer was re-extracted with DCM (3×100 mL). The combined organic washes were dried using sodium sulfate and then filtered. The solution was concentrated in vacuo to dryness and was used in next step without further purification (27.4 gm, 85%). $^1$H NMR (250 MHz, CDCl$_3$) δ 3.30 (s, 2H), 2.83-2.76 (m, 2H), 2.72-2.64 (m, 2H), 1.60 (b, 3H), 1.47 (s, 9H). $^{13}$C NMR (63 MHz, CDCl$_3$) ppm 171.54, 80.59, 51.70, 51.21, 41.34, 27.78.

tert-Butyl N-[2-(N-9-fluorenylmethoxycarbonyl)aminoethyl]glycinate hydrochloride 3 (FIG. 20B). Compound 2 (22 gm, 0.13 mol) was dissolved along with DIEA (22 mL, 0.13 mol) in DCM (1000 mL) and N-(9-fluorenylmethoxycarbonyloxy) succinimide (41 gm, 0.12 mol) in 300 mL DCM was added dropwise over one hour. The reaction contents were stirred overnight and washed with (3×100 mL) 1M HCl solution and brine solution (100 mL). The organic contents were dried using Na$_2$SO$_4$ and filtered. The solution was partially concentrated to 50 mL and cooled in deep freezer (−20° C.) for overnight. The white precipitate formed was filtered and washed with DCM. The precipitates were vacuum dried to give compound 3 as the hydrochloride salt (43.1 gm, 90%). $^1$H NMR (400 MHz, DMSO d$_6$) δ 9.51 (s, 2H), 7.88 (d, J=7.5 Hz, 2H), 7.70 (d, J=7.4 Hz, 2H), 7.65 (d, J=5.5 Hz, 1H), 7.41 (t, J=7.4 Hz, 2H), 7.33 (t, J=7.3 Hz, 2H), 4.31 (d, J=6.7 Hz, 2H), 4.23 (d, J=6.6 Hz, 1H), 3.86 (s, 2H), 3.49-3.26 (m, 2H), 3.02 (t, J=5.9 Hz, 2H), 1.45 (s, 9H). $^{13}$C NMR (101 MHz, DMSO d$_6$) ppm 165.52, 156.21, 143.77, 140.70, 127.60, 127.04, 125.17, 120.09, 82.91, 65.64, 54.91, 47.19, 46.63, 46.37, 36.59, 27.59. HRMS m/z (ESI): calcd. for C$_{23}$H$_{29}$N$_2$O$_4$ [M+H]$^+$ 397.2122, found 397.2120.

tert-Butyl N-[2-(N-9-fluorenylmethoxycarbonyl)aminoethyl N-methylsulfonamido glycinate 4 (FIG. 20C). Compound 3 (5.0 gm, 11.5 mmol) was suspended in 50 mL of THF and DIEA (4.0 mL, 23.1 mmol) was added to it at 0° C. Methanesulfonyl chloride (0.9 mL, 11.5 mmol) was added dropwise for period of 10 mins. The reaction mixture was stirred for two hours and allowed to warm to room temperature. The mixture was evaporated to dryness in vacuum and the residue was partitioned between DCM and water. The organic layer was partially concentrated and kept in the refrigerator overnight. The white precipitate that formed was filtered and dried in vacuuo. (4.8 gm, 88%) $^1$H NMR (250 MHz, CDCl$_3$) δ 7.76 (d, J=7.1 Hz, 2H), 7.61 (d, J=7.3 Hz, 2H), 7.44-7.27 (m, 5H), 5.48 (s, 1H), 4.38 (d, J=7.1 Hz, 2H), 4.28-4.18 (m, 1H), 4.02 (s, 2H), 3.38 (d, J=12.6 Hz, 4H), 3.01 (s, 3H), 1.48 (s, 9H). $^{13}$C NMR (63 MHz, CDCl$_3$) ppm 169.04, 156.58, 143.93, 141.30, 127.69, 127.09, 125.18, 119.96, 82.97, 66.95, 49.45, 47.94, 47.19, 39.71, 39.20, 28.04. HRMS m/z (ESI): calcd. for C$_{24}$H$_{31}$N$_2$O$_6$SNa [M+Na]$^+$ 497.1717, found 497.1712.

Figure 20D:
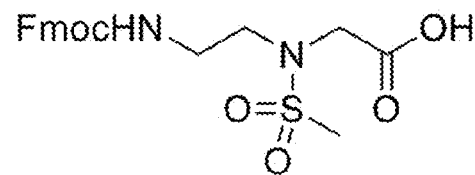

2-(N-(2-(((9H-fluoren-9-yl)methoxy)carbonylamino) ethyl)methylsulfonamido)acetic acid 5 (FIG. 20D).

Compound 4 (4.8 gm, 10 mmol) was dissolved in 1,4-dioxane and 4M HCl was added to it. After completion of the reaction, reaction contents were filtered to give compound 2.5 as white solid in quantitative yield (4.1 gm). $^1$H NMR (400 MHz, DMSO d$_6$) δ 12.93 (s, 1H), 7.90 (d, J=7.5 Hz, 2H), 7.69 (d, J=7.4 Hz, 2H), 7.43 (t, J=7.4 Hz, 2H), 7.34 (t, J=7.3 Hz, 2H), 4.32 (d, J=6.9 Hz, 2H), 4.23 (t, J=6.8 Hz, 1H), 4.01 (s, 2H), 3.36 (s, 1H), 3.29 (t, J=6.3 Hz, 2H), 3.20 (dd, J=12.0, 6.0 Hz, 2H), 2.98 (s, 3H). $^{13}$C NMR (101 MHz, DMSO) ppm 170.99, 156.13, 143.88, 140.73, 127.60, 127.06, 125.13, 120.10, 65.45, 48.25, 46.98, 46.74, 39.02, 38.87. HRMS m/z (ESI): calcd. for C$_{20}$H$_{23}$N$_2$O$_6$S [M+H]$^+$ 419.1271, found 419.1278.

Figure 20E:
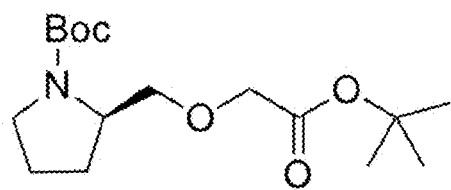

1-tert-butyl 2-((2-tert-butoxy-2-oxoethoxy)methyl)pyrrolidine-1-carboxylate 7 (FIG. 20E). To a solution of 6 (0.5 gm, 2.5 mmol) in toluene (10 mL) were added 30% NaOH solution (6 mL), tert-butyl bromoacetate (0.73 mL, 5.0 mmol) and TBAI (0.46 gm, 1.2 mmol) at 0° C. The reaction was carried out for 3 hrs until the TLC showed complete consumption of starting material. The reaction mixture was diluted with water (5 mL) before extracting with ethyl acetate (3×20 mL). The combined organic layer was washed with 1M HCl (10 mL), brine (10 mL) and dried over Na$_2$SO$_4$. The organic layer was concentrated to leave a residue which was further purified by column chromatography to give compound 7 (0.6 gm) in 77% yield. $^1$H NMR (CDCl$_3$, 400 MHz): δ 3.70 (s, 1H), 3.37 (m, 1H), 3.08 (m, 2H), 1.81-1.67 (m, 4H), 1.22 (s, 9H), 1.21 (s, 9H). $^{13}$C NMR (CDCl$_3$, 100 MHz): δ 169.3 (1C), 154.2 (1C), 80.9 (1C), 78.9 (1C), 71.7 (1C), 68.7 (1C), 56.1 (1C), 46.4 (1C), 28.4 (1C), 28.2 (3C), 27.8 (3C), 23.0 (1C). HRMS m/z (ESI): calcd. for C$_{16}$H$_{30}$NO$_5$ [M+H]$^+$ 316.2119, found 316.2164.

Figure 20F:
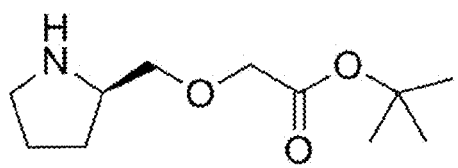

1-tert-butyl 2-(pyrrolidin-2-ylmethoxy) acetate 8 (FIG. 20F). Compound 7 (0.6 gm, 1.8 mmol) was dissolved in 15 mL DCM and 5 mL trifluoroacetic acid was added to it. The reaction contents were stirred until the starting material was completely consumed. The reaction mixture was concentrated to dryness in vacuo and was used in the next step without further purification.

Figure 20G:
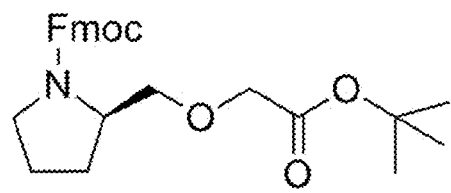

1-(9H-fluoren-9-yl)methyl 2-((2-tert-butoxy-2-oxoethoxy)methyl)pyrrolidine-1-carboxylate 9 (FIG. 20G). Compound 8 (0.5 gm, 1.8 mmol) was dissolved in 20 mL DCM and DIEA (1.0 mL, 5.4 mmol) was added to it. The reaction mixture was cooled to 0° C. and FmocOSu (0.6 gm, 1.8 mmol) was added to it. The reaction contents were allowed to warm to room temperature and stirred for two hours. The reaction mixture was concentrated in vacuo and residue was partitioned between DCM (20 mL) and H$_2$O (15 mL). The organic layer was dried, filtered, concentrated and chromatographed using EtOAc/Hexane (4:1) as eluent to give compound 9 (0.55 gm) in 79% yield. $^1$H NMR (CDCl$_3$, 400 MHz): δ 7.74 (d, J=8 Hz, 2H), 7.58 (d, J=8 Hz 2H), 7.37 (t, J=8 Hz, 2H), 7.29 (t, J=8 Hz, 2H), 4.54 (d, J=4 Hz, 1H), 4.36 (m, 1H), 4.22 (m, 1H), 3.96 (s, 1H), 3.74-3.55 (m, 3H), 3.44-3.33 (m, 2H), 3.24-3.10 (m, 1H), 2.10-1.75 (m, 4H), 1.46 (s, 9H). $^{13}$C NMR (CDCl$_3$, 100 MHz): δ 169.5 (1C), 154.9 (1C), 144.1 (2C), 141.3 (2C), 127.6 (2C), 127.0 (2C), 125.0 (2C), 119.9 (2C), 81.4 (1C), 71.6 (1C), 68.9 (1C), 66.7 (1C), 56.7 (1C), 47.4 (1C), 46.8 (1C), 28.3 (1C), 28.1 (3C), 23.4 (1C). HRMS m/z (ESI): calcd. for C$_{26}$H$_{32}$NO$_5$ [M+H]$^+$ 438.2275, found 438.2218.

Figure 20H:
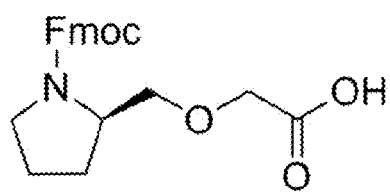
Figure 21:
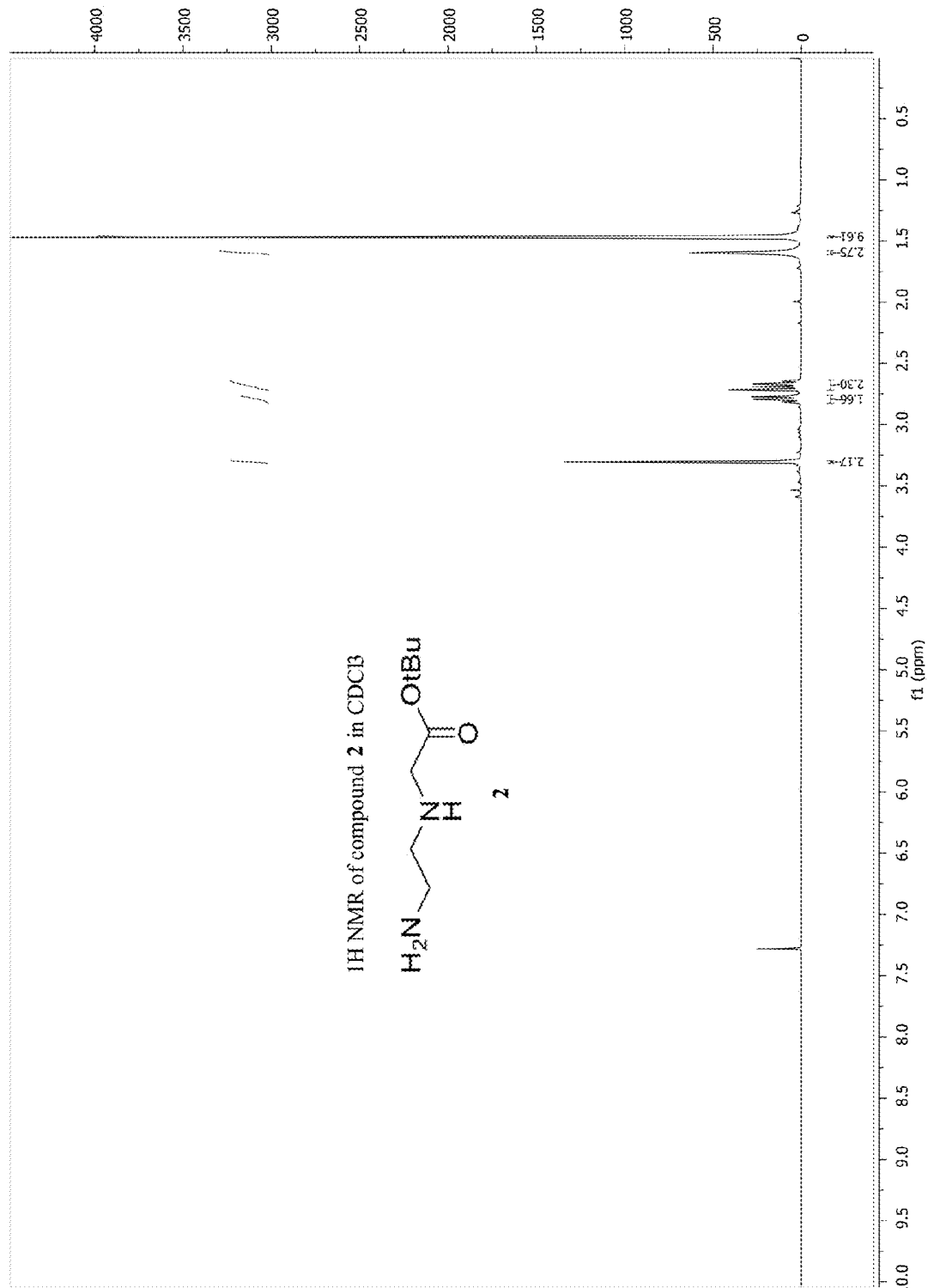
FIGS. 21-32 are NMR spectra of compounds 2, 3, 5, 7, 9, and 10.
Figure 22:
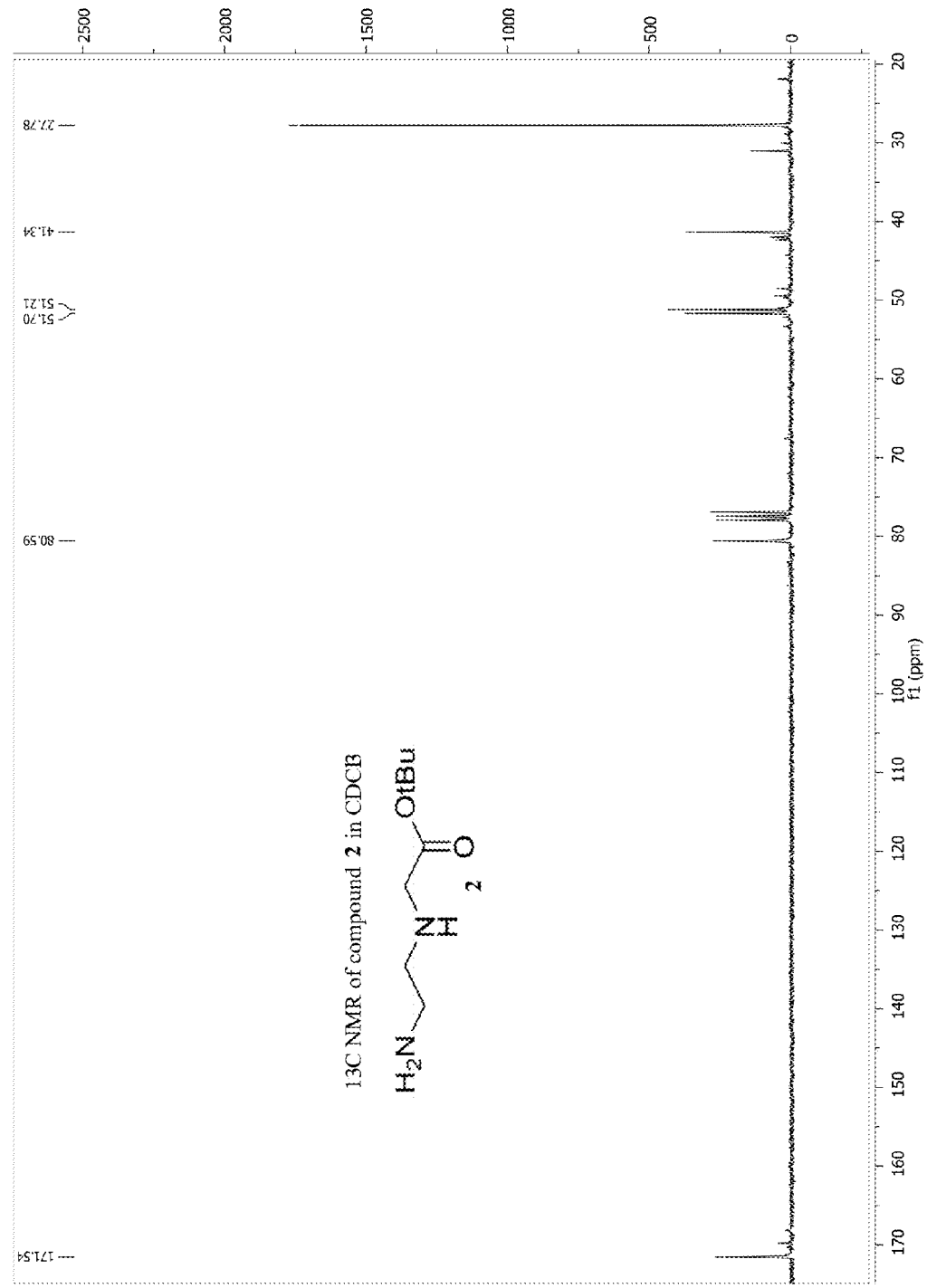
Figure 23:
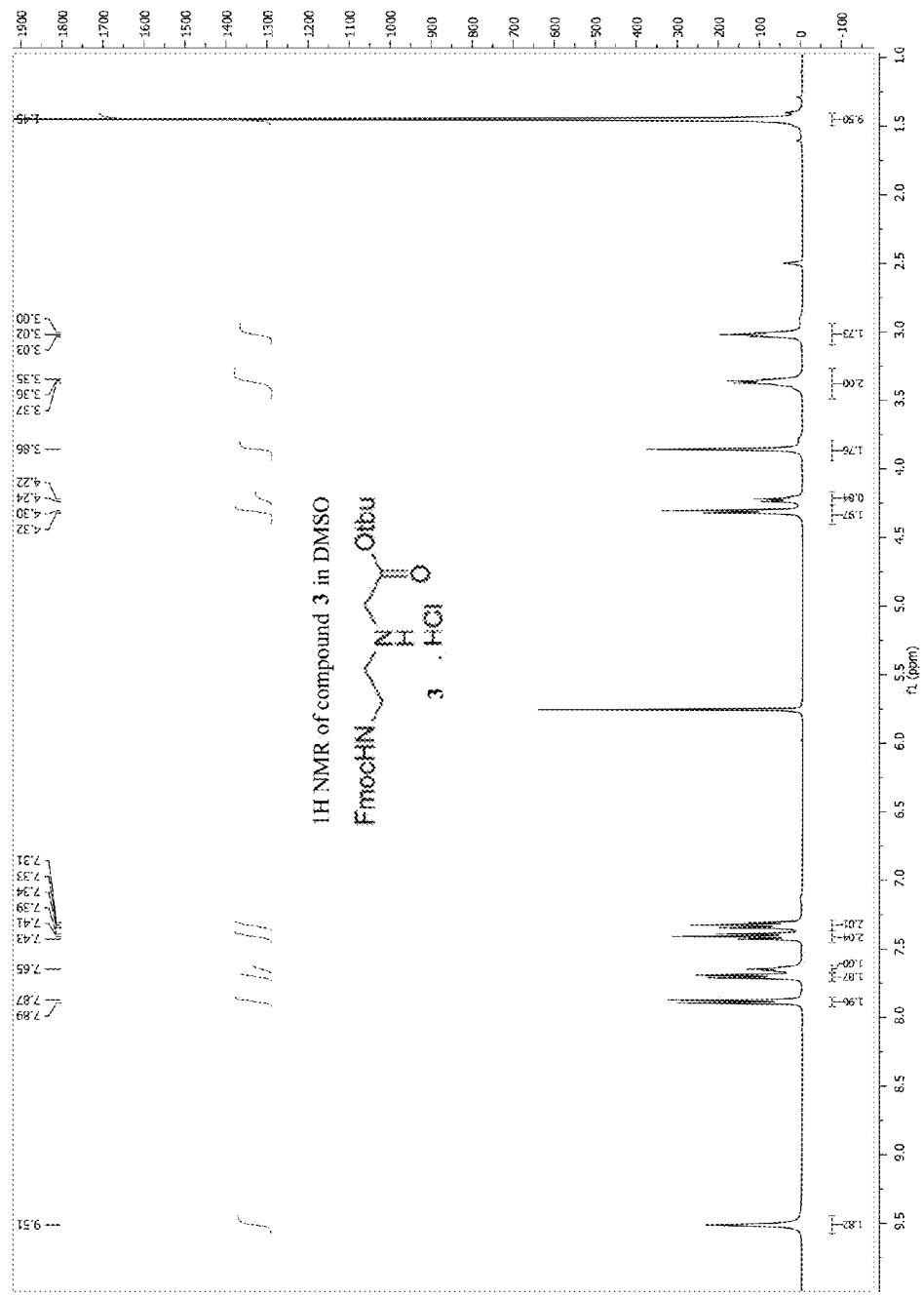
Figure 24:
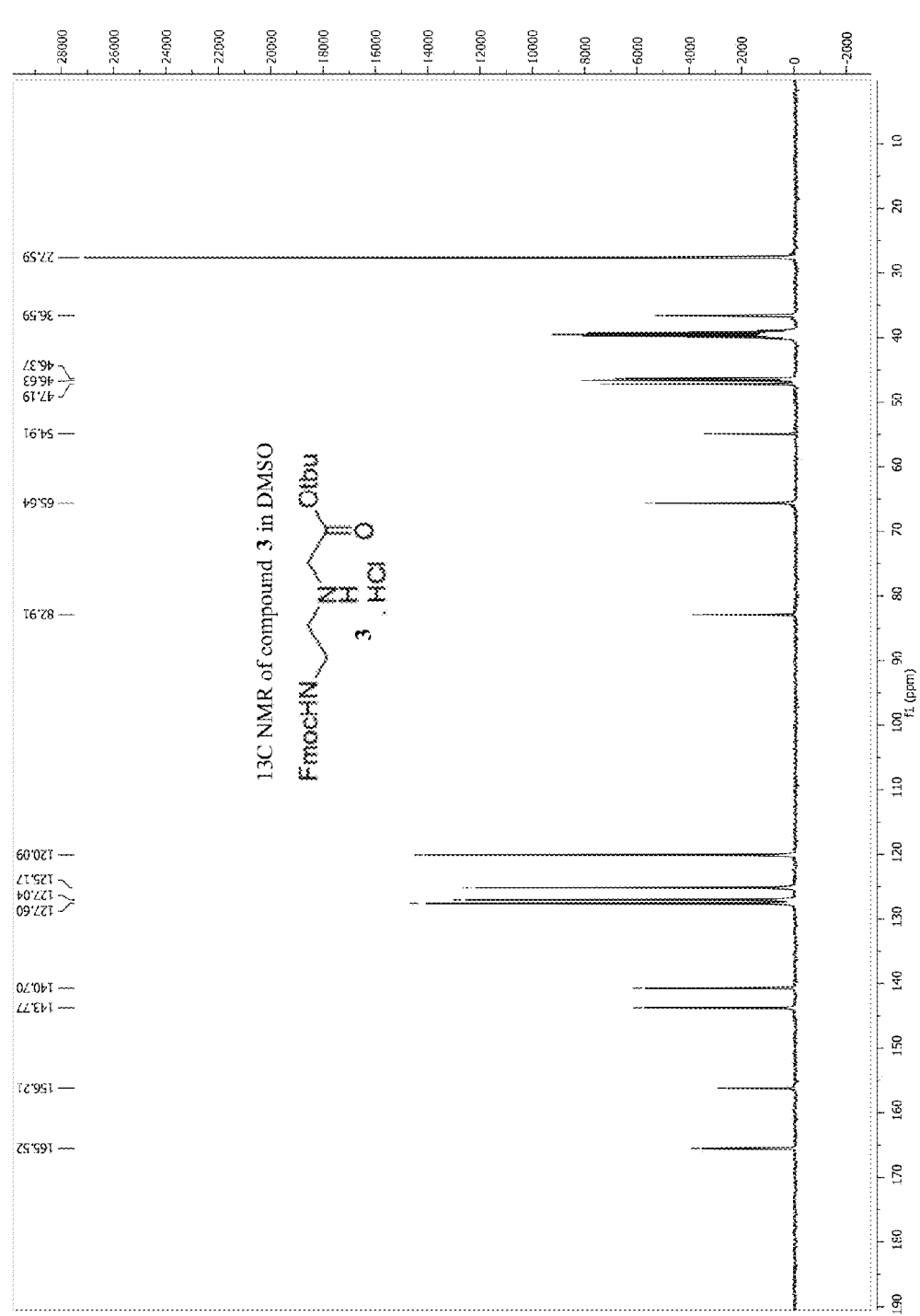
Figure 25:
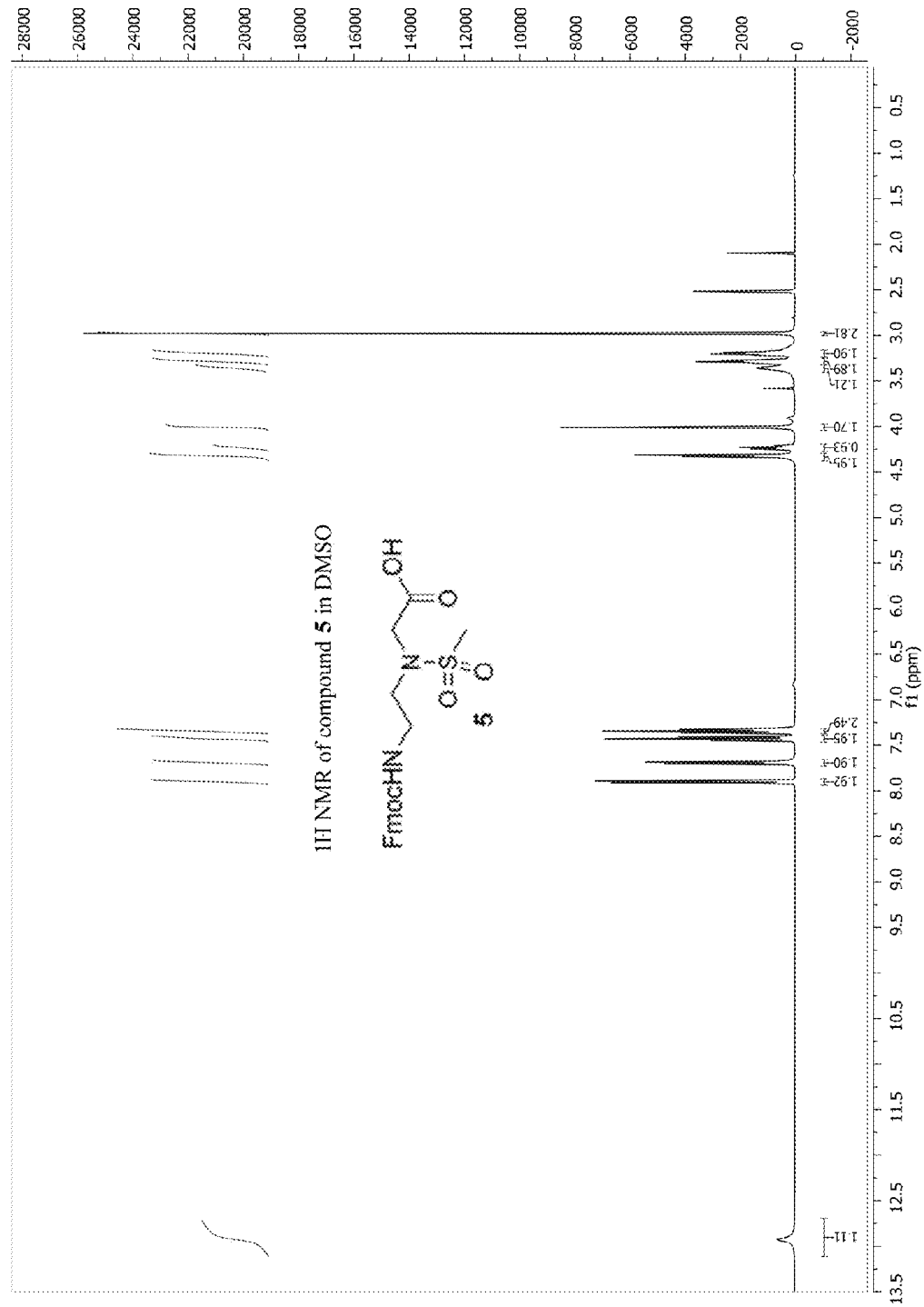
Figure 26:
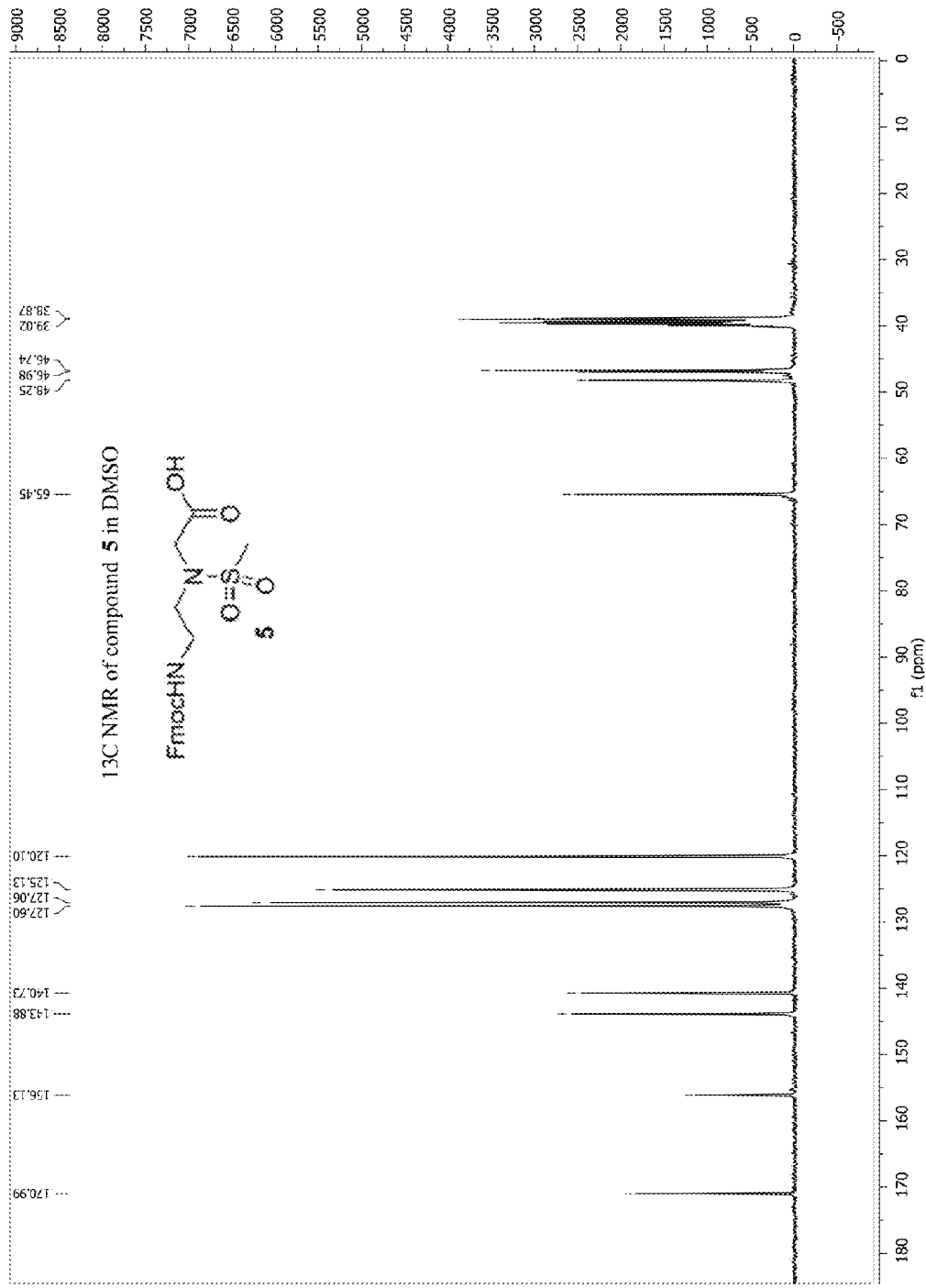
Figure 27:
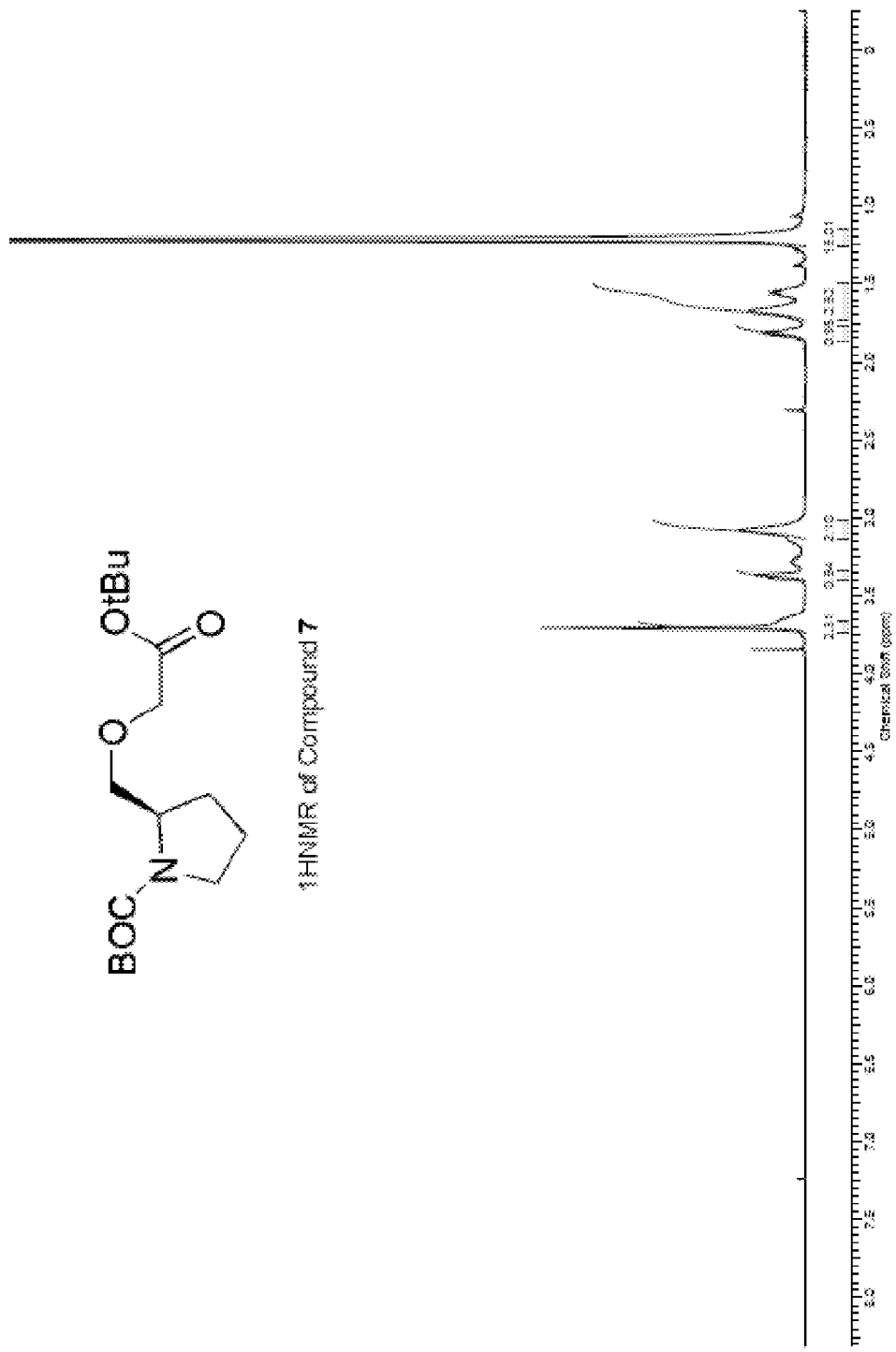
Figure 28:
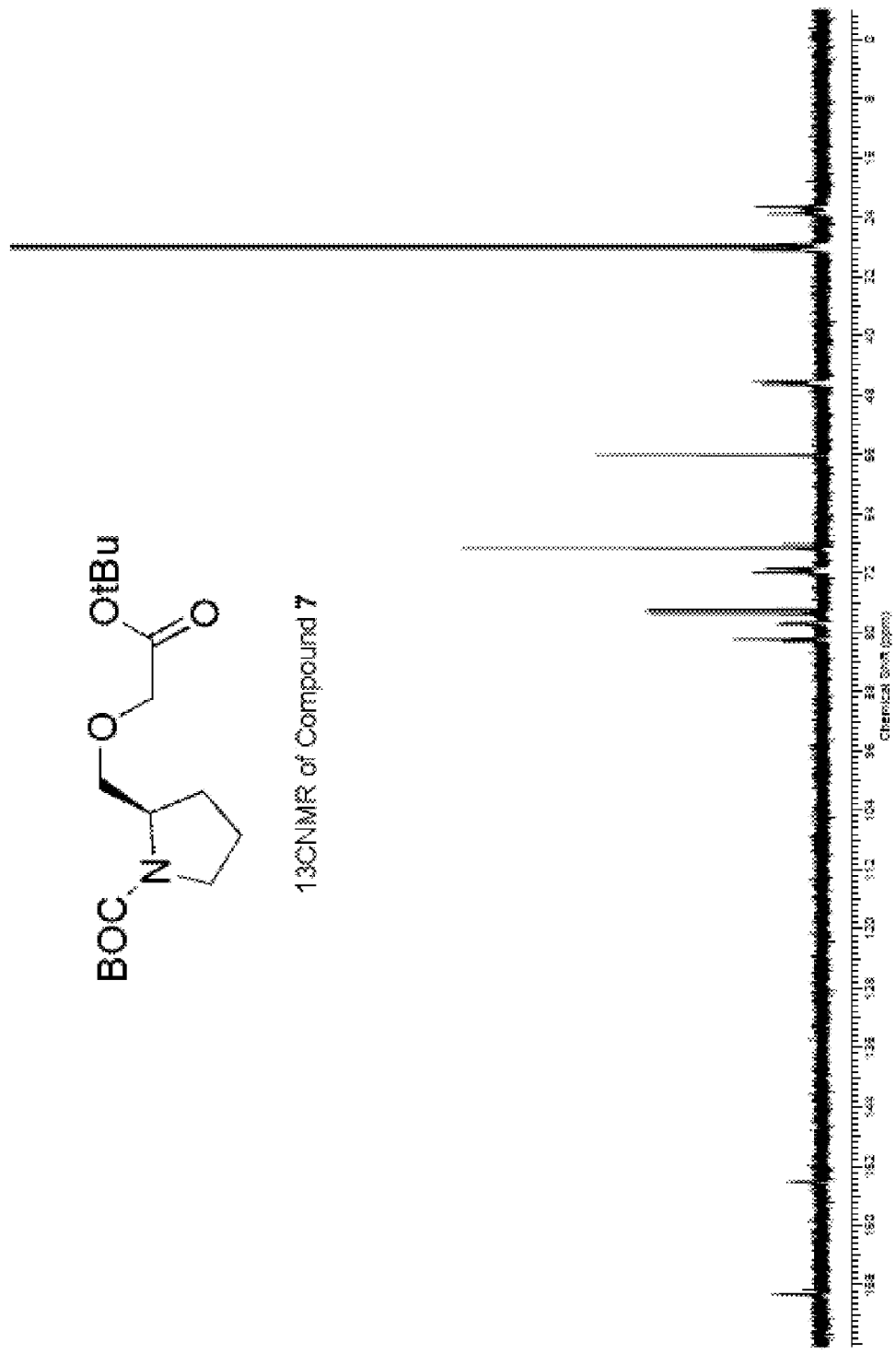
Figure 29:
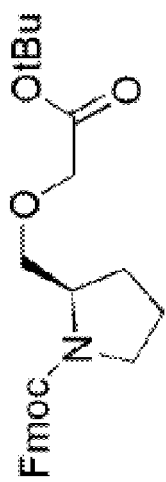
Figure 29:
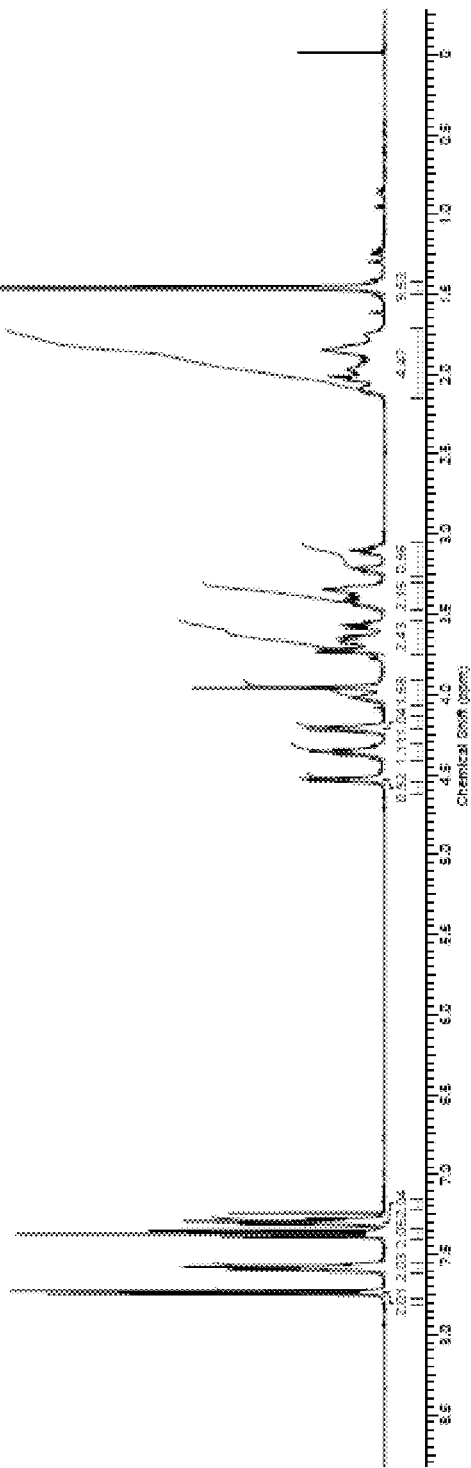
Figure 30:
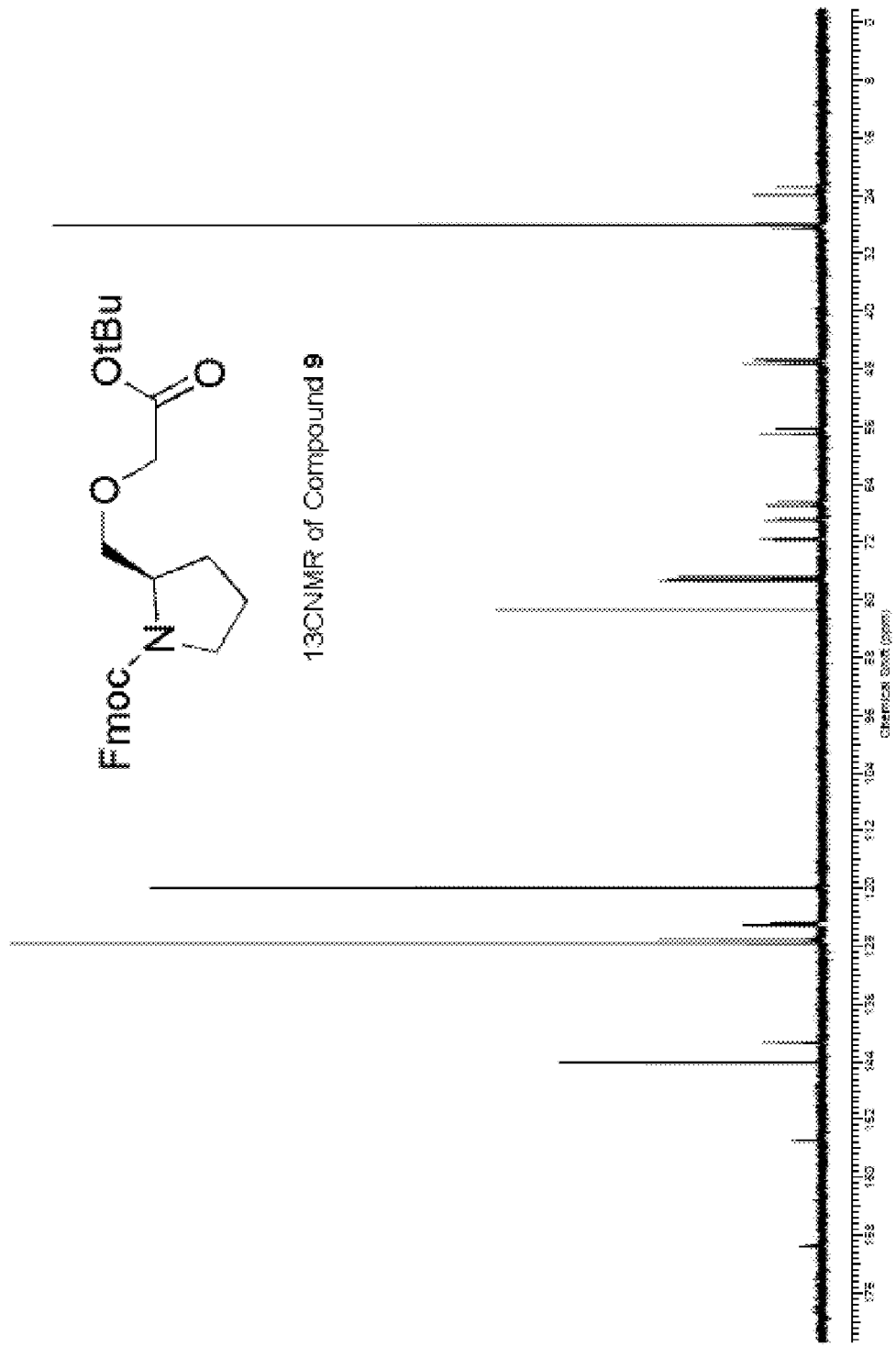
Figure 31:
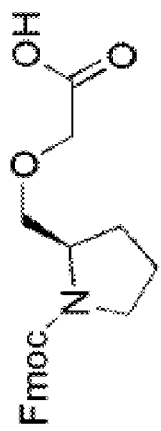
Figure 31:
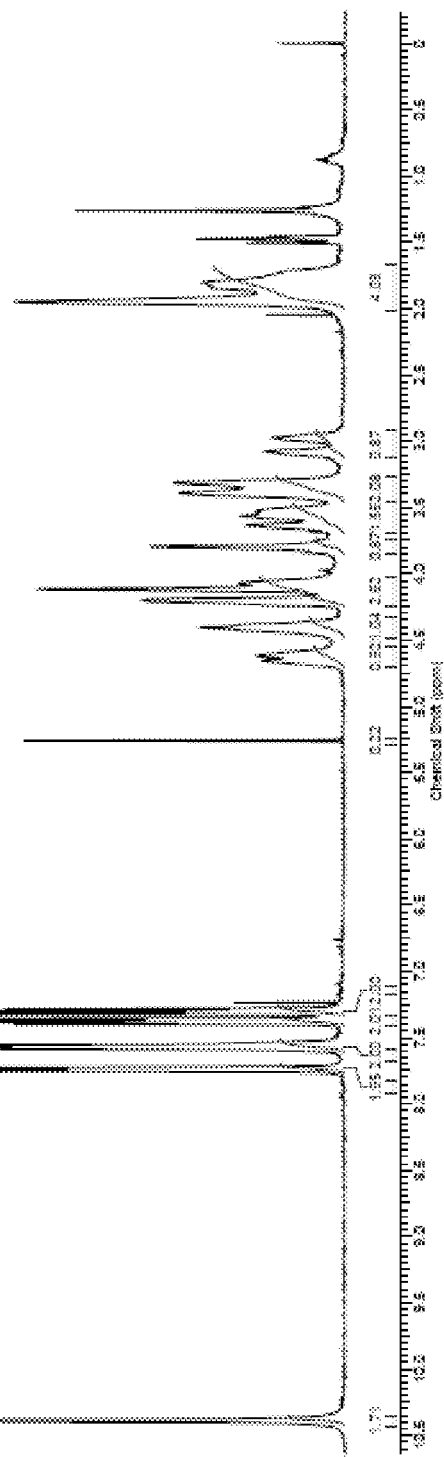
Figure 32:
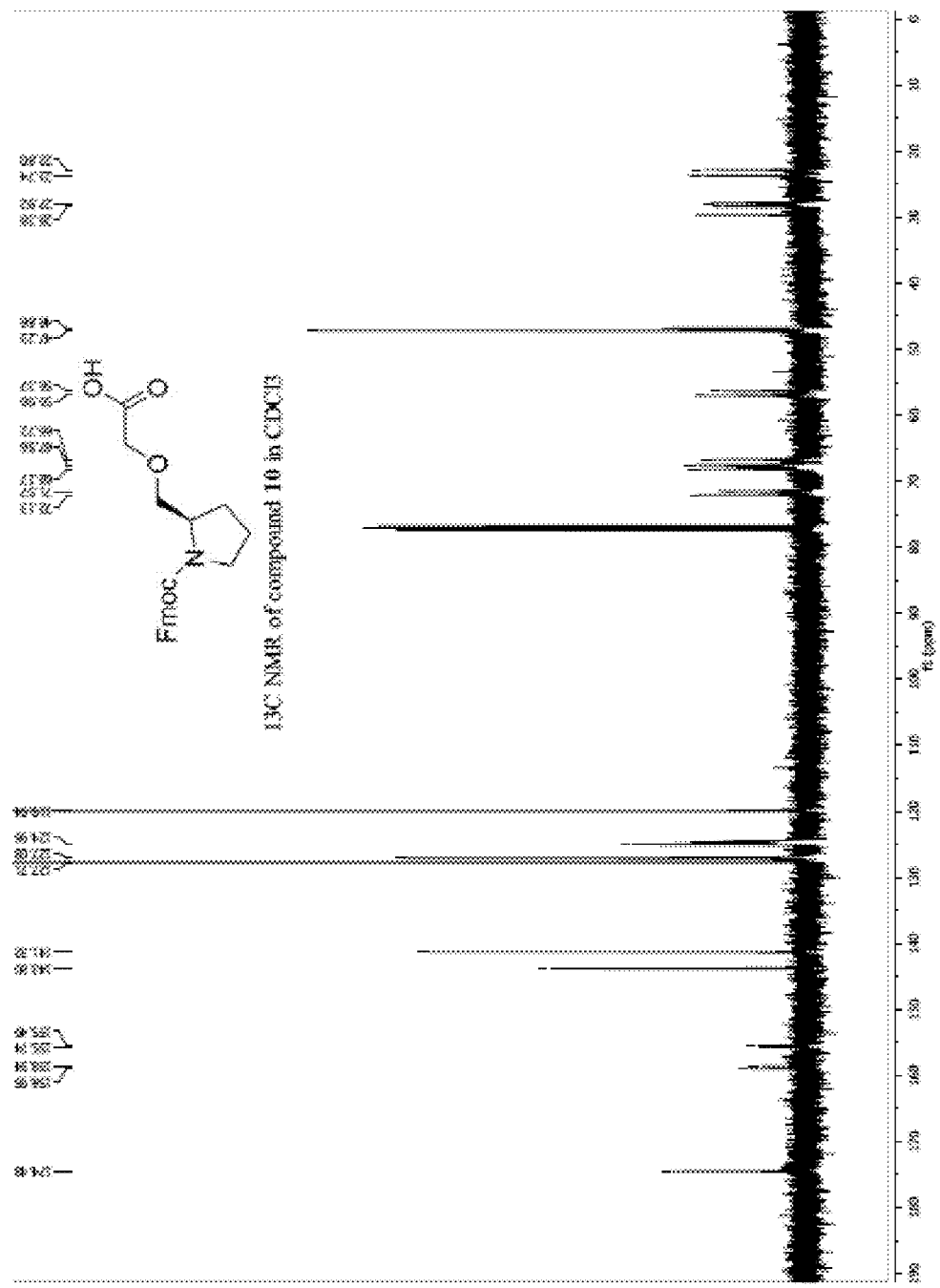
Figure 33A:
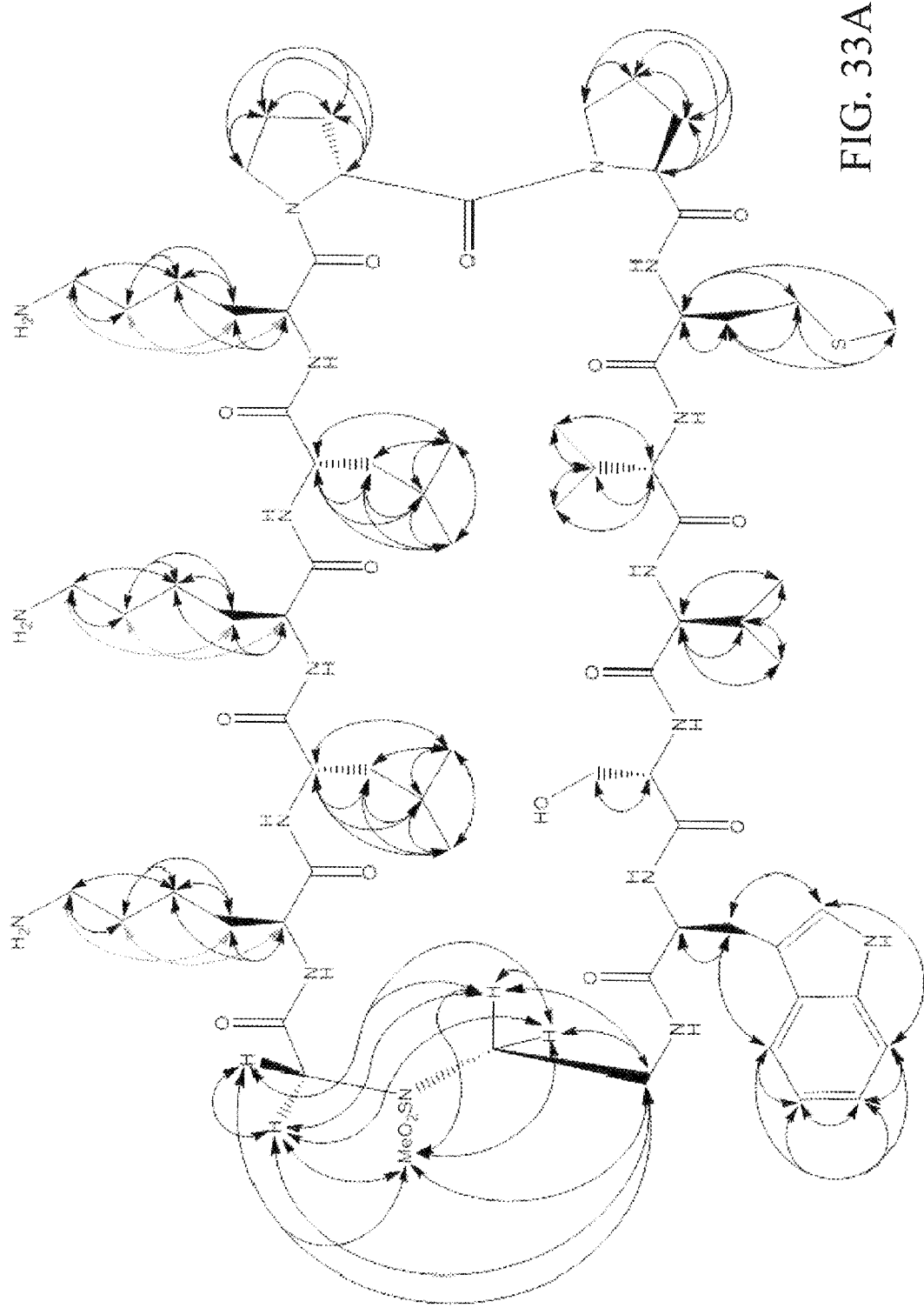
FIGS. 33A-33C show peptides structural characterization via NOE Peptide 1 NOEs.
Figure 33B:
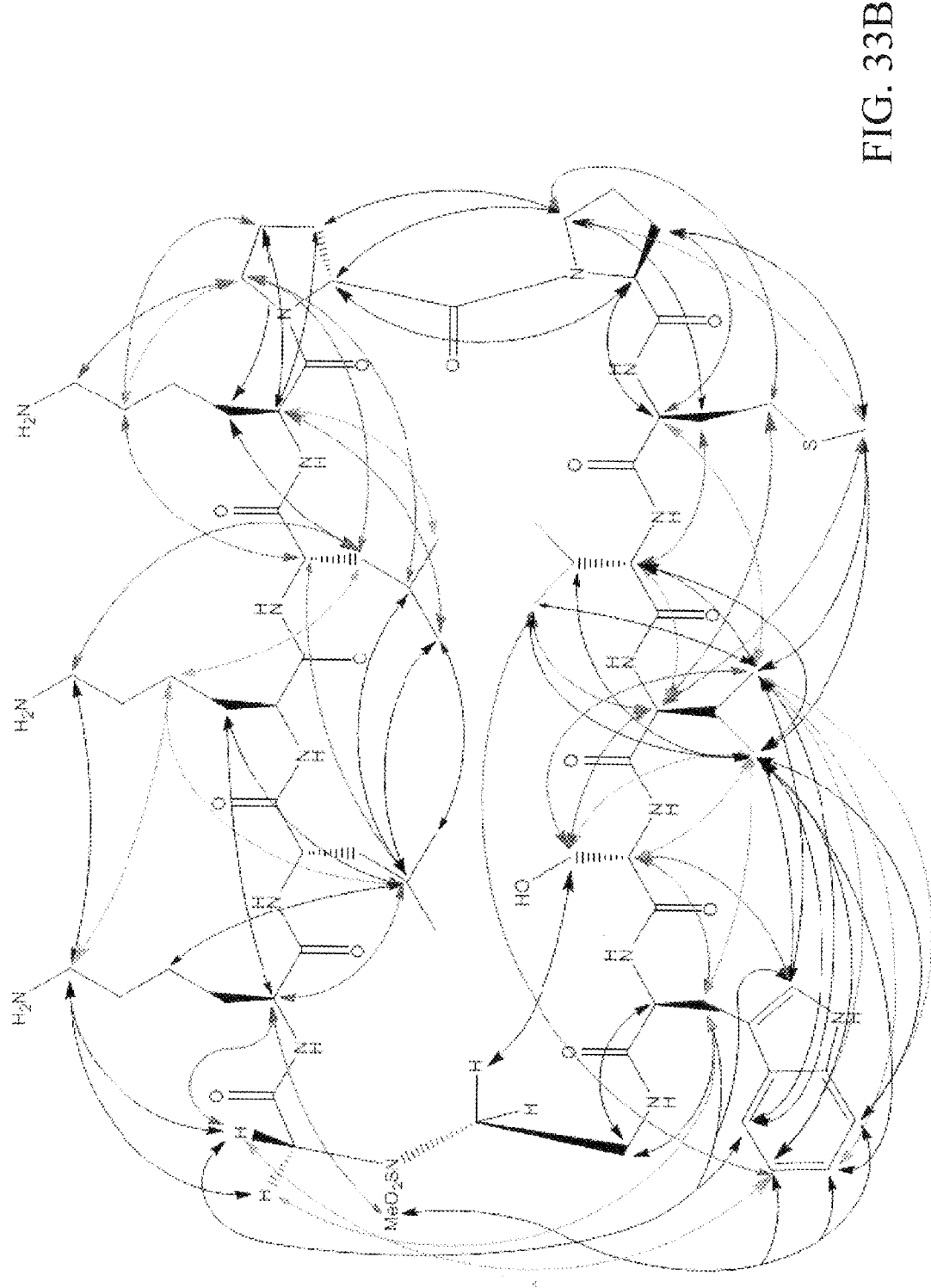
Figure 33C:
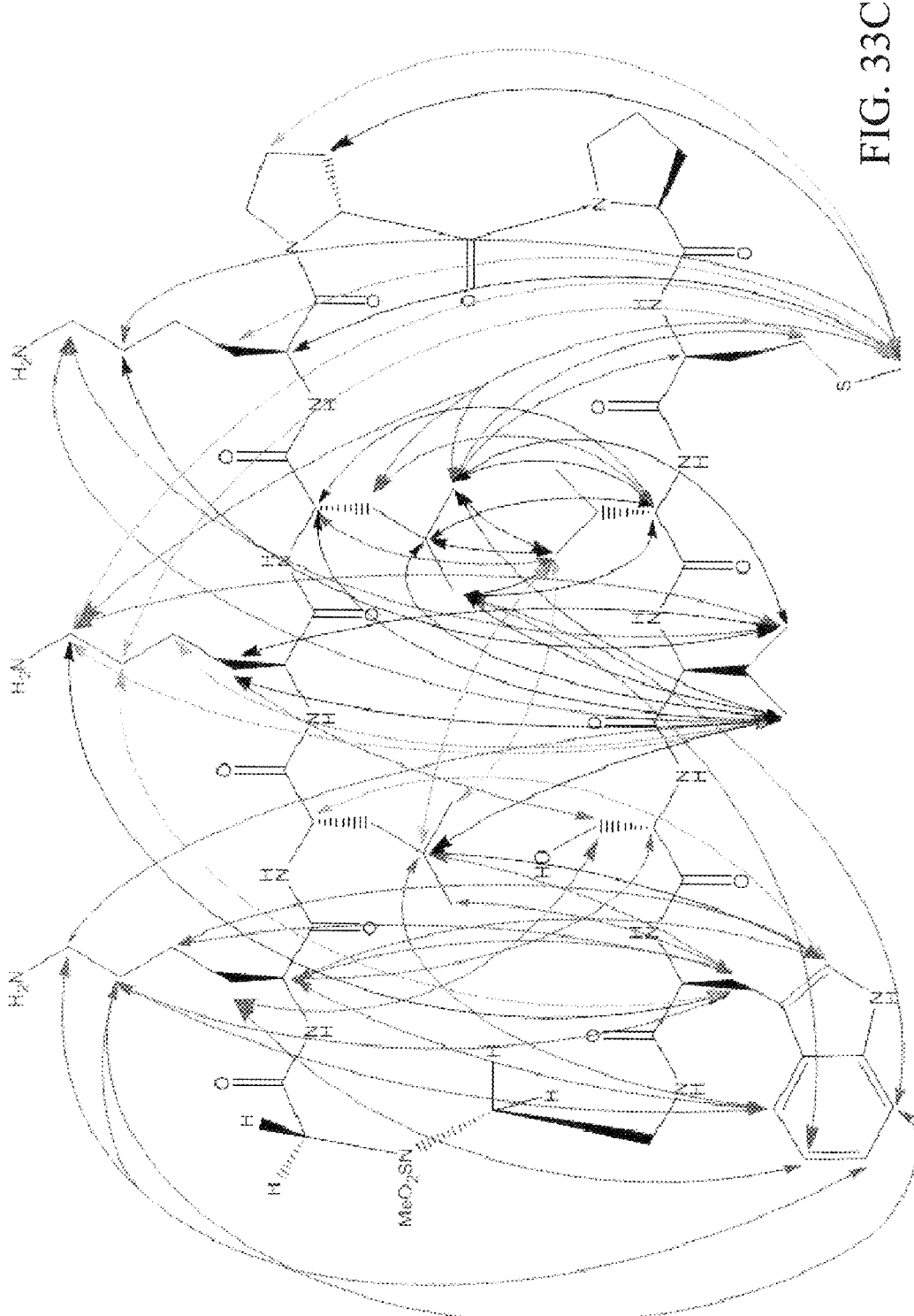
Figure 34A:
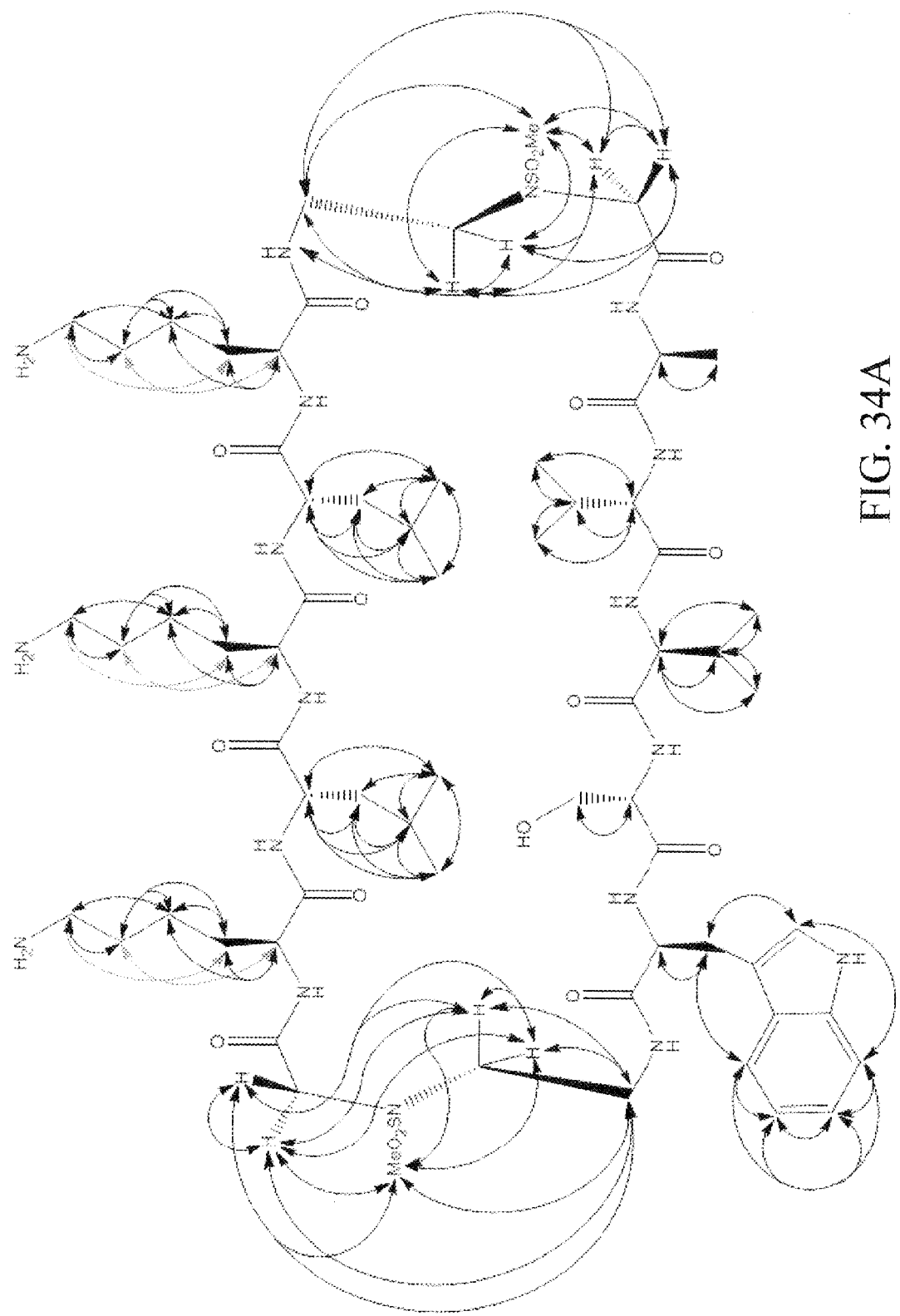
FIGS. 34A-34C show peptide 7 NOEs.
Figure 34B:
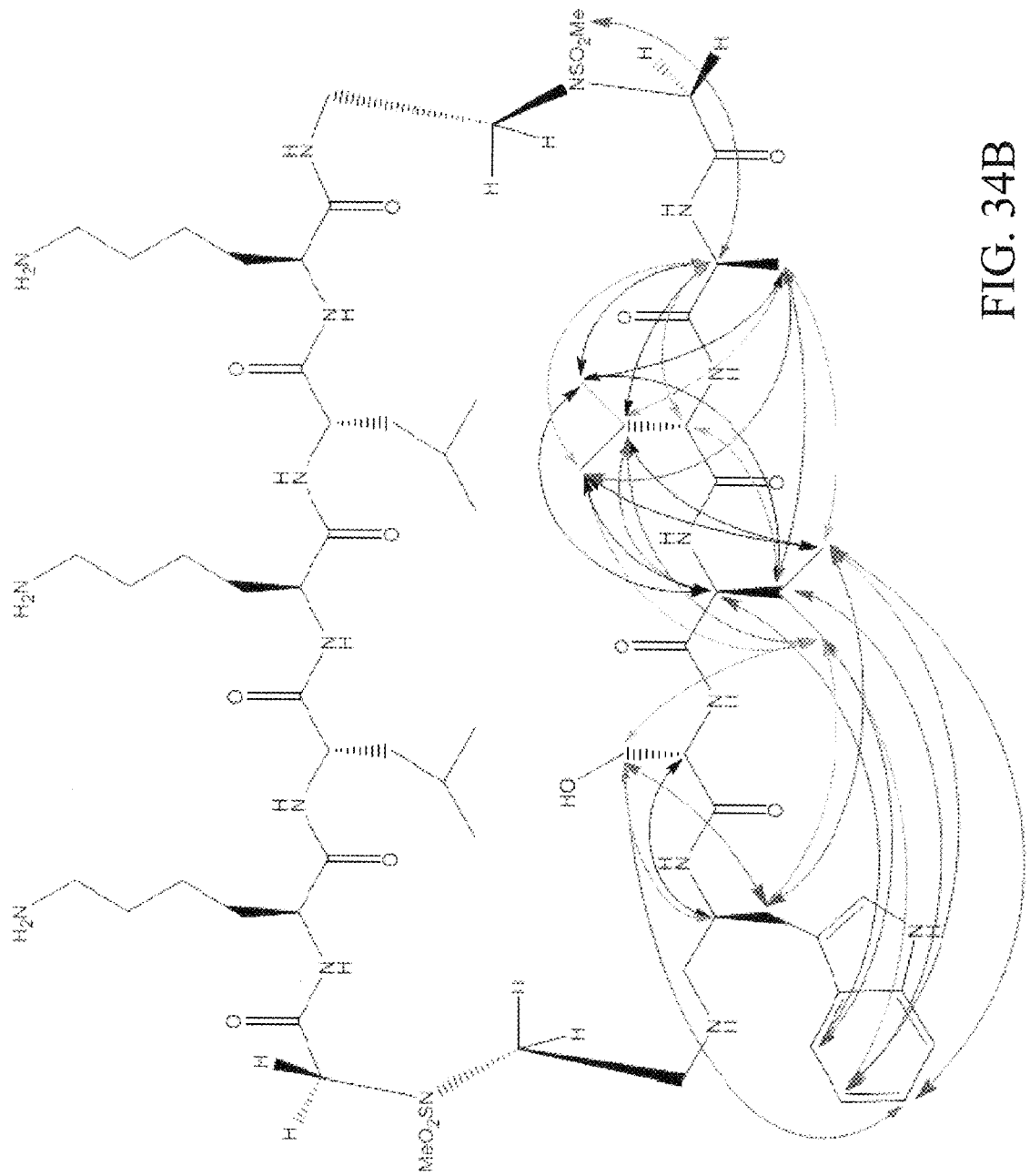
Figure 34C:
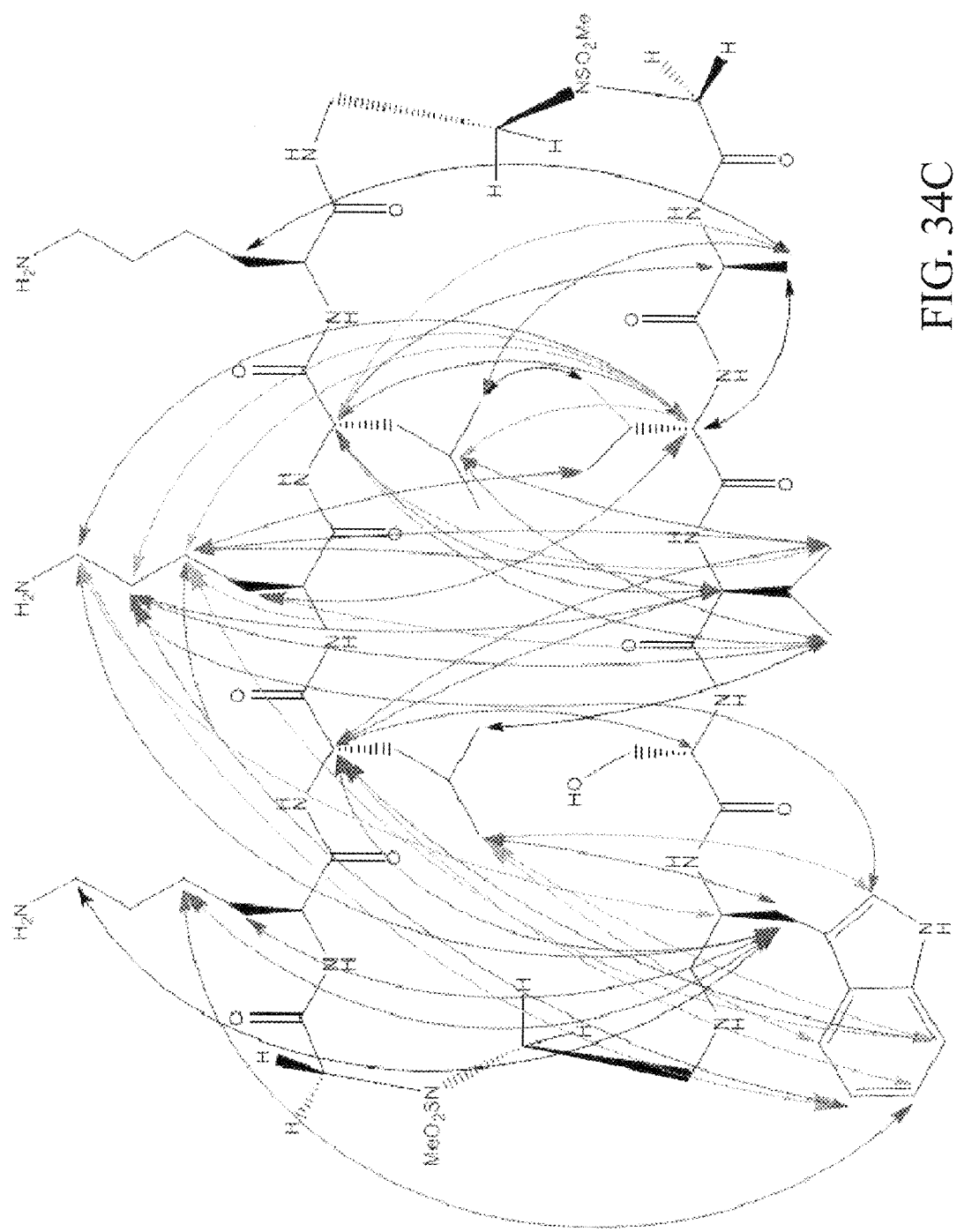
Figure 35A:
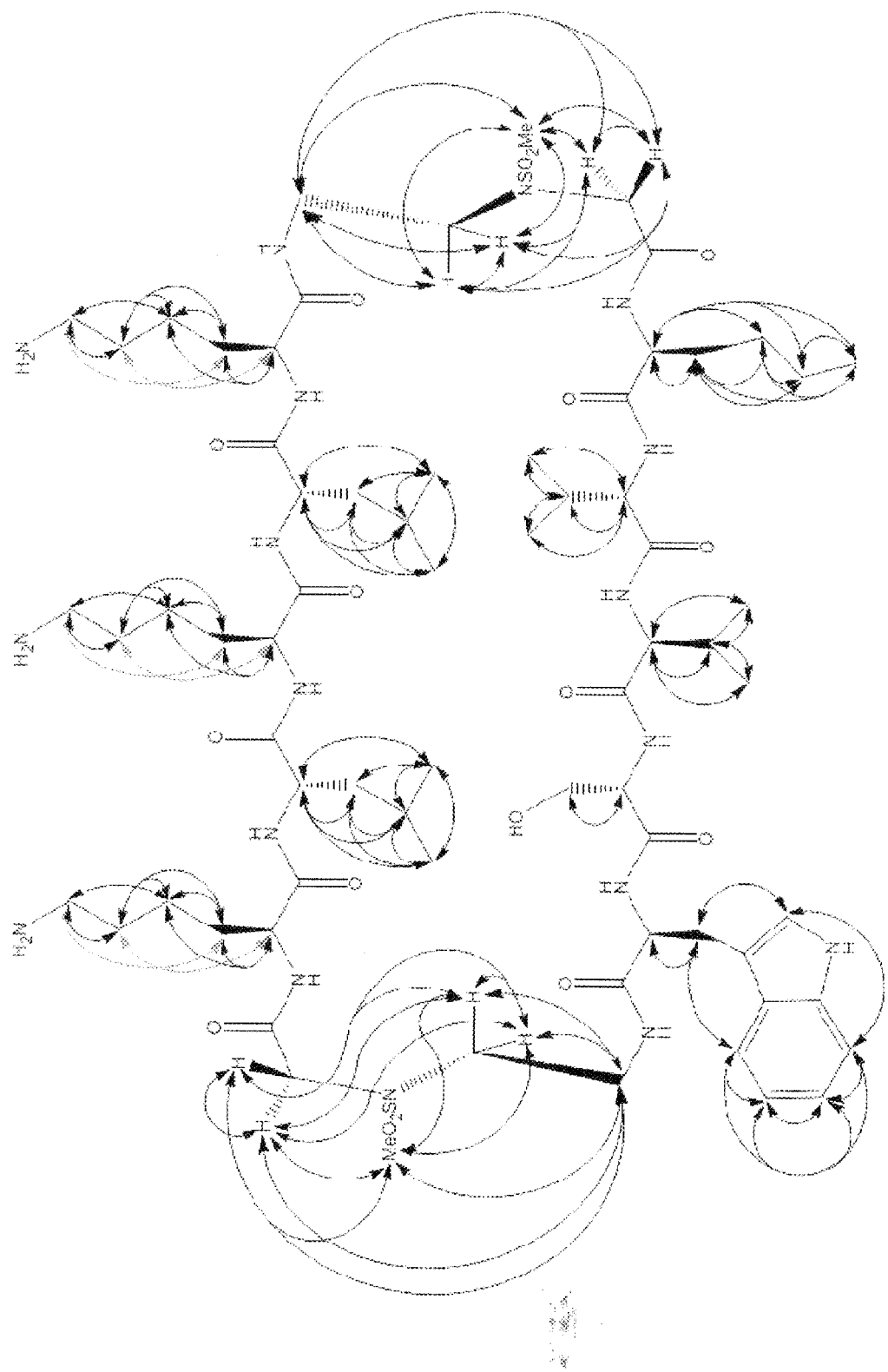
FIGS. 35A-35C show peptide 8 NOEs.
Figure 35B:
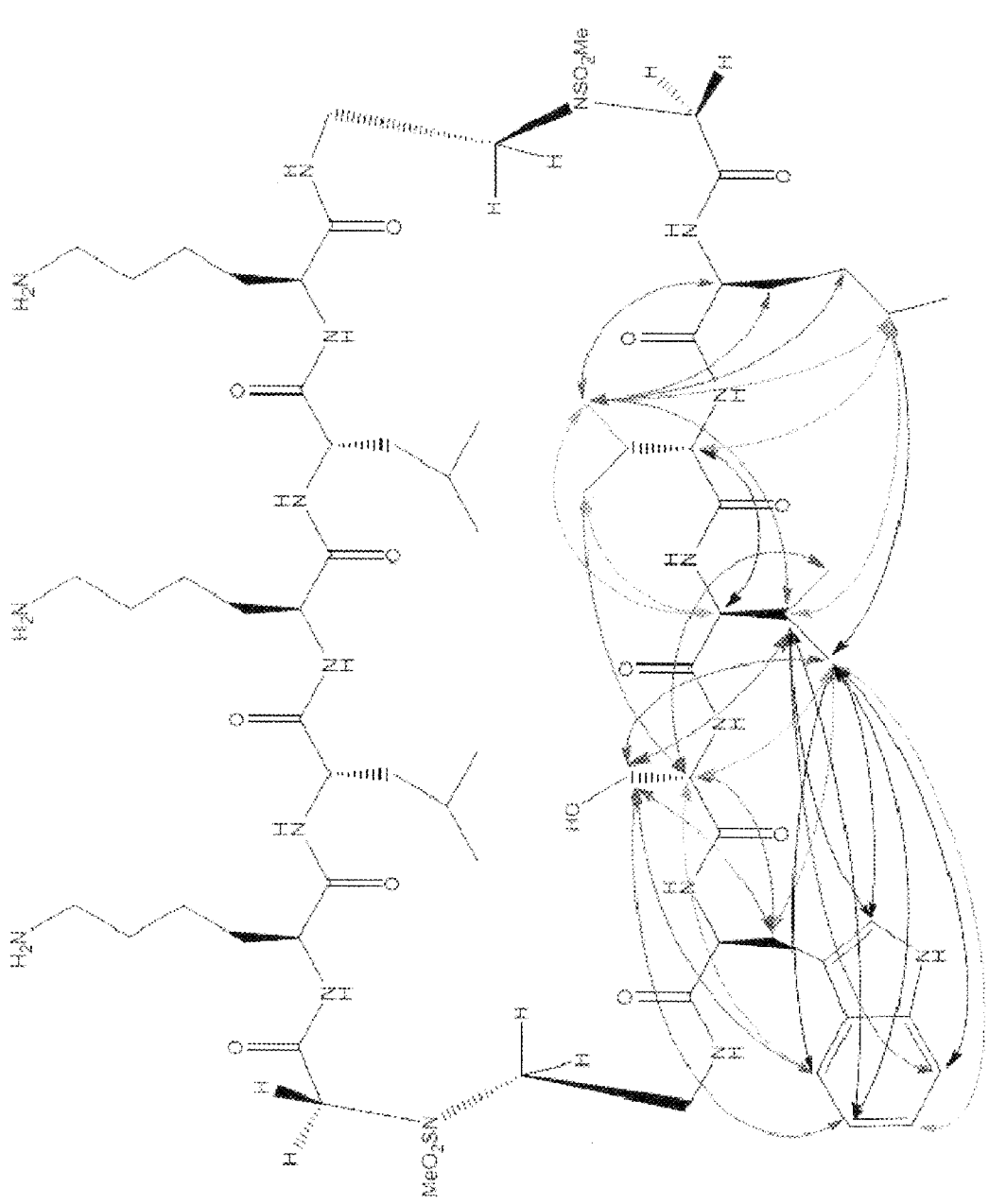
Figure 35C:
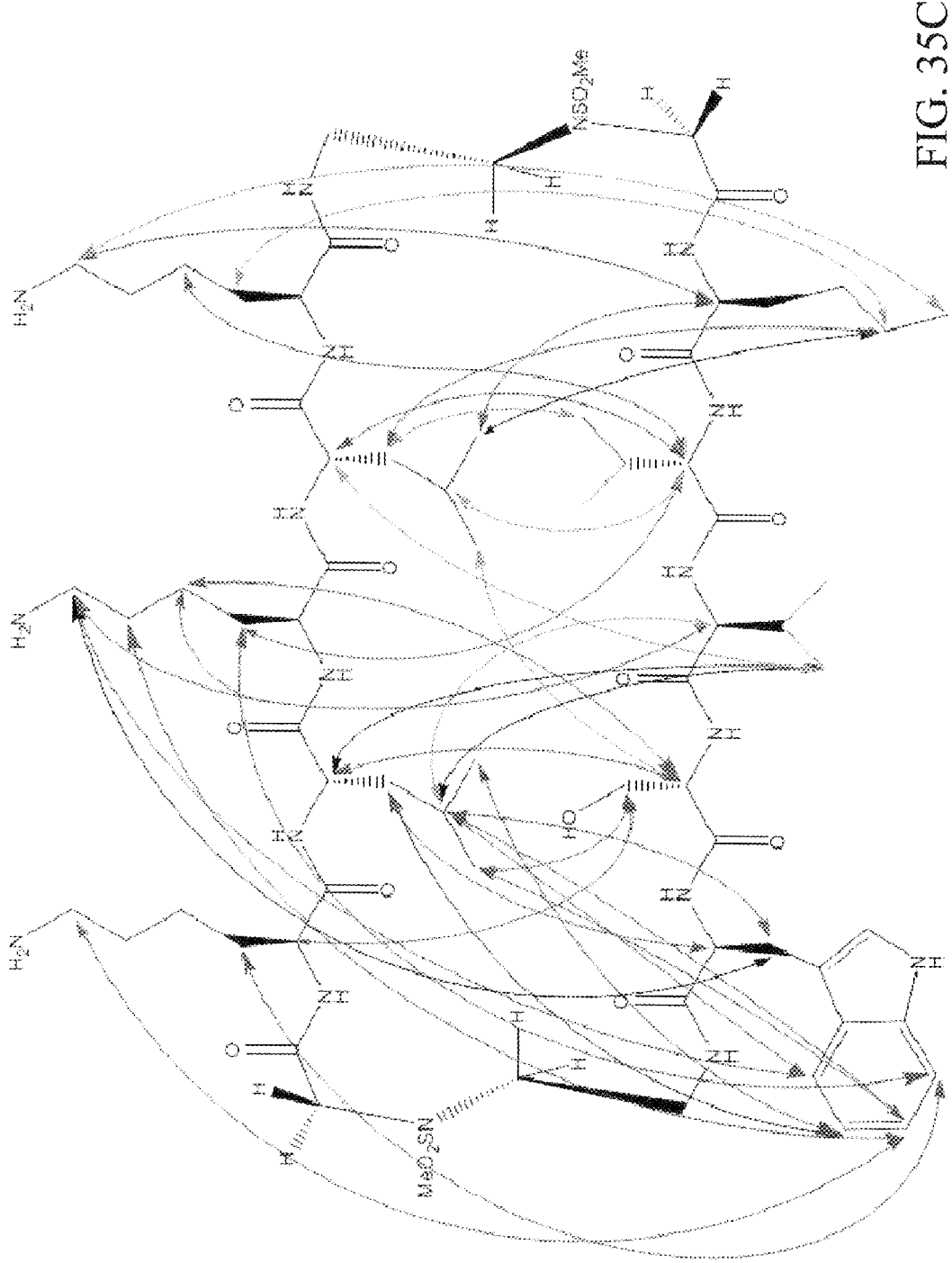
Figure 36A:
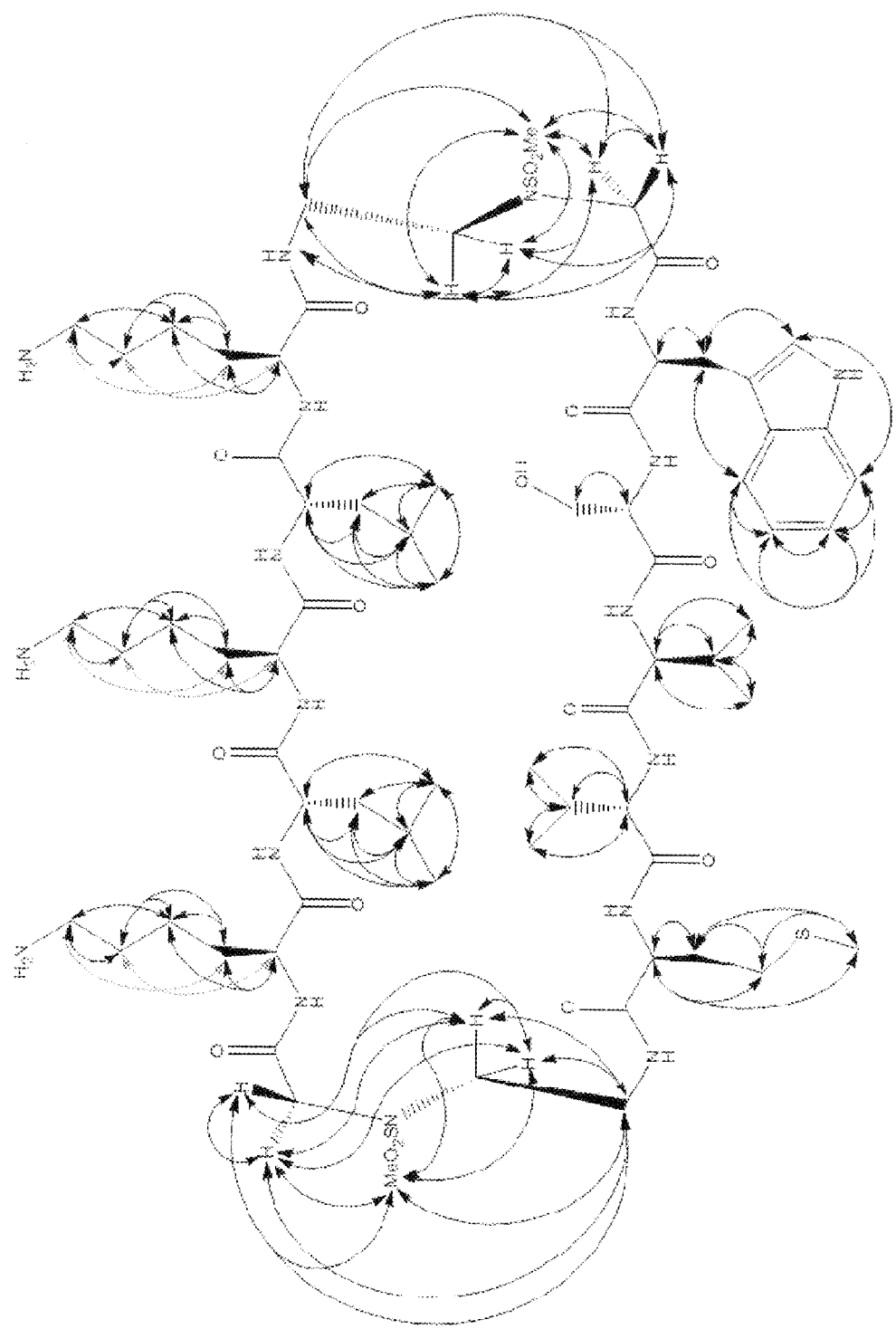
FIGS. 36A-36C show peptide 10 NOEs.
Figure 36B:
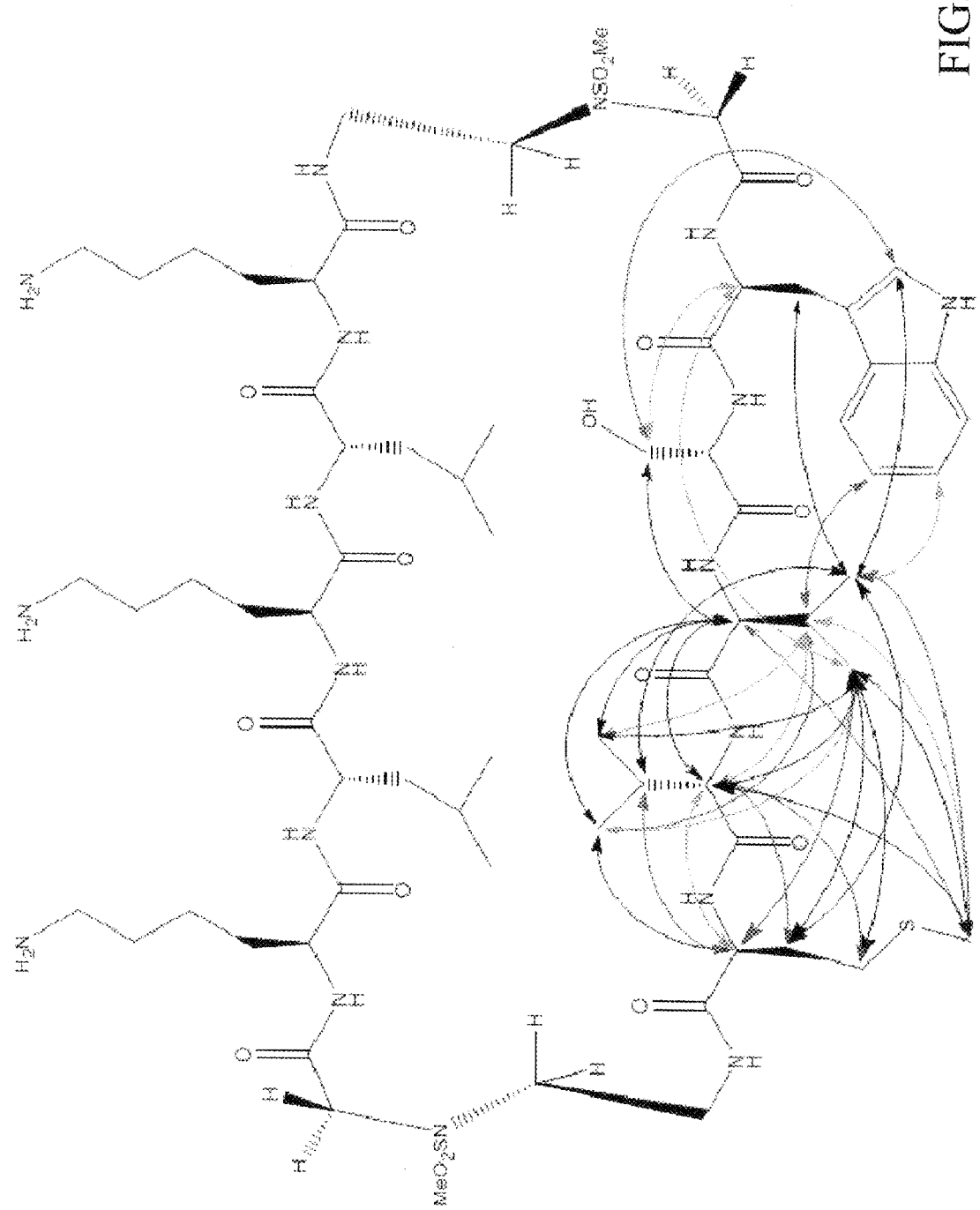
Figure 36C:
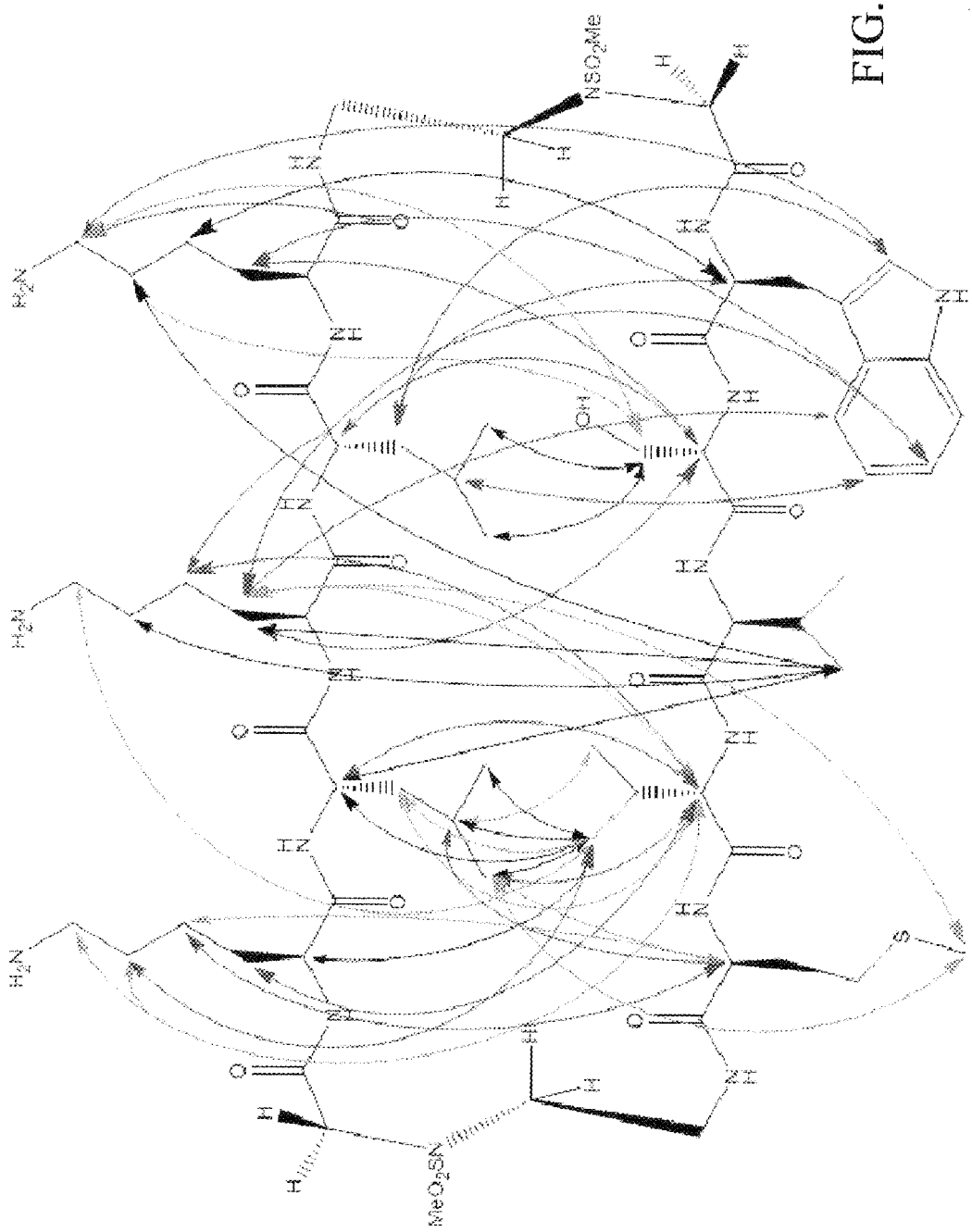
Figure 37A:
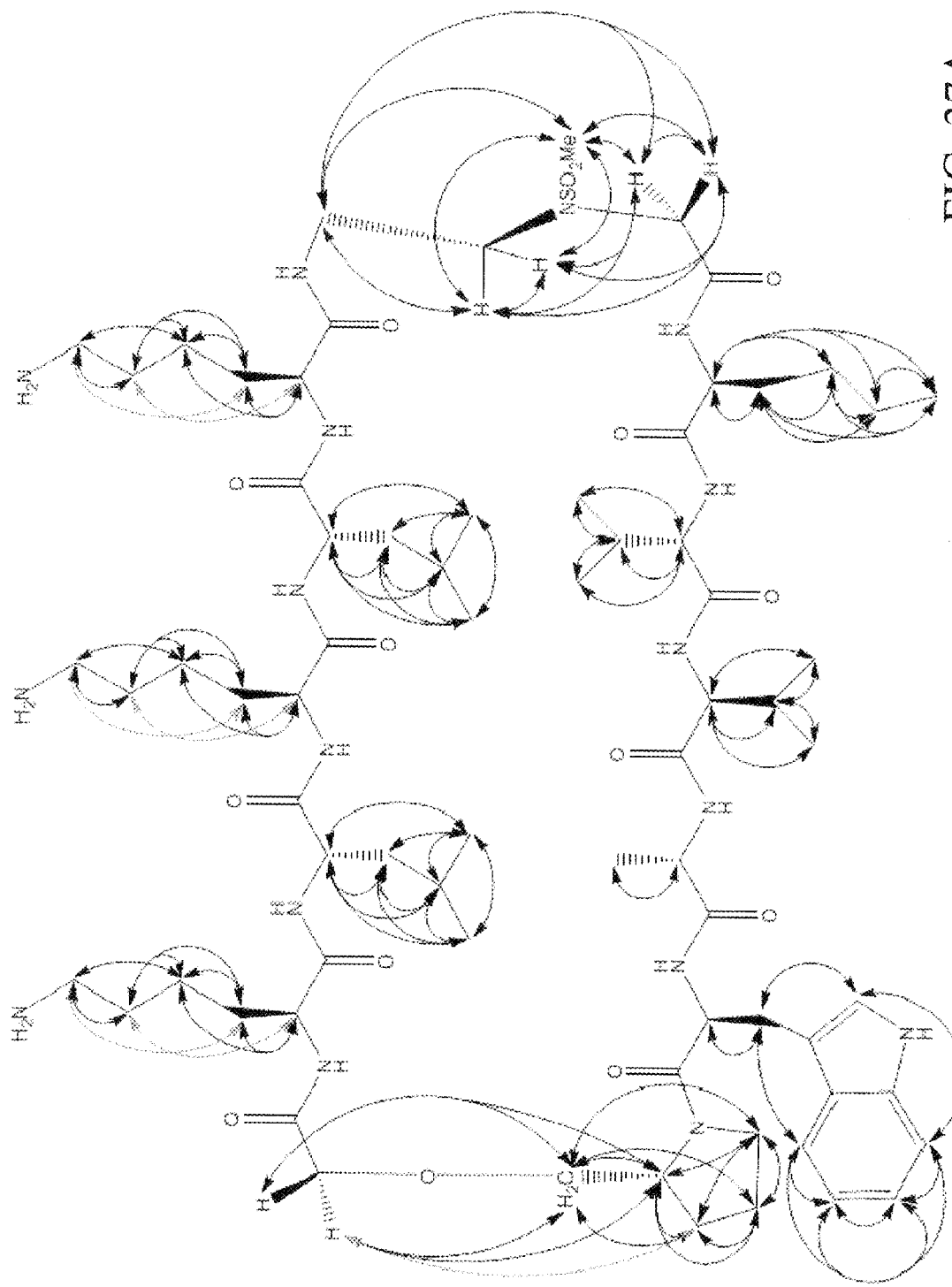
FIGS. 37A-37C show peptide 16 NOEs.
Figure 37B:
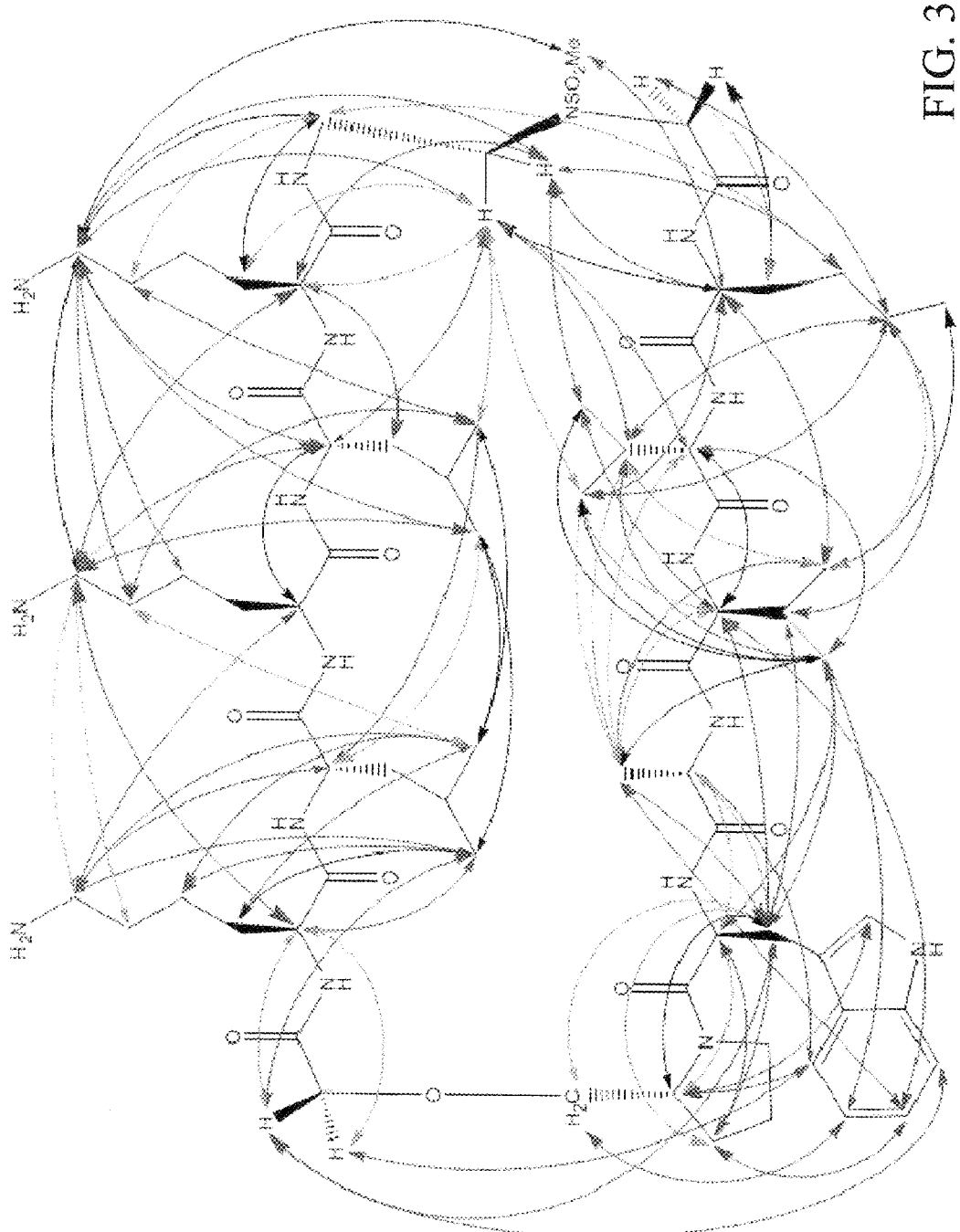
Figure 37C:
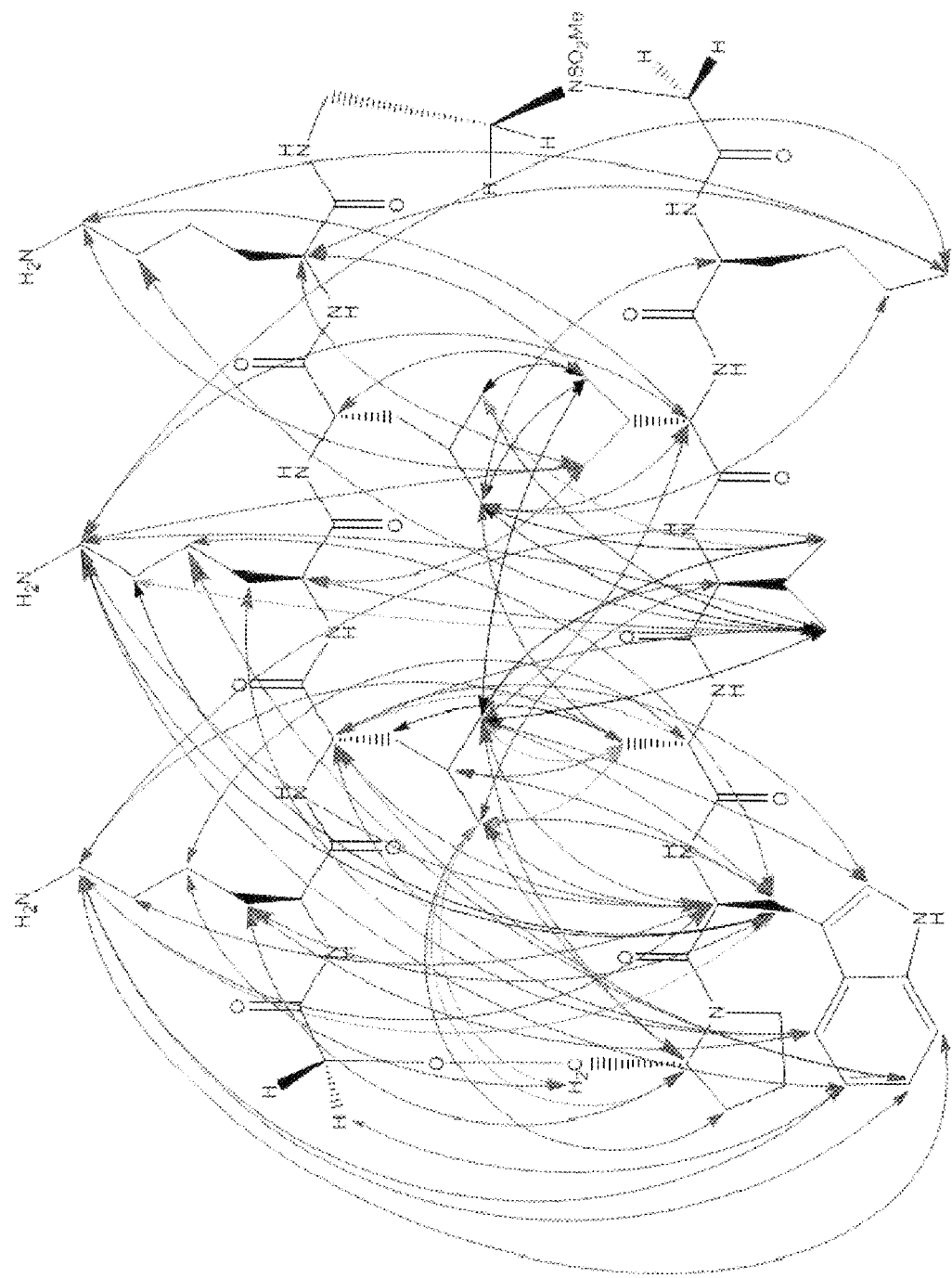

1-2-((1-(((9H-fluoren-9-yl)methoxy)carbonyl)pyrrolidin-2-yl)methoxy)aceticacid 10 (FIG. 20H). Compound 9 (0.6 gm, 1.3 mmol) was dissolved in 10 mL DCM and 10 mL trifluoroacetic acid was added to it. The reaction contents were stirred until the starting material was completely consumed to give compound 10 in quantitative yield. $^1$H NMR (CDCl$_3$, 400 MHz): δ 10.390 (s, 1H), 7.74 (d, J=8 Hz, 2H), 7.57 (d, J=8 Hz 2H), 7.38 (t, J=8 Hz, 2H), 7.30 (t, J=8 Hz, 2H), 4.64 (d, J=16 Hz, 1H), 4.41 (m, 1H), 4.24-4.01 (m, 3H), 3.80 (s, 1H), 3.60 (m, 1H), 3.36 (d, J=28 Hz, 2H), 3.05 (d, J=44 Hz, 1H), 1.95-1.75 (m, 4H). $^{13}$C NMR (CDCl$_3$, 100 MHz): δ 174.5 (1C), 155.5 (1C), 143.8 (2C), 141.3 (2C), 127.7 (2C), 127.1 (2C), 124.8 (2C), 119.9 (2C), 71.8 (1C), 68.0 (1C), 67.2 (1C), 56.6 (1C), 47.2 (1C), 46.8 (1C), 28.1 (1C), 23.3 (1C). HRMS m/z (ESI): calcd. for C$_{22}$H$_{24}$NO$_5$ [M+H]$^+$ 382.1649, found 382.1672.

All patents, patent applications, provisional applications, and publications referred to or cited herein, supra or infra, are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Figure 3A:
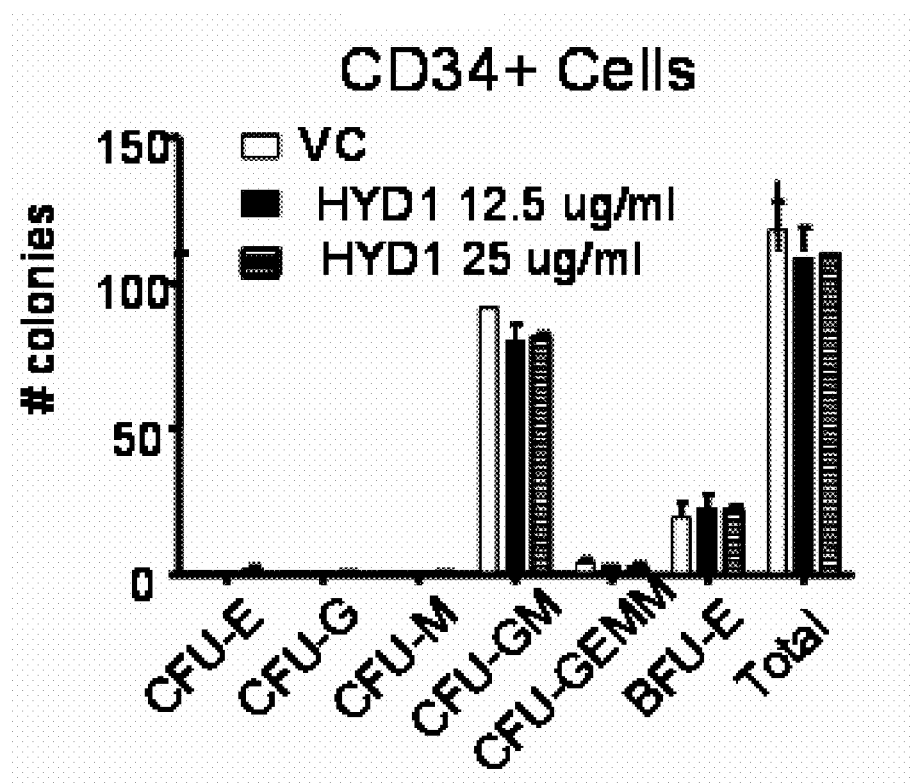
FIG. 3(A) is a graph showing HYD1 is more potent in MM cells (H929) compared to normal hematopoietic cells. CD34 positive cells were isolated from the peripheral blood of a normal donor. HYD1 treatment did not inhibit differentiation or colony formation of CD34 positive cells.
Figure 3B:
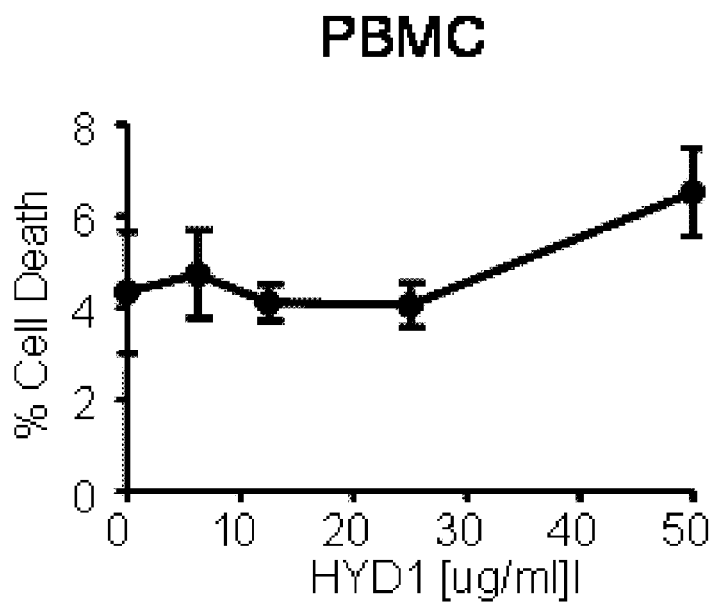
FIG. 3(B) is a graph showing HYD1 is more potent in MM cells (H929) compared to normal hematopoietic cells. Peripheral blood mononuclear cells (PBMC) were isolated from a normal donor. Cells were treated with 6.25, 12.5, 25 and 50 ug/ml for six hours and cell death was measured by annexin V positivity and FACS analysis.
Figure 3C:
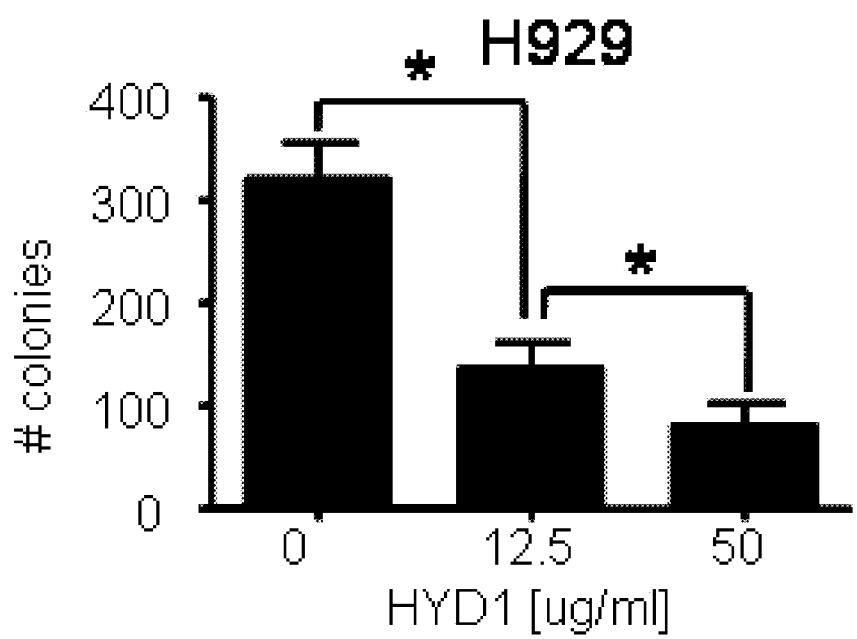
FIG. 3(C) is a graph showing HYD1 is more potent in MM cells (H929) compared to normal hematopoietic cells. H929 cells are more sensitive to HYD1 induced inhibition of colony growth compared to normal CD34 positive cells. Similar to H929 cells, U226, 8226 and MM1S myeloma cells were all sensitive to HYD1 induced cell death.
Figure 6:
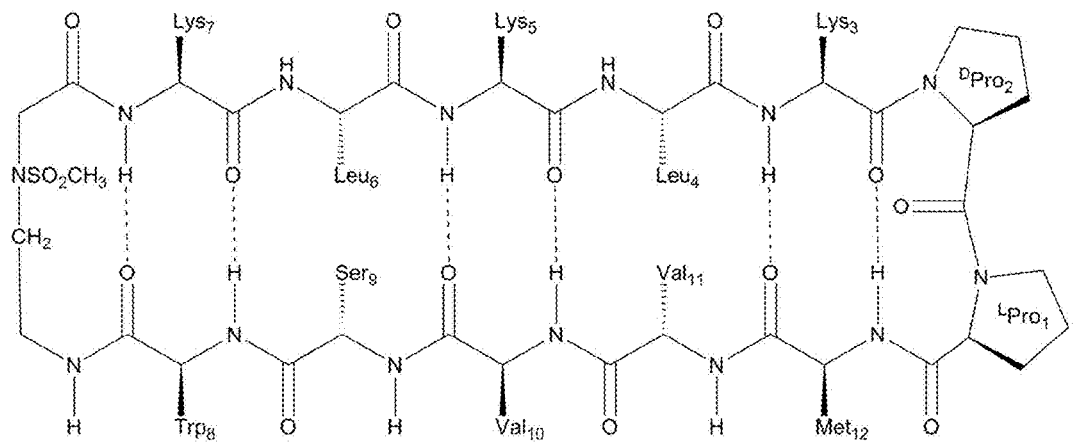
FIG. 6 is a diagram of the general cyclic III peptide for Table 5 (SEQ ID NOs:10, 270, 271, 272, 273, 274, 275, 1, 276, and 277).

Integrin Interaction Inhibitor Activity in Normal Hematopoietic Progenitor Cells and In Vivo Activity A colony forming assay was used to compare integrin interaction inhibitors induced cell death in normal hematopoietic cells and MM cells. CD34$^+$ hematopoietic progenitor cells were isolated from peripheral blood and treated for 2 hrs with integrin interaction inhibitors (12.5 and 50 µg/ml) and then plated in a methylcellulose media supplemented with growth factors supporting myeloid and erythroid colonies. Colonies were counted on day 12 post-plating. As shown in FIG. 3A, integrin interaction inhibitors did not inhibit colony formation of normal CD34$^+$ cells. In addition, we evaluated the toxicity of integrin interaction inhibitors in normal peripheral blood mononuclear cells (PBMC). As shown in FIG. 3B, 6 hours treatment with increasing concentration of integrin interaction inhibitors did not induce cell death up to doses of 50 µg/ml in PBMC. Finally as shown in FIG. 3C, and consistent with other endpoints of cell death, integrin interaction inhibitors did inhibit colony formation of H929 cells at doses ranging from 12.5-50 µg/ml integrin interaction inhibitors. The data indicate that integrin interaction inhibitors targets MM cells preferentially when compared to normal hematopoietic cells. Further, recent reports using the SCID-Hu multiple myeloma in vivo model show that integrin interaction inhibitor-treated mice demonstrated significant reduction in tumor burden compared to control mice (P<0.05, repeated measures test).

Recent studies demonstrated that integrin interaction inhibitor-induced cell death was necrotic in nature as shown by: (a) decrease in mitochondrial membrane potential ($\Delta_{\psi m}$); (b) loss of total cellular ATP, and; (c) increase in reactive oxygen species (ROS) production. Moreover, integrin interaction inhibitor treatment does not result in apoptotic cell death as it did not trigger the activation of caspases or the release of apoptosis-inducing factor (AIF) and Endonuclease G (Endo G) from the mitochondria, nor did it induce double stranded DNA breaks. Integrin interaction inhibitors did initiate autophagy in cells; however, autophagy was found to be an adaptive response contributing to cell survival rather than the cause of cell death. It was further shows that N-acetyl-L-cysteine (NAC), a thiol containing free radical scavenger, partially protects MM cells from integrin interaction inhibitor-induced death.

Figure 4:
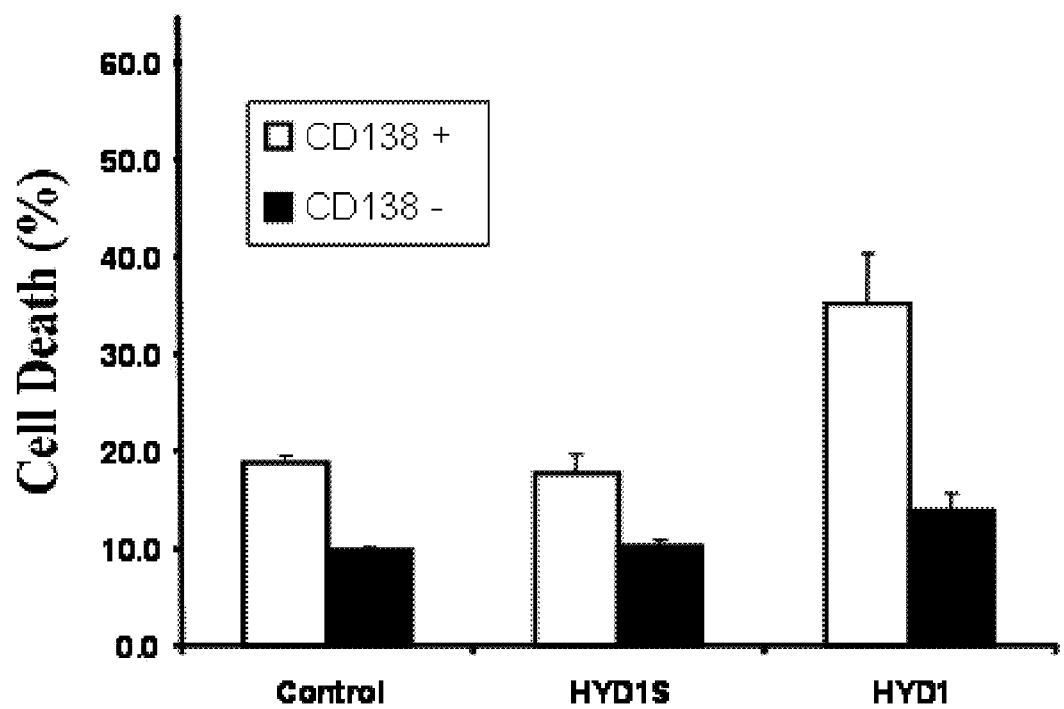
FIG. 4 is a graph showing HYD1 but not the scrambled control peptide (HYD1S) induces preferential cell death in MM cells. CD138 positive (myeloma) and negative cells were collected, isolated from a BM aspirate, and treated with 50 μg/ml for 24 h; 24 hours after drug treatment, cell death was determined by Annexin V/PI staining and FACS analysis.

As shown in FIG. 4, integrin interaction inhibitors induce cell death in primary myeloma patient specimens. Furthermore, integrin interaction inhibitors showed increased potency in the 138 myeloma population compared to the CD138 negative presumably normal hematopoietic cells obtained from the bone marrow aspirate.

N- and C-terminus truncation studies have been performed, which identified MVISW (SEQ ID NO:279) as the likely core region of the integrin interaction inhibitor required for biological activity. Using this information and the finding that V for I replacement gave a more active integrin interaction inhibitor analog, a cyclized version of the integrin interaction inhibitor was developed that is designed to display the core sequence (MVVSW) (SEQ ID NO:33) in an extended or beta-sheet-like conformation. Side chain-side chain or N- to C-terminus cyclization of linear peptides to constrain the number of conformations available to the linear peptide is a well-known strategy that increases the affinity of the cyclized peptide for its target when the constraint stabilizes the bound conformation of the peptide, but the cyclic beta-hairpin further constrains the recognition portion of the cyclic peptide specifically into a extended or beta-sheet-like conformation.

TABLE 4

Structure activity relationship in H929 myeloma cells of cyclic integrin interaction inhibitor derivatives.

| SEQ ID NO. | peptide | R1 | R2 | R3 | R4 | R5 | T1 | R6 | R7 | R8 | R9 | R10 | T2 | IC50 |
|---|---|---|---|---|---|---|---|---|---|---|---|---|---|---|
| | INTEGRIN INTERACTION INHIBITORS | | | | | | | | | | | | | 31.8 μM |
| 10 | L-cINTEGRIN INTERACTION INHIBITORS | K | L | K | L | K | X | W | S | V | V | M | X | 13.9 μM |
| 270 | L-cINTEGRIN INTERACTION INHIBITORSa6 | K | L | K | L | K | X | A | S | V | V | M | X | 55.0 μM |
| 271 | L-cINTEGRIN INTERACTION INHIBITORSa7 | K | L | K | L | K | X | W | A | V | V | M | X | 4.0 μM |
| 272 | L-cINTEGRIN INTERACTION INHIBITORSa8 | K | L | K | L | K | X | W | S | A | V | M | X | 11.0 μM |
| 273 | L-cINTEGRIN INTERACTION INHIBITORSa9 | K | L | K | L | K | X | W | S | V | A | M | X | 5.6 μM |
| 274 | L-cINTEGRIN INTERACTION INHIBITORSa10 | K | L | K | L | K | X | W | S | V | V | A | X | 8.9 μM |
| 275 | L-cINTEGRIN INTERACTION INHIBITORSn10 | K | L | K | L | K | X | W | S | V | V | NL | X | 2.7 μM |
| 1 | rL-cINTEGRIN INTERACTION INHIBITORS | K | L | K | L | K | X | M | V | V | S | W | X | 6.7 μM |

T1, T2 = beta-turn 1 or 2;
X = $H_3CSO_2N$;
NL = nor-Leu

Table 4 legend: Structure activity relationship in H929 myeloma cells of cyclic INTEGRIN INTERACTION INHIBITORS derivatives. The minimal bioactive core sequence of INTEGRIN INTERACTION INHIBITORS WSVVM (SEQ ID NO:85) was cyclized using 2 novel reduced amide bond beta turn promoters and KLKLK (SEQ ID NO:27) as the non-recognition sequence. H929 cells were treated with varying concentrations of the indicated peptide for 24 h. Cell viability was determined using Topro-3 staining and FACS analysis after drug treatment. $IC_{50}$ values were generated from linear regressions generated from the dose response curves (n=mean of 3 independent experiments). The cyclized analog L-cINTEGRIN INTERACTION INHIBITORS is 2.5-fold more potent than the linear peptide. The alanine scan showed that residues 6, 8, 10 (L-cINTEGRIN INTERACTION INHIBITORSa6, L-cINTEGRIN INTERACTION INHIBITORSa8, L-cINTEGRIN INTERACTION INHIBITORSa10) decrease in activity and residues 7 and 9 (L-cINTEGRIN INTERACTION INHIBITORSa7, L-cINTEGRIN INTERACTION INHIBITORSa9, L-cINTEGRIN INTERACTION INHIBITORSn10) increase in activity and the retro-inverso peptide (rL-cINTEGRIN INTERACTION INHIBITORS) increases in activity relative to the inverso peptide (L-cINTEGRIN INTERACTION INHIBITORS). Also the nor-leucine replacement of methionine (L-cINTEGRIN INTERACTION INHIBITORSn10) gave the most potent peptide to date.

EXAMPLE 2

Reducing α4 Integrin Expression Confers Resistance to Integrin Interaction Inhibitor-Induced Cell Death Currently, 11 α binding partners for β1 integrin have been identified. An integrin interaction inhibitor-resistant cell line was recently developed by chronically exposing H929 parental MM cells to increasing concentrations of integrin interaction inhibitors. The resistant phenotype correlated with reduced α4 integrin expression and ablated α4 mediated adhesion to the extracellular matrix fibronectin and VCAM1 (data not shown). The cell line was initially tested to determine whether α4 expression is required for integrin interaction inhibitor-mediated cell death. As shown in FIGS. 3A-3B, reducing α4 levels in H929 cells using shRNA partially blocked integrin interaction inhibitor-induced cell death. The fact that reducing α4 levels did not abrogate integrin interaction inhibitor-induced cell death suggests that additional αXβ1 heterodimers may also contribute to cell death.

EXAMPLE 3

Peptide Design

Using combinatorial peptide libraries and a functional binding assay, several peptides have been identified that inhibited α2β1 and α6β1 integrin mediated adhesion of prostate cancer cells to fibronectin, laminin and collagen IV.[1] They identified an all D-amino acid containing peptide referred as HYD1 (KIKMVISWKG) (SEQ ID NO:278) that blocks binding of epithelial prostate carcinoma cells to extracellular matrix components.[2,3] Hazlehurst and co-workers have truncated the N- and C-termini and alanine scan studies identified MVISW (SEQ ID NO:279) as the likely core region of linear D-HYD1 required for biological activity. Using this information and the finding that Val for Ile replacement gave a more active D-HYD1 analog, we had developed a cyclized version of D-HYD1 that was designed to display the core sequence (MVVSW) (SEQ ID NO:33) in the recognition strand and (KLKLK) (SEQ ID NO:27) as the non-recognition strand. The pentapeptide (KLKLK) (SEQ ID NO:27) was selected as the non-recognition strand to improve the solubility. N- to C-terminus cyclization of linear peptides was done to restrict the number of conformations available to the linear peptide which increases the affinity of the cyclized peptide for its target when the constraint stabilizes the bound conformation of the peptide. We synthesized cyclic D-HYD1 using a novel methylsulfonamide aminoethyl glycine linker $T_1$ that connects two anti-parallel strands. As per the cell inhibition assay TOPRO 3, the cyclic D-HYD1 peptide ($IC_{50}$=30 μM) was found to be twice as active as linear D-HYD1 against H929 cells. The inverso-(peptide 2, Table 4) and partially modified retro-inverso (PMRI) (peptide 10) pentapeptide sequences of the recognition strand of cyclic III (Integrin Interaction Inhibitors also known as cyclic L-HYD1) peptide analogs were subsequently investigated for their potential to block beta integrin mediated cell adhesion. The retro-inverso design of biologically active peptides is a well-known strategy to design all D-amino acid peptides from potentially bioactive all L-peptide sequences with increased stability[4-7]. Our retro-inverso peptide analogs have a similar placement of side chain residues as observed for cyclic D-HYD1 and hence similar or greater bioactivity was anticipated for these retro-inverso analogs. It was found that partially modified retro-inverso analogs had better bioactivity than cyclic D-HYD1 analogs whereas cyclic III peptides were twice as active as cyclic D-HYD1 (Table 7).

EXAMPLE 4

Colony Forming Assay

A colony forming assay was used to compare induced cell death in H929 multiple myeloma cells. Cells were treated with integrin interaction inhibitors, shown in FIG. 5 and Table 4, and cell death was measured following 24 hour peptide treatment by TOPRO-3 staining and FACS analysis.

An alanine scan of III showed that Tryptophan, Valine and Methionine are critical for the bioactivity of the peptide. Replacement of Methionine with Nor-leucine gave III with enhanced bioactivity. The retro-inverso analog of III has comparable bioactivity for inducing cell death.

TABLE 5

Figure 5:
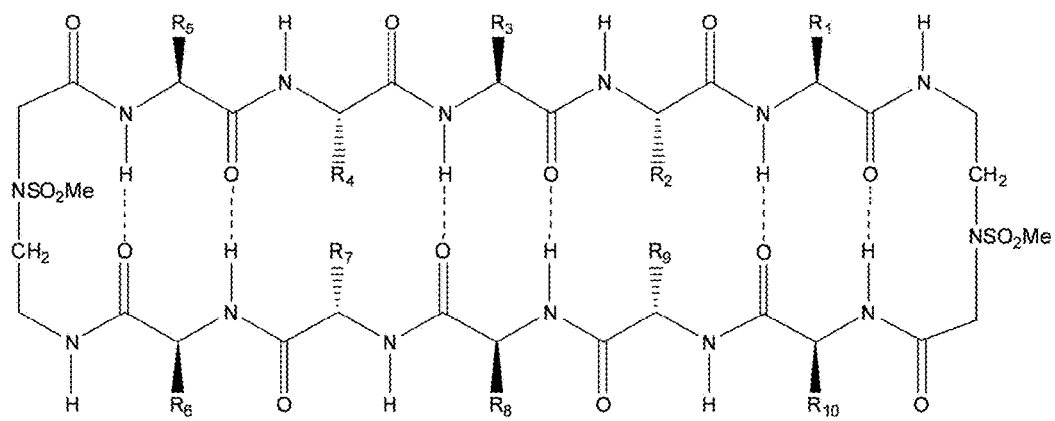
FIG. 5 is a diagram of the general cyclic III peptide for Table 4 (SEQ ID NOs:10, 270, 271, 272, 273, 274, 275, and 1).

SAR studies of III in H929 multiple myeloma cells. Variations of the compound III, seen in FIG. 5, are shown. Cell death was measured following 24 hour peptide treatment by TOPRO-3 staining and FACS analysis. Shown is the mean $IC_{50}$ value and standard deviation of three independent experiments.

| SEQ ID NO. | III | R1 | R2 | R3 | R4 | R5 | R6 | R7 | R8 | R9 | R10 | IC50 (μM) |
|---|---|---|---|---|---|---|---|---|---|---|---|---|
| 10 | 1 | K | L | K | L | K | W | S | V | V | M | 15.5 +/− 7.7 |
| 270 | 2 | K | L | K | L | K | A | S | V | V | M | 57.1 +/− 22 |
| 271 | 3 | K | L | K | L | K | W | A | V | V | M | 4.1 +/− 1.9 |
| 272 | 4 | K | L | K | L | K | W | S | A | V | M | 19.0 +/− 6.9 |
| 273 | 5 | K | L | K | L | K | W | S | V | A | M | 6.2 +/− 2.7 |
| 274 | 6 | K | L | K | L | K | W | S | V | V | A | 31.1 +/− 7.6 |
| 275 | 7 | K | L | K | L | K | W | S | V | V | * | 2.6 +/− 1.3 |
| 1 | 8 | K | L | K | L | K | M | V | V | S | W | 5.9 +/− 3.4 |
| 276 | 9 | K | L | K | L | K | W | Y | V | V | * | 2.9 +/− 1.3 |
| 277 | 10 | K | L | K | L | K | W | S | V | V | W | 5.9 |

The structure of the integrin interaction inhibitors showed that integrin interaction inhibitors exhibited secondary β-sheet structure with minima around 200 nm and absorption maxima around 186 nm, as seen in FIG. 6 and Table 5.

TABLE 6

NMR studies of Integrin Interaction Inhibitors

| Residue | $H_\alpha$ (ppm) | $H_\beta$ (ppm) | $H_\gamma$ (ppm) | $H_\delta$ (ppm) | $H_\epsilon$ (ppm) |
|---|---|---|---|---|---|
| Tryptophan | 4.692 | 3.128, 3.226 | | | |
| Serine | 4.599 | 3.837 | | | |
| Valine | 4.267 | 1.989 | 0.802, 0.880 | | |
| Valine | 4.13 | 1.94 | 0.665, 0.875 | | |
| Methionine | 4.482 | 2.107 | 2.434, 2.551 | | 2.121 |

TABLE 6-continued

NMR studies of Integrin Interaction Inhibitors

| Residue | $H_\alpha$ (ppm) | $H_\beta$ (ppm) | $H_\gamma$ (ppm) | $H_\delta$ (ppm) | $H_\epsilon$ (ppm) |
|---|---|---|---|---|---|
| L-Proline | 4.531 | 2.219, 2.111 | 2.077, 1.940 | 3.949, 3.705 | |
| D-Proline | 4.731 | 2.287, 2.155 | 2.004, 1.896 | 3.793, 3.539 | |
| Lysine | 4.541 | 1.789, 1.662 | 1.349, 1.242 | 1.564 | 2.864 |
| Leucine | 4.985 | 1.73 | 1.53 | 0.851, 0.777 | |
| Lysine | 4.291 | 1.794, 1.667 | 1.403, 1.261 | 1.564 | 2.947 |
| Leucine | 4.536 | 1.569 | 1.505 | 0.812, 0.811 | |
| Lysine | 4.379 | 1.784, 1.745 | 1.403 | 1.667 | 2.977 |
| Aeg turn promoter | $CH_2$ | $3.162^E$ | $3.348^A$ | | |
| | $CH_2$—$CH_2$ $SO_2Me$ | $3.563^{NH}$ 3.03 | $3.866^{SO}$ | | |

Figure 7:
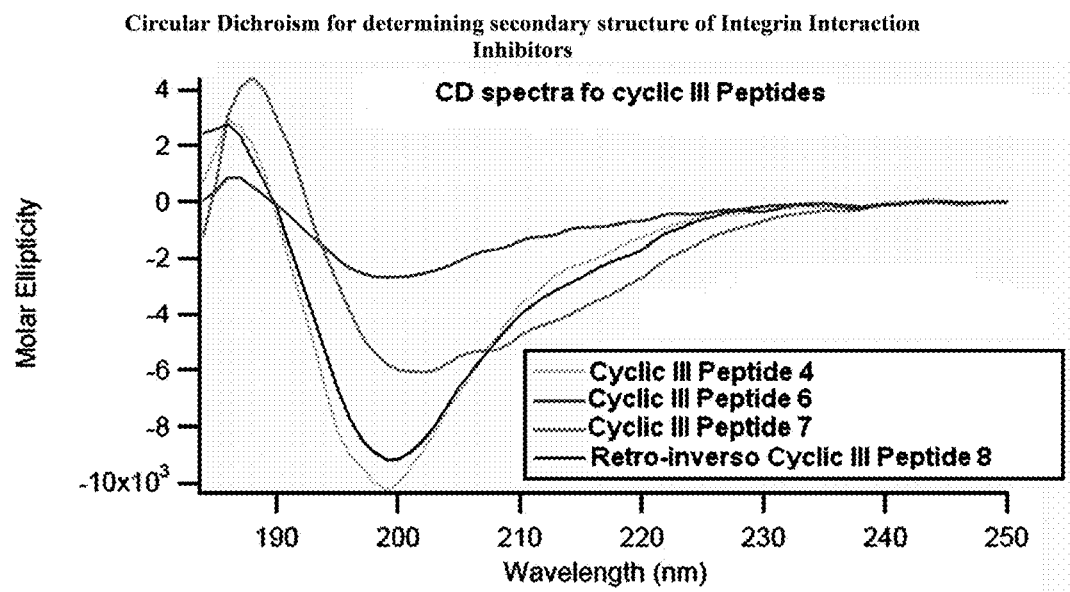
FIG. 7 is a graph showing the circular dichroism studies for/integrin interaction inhibitors in 7 mM Sodium Acetate buffer at a concentration of 200 μM at pH 7.

To determine the chirality of the compounds, circular dichroism of different compound III isoforms was detected, as seen in FIG. 7.

The integrin interaction inhibitors shown herein have better bioactivity than its parent linear peptides. NMR and circular dichroism studies are consistent with integrin interaction inhibitors adopting a secondary β-sheet structure.

Administration of different integrin interaction inhibitors with traditional chemotherapeutic agents that induce ROS was also found to interact synergistically with and additive with agents that activate the apoptotic pathway. As shown in Table 7, a strong synergism exists with doxorubicin, the HDAC inhibitor SAHA and arsenic trioxide. All three of these compounds are reported to increase ROS levels. Additionally, modest synergy was observed with the topoisomerase II inhibitor etopside. Doxorubicin showed the greatest level of synergy, seen in Table 7.

EXAMPLE 5

Structure-Activity Relationship (SAR) Studies for Cyclic III Peptides

In an effort to optimize the bioactivity of cyclic III, it was essential to determine the key residues most critical to the bioactivity of the cyclic III peptides. The key residues in the cyclic III peptides that are responsible for the biological activity were identified by performing a sequential Alanine substitution analysis on the recognition strand of the inverso and retro-inverso peptide analogs.

As shown in Table 8, bioactivity data of inverso cyclic III peptide analogs (peptides 3-7) revealed Tryptophan, Valine and Methionine in peptides 3, 5 and 7 respectively as key residues critical for the binding of cyclic III to integrins. Replacement of the Serine residue with the more hydropho-

TABLE 7

Combination Index (CI) Summary for Combinations in Myeloma Cell Lines.

| Treatment | Treatment regimen | U266 | Treatment | Treatment regimen | U266 |
|---|---|---|---|---|---|
| integrin interaction inhibitor & SAHA | Concurrent | 0.497 ± 0.155 (n = 3) +++ | INTEGRIN INTERACTION INHIBITORS&Vel | Concurrent | 1.056 ± 0.23 (n = 4) ± |
| integrin interaction inhibitor & Etoposide | Concurrent | 0.843 ± 0.439 (n = 3) ++ | INTEGRIN INTERACTION INHIBITORS&Dox | Concurrent | 0.365 ± 0.28 (n = 5) +++ |
| integrin interaction inhibitor & Arsenic | Concurrent | 0.620 ± 0.328 (n = 2) +++ | INTEGRIN INTERACTION INHIBITORS&PLAM | Concurrent | 5.102 ± 6.365 (n = 3) ---- |

Legend: Values indicate average calculated CI range for 3-5 replicate experiments (----, strong antagonism; ---, antagonism; --, moderate antagonism; -, slight antagonism; +/-, nearly additive; +, slight synergism; ++, moderate synergism; +++, synergism).
Synergistic growth inhibition was noted when U226 cells were treated with integrin interaction inhibitor in combination with SAHA, arsenic trioxide, doxorubicin, and etoposide. U226 cells were treated concurrently with varying concentrations of 2 drugs for 72 hours, and cell viability was measured by the CT-Blue assay (Promega). Data generated were used to calculate a Chou and Talalay Combination Index (CI).

Figure 8:
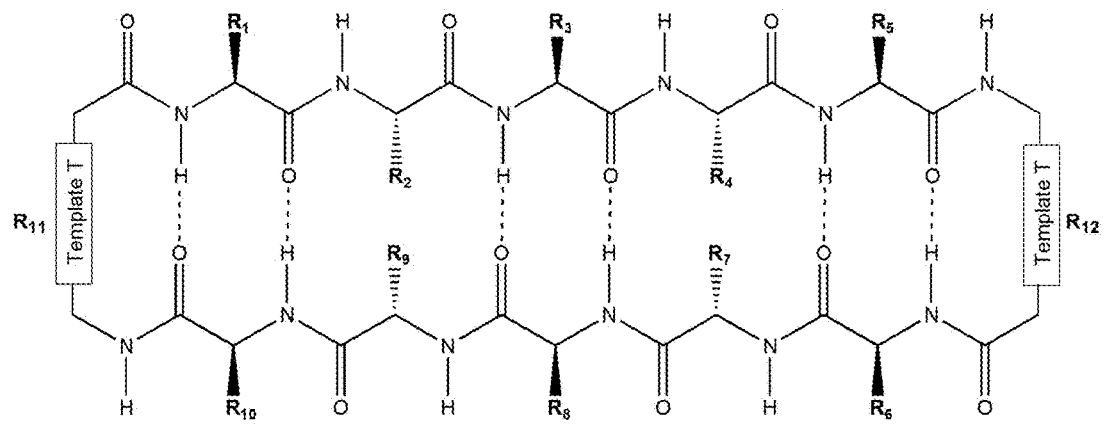
FIG. 8 shows the structure of an embodiment of the integrin interaction inhibitors of the invention, wherein $R_1$ is K; R$_2$ is L; R$_3$ is K; R$_4$ is L; R$_5$ is K; R$_6$ is selected from the group consisting of W, A, and M; R$_7$ is selected from the group consisting of S, A, Y, and V; R$_8$ is selected from the group consisting of V and A; R$_9$ is selected from the group consisting of V, A, and S; and R$_{10}$ is selected from the group consisting of M, A, W, and nor-Leu (Table 8; SEQ ID NOs:1-16, 49, and 18-26).

Bioavailability studies and human bone marrow xenograft inhibition of tumor growth studies are conducted in SCID mice using integrin interaction inhibitors with the highest activity. Cyclized derivatives are tested to determine whether the increased specificity towards tumor compared to normal cells and determine whether derivatives induce caspase independent cell death. Testing is also performed to determine whether alpha 4 integrin expression is required for cell death.

bic Alanine in peptide 4 significantly improved the bioactivity of cyclic III analog. Furthermore, oxidation of Methionine side chain has been observed during peptide isolation for some cyclic III analogs. This problem was overcome by replacing the Methionine side chain with a structurally similar and chemically stable side chain such as Norleucine. Introduction of the hydrophobic Norleucine into the recognition strand of peptide 8 resulted in a further increase of the peptide's bioactivity. Hence, the pentapeptide sequence WAVVN* (N*=Norleucine) (SEQ ID NO:54) was established as the lead recognition strand of inverso cyclic III peptide analog. After the determination of critical residues responsible for the bioactivity of inverso cyclic III peptide, efforts were made to further enhance the bioactivity by making slight changes such as increasing the hydrophobicity or slightly decreasing the hydrophobicity in the recognition strand. Cress and co-workers have previously reported that another peptide RZ-3 (KMVIYWKAG) (SEQ ID NO:280) similar to HYD1 inhibited adhesion of prostate tumor cells to extracellular matrix (ECM) proteins or to human dermal fibroblasts[8]. To further optimize the recognition strand for the enhancement of bioactivity of cyclic III peptide design, cyclic peptide 9 (N*VVYW) (SEQ ID NO:40) was synthesized with a design similar to the one found in the RZ-3 core sequence of the recognition strand. Peptide 9 had a similar bioactivity as the inverso cyclic III peptide 8. (FIG. 8)

amino acid (proline or 2-piperidine carboxylic acid derivative) as a constrained turn promoter should further reduce the degrees of freedom available to the cyclic peptide and possibly increase its affinity for binding to the target. Conformational search and energy minimization studies suggested that the introduction of the five membered ring D-Proline derivatized ether-peptidomimetic was favorable in stabilizing and sustaining the intramolecular hydrogen-bonding within the cyclic III analog. Based on this information, the inventors synthesized cyclic III peptide analog 16 with bioactivity of 1 μM. This peptide provided the best lead scaffold which was further optimized for an improvement in binding affinity towards H929 multiple myeloma cells.

TABLE 8

Structure-Activity relationship studies of cyclic III peptide analogs

| SEQ ID NO. | Peptide | $R_1$ | $R_2$ | $R_3$ | $R_4$ | $R_5$ | $R_6$ | $R_7$ | $R_8$ | $R_9$ | $R_{10}$ | $R_{11}$ | $R_{12}$ | $IC_{50}$ (μM) |
|---|---|---|---|---|---|---|---|---|---|---|---|---|---|---|
| 1 | 1 | K | L | K | L | K | M | V | V | S | W | $T_1$ | $T_2$ | 15 |
| 2 | 2 | K | L | K | L | K | M | V | V | S | W | $T_1$ | $T_1$ | 15 |
| 3 | 3 | K | L | K | L | K | M | V | V | S | A | $T_1$ | $T_1$ | 57 |
| 4 | 4 | K | L | K | L | K | M | V | V | A | W | $T_1$ | $T_1$ | 4 |
| 5 | 5 | K | L | K | L | K | M | V | A | S | W | $T_1$ | $T_1$ | 19 |
| 6 | 6 | K | L | K | L | K | M | A | V | S | W | $T_1$ | $T_1$ | 6 |
| 7 | 7 | K | L | K | L | K | A | V | V | S | W | $T_1$ | $T_1$ | 31 |
| 8 | 8 | K | L | K | L | K | N* | V | V | S | W | $T_1$ | $T_1$ | 3 |
| 9 | 9 | K | L | K | L | K | N* | V | V | Y | W | $T_1$ | $T_1$ | 3 |
| 10 | 10 | K | L | K | L | K | W | S | V | V | M | $T_1$ | $T_1$ | 6 |
| 11 | 11 | K | L | K | L | K | W | A | V | V | N* | $T_1$ | $T_1$ | 12 |
| 12 | 12 | K | L | K | L | K | W | A | V | V | A | $T_1$ | $T_1$ | 69 |
| 13 | 13 | K | L | K | L | K | W | A | V | A | N* | $T_1$ | $T_1$ | 26 |
| 14 | 14 | K | L | K | L | K | W | A | A | V | N* | $T_1$ | $T_1$ | 41 |
| 15 | 15 | K | L | K | L | K | A | A | V | V | N* | $T_1$ | $T_1$ | 3 |
| 16 | 16 | K | L | K | L | K | N* | V | V | A | W | $T_3$ | $T_1$ | 1 |
| 49 | 17 | K | L | Q | L | K | N* | V | V | A | W | $T_3$ | $T_1$ | 13 |
| 18 | 18 | Q | L | K | L | K | N* | V | V | A | W | $T_3$ | $T_1$ | ND |
| 19 | 19 | K | L | K | L | Q | N* | V | V | A | W | $T_3$ | $T_1$ | 19 |
| 20 | 20 | K | Q | K | L | K | N* | V | V | A | W | $T_3$ | $T_1$ | 18 |
| 21 | 21 | K | L | K | Q | K | N* | V | V | A | W | $T_3$ | $T_1$ | 25 |
| 22 | 22 | K | L | K | L | K | W | A | V | V | N* | $T_3$ | $T_3$ | 17 |
| 23 | 23 | K | X | K | X | K | W | A | V | V | N* | $T_3$ | $T_3$ | >150 |
| 24 | 24 | K | L | K | L | K | N* | V | L | A | W | $T_3$ | $T_1$ | 10 |
| 25 | 25 | K | L | K | L | K | N* | V | I | A | W | $T_3$ | $T_1$ | 10 |
| 26 | 26 | K | L | K | L | K | N* | V | F | A | W | $T_3$ | $T_1$ | 9 |

$T_1$, $T_2$, $T_3$ = Linker 1, 2 or 3;
$T_1$ = $NH_2CH_2CH_2N(SO_2Me)CH_2COOH$;
$T_2$ = LPro-DPro
N* = Norleu
X = Sarcosine
$T_3$ = $N(CH_2)_3CHCH_2OCH_2COOH$ After determining that the replacement of the Serine and Methionine residues with the Alanine and Norleucine residues respectively yielded inverso cyclic III peptides with improved bioactivity, we attempted to study the structure activity relationship for the retro-inverso cyclic III analog (peptides 12-15). A sequential Alanine scan was carried out with (WAVVN*) (SEQ ID NO:54) as the core sequence in the recognition strand. It was found that replacement of Norleucine and Valine in peptides 12 & 13 respectively were critical for the bioactivity of the retro-inverso peptides. There was an unexpected improvement in bioactivity for peptide 15 where Tryptophan was substituted for Alanine.

Inverso cyclic peptide design was further improved by bringing additional restraint into the cyclic peptide by introduction of a constrained turn promoter ($T_3$) at one turn and the methylsulfonamido aminoethyl glycine linker ($T_1$) as the other turn. The introduction of an ether-peptidomimetic The non-recognition strand of cyclic III peptide was also optimized to determine if it has any effect on the bioactivity. A side chain anchoring strategy was explored for easy preparation of this series of cyclic peptides. Various research groups have applied this solid phase strategy to synthesize monomers[9-17]. This strategy involves side chain anchoring of trifunctional amino acids such as Lysine, Glutamic Acid, Glutamine, Aspartic and Asparagine for peptide elongation and on resin peptide cyclization. A sequential Glutamine substitution analysis on the non-recognition strand of the inverso cyclic III analogs (peptides 17-21) revealed that these residues did not significantly alter the binding of the peptide to its target. A similar bioactivity observed for the cyclic D-HYD1 and the cyclic III peptide 1 suggests extensive peptide backbone interactions are absent or minimal since these two analogs have opposite backbone sequences. This hypothesis was tested by replacing the amino acid residues that have exo amide hydrogens with N-methylated amino acid residues. The inventors first replaced all of the Leucine residues in the non-recognition strand with Sarcosine (peptide 23). The inventors anticipated that N-methylation of the exo amides will not significantly change the beta-hairpin conformation but it should stabilize the cyclic beta-hairpin and eliminate possible peptide aggregation due to beta-sheet like dimerization or oligomerization of one or more cyclic III analogs. The poor bioactivity of peptide 23 led us to believe that the introduction of too many constraints in the molecule might have caused disruption of the internal hydrogen bonding which stabilizes the cyclic peptide. Efforts have been made to further enhance the bioactivity by varying hydrophobicity in the recognition strand of the lead peptide by incorporating hydrophobic residues at position 9 (peptide 24-26).

EXAMPLE 6

Synthesis of Linkers and Cyclic III Peptides

Figure 9:
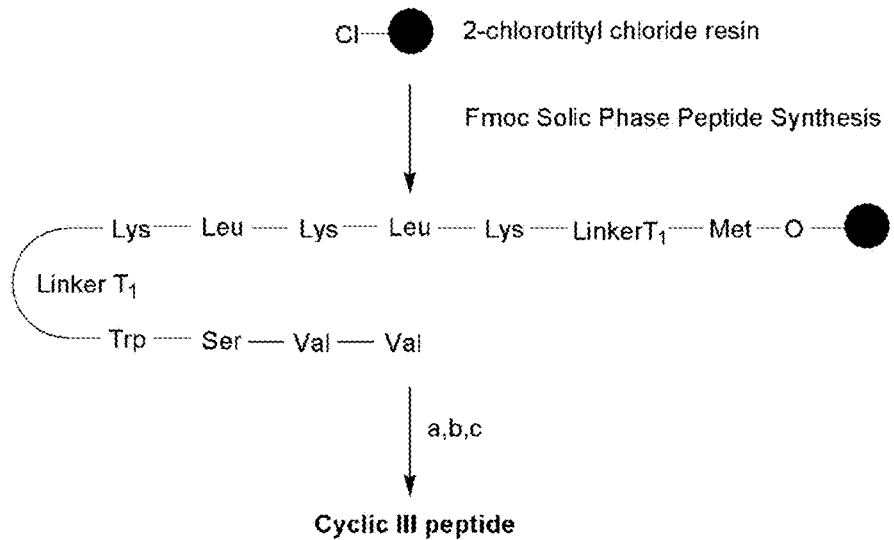
FIG. 9 is Scheme 1: Solid-Phase synthesis of cyclic III peptide using solution phase cyclization strategy.
Figure 10:
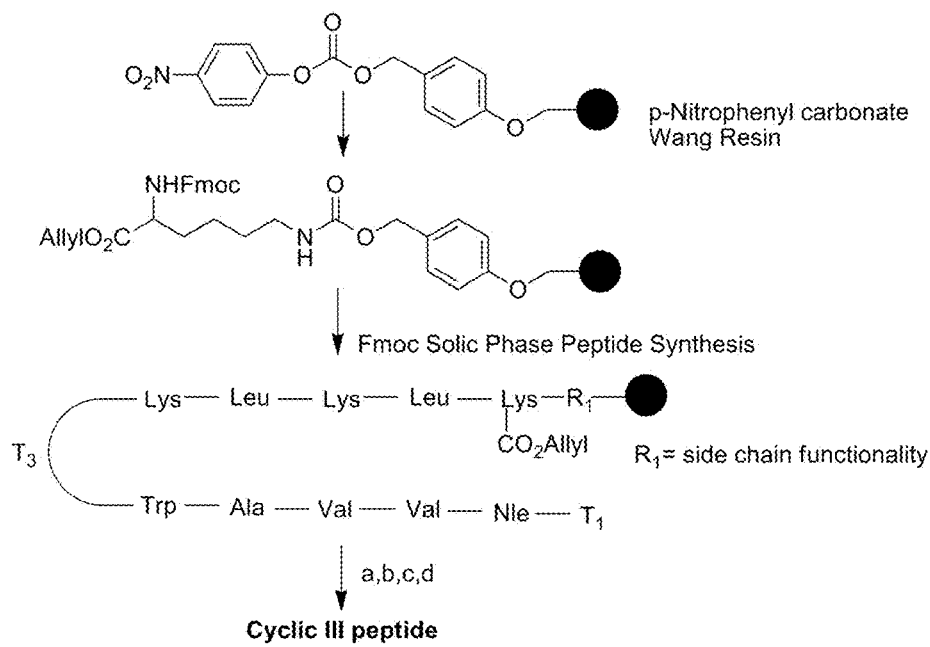
FIG. 10 is Scheme 2: Solid-Phase synthesis of cyclic III peptide analogs using side chain anchoring strategy.

Cyclic peptides 1-15 were synthesized on 2-chlorotrityl chloride resin as solid support and Fmoc solid phase peptide synthesis strategy was used as shown in Scheme 1 (FIG. 9). The linear peptides were synthesized and selectively cleaved from the resin without cleaving the side chain Boc-groups using trifluoroethanol as the cleaving agent. The linear peptide was then cyclized in solution under dilute conditions to afford crude cyclized peptide in modest yields. In order to synthesize a series of cyclic III peptide analogs with better yields, an efficient protocol for peptide cyclization on resin was explored. An alternative peptide cyclization procedure was developed using a side-chain attachment strategy for preparing peptides 16-26. As shown in Scheme 2 (FIG. 10), the $N^\epsilon$-amino group of the Lysine was attached to carbonate Wang resin. The α-carboxyl group was protected with an orthogonal allyl protecting group. After synthesis of the protected linear peptide using our Fmoc-based strategy, the C-terminus α-carboxyl group and Fmoc group from N-terminus were deprotected. The linear peptide was then cyclized on resin and subsequently released from the resin using TFA. For the Glutamine scan of peptides 17-22, we anchored the γ-side chain carboxyl group of Glutamic Acid to Rink amide resin. The on resin cyclization strategy of synthesizing cyclic peptides enabled us to synthesize and screen a moderate library of cyclic peptides very efficiently and in excellent yields.

Figure 11:
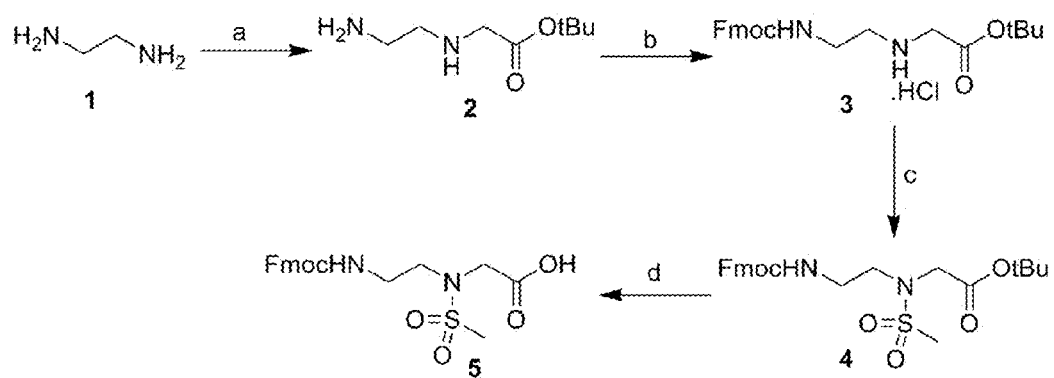
FIG. 11 is Scheme 3: Synthesis of the methylsulfonamido aminoethyl glycine linker T$_1$.
Figure 12:
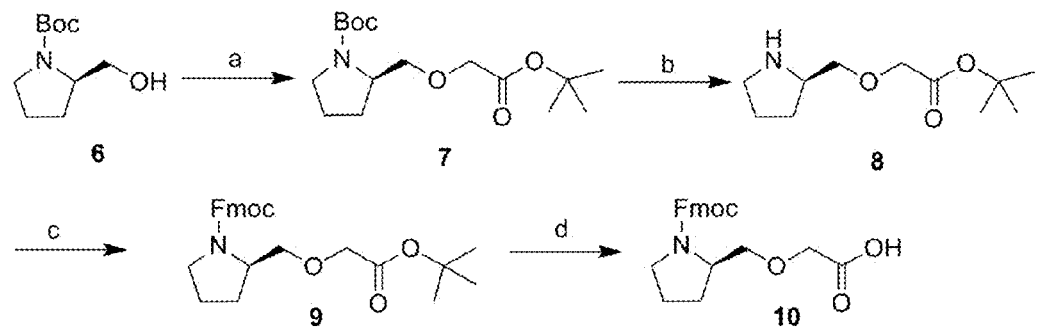
FIG. 12 is Scheme 4: Synthesis of the ether peptidomimetic amino acid linker T$_3$.

Scheme 3 describes the synthesis of the methylsulfonamide aminoethyl glycine linker $T_1$ (FIG. 11). Selective mono-alkylation of excess ethylene diamine with tert-butyl bromoacetate was carried out under dilute conditions to give compound 2 in 85% yield[18]. Compound 2 was used in the next step without further purification and selective Fmoc protection of the primary amine was achieved to give crude Fmoc-protected aminoethyl glycinate 3. The crude reaction was then washed with dilute hydrochloric acid and stored overnight in the deep freezer which resulted in the precipitation of pure compound 3 as the hydrochloride salt that can be stored for several months in the refrigerator without decomposing. Mesylation of the secondary amine with methanesulfonyl chloride afforded compound 4 that precipitates from an ethyl acetate solution under cold conditions. Deprotection of the t-butyl group was achieved by employing 4M HCl in dioxane to give the desired compound 5 in excellent yield. The ether peptidomimetic amino acid linker $T_3$ was prepared from commercially available Boc-D-Prolinol (Scheme 4, FIG. 12). First, O-alkylation of 6 with tert-butyl bromoacetate afforded compound 7 in 77% yield[19,20]. Selective removal of the Boc protecting group in compound 7 using trifluoroacetic acid in DCM (1:4) gave compound 8. Fmoc-group protection of the secondary amine in compound 8 with FmocOSu followed by acidic cleavage of the tert-butyl ester group gave the Proline derived ether-peptidomimetic 10 in 79% yield.

EXAMPLE 7

Structural Determination of Cyclic Peptides: Circular Dichroism Studies

Figure 13:
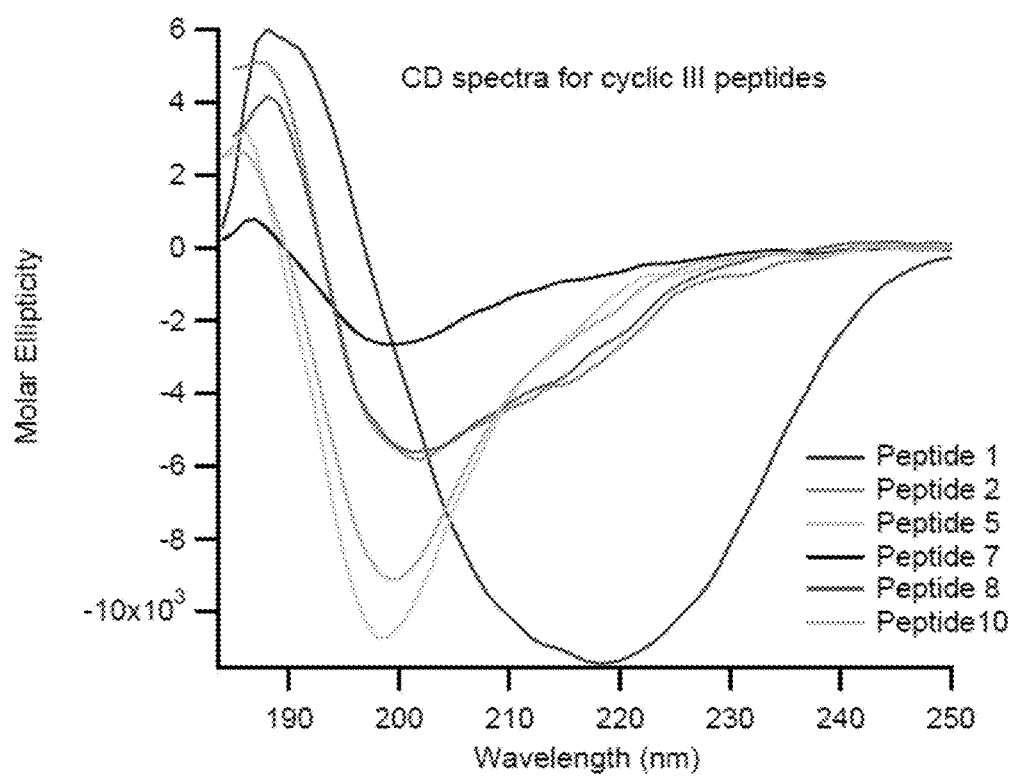
FIG. 13 are results of circular dichroism studies for cyclic III peptides 1, 2, 5, 7, 8 and 10 in 7 mM sodium acetate buffer at a concentration of 200 µM at pH 7.

Circular dichroism (CD) is a sensitive measure of the secondary structure of peptides and proteins. Various reports cited in the literature have shown that CD spectra taken from 260-190 nm is analyzed for different secondary structures of peptides and proteins i.e. α-helix, parallel and antiparallel β-sheet, β-turn, etc[21,22]. Peptides with a β-sheet structure usually exhibit an absorption minima around 210 nm and a relatively strong absorption maxima around 190 nm. As seen in FIG. 13, CD spectra of peptide 1 shows an absorption minima around 215 nm, which suggests a more stable β-sheet conformation for this peptide whereas peptide 2 displays a negative band around 202-204 nm, which suggests that this peptide deviates from a stable β-sheet conformation and moves towards a more random structure. This can be attributed to the D-Pro-L-Pro turn in peptide 1 which is very structurally rigid thus forcing the peptide into a β-hairpin conformation. In opposite of this rigid turn, the methylsulfonamido linker in peptide 2 is more flexible, allowing the residues to be less structurally rigid and thereby deviate from the β-hairpin conformation. All cyclic III peptides 2-16 display similar CD bands: negative absorption minima around 202 nm and strong positive absorption maxima around 190 nm. Therefore, the inventors can conclude that all of these cyclic peptides have adopted a semi β-sheet structure.

EXAMPLE 8

Structural Determination of Cyclic Peptides: NMR Studies for Structural Determination of Cyclic Peptides in Solution Complete peak assignments were only done for cyclic peptides 1, 5 and 16. Assignments for both the recognition sequence and the non-recognition sequence, omitting the turns, were done for the remainder of the peptides. In an effort to de-clutter the 2D spectra sets, the NMR experiments were run in 100% $D_2O$ to remove the exchangeable amide and Lysine ε-NH protons from the spectrum. Even without information from the amide and Lysine ε-NH protons, the results from the NMR experiments clearly show that the peptides have all adopted a β-hairpin structure.

Supporting the CD results, both the chemical shifts of the amino acid α-hydrogen protons ($H_\alpha$) and the NOE data indicate that the peptides are in a β-hairpin conformation. The NMR results agree with previous empirical analysis which has shown that when β-sheets are formed, there is a downfield shift in the $H_\alpha$ resonances[23,24]. The majority of the amino acid $H_\alpha$'s in our peptides are shifted significantly downfield such that their values indicate a β-hairpin conformation (Table 9).

TABLE 9

α-Proton Chemical Shifts (ppm) of selective cyclic peptide analogs

| | Position | | | | | | | | | | | |
|---|---|---|---|---|---|---|---|---|---|---|---|---|
| | $R_1$ | $R_2$ | $R_3$ | $R_4$ | $R_5$ | $R_6$ | $R_7$ | $R_8$ | $R_9$ | $R_{10}$ | $R_{11}$ | $R_{12}$ |
| 1 | 4.38 | 4.54 | 4.29 | 4.99 | 4.54 | 4.48 | 4.13 | 4.27 | 4.60 | 4.69 | $3.56^S$ $3.86^R$ | L-Pro 4.53 D-Pro 4.74 |
| 2 | 4.26 | 4.35 | 4.08 | 4.28 | 4.57 | 4.64 | 4.66 | 4.32 | 4.46 | 4.70 | — | — |
| 5 | 4.31 | 4.16 | 4.07 | 4.04 | 4.42 | 4.60 | 4.58 | 4.53 | 4.60 | 4.61 | $3.89^S$ $4.06^R$ | $3.47^S$ $4.05^R$ |
| 7 | 4.44 | 4.31 | 4.08 | 4.28 | 4.52 | 4.42 | 4.63 | 4.18 | 4.70 | 4.67 | — | — |
| 8 | 4.29 | 4.29 | 4.09 | 4.38 | 4.59 | 4.45 | 4.67 | 4.64 | 4.45 | 4.60 | — | — |
| 10 | 4.17 | 4.53 | 4.05 | 4.37 | 4.35 | 4.83 | 4.51 | 4.52 | 4.10 | 4.45 | — | — |
| 16 | 4.55 | 4.78 | 4.32 | 4.63 | 4.17 | 4.34 | 4.44 | 4.55 | 4.70 | 5.05 | 4.232 | $3.94^S$ $4.08^R$ |

$^R$= Pro-R,
$^S$= Pro-S $H_\alpha$ and NOE NMR analysis of peptide 1, which contains both the Robinson β-hairpin turn promoter template (D-Pro-L-Pro)[25] and the methylsulfonamido aminoethyl glycine turn, confirms the structure of this peptide as a β-sheet. This peptide was then remade using the methylsulfonamido aminoethyl glycine in place of the Robinson template as the β-hairpin turn promoter to give peptide 2. The resulting $H_\alpha$ chemical shifts for this peptide show it is also a β-sheet.

A comparison between the $H_\alpha$ shifts of these two peptides reveals many similarities. Most of the $H_\alpha$'s on the non-recognition side of peptide 2 have shifted upfield relative to 1, suggesting that the structure is less like a β-sheet. While three of these residues have only shifted about 0.2 ppm or less upfield, Leu4's shift of about 0.7 ppm suggests a fair amount of structural change. Interestingly, the only $H_\alpha$ on the non-recognition strand that has an upfield shift is Lys1. More importantly however, all but one of the $H_\alpha$'s on the recognition side of the peptide have shifted downfield indicating a β-sheet conformation. The $H_\alpha$ of Ser9 is the only one that has shifted upfield. Looking at the fact that the $H_\alpha$'s on residues Met6 and Lys5 have shifted downfield after the β-hairpin turn promoter was changed from the Robinson template to our methylsulfonamido aminoethyl glycine turn, it suggests that our turn promoter allows for more β-hairpin-like character at this end of the peptide. Thus, our turn may be a better β-hairpin promoter for certain peptide sequences.

Although most of the $H_\alpha$ shifts were small, about 0.2 ppm or less, there was a large shift in two of the $H_\alpha$'s which appears to be highly structurally significant. While the Leu4's $H_\alpha$ shifted upfield 0.704 ppm, Val7's $H_\alpha$ shifted downfield 0.532 ppm. This suggests that the Leucine is not adopting a predominantly β-sheet conformation. This is most likely due to steric interactions from the γ-protons of Val7 which is directly across from Leu4. Presumably as a direct result of Leu4's structural conformational change, Lys3's $H_\alpha$ is shifted 0.215 ppm (the second largest shift) upfield which removes a small amount of its β-sheet character and thus is further evidence supporting this claim.

An examination of the other peptides reveals a similar phenomenon. The Leu4 $H_\alpha$ is always shifted upfield and the residue in position 7 is always shifted downfield in comparison with peptide 1. This can be explained by the fact that the D-Pro-L-Pro turn in the Robinson template is very structurally rigid, forcing those residues close to it into a β-hairpin conformation. However, our turn is much more flexible, thus allowing the residues close to the turn to be less rigid in their orientations. It is probably this flexibility that allows the Leu4 $H_\alpha$ to deviate from the β-sheet configuration. NOE analysis supports this view. In peptide 1, strong NOEs were observed between the $H_\alpha$'s of Leu4 and Val7. However, in peptide 2 the NOE between the $H_\alpha$'s of Leu4 and Val7 was only of low intensity. In its place, there was a semi-strong NOE between the $H_\alpha$ of Leu4 and only 1 γ-$CH_3$ group of Val7. This significant reduction in the NOE cross-peak intensity between the Leu and Val $H_\alpha$'s combined with the appearance of a new strong cross-peak between the two Leu $H_\alpha$'s is strong evidence in support of the flexibility of our turn.

The inventors also investigated the use of our ether peptidomimetic amino acid linker ($T_3$) as a β-turn promoter. This promoter is similar to the Robinson template in the fact that they both contain Pyrrolidine rings however; $T_3$ has a higher degree of flexibility than the D-Pro-L-Pro turn due to the fact that $T_3$ contains only 1 ring. An empirical analysis of the $H_\alpha$'s in peptide 16 shows more resonances adopting a β-sheet conformation than any other peptide. This shows that the rigid $T_3$ linker is quite capable of inducing a β-turn while retaining enough malleable character to allow all of the other residues enough conformational flexibility to adopt a β-sheet. This is opposed to the Robinson template which does not confirm the same flexibility thus fewer residues empirically display β-sheet characteristics.

Comparing the $H_\alpha$'s of peptides 1 and 16 reveals a number of striking similarities and further demonstrates linker $T_3$'s ability to induce a β-turn. Focusing on the non-recognition strands, a comparison of the $H_\alpha$ of the Lysine residues closest to their respective turns (1 Lys5 vs. 16 Lys1) reveals almost no chemical shift difference; 16 Lys1 is shifted downfield by only 0.009 ppm. Moving further away from the respective turns, the chemical shift difference between the two Lys3 $H_\alpha$'s increases slightly to 0.029 ppm implying 16 has slightly more β-sheet character at this residue. Generally, as is the case for 1, the $H_\alpha$ of the Lysine furthest from the turn is slightly downfield of Lys3's $H_\alpha$. In peptide 16 however, Lys5's $H_\alpha$ is considerably upfield of Lys3. The difference in chemical shifts between the furthest Lysines (1 Lys1 vs. 16 Lys5) is greater than 0.2 ppm. Additionally the $H_\alpha$'s of both Lys5 and Nle6 in 16 are significantly upfield of the same protons in peptide 8. Combined, these facts show that this end of the turn, from Lys5 through the turn to Nle6, adopts slightly less of a β-sheet conformation in 16. This is most likely caused by trying to relieve a conformational strain generated by either the methylsulfonamido aminoethyl glycine turn or by Lysine's side chain interactions with the other residues pulling the $H_\alpha$'s out of a β-sheet. It should be noted however that all of the protons in the $T_1$ linker of 16 have been significantly shifted downfield of those in the $T_1$ linker of 1, further confirming the superiority of the $T_3$ linker over the Robinson template.

However, the Leucine residues in the non-recognition strand are in striking contrast from the Lysine residues. In 16 the $H_\alpha$ of Leu2, the one closest to the constrained ring turn, is very upfield (by about 0.205 ppm) from the corresponding $H_\alpha$ of Leu4 in 1 even though they shouldn't be that different. This is especially true given the fact that the chemical shifts of the Lysine $H_\alpha$'s right next to the rigid turns in each peptide are almost exactly identical. This is most likely due to the difference in rigidity between the two linkers as discussed above.

Moving on to the recognition strand, as is expected, there is a downfield shift of Trp's $H_\alpha$ in 16 vs. 1 which is clearly due to its proximity to the rigid β-turn. With regards to the Valine residues, we would expect them to follow a similar trend. Taking into consideration the fact that in peptide 1, the Valine at residue 7 is very close (two residues away) to the Proline-Proline turn, it stands to reason that it's $H_\alpha$ should be much more downfield than the same residue on peptide 16 which is much further away (four residues away, twice as far) from its constrained ring turn. However, the $H_\alpha$'s for both Val7 and Val8 in 16 are shifted significantly downfield (0.28 and 0.31 ppm respectively) from those in peptide 1. In a comparison of the $H_\alpha$'s of the Valines at residue 8 between the two peptides, we would expect their $H_\alpha$ chemical shifts to be fairly similar given their central (and identical) location on the recognition strand of the peptide. This however is clearly not the case which indicates that 16's recognition strand contains more β-sheet character at this middle point than peptide 1's does. Therefore, extrapolation of these findings clearly indicates that the entire recognition strand in peptide 16 has adopted a β-sheet conformation.

The replacement of the Robinson template by our turn $T_1$ slightly increases the distance between the two sides of the β-sheet. This is due to the fact that this turn isn't rigidly fixed into a certain conformation thereby allowing the chain to expand and contract, much like an accordion. It is this accordion-like action that allows the distance between the two sides of the β-sheet to change. This change in distance can be seen by the decrease in NOE intensity between the Leu and Val residues mentioned previously. NOEs also show the disappearance of the following; a strong NOE between the ε protons of Meth and the $H_\alpha$ of Lys5, a strong NOE between the $\gamma_1$ protons of Val8 and the β and β' protons of Lys3. Also, the intensity of the NOE interaction between the $\gamma_2$ protons of Val8 and the β proton of Lys3 dropped from being semi-strong to being very weak upon replacement of the Robinson turn.

Figure 14C:
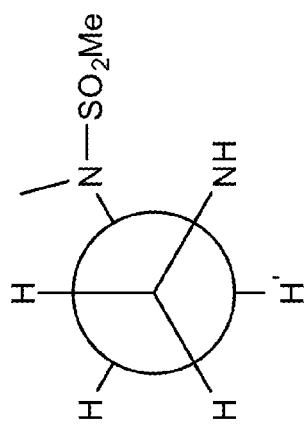
FIGS. 14A-C.
Figure 14B:
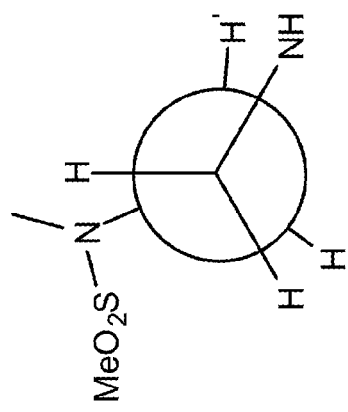
Figure 14A:
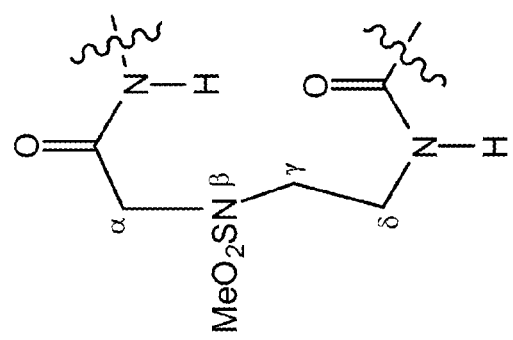

The methylsulfonamido aminoethyl glycine turn itself can be broken down into two parts for discussions sake. The first part is the $CH_2$ side between the carbonyl and the N-Mesyl group, which we will refer to as the α-protons. The second part is the $CH_2$—$CH_2$ side between the N-Mesyl group and the amide NH, which will be referred to as the γ and δ-protons as shown in FIG. 14A.

The flexibility of the turn is not just limited to adjusting the distance between the two sides. Rather, NOE analysis shows the existence of 2 distinct conformations. Newman projections of the two different conformations viewed down the δ-γ bond showing specific steric interactions can be seen in FIGS. 14A-C. The first conformation (FIG. 14B) exists as an eclipsed conformer which puts it in the higher energy state of the two. However, the bulky N-Ms group points down and away from the β-sheet, eliminating all steric interactions and placing it in the lowest energy state. The second conformation (FIG. 14C) exists as the staggered conformer, thus being the lower energy of the two. This time however, the bulky N-Ms group points directly into the center of the β-sheet causing large amounts of steric interactions with the sheet's backbone forcing the N-Ms group into a very high energy state. Therefore, it can be assumed that the bulky N-Ms group drives the turn's preference for the (FIG. 14B) conformation, picking the lower total energy conformer with the least amount of steric interactions.

Interestingly, conformer (FIG. 14B) may also be slightly favored because the Pro-R γ-proton (labeled as H') is eclipsed with the amide NH and the Pro-R δ-proton is eclipsed with the nitrogen from the N-Ms group. The proton attached to the amide NH is pointed out away from the backbone of the peptide while the lone pair on this nitrogen is pointed upwards towards the inside of the β-sheet. Additionally, the lone pair on the nitrogen from the N-Ms group points out towards the middle of the two δ-protons. There is the potential for a favorable attractive interaction between the lone pairs on these nitrogens and their respective eclipsed protons[26,27]. This would forgive some of the strain caused from being in the eclipsed conformation further reducing the total energy of the (FIG. 14B) conformation making it the more favorable one.

Indeed, this favorable attractive interaction is supported by the chemical shifts of the respective protons. In peptide 5 for both turns, the Pro-R γ-protons are shifted downfield relative to the Pro-S γ-protons meaning a decrease in shielding as is expected with the interaction of the lone pair of electrons on the amide nitrogen.

For all but one of the peptides, the turn's geminal γ-protons are non-identical giving rise to a Pro-R proton and a Pro-S proton. Peptide 1 is the only one where these protons are identical. This is most likely caused by the Robinson turn locking the methylsulfonamido aminoethyl glycine turn into a more rigid conformation. Observations that support this analysis can be seen by the significant (0.08 ppm and greater) upfield shift of both the γ and δ resonances in 1 vs. those in 5. The α protons of peptide 1 also experience large (0.18 ppm and greater) upfield shift in comparison to those in peptide 5, with the exception of the Pro-S α proton in residue 12 of peptide 5. Thus, this side of the peptide looks less like a β-sheet when the Robinson turn is used to induce the β-hairpin.

Figure 15:
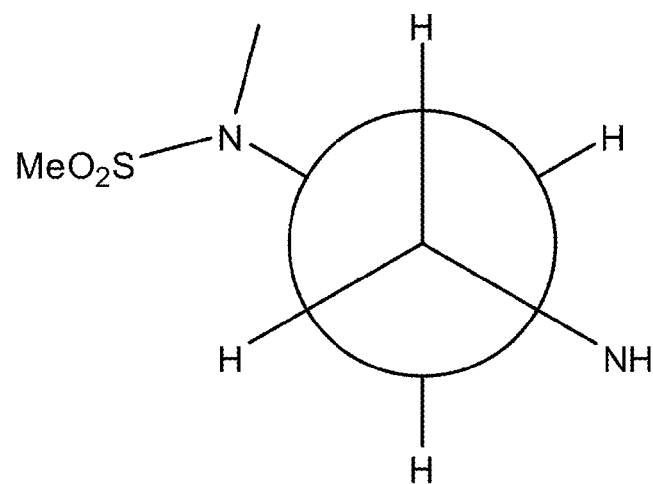
FIG. 15 is a Newman Projection of the structurally locked β-turn viewed down the δ-γ bond.

Because only one peak is seen for the γ-protons in peptide 1's turn, they must exist in somewhat similar environments and the turn's conformation must be different enough from the two mentioned above. Supported by NOEs, FIG. 15 is a Newman projection viewed down the δ-γ bond of the $T_1$ linker and shows what this altered conformation might look like.

Figure 16:
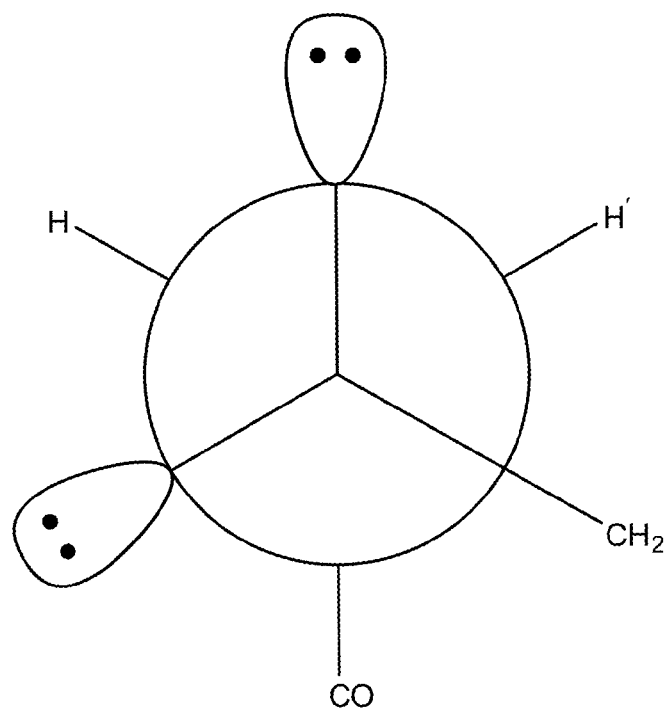
FIG. 16 is a Newman Projection of the T$_3$ β-turn viewed down the O-α' bond. The Pro-R α' proton is labeled as H'.

The final turn promoter, $T_3$, contains characteristics of both turns $T_1$ and $T_2$. In $T_3$, the $CH_2$ α to the carbonyl (herein referred to as α') has a Pro-R and Pro-S proton much like the α-position in the $T_1$ linker. However, the chemical shifts of these two protons are opposite of those in any of the $T_1$ linkers such that in $T_3$, the Pro-S proton is the more downfield one rather than being the more upfield one. As shown in FIG. 16, this has to do with the two lone pairs on the ether oxygen which are pointing away from the center of the β-sheet and encompass the Pro-S proton causing its chemical shift to move downfield. Additionally, the difference here in chemical shifts between the Pro-R and Pro-S protons is only 0.044 ppm while the differences between the $T_1$ α protons are between 0.13 and 0.58 ppm. Therefore, this means that the Pro-R and Pro-S protons are in fairly similar chemical environments. This is clearly the case as the Newman projection shows because one of the lone pairs on the oxygen is also close to the Pro-R proton which would also account for the significant downfield shift of this proton as well.

EXAMPLE 8

Peptide Structural Characterization Via NOE

Figure 17A:
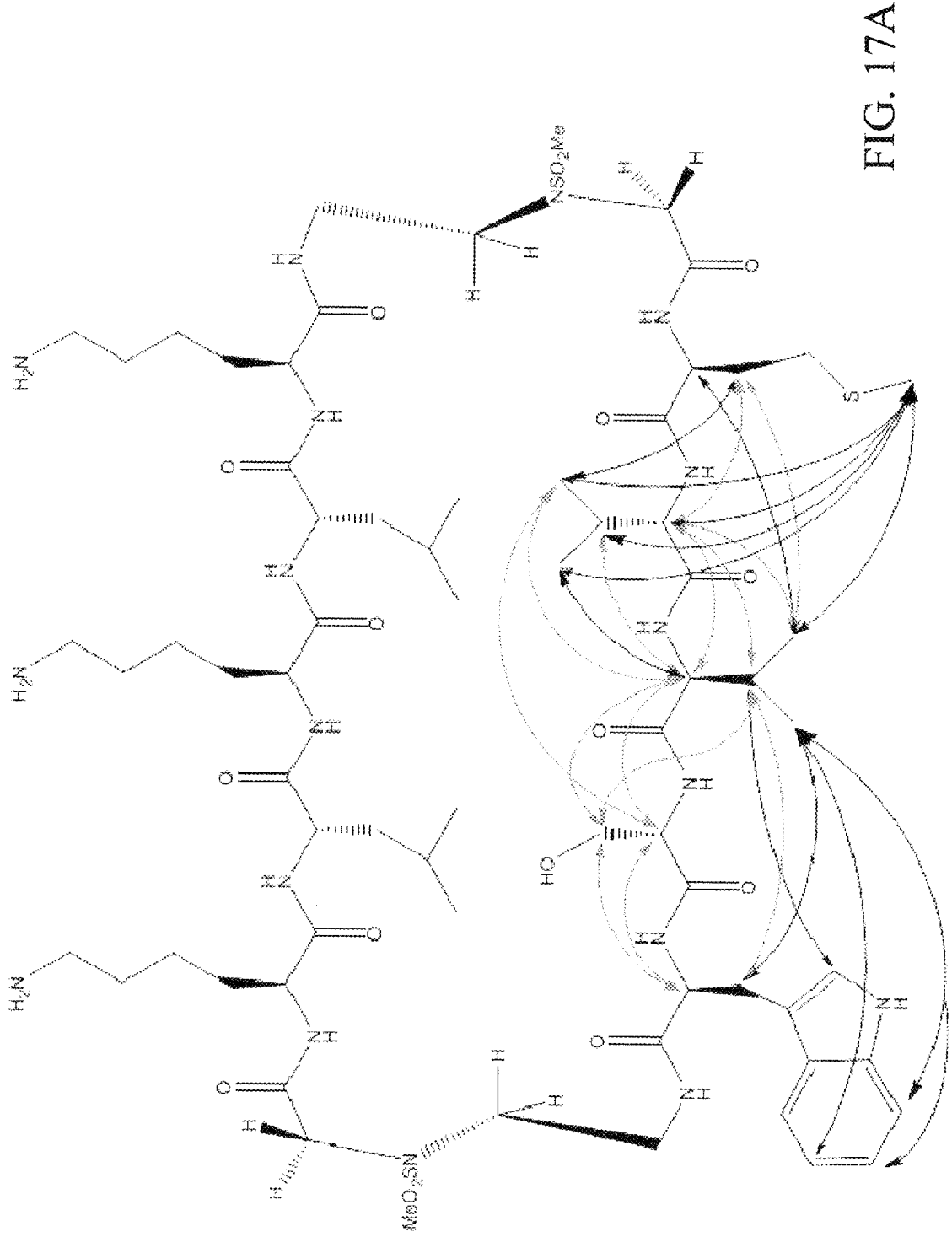
FIGS. 17A-17B are peptide 2 NOEs.
Figure 17B:
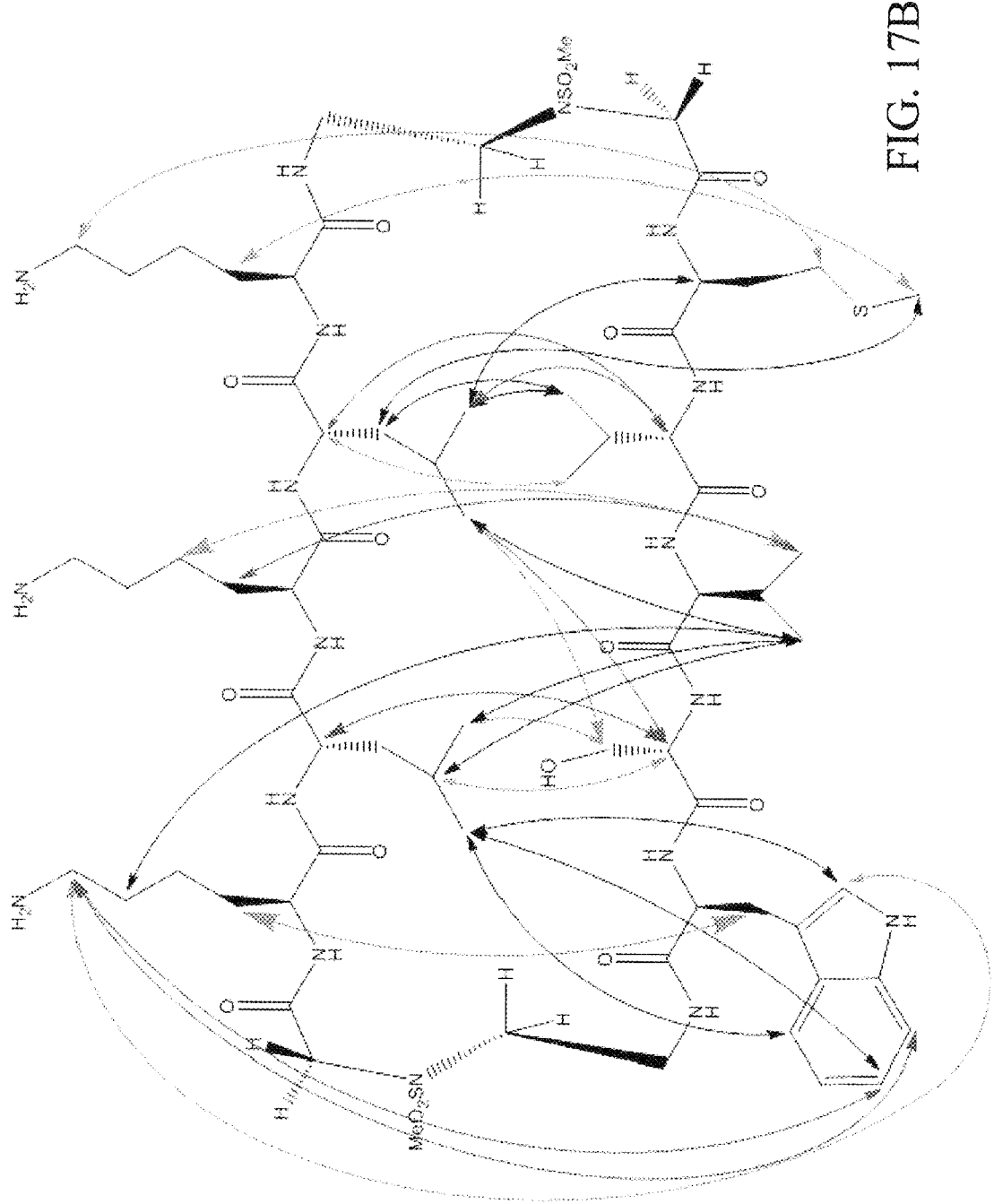
Figure 18A:
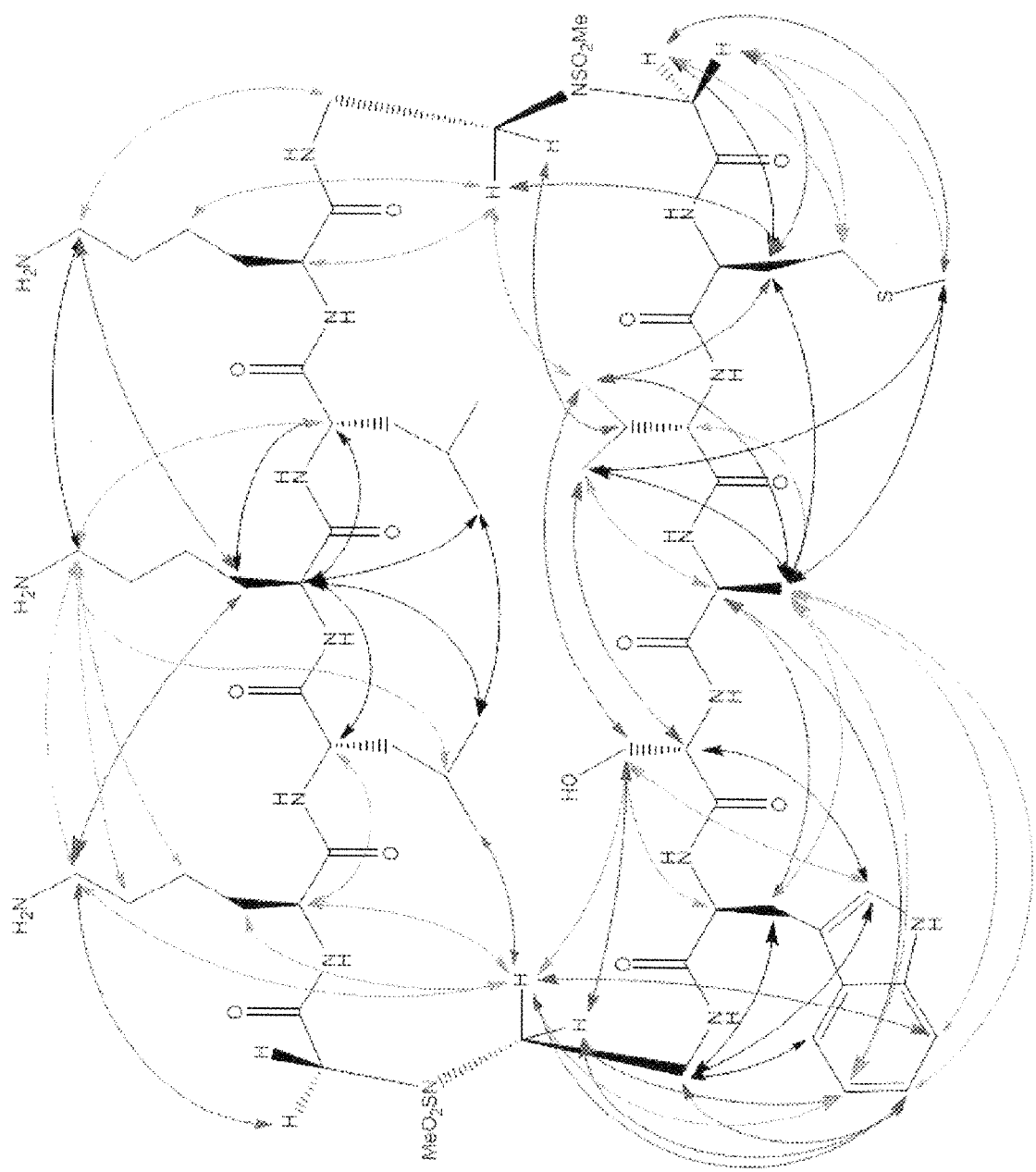
FIGS. 18A-18B are peptide 5 NOEs.
Figure 18B:
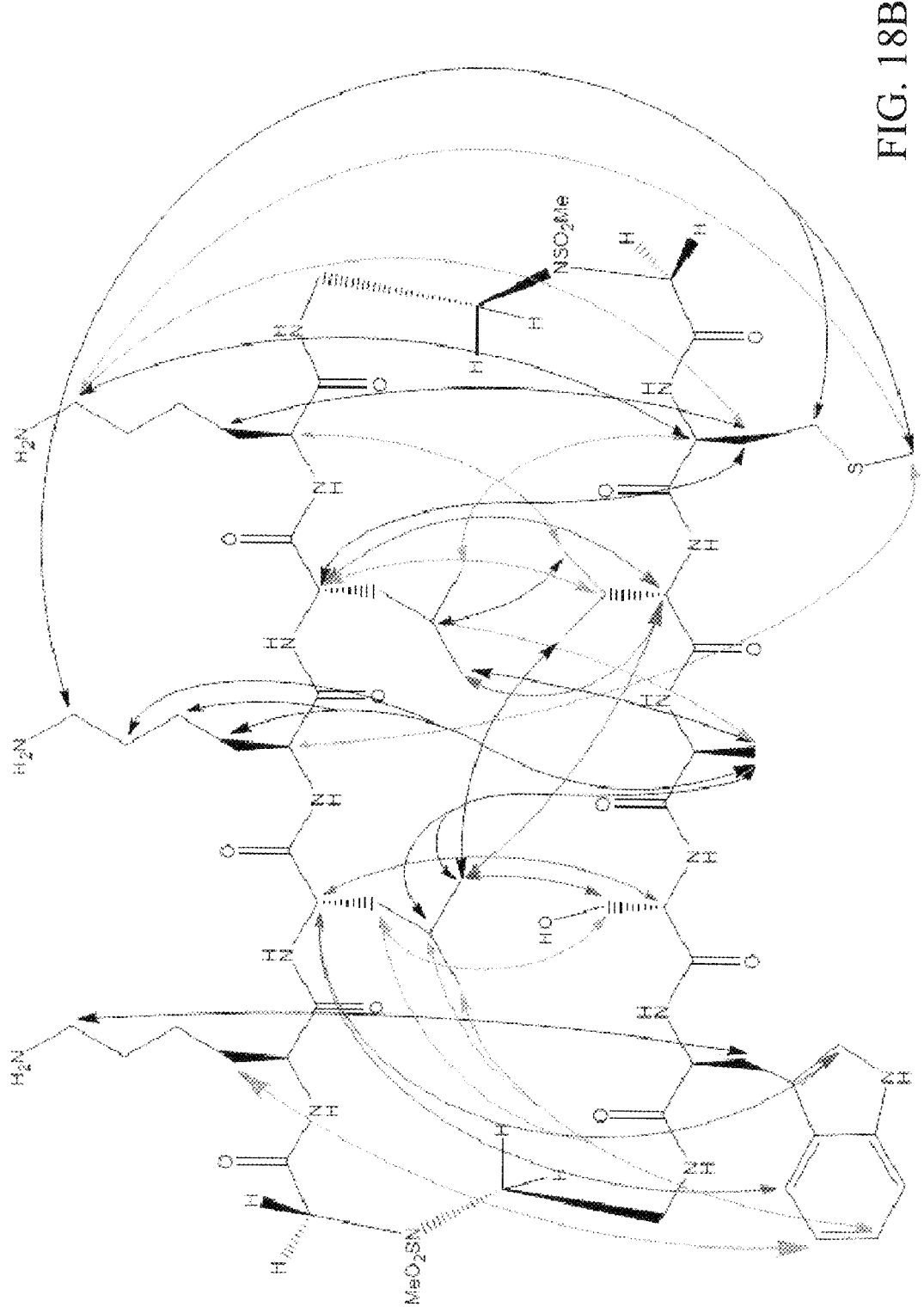

In conjunction with the chemical shifts of the α-protons, the NOE data was used to help determine the 3D structure of peptides. FIGS. 17A-B and 18A-B show the NOEs found for peptides 2 and 5, respectively. Analysis of peptide 5 was used as a general model for all the peptides. Cross-strand analysis reveals many NOEs between the Trp10 and Lys1 residues, specifically between Trp4H-LysεH, Trp5H-LysβH, Trp5H-LysεH, Trp6H-LysγH and TrpβH-LysεH to name a few. These suggest that the Tryptophan ring sits between the two strands at an angle with the indole ring facing the rest of the peptide. Additionally, peptide 2 also shows a NOE between TrpβH-LysβH, evidence that the ring spends part of its time in an alternate position between the two strands. FIGS. 17A and 17B show peptide 2 NOEs: (FIG. 17A) Same-strand NOEs; (FIG. 17B) Cross-strand NOEs. (Black=strong, Green=Medium, Red=Weak). FIGS. 18A and 18B show peptide 5. NOEs: (FIG. 18A) Same-strand NOEs; (FIG. 18B) Cross-strand NOEs. (Black=strong, Green=Medium, Red=Weak)

Chemical shift analysis supports these two Trp positions, showing that the Tryptophan ring occupies one of the two positions depending on the adjacent residues. With the exception of the $H_\alpha$'s, all of the protons in Lys1 are downfield of their respective ones in either Lys3 or Lys5 even though Lys1 is cross-strand from Trp10 which would suggest an upfield shift due to an interaction with the face of the aromatic rings. The first, and main, position Trp occupies is one that deals with those peptides that contain a Valine at residue 8. Here, the aromatic ring of Trp10 and the hydrophobic γ-methyl groups of Val8 are oriented with each other such that one face of the Tryptophan ring is interacting with the Valine via intra-pair van der Waal's contacts while the other face is interacting slightly with the Lys1 protons via cation-π interaction causing the γ-methyl's to slightly shift upfield[28,29]. This is confirmed by the chemical shifts of the Valine in position 8 because the protons interacting with the Tryptophan ring shift a certain amount upfield relative to their proximity to the Tryptophan ring as is expected due to the increased shielding from the ring. However, peptide 7 does not follow this model. While the Val8 $H_\alpha$ does shift upfield, the β and γ-protons shift downfield which means the face of the Tryptophan ring is not interacting with that Valine to the same extent as the other peptides. This downfield shift is also seen in peptide 16. In peptide 7, all of Lys3's protons shift upfield with the exception of the $H_\alpha$ and new prominent NOEs can be seen between Lys3 and Trp10. This combined with the fact that there was very little shift, up or downfield, of Lys1's protons means the faces of the Tryptophan ring are now interacting with Lys 1 and Lys3 rather than with Lys1 and Val8. This is probably due to the replacement of the Methionine with an Alanine at position 6 thus reducing the van der Waal's interactions and eliminating the hydrogen bonding between positions 3 and 6.

The second position Trp occupies is found in peptide 5, which lacks a Valine at residue 8. Here, the Tryptophan ring sits between the two strands partially over the turn and is at an angle with the indole ring facing the rest of the peptide.

In this orientation, there is less interaction between the face of the Tryptophan ring and the protons of Lys1. Therefore, the Lys1 resonances are shifted slightly downfield. Regardless of the presence or absence of a Valine at residue 8, the Lys5 and Lys3 resonances are more upfield due to interactions with each other and the Methionine.

Interestingly, peptide 5 shows only a small NOE between the $H_\alpha$'s of Leu2 and Ser9, much like the Leu4-Val7 interaction mentioned above. There are, however, a few notable NOEs between Leu2 and Ser9 which include SerβH-LeuδH, SerβH-LeuβH and SerβH-Leuβ'H. These imply that the Leucine is oriented such that the β-protons point into the β-sheet while the δ-methyl's are pointing down and away from the β-sheet. It is also important to note the chemical shift of the Serine $H_\alpha$. There is no difference in the Serine $H_\alpha$ chemical shift between peptides 1 and 5. This is due to the fact that in 1, the Robinson turn helps to keep everything in a tight β-sheet and so the Serine $H_\alpha$ is most likely artificially changed due to the Tryptophan ring current effects while in 5, the Tryptophan ring is over the turn. However, in peptides 2 and 8, the Tryptophan ring is above the Serine $H_\alpha$ shielding it and causing an upfield shift. In peptide 7, the Serine $H_\alpha$ is significantly downfield suggesting that the Tryptophan ring isn't sitting above it; this is supported by the NOE data. NOE data for peptide 16 suggests that while the Tryptophan ring is over the β-sheet, it may be in a more vertical position over Leu2 and Ala9 interacting with the Lys1 and Lys3 side chains. This possible ring orientation is supported by the downfield shift of Alanine's $H_\alpha$.

In peptide 5, the NOEs between the Ala8 and Lys3 residues are of significant intensity. The Alanine β-proton shows an NOE with the β, β', γ and δ-protons of Lys3. Although the other peptides possess a Valine at position 8, they show the same NOEs with Lys3 and some even show NOEs to Lys1 and Lys5. These cross-strand and diagonal cross-strand NOEs imply that all of the Lysine's are oriented over the β-sheet itself and that when there is a Valine in position 8, it's γ-methyl groups are aligned with the β-sheet and point in opposite directions.

The Valine in position 7 has several cross-strand NOEs, while most are with Leu4 there is one with Leu2 which is quite intense. A few of those with Leu4 include Valγ$_2$H-LeuγH, Valγ$_2$H-LeuδH, Valγ$_2$H-LeuβH, ValβH-LeuαH and ValαH-LeuδH. The NOE with Leu2 is between Valγ$_1$H and LeuδH. Although the intensity of the NOE between the $H_\alpha$'s of Val7 and Leu4 is quite low, the strengths of the NOEs just mentioned provide compelling evidence that the structure of this part of the peptide is indeed a β-sheet.

NOEs from peptide 5's Met6 describe an interesting side-chain shape and a particular orientation with Lys5. Some of these include MetεH-LysαH, Metβ'H-Lysβ'H, Metβ'H-LysεH and MetαH-LysεH. Since these residues are attached to either side of the turn, their cross-strand NOEs are proof that the turn does in fact make a β-sheet rather than a random coil. Additionally, NOEs are also observed between Met6 and Lys3. Some of the most significant ones are MetεH-LysεH, MetγH-LysεH and MetβH-LysεH. These diagonal cross-strand NOEs help to reinforce the fact that these peptides exist as β-sheets despite the lack of a strong NOE between the $H_\alpha$'s of Leu4 and Val7. These NOEs suggest that the Methionine side chain is specifically interacting with these two Lysine side chains. In addition to the standard Van der Waals interactions, weak hydrogen bonding may exist between the Methionine sulfur and the Lysine ε-NH protons holding the chains closer in space thus giving rise to more and stronger NOEs between the chains[30]. This idea is supported by the fact that when Methionine is replaced by Norleucine in 8, both the amount and the intensity of the cross-strand NOEs decrease significantly. Furthermore, both the ε and γ-methylenes of Lys5 experience a significant downfield shift upon the replacement with Norleucine. Replacing the Methionine residue with a more hydrophobic one removes the hydrogen bonding and causes a change in the side chain conformation, which is evident in peptide 8.

EXAMPLE 9

Constrained Conformation Search with MacroModel

Figure 38:
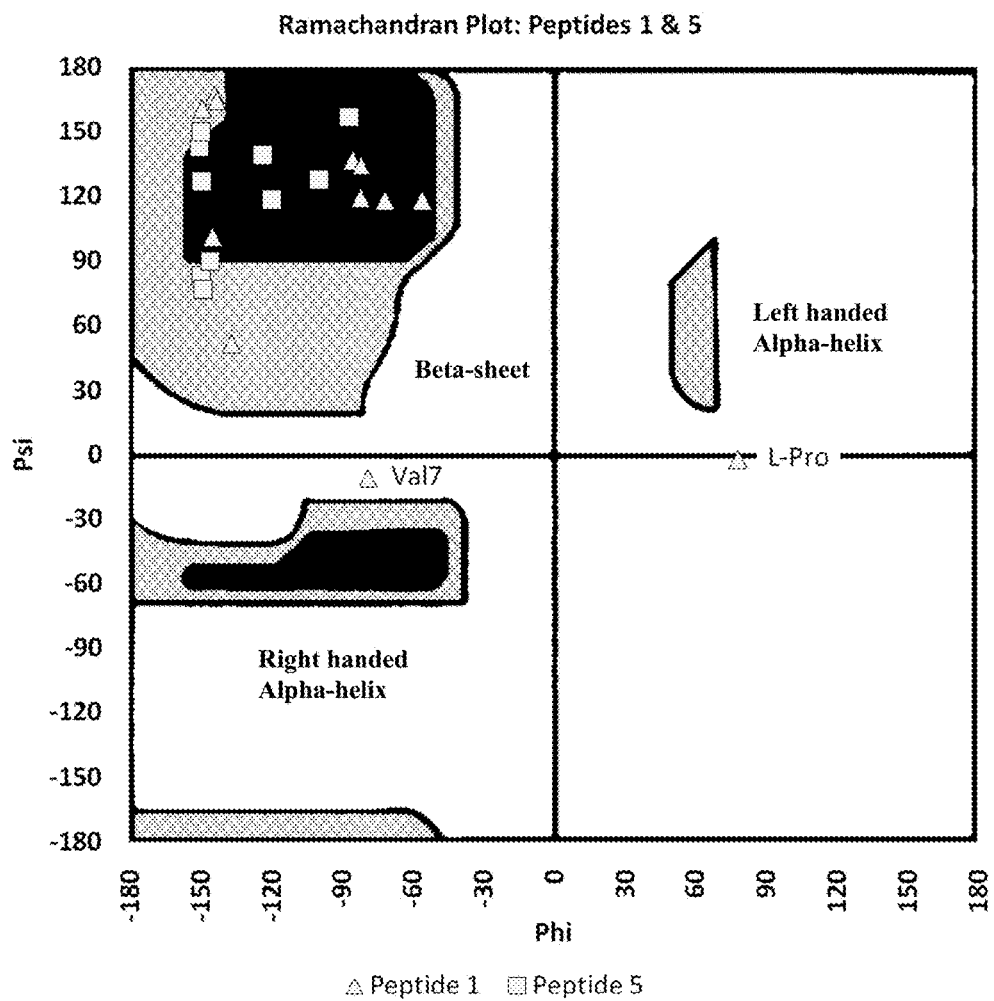
FIG. 38 shows a Ramachandran plot of peptides 1 and 5. All of the peptide 5 amino acids are in the Beta-sheet region while two amino acids (Val7, L-Pro) of peptide 1 are in the "disallowed regions."[4] The L-Pro phi/psi angles are consistent with the L-Pro phi-psi angles of the cyclic peptide structure published by Fasan et al (PDB 2AXI).[5]

Structures of peptides 1 and 5 were built with Maestro[31]. NOE-derived distance constraints were applied to optimize the peptide structures with MacroModel[32] to produce 891 and 920 structures within a 100 kJ/mol range for peptides 1 and 5, respectively. The conformations were reduced in number based on RMSD to 61 and 87 structures of which the 20 lowest energy representative structures shown in FIGS. 19A and 19B were analyzed. Both sets of calculated structures reveal a twisting of the β-hairpin structure. Further, peptide 1 has a more subtle twist close to its rigid D-Pro-L-Pro linker while the β-hairpin is more contorted near linker $T_1$. The Ramachandran plot places all phi/psi angles of peptide 5 in the β-sheet region while 2 amino acids, L-Pro and Val 7, of peptide 1 are in the disallowed region (see FIG. 38). The averaged energies offer explanation to these structural differences: solvation and electrostatics contribute 80% of the difference in the average energies of the calculated structures (see Table S9). The flexibility of the linker $T_1$ in comparison to the rigid D-Pro-L-Pro linker allow for a more solvated conformation when in solution, an entropic gain (from less ordered waters) that translates into lower electrostatic and solvation energies. Further, peptide 5 has lower stretch, bend, and torsion energies than peptide 1 accounting for less than 20% of the average energy difference (supporting information, Table S9). Overall, the average energies from the calculated structures indicate more conformational flexibility of peptide 5 over peptide 1.

Figure 19A:
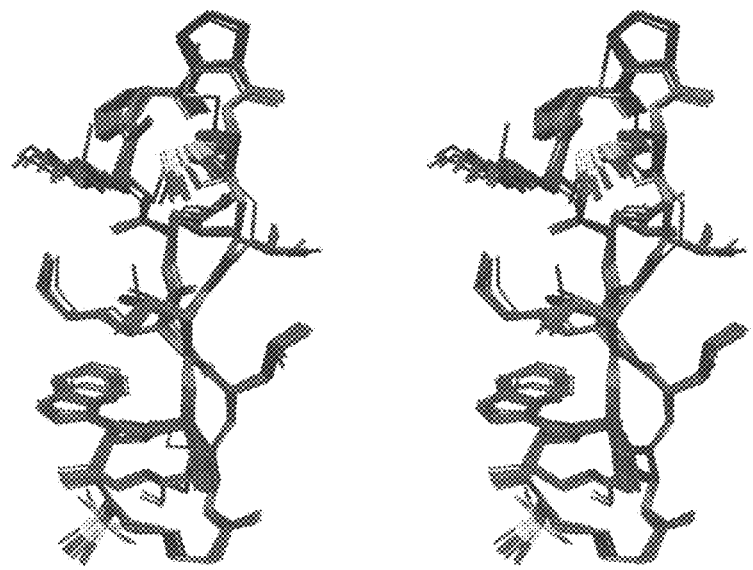
FIGS. 19A-19B are stereoviews of the 20 lowest energy structures for NOE-constrained calculated structure of peptides 1 (green carbon atoms) (19A) and 5 (gold carbon atoms) (19B). N=blue, O=red, S=yellow; hydrogens omitted for clarity. Thin wire representations prepared with Maestro.
Figure 19B:
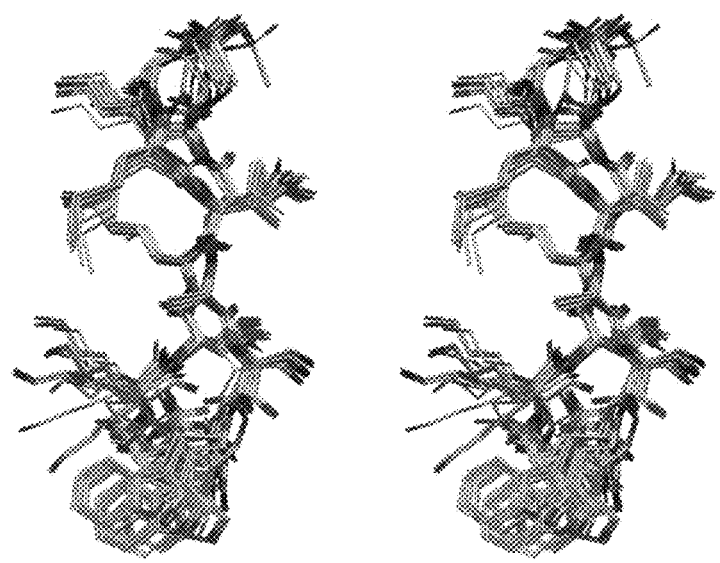

FIGS. 19A and 19B show stereoviews of the 20 lowest energy structures for NOE-constrained calculated structure of peptides 1 (green carbon atoms) and 5 (gold carbon atoms), respectively. N=blue, O=red, S=yellow; hydrogens omitted for clarity. Thin wire representations prepared with Maestro.

EXAMPLE 10

Biotin-HYD1 Interacts with CD44

The inventors used biotin-HYD1 as bait to pulldown binding complexes contained within membrane extracts of H929 MM cells. The pull down assay was directly coupled with an unbiased Mass-Spec analysis to identify HYD1 binding partners. Before performing these studies, the inventors confirmed that biotinylation of HYD1 did not inhibit the bioactivity of the compound, as the $IC_{50}$ value for biotin-HYD1 was slightly decreased in H929 cells. NeutrAvidin beads were used to reduce non-specific binding. The control sample consisted of incubating the membrane extract with biotin and subsequently subjecting the sample to NeutraAvidin beads similar to the biotin-HYD1 sample. In the 30 ug of membrane extract, the only cell surface protein that the inventors identified that was specific for the biotin-HYD1 sample was CD44. The binding experiment was repeated using 300 ug of membrane extract. In the scaled up reaction, α4 integrin, β1 integrin, NCAM and syndecan-1 were indentified by Mass-Spec analysis. As shown in FIG. 44, Western blot analysis was used to confirm that biotin-HYD1 and not biotin interacted with CD44 (antibody used is a pan CD44 antibody). The inventors next determined whether α4 integrin could be detected by western blot analysis. As shown in FIG. 45A, the inventors were able to show that α4 was present in the complex; however, stripping the blot and reprobing the membrane revealed that the Biotin-HDY1 complex contains more CD44 compared to α4 integrin (see FIG. 45B). To determine whether CD44 was indeed a direct binding partner of CD44 the inventors used recombinant CD44 and an ELISA as a readout of binding. The recombinant CD44 protein (purchased from Abnova) corresponds to Isoform 4 on Swiss Prot. The amino acid sequence is missing 224-266 and 223 is substituted S for T relative to the longest CD44 variant referred to as epican. As shown in FIG. 46, the inventors were able to capture CD44 in biotin-HYD1 NeutraAvidin coated 96-well plates. Again, Biotin-coated NetraAvidin showed relatively no binding of CD44. Collectively, these data indicate that CD44 is the likely direct binding target of CD44. Both U226 and H929 cells which are relatively sensitive to HYD1 are reported to express the CD44s (standard form) and the variant forms CD44v3 and CD44v9.

Figure 43:
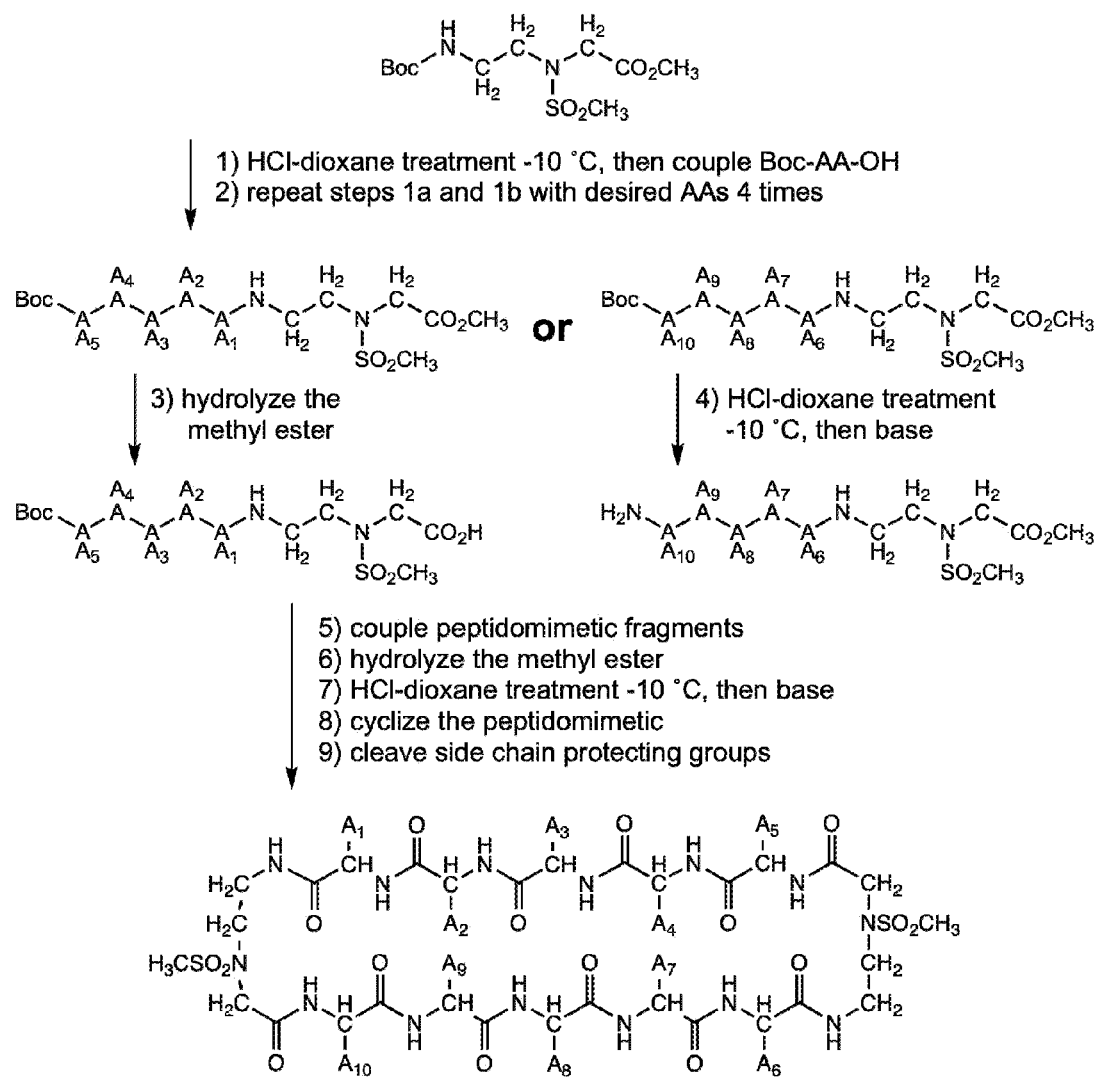
FIG. 43 is an embodiment of a synthesis scheme for cyclized peptides. The optimized recognition sequence and the non-recognition sequence are synthesized via standard solution-phase peptide synthesis techniques with a convergent fragment coupling at the beta-turn promoter carboxylate groups which cannot be racemized during fragment coupling or during cyclization. The c-HYD1 peptide is very amenable to convergent solution-phase peptide synthesis methods. The beta-turn promoters in our most active c-HYD1 analog have achiral glycine-like carboxylic acid functional groups that cannot undergo racemization and are therefore excellent sites for peptide fragment coupling, which allows a convergent synthetic approach to making the c-HYD1 analogs. The scheme in FIG. 43 is an example of a synthesis approach. Strand A1-A5 and A6-A10 can be the recognition and non-recognition sequences, respectively, or vice versa. The non-recognition sequence position A3 or A8 will have an orthogonal protecting group such as the alloc group which will allow easy derivatization with biotin, FAM1, dimerization, or oligomerization. The inventors have already determined that derivatization of that Lys group does not negatively effect bioactivity.

The inventors will verify that biotin conjugated c-HYD1 preferentially binds CD44 in myeloma compared to normal hematopoietic cells. The inventors have synthesized biotin conjugated c-HYD1 derivatives using standard solid-phase peptide synthesis methods and will scale-up synthesis using the solution-phase peptide synthesis methods shown in FIG. 43. The inventors will use this reagent to verify that c-HYD1 increases the affinity and specificity for CD44 in MM cell lines compared to normal peripheral blood mononuclear cells. The inventors anticipate that biotin-c-HYD1 will pull down CD44v in MM cell lines but not in membrane extracts obtained from normal mononuclear cells. The c-HYD1 peptide is very amenable to convergent solution-phase peptide synthesis methods. The beta-turn promoters in our most active c-HYD1 analog have achiral glycine-like carboxylic acid functional groups that cannot undergo racemization and are therefore excellent sites for peptide fragment coupling, which allows a convergent synthetic approach to making the c-HYD1 analogs. The scheme in FIG. 43 shows our proposed approach.

Strand A1-A5 and A6-A10 can be the recognition and non-recognition sequences, respectively, or vice versa. The non-recognition sequence position A3 or A8 will have an orthogonal protecting group such as the alloc group which will allow easy derivatization with biotin, FAM1, dimerization, or oligomerization. The inventors have determined that derivatization of that Lys group does not negatively effect bioactivity.

TABLE S1

Analytical Data for cyclic III peptides

| Peptide | Sequence | SEQ ID NO: | Purity % | HPLC Retention Time (min) | MALDI-TOF Data (m/z) |
|---|---|---|---|---|---|
| 1 | KLKLKT$_2$MVVSWT$_1$ | 1 | 95 | 24.71 | 1585.962 |
| 2 | KLKLKT$_1$MVVSWT$_1$ | 2 | 98 | 25.4 | 1569.488 |
| 3 | KLKLKT$_1$MVVSAT$_1$ | 3 | ND | ND | 1455.166 |
| 4 | KLKLKT$_1$MVVAWT$_1$ | 4 | 99 | 25.29 | 1544.208 |
| 5 | KLKLKT$_1$MVASWT$_1$ | 5 | 99 | 30.45 | 1542.172 |
| 6 | KLKLKT$_1$MAVSWT$_1$ | 6 | ND | ND | 1542.240 |
| 7 | KLKLKT$_1$AVVSWT$_1$ | 7 | 93 | 23.64 | 1510.291 |
| 8 | KLKLKT$_1$N*VVSWT$_1$ | 8 | 95 | 26.93 | 1552.286 |
| 9 | KLKLKT$_1$N*VVYWT$_1$ | 9 | 99 | 26.52 | 1628.341 |
| 10 | KLKLKT$_1$WSVVMT$_1$ | 10 | 93 | 23.21 | 1572.091 |
| 11 | KLKLKT$_1$WAVVN*T$_1$ | 11 | 98 | 25.13 | 1536.172 |
| 12 | KLKLKT$_1$WAVVAT$_1$ | 12 | 84 | 24.11 | 1494.242 |
| 13 | KLKLKT$_1$WAVAN*T$_1$ | 13 | 97 | 25.93 | 1508.098 |
| 14 | KLKLKT$_1$WAAVN*T$_1$ | 14 | 87 | 23.52 | 1508.200 |
| 15 | KLKLKT$_1$AAVVN*T$_1$ | 15 | 91 | 25.96 | 1421.254 |
| 16 | KLKLKT$_1$N*VVAWT$_3$ | 16 | 98 | 25.68 | 1499.181 |
| 17 | KLKQKT$_1$N*VVAWT$_3$ | 17 | 97 | 34.62 | 1499.313 |
| 18 | QLKLKT$_1$N*VVAWT$_3$ | 18 | 90 | 30.15 | 1499.100 |
| 19 | KLKLQT$_1$N*VVAWT$_3$ | 19 | 97 | 29.74 | 1615.162 |
| 20 | KQKLKT$_1$N*VVAWT$_3$ | 20 | 87 | 29.97 | 1514.242 |
| 21 | KLKQKT$_1$N*VVAWT$_3$ | 21 | 90 | 29.99 | 1301.070 |
| 22 | KLKLKT$_3$WAVVN*T$_3$ | 22 | 93 | 27.54 | 1462.073 |
| 23 | KXKXKT$_3$WAVVN*T$_3$ | 23 | 86 | 19.69 | 1378.046 |
| 24 | KLKLKT$_1$N*VLAWT$_3$ | 24 | 91 | 35.33 | 1513.344 |
| 25 | KLKLKT$_1$N*VIAWT$_3$ | 25 | 93 | 34.98 | 1513.375 |
| 26 | KLKLKT$_1$N*VFAWT$_3$ | 26 | 97 | 36.05 | 1547.507 |

TABLE S2

NMR assignments for peptide 1

|  | α | β | γ | δ | ε |
|---|---|---|---|---|---|
| L-Pro-T$_2$ | 4.531 | 2.219, 2.111 | 2.077, 1.940 | 3.949, 3.705 |  |
| D-Pro-T$_2$ | 4.741 | 2.287, 2.155 | 2.004, 1.896 | 3.793, 3.539 |  |
| Lys-1 | 4.379 | 1.784, 1.745 | 1.403 | 1.667 | 2.977 |
| Leu-2 | 4.536 | 1.569 | 1.505 | 0.812, 0.811 |  |
| Lys-3 | 4.291 | 1.794, 1.667 | 1.403, 1.261 | 1.564 | 2.947 |
| Leu-4 | 4.985 | 1.730 | 1.530 | 0.851, 0.777 |  |
| Lys-5 | 4.541 | 1.789, 1.662 | 1.349, 1.242 | 1.564 | 2.864 |
| Linker T$_1$ | 3.563$^S$, 3.866$^R$ |  | 3.348 | 3.162 | SO$_2$Me = 3.030 |
| Met-6 | 4.482 | 2.107 | 2.551, 2.434 |  | 2.121 |
| Val-7 | 4.130 | 1.940 | 0.875, 0.665 |  |  |

TABLE S2-continued

| | NMR assignments for peptide 1 | | | | |
|---|---|---|---|---|---|
| | α | β | γ | δ | ε |
| Val-8 | 4.267 | 1.989 | 0.880, 0.802 | | |
| Ser-9 | 4.599 | 3.837 | | | |
| Trp-10 | 4.692 | 3.226, 3.128 | 7.121, 7.146, 7.229, 7.473, 7.561 | (5H, 2H, 6H, 7H, 4H) | |

TABLE S3

| | NMR assignments for peptide 2 | | | | |
|---|---|---|---|---|---|
| | α | β | γ | δ | ε |
| Lys-1 | 4.262 | 1.823, 1.774 | 1.432, 1.402 | 1.642 | 2.976 |
| Leu-2 | 4.349 | 1.554 | 1.427 | 0.782, 0.767 | |
| Lys-3 | 4.076 | 1.759, 1.642 | 1.373, 1.285 | 1.588 | 2.874 |
| Leu-4 | 4.281 | 1.945 | 1.622 | 0.923, 0.845 | |
| Lys-5 | 4.574 | 1.765, 1.657 | 1.286 | 1.589 | 2.879 |
| Met-6 | 4.643 | 2.155, 1.989 | 2.575, 2.522 | | 2.072 |
| Val-7 | 4.662 | 1.637 | 0.874, 0.801 | | |
| Val-8 | 4.320 | 1.911 | 0.816, 0.772 | | |
| Ser-9 | 4.462 | 3.778 | | | |
| Trp-10 | 4.701 | 3.172 | 7.140, 7.121, 7.238, 7.473, 7.590 | (5H, 2H, 6H, 7H, 4H) | |

TABLE S4

| | NMR assignments for peptide 5 | | | | |
|---|---|---|---|---|---|
| | α | β | γ | δ | ε |
| Linker T$_1$ | 3.891$^S$, 4.062$^R$ | | 3.500$^S$, 3.612$^R$ | 3.236 | SO$_2$Me = 3.045 |
| Lys-1 | 4.311 | 1.823 | 1.452 | 1.691 | 2.996 |
| Leu-2 | 4.160 | 1.525, 1.418 | 1.359 | 0.768, 0.645 | |
| Lys-3 | 4.072 | 1.740, 1.613 | 1.281, 1.149 | 1.506 | 2.776 |
| Leu-4 | 4.042 | 1.994 | 1.955 | 0.929, 0.904 | |
| Lys-5 | 4.423 | 1.770, 1.657 | 1.305 | 1.589 | 2.879 |
| Linker T$_2$ | 3.465$^S$, 4.047$^R$ | | 3.490$^S$, 3.529$^R$ | 3.334 | SO$_2$Me = 3.050 |
| Met-6 | 4.599 | 2.234, 1.999 | 2.664, 2.532 | | 2.077 |
| Val-7 | 4.575 | 1.618 | 0.924, 0.797 | | |
| Ala-8 | 4.531 | 1.183 | | | |
| Ser-9 | 4.599 | 3.822, 3.720 | | | |
| Trp-10 | 4.609 | 3.206, 3.123 | 7.151, 7.160, 7.239, 7.473, 7.654 | (5H, 2H, 6H, 7H, 4H) | |

TABLE S5

| | NMR assignments for peptide 7 | | | | |
|---|---|---|---|---|---|
| | α | β | γ | δ | ε |
| Lys-1 | 4.438 | 1.823, 1.779 | 1.423 | 1.662 | 2.977 |
| Leu-2 | 4.311 | 1.946 | 1.892 | 0.836, 0.763 | |
| Lys-3 | 4.081 | 1.750, 1.638 | 1.339, 1.261 | 1.555 | 2.845 |
| Leu-4 | 4.282 | 1.540 | 1.427 | 0.787, 0.768 | |
| Lys-5 | 4.516 | 1.745, 1.647 | 1.291 | 1.564 | 2.869 |
| Ala-6 | 4.419 | 1.383 | | | |
| Val-7 | 4.629 | 1.623 | 0.865, 0.792 | | |
| Val-8 | 4.184 | 1.950 | 0.934, 0.860 | | |
| Ser-9 | 4.697 | 3.803, 3.754 | | | |
| Trp-10 | 4.668 | 3.172, 3.153 | 7.146, 7.141, 7.244, 7.478, 7.615 | (5H, 2H, 6H, 7H, 4H) | |

TABLE S6

NMR assignments for peptide 8

| | α | β | γ | δ | ε |
|---|---|---|---|---|---|
| Lys-1 | 4.287 | 1.799, 1.691 | 1.437, 1.379 | 1.623 | 2.943 |
| Leu-2 | 4.292 | 1.579 | 1.467 | 0.821, 0.807 | |
| Lys-3 | 4.086 | 1.750, 1.682 | 1.369, 1.266 | 1.584 | 2.869 |
| Leu-4 | 4.375 | 1.985 | 1.618 | 0.914, 0.836 | |
| Lys-5 | 4.590 | 1.731, 1.638 | 1.388, 1.310 | 1.589 | 2.943 |
| Nor-6 | 4.453 | 1.794 | 1.711 | 1.276 | 0.851 |
| Val-7 | 4.673 | 2.038 | 0.895, 0.880 | | |
| Val-8 | 4.639 | 1.589 | 0.861, 0.811 | | |
| Ser-9 | 4.453 | 3.802 | | | |
| Trp-10 | 4.595 | 3.246, 3.207 | 7.112, 7.141, 7.239, 7.483, 7.581 | (2H, 5H, 6H, 7H, 4H) | |

TABLE S7

NMR assignments for peptide 10

| | α | β | γ | δ | ε |
|---|---|---|---|---|---|
| Lys-1 | 4.174 | 1.770, 1.652 | 1.345 | 1.379 | 2.967 |
| Leu-2 | 4.531 | 1.657 | 1.535 | 0.895, 0.851 | |
| Lys-3 | 4.052 | 1.731, 1.608 | 1.354 | 1.535 | 2.943 |
| Leu-4 | 4.365 | 1.633 | 1.525 | 0.905, 0.875 | |
| Lys-5 | 4.345 | 1.819, 1.770 | 1.437, 1.393 | 1.687 | 2.977 |
| Trp-6 | 4.834 | 3.436, 3.212 | 7.141, 7.234, 7.268, 7.493, 7.630 | (5H, 6H, 2H, 7H, 4H) | |
| Ser-7 | 4.512 | 3.774, 3.754 | | | |
| Val-8 | 4.517 | 1.496 | 0.816, 0.782 | | |
| Val-9 | 4.096 | 2.009 | 0.939, 0.924 | | |
| Met-10 | 4.453 | 2.048, 1.941 | 2.562, 2.498 | | 2.083 |

TABLE S8

NMR assignments for peptide 16

| | α | β | γ | δ | ε |
|---|---|---|---|---|---|
| Prolinol-T$_1$ | 4.232 | 3.426 | 1.544 | 1.754 | α-CH$_2$—O: 3.704 |
| O—CH$_2$—CO | 4.022$^S$, 3.978$^R$ | | | | |
| Lys-1 | 4.550 | 1.994, 1.935 | 1.525, 1.495 | 1.730 | 3.010 |
| Leu-2 | 4.780 | 1.725, 1.642 | 1.427 | 0.889, 0.792 | |
| Lys-3 | 4.320 | 1.852, 1.759 | 1.393, 1.344 | 1.627 | 2.918 |
| Leu-4 | 4.634 | 1.701 | 1.564 | 0.831, 0.816 | |
| Lys-5 | 4.169 | 1.828, 1.715 | 1.422, 1.383 | 1.661 | 2.971 |
| Linker T$_2$ | 3.944$^S$, 4.076$^R$ | | 3.538$^S$, 3.445$^R$ | 3.284 | SO$_2$Me = 3.064 |
| Nor-6 | 4.340 | 1.720 | 1.647 | 1.281 | 0.860 |
| Val-7 | 4.442 | 2.106 | 0.938, 0.928 | | |
| Val-8 | 4.545 | 1.950 | 0.933, 0.875 | | |
| Ala-9 | 4.697 | 1.285 | | | |
| Trp-10 | 5.054 | 3.309, 2.952 | 7.223, 7.175, 7.258, 7.497, 7.658 | (5H, 6H, 2H, 7H, 4H) | |

TABLE S8

NOE-derived constraints and statistics of NMR structure calculations for peptides 1 and 5.

| | Peptide 1 | Peptide 5 |
|---|---|---|
| NOE upper-distance limits | 40 | 40 |
| Intraresidue | 7 | 3 |
| Sequential | 12 | 6 |
| Dihedral angle restraints (HN—C=O) | 13 | 12 |
| Mean RMSD values (Å) | | |
| Backbone atoms | 0.14 ± 0.08 | 0.45 ± 0.11 |
| Heavy atoms | 0.30 ± 0.18 | 0.72 ± 0.23 |

TABLE S9

Energies for calculated structures of peptides 1 & 5 (kJ/mol)

| | Difference | %$_{Diff.}$[a] | Peptide 1 | Peptide 5 |
|---|---|---|---|---|
| Force Field | −355.91 | 56% | −851.684 | −1207.6 |
| Stretch | −8.63 | 1% | 28.68 | 20.05 |
| Bend | −45.21 | 7% | 127.12 | 81.91 |
| Torsion | −61.43 | 10% | 166.57 | 105.14 |
| Improper Torsion | 2.08 | 0% | 4.91 | 7.00 |
| VDW | −11.62 | 2% | −112.20 | −123.82 |
| Electrostatic | −234.96 | 37% | −1066.77 | −1301.73 |
| Solvation | −274.66 | 43% | −1337.53 | −1612.19 |
| Total | −633.91 | | −2189.22 | −2823.13 |

[a]Percent difference based on average total energy difference.

ADDITIONAL REFERENCES

DeRoock, I. B., Sroka, T. C., Lam, T., Bair, E. L., Cress, A. E. *Cancer Research,* 61, 3308-3313 (2001).

Sroka, T. C., Penningtion, M. E., Cress, A. E. *Carcinogenesis,* 27(9), 1748-1757 (2006).

Nair R N, Mr. Emmons M F, Cress A E, Argilagos R F, Lam K, Kerr W, Wang H G, Dalton W S, Hazlehurst L A Molecular Cancer Therapeutics. 2009; 8(8):2441-51.

The disclosures of all publications cited above are expressly incorporated herein by reference, each in its entirety, to the same extent as if each were incorporated by reference individually.

Pennington, M. E.; Lam, K. S.; Cress, A. E., The use of a combinatorial library method to isolate human tumor cell adhesion peptides. *Mol. Diversity* 1996, 2 (1/2), 19-28.

Sroka Thomas, C.; Marik, J.; Pennington Michael, E.; Lam Kit, S.; Cress Anne, E., The minimum element of a synthetic peptide required to block prostate tumor cell migration. *Cancer Biol Ther* 2006, 5 (11), 1556-62.

Sroka Thomas, C.; Pennington Michael, E.; Cress Anne, E., Synthetic D-amino acid peptide inhibits tumor cell motility on laminin-5. *Carcinogenesis* 2006, 27 (9), 1748-57.

Chorev, M.; Goodman, M., A dozen years of retro-inverso peptidomimetics. *Acc. Chem. Res.* 1993, 26 (5), 266-73.

Fletcher, M. D.; Campbell, M. M., Partially Modified Retro-Inverso Peptides: Development, Synthesis and Conformational Behavior. *Chem. Rev.* (Washington, D.C.) 1998, 98 (2), 763-795.

Nair, D. T.; Kaur, K. J.; Singh, K.; Mukherjee, P.; Raj agopal, D.; George, A.; Bal, V.; Rath, S.; Rao, K. V. S.; Salunke, D. M., Mimicry of native peptide antigens by the corresponding retro-inverso analogs is dependent on their intrinsic structure and interaction propensities. *J. Immunol.* 2003, 170 (3), 1362-1373.

Taylor, E. M.; Otero, D. A.; Banks, W. A.; O'Brien, J. S., Retro-inverso prosaptide peptides retain bioactivity, are stable in vivo, and are blood-brain barrier permeable. *J. Pharmacol. Exp. Ther.* 2000, 295 (1), 190-194.

DeRoock, I. B.; Pennington, M. E.; Sroka, T. C.; Lam, K. S.; Bowden, G. T.; Bair, E. L.; Cress, A. E., Synthetic peptides inhibit adhesion of human tumor cells to extracellular matrix proteins. *Cancer Res.* 2001, 61 (8), 3308-3313.

Ficht, S.; Payne, R. J.; Guy, R. T.; Wong, C.-H., Solid-phase synthesis of peptide and glycopeptide thioesters through side-chain-anchoring strategies. *Chemistry—A European Journal* 2008, 14 (12), 3620-3629.

Crimmins, M. T.; Zuercher, W. J Solid-phase synthesis of carbocyclic nucleosides. *Organic letters* 2000, 2 (8), 1065-7.

Dressman, B. A.; Spangle, L. A.; Kaldor, S. W., Solid phase synthesis of hydantoins using a carbamate linker and a novel cyclization/cleavage step. *Tetrahedron Letters* 1996, 37 (7), 937-40.

His, S.; Meyer, C.; Cossy, J.; Emeric, G.; Greiner, A., Solid phase synthesis of amides by the Beckmann rearrangement of ketoxime carbonates. *Tetrahedron Letters* 2003, 44 (47), 8581-8584.

Meester, W. J. N.; Rutjes, F. P. J. T.; Hermkens, P. H. H.; Hiemstra, H., Synthesis of homoallylic amines via N-acyliminium ion reactions on solid support. *Tetrahedron Letters* 1999, 40 (8), 1601-1604.

Park, K.-H.; Cox, L. J., Solid-phase synthesis of 1,2,4-triazolidine-3,5-diones. *Tetrahedron Letters* 2002, 43 (21), 3899-3901.

Rabinowitz, M.; Seneci, P.; Rossi, T.; Dal Cin, M.; Deal, M.; Terstappen, G., Solid-phase/solution-phase combinatorial synthesis of neuroimmunophilin ligands. *Bioorganic & Medicinal Chemistry Letters* 2000, 10 (10), 1007-1010.

Wang, C.-C.; Li, W.-R., Traceless Solid-Phase Synthesis of Substituted Benzimidazolones. *Journal of Combinatorial Chemistry* 2004, 6 (6), 899-902.

Wang, P.; Miranda, L. P., Fmoc-protein synthesis: preparation of peptide thioesters using a side-chain anchoring strategy. *International Journal of Peptide Research and Therapeutics* 2005, 11 (2), 117-123.

Thomson, S. A.; Josey, J. A.; Cadilla, R.; Gaul, M. D.; Hassman, C. F.; Luzzio, M. J.; Pipe, A. J.; Reed, K. L.; Ricca, D. J.; et al., Fmoc mediated synthesis of peptide nucleic acids. *Tetrahedron* 1995, 51 (22), 6179-94.

Kuwahara, M.; Arimitsu, M.; Shigeyasu, M.; Saeki, N.; Sisido, M., Hybridization between Oxy-Peptide Nucleic Acids and DNAs: Dependence of Hybrid Stabilities on the Chain-Lengths, Types of Base Pairs, and the Chain Directions. *J. Am. Chem. Soc.* 2001, 123 (20), 4653-4658.

Kuwahara, M.; Arimitsu, M.; Sisido, M., Synthesis of delta-amino acids with an ether linkage in the main chain and nucleobases on the side chain as monomer units for oxy-peptide nucleic acids. *Tetrahedron* 1999, 55 (33), 10067-10078.

Creighton, T. E. *Protein: Structures and Molecular Properties,* 2nd ed.; W. H.Freeman and Co.: New York, 1993.

Tilstra, L.; Mattice, W. L. In *Circular Dichroism and the Conformational Analysis of Biomolecule.* Fasman, G. D. ed; Plenum Press: New York, 1996.

Wishart, D. S.; Sykes, B. D.; Richards, F. M., The chemical shift index: a fast and simple method for the assignment of protein secondary structure through NMR spectroscopy. *Biochemistry* 1992, 31 (6), 1647-51.

Wishart, D. S.; Sykes, B. D.; Richards, F. M., Relationship between nuclear magnetic resonance chemical shift and protein secondary structure. *Journal of Molecular Biology* 1991, 222 (2), 311-33.

Favre, M.; Moehle, K.; Jiang, L.; Pfeiffer, B.; Robinson, J. A., Structural Mimicry of Canonical Conformations in Antibody Hypervariable Loops Using Cyclic Peptides Containing a Heterochiral Diproline Template. *Journal of the American Chemical Society* 1999, 121 (12), 2679-2685.

Bertrand, R. D.; Compton, R. D.; Verkade, J. G., Unusual behavior of hexafluorobenzene and benzene in the aromatic nuclear magnetic resonance shift effect. *J. Amer. Chem. Soc.* 1970, 92 (9), 2702-9.

Yamamoto, Y.; Iwafune, K.; Nanai, N.; Osawa, A.; Chujo, R.; Suzuki, T., NMR study of *Galeorhinus japonicus* myoglobin. Proton NMR study of molecular structure of the heme cavity. *European Journal of Biochemistry* 1991, 198 (2), 299-306.

Hutchinson, E. G.; Sessions, R. B.; Thornton, J. M.; Woolfson, D. N., Determinants of strand register in antiparallel beta-sheets of proteins. *Protein Science* 1998, 7 (11), 2287-2300.

Hughes, R. M.; Waters, M. L., Influence of N-Methylation on a Cation-pi Interaction Produces a Remarkably Stable beta-Hairpin Peptide. *Journal of the American Chemical Society* 2005, 127 (18), 6518-6519.

Zhou, P.; Tian, F.; Lv, F.; Shang, Z. *Proteins Struct. Funct. Bioinf.* 2009, 76, 151-163.

Maestro, 8.5 ed.; Schrödinger, LLC: New York, N.Y., 2008.

MacroModel, 9.8 ed.; Schödinger, LLC: New York, N.Y., 2010.

Wüthrich, K. *NMR of Proteins and Nucleic Acids*; Wiley-Interscience Publication: New York, 1986.

Maestro, 8.5 ed.; Schrödinger, LLC: New York, N.Y., 2008.

MacroModel, 9.8 ed.; Schödinger, LLC: New York, N.Y., 2010.

Halgren, T. A.; Murphy, R. B.; Jorgensen, W. L.; Friesner, R. A. *Abstracts of Papers of the American Chemical Society* 2000, 220, 2.

Fasan, R.; Dias, R. L.; Moehle, K.; Zerbe, O.; Obrecht, D.; Mittle, P. R.; Grütter, M. G.; Robinson, J. A. *Chembiochem.* 2006, 7, 515.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

---

We claim:

1. A method of treating multiple myeloma or lung cancer in a subject, comprising administering an effective amount of a cyclic compound and at least one other anti-cancer agent to the subject, wherein the cyclic compound comprises a recognition sequence and a non-recognition sequence, wherein said recognition sequence is joined to said non-recognition sequence by a first linker and a second linker, wherein said non-recognition sequence is five amino acids selected from KLKLK (SEQ ID NO:27), KLQLK (SEQ ID NO:28), QLKLK (SEQ ID NO:29), KLKLQ (SEQ ID NO:281), KQKLK (SEQ ID NO:30), KLKQK (SEQ ID NO:282), KXKXK (SEQ ID NO:31), or ELKLK (SEQ ID NO:32), where X=sarcosine and said recognition sequence is five amino acids selected from MVVSW (SEQ ID NO:33), MVVSA (SEQ ID NO:34), MVVAW (SEQ ID NO:35), MVASW (SEQ ID NO:36), MAVSW (SEQ ID NO:37), AVVSW (SEQ ID NO:38), N*VVSW (SEQ ID NO:39), N*VVYW (SEQ ID NO:40), N*VVAW (SEQ ID NO:41), AVVAW (SEQ ID NO:42), N*AVAW (SEQ ID NO:43), N*VAAW (SEQ ID NO:44), N*VLAW (SEQ ID NO:45), N*VIAW (SEQ ID NO:46), N*VFAW (SEQ ID NO:47), or WSVVW (SEQ ID NO:48), where N*=norleucine, and where said first linker and said second linker are independently selected from the structures:

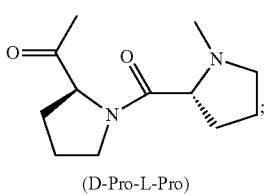

(D-Pro-L-Pro)

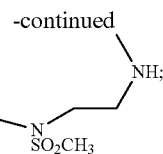

(methylsulfonamido aminoethylglcine) or

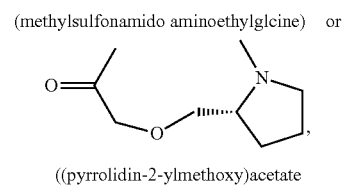

((pyrrolidin-2-ylmethoxy)acetate wherein no more than one of said first linker and said second linker is D-Pro-L-Pro.

2. The method of claim 1, wherein the at least one other anti-cancer agent comprises a cytotoxic agent, chemotherapeutic agent, or anti-signaling agent.

3. The method of claim 1, wherein the at least one other anti-cancer agent comprises bortezomib, or a pharmaceutically acceptable salt thereof.

4. The method of claim 1, wherein the cyclic compound has one of the following structures:

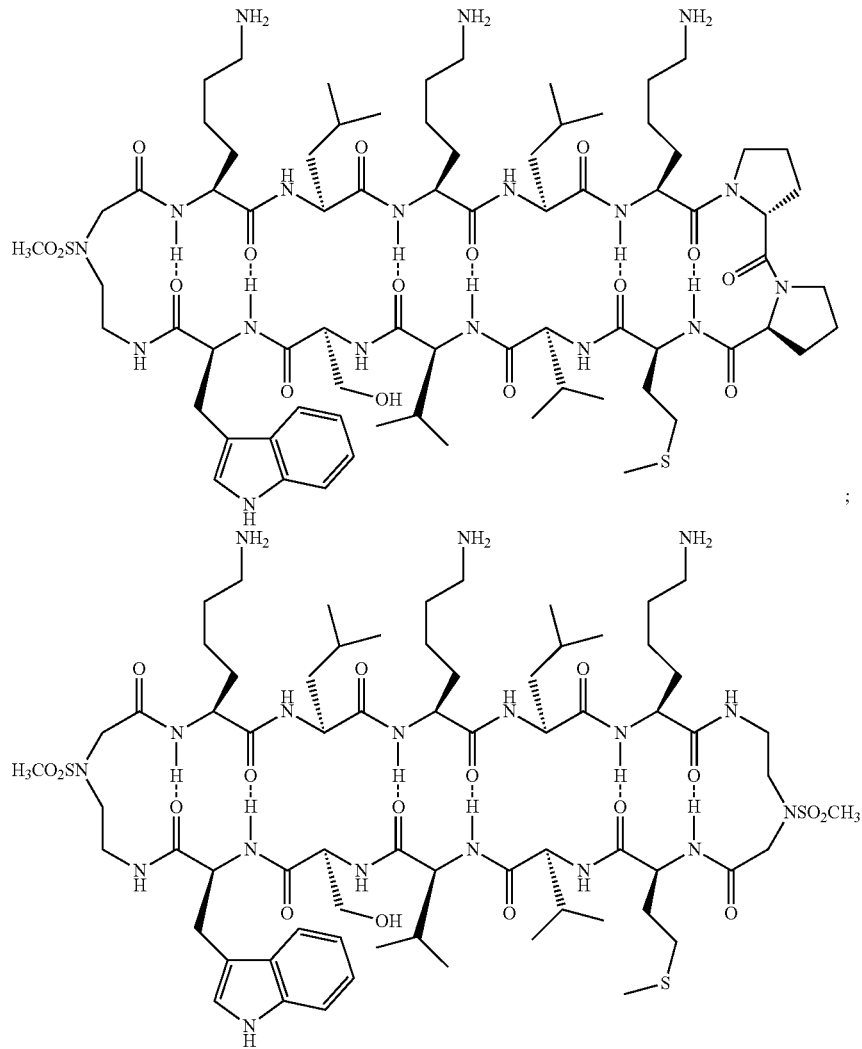

-continued
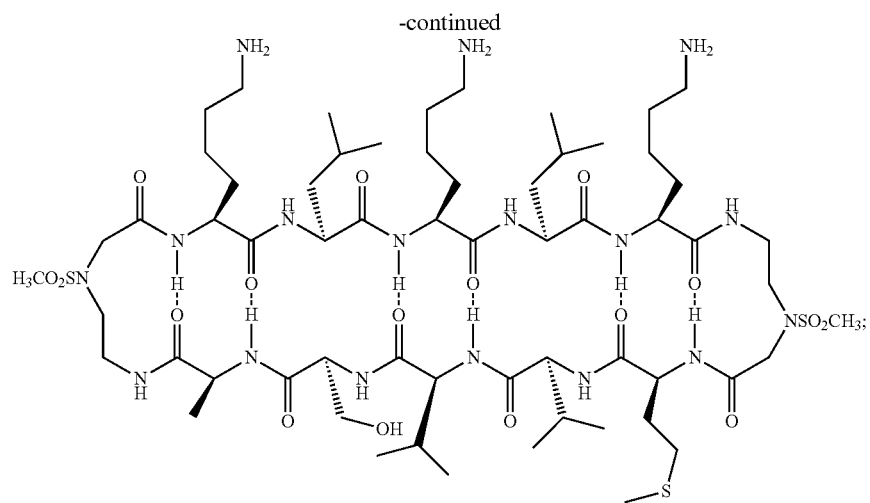
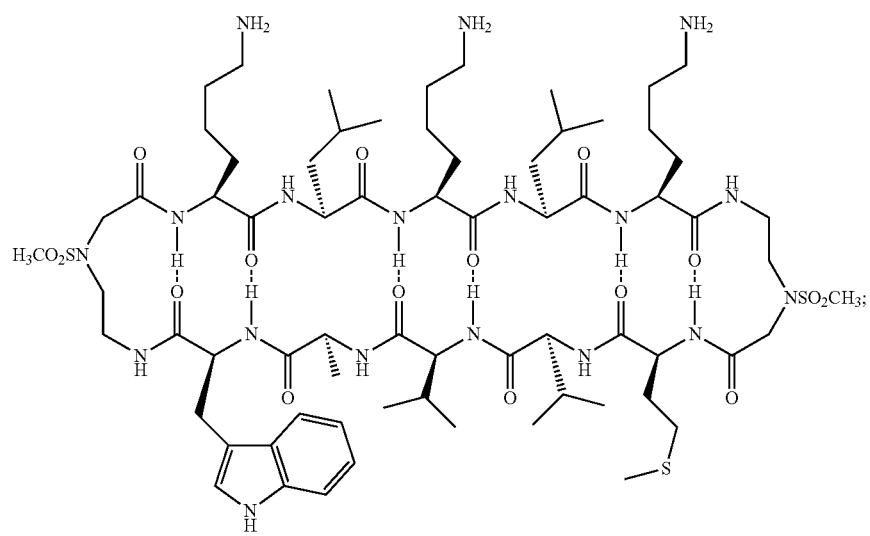
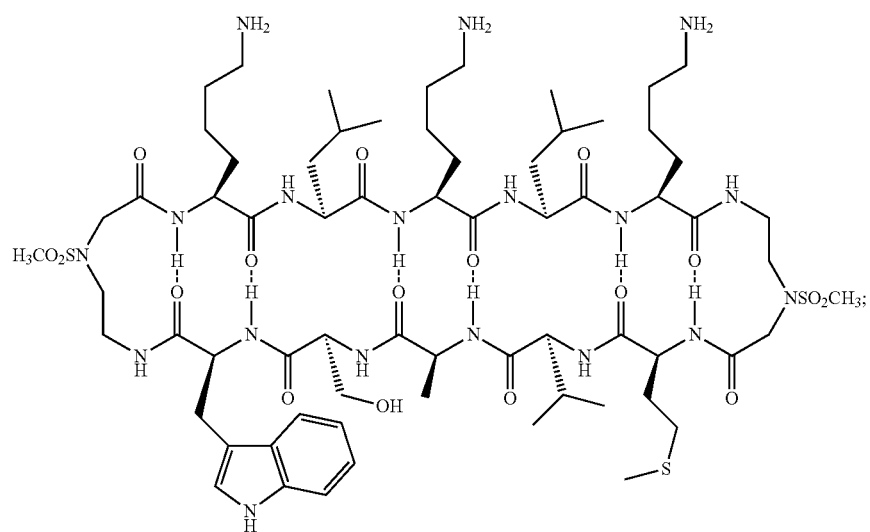

-continued
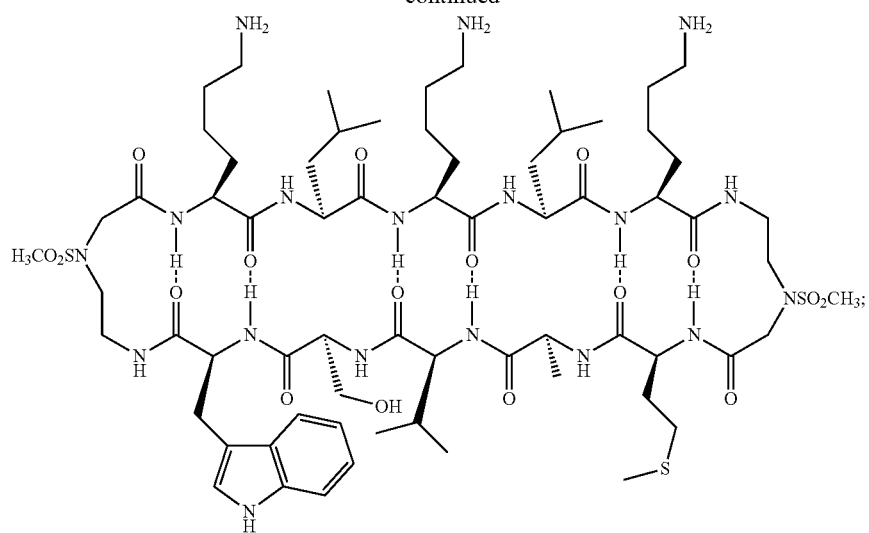
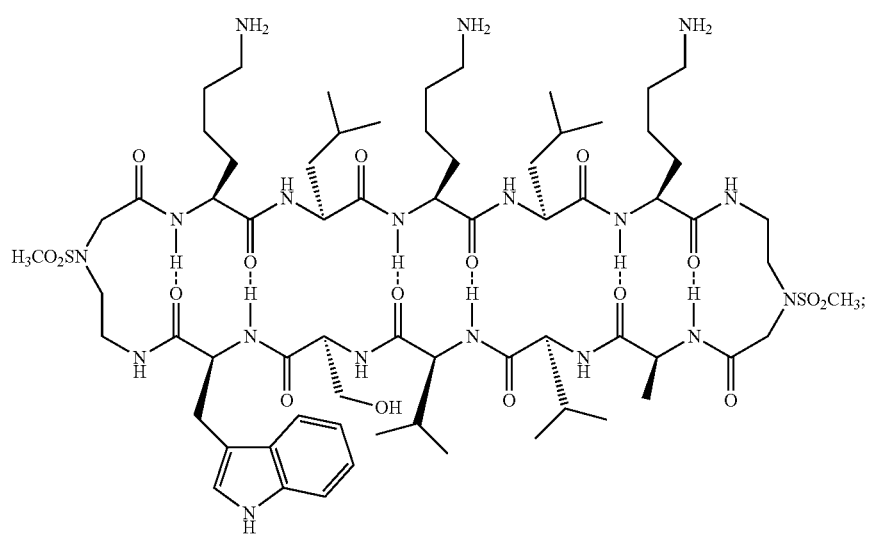
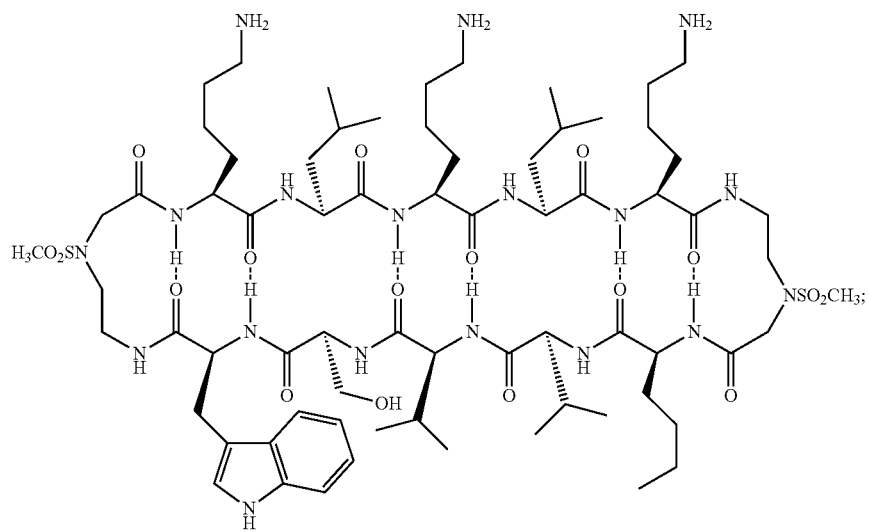

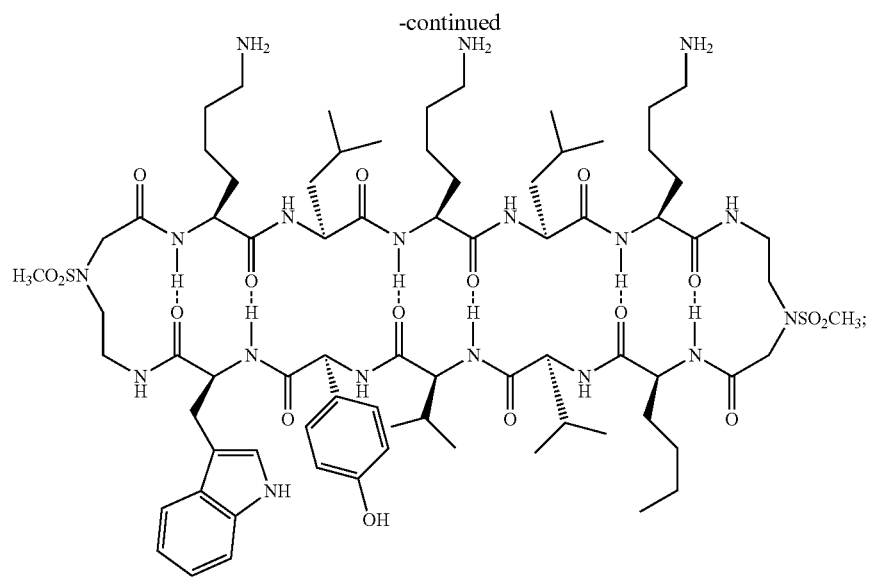
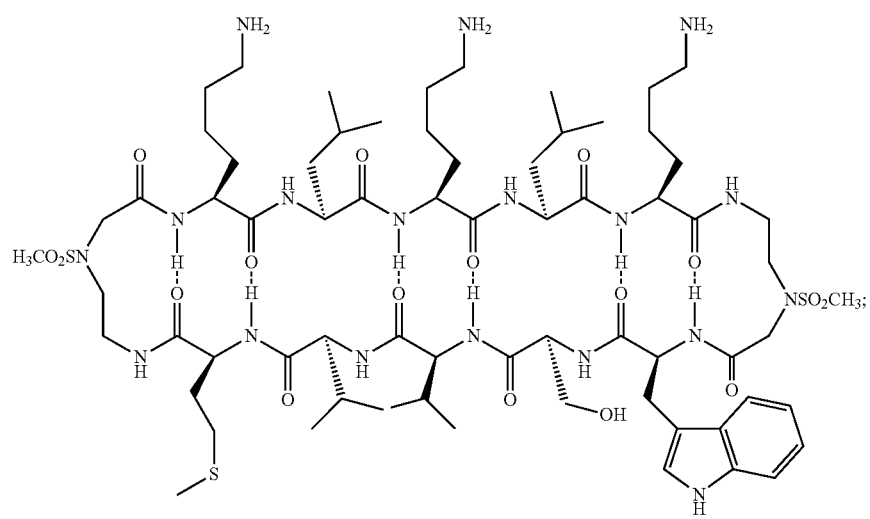
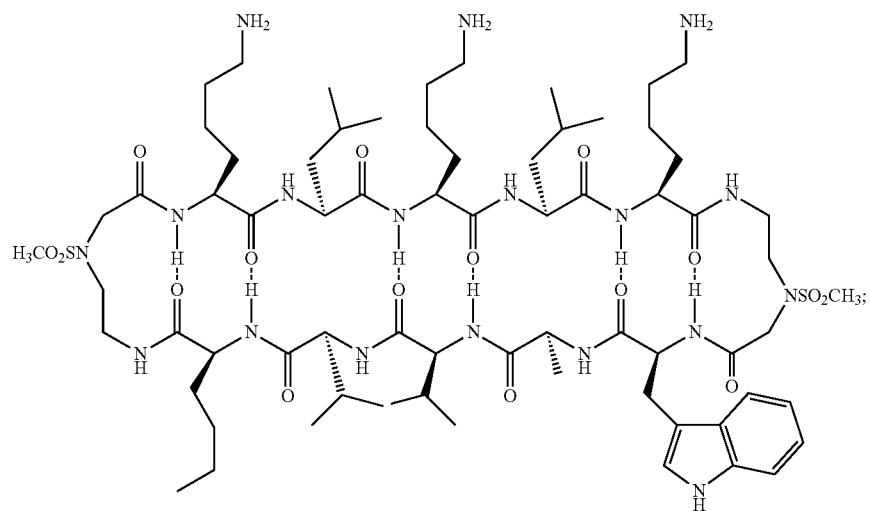

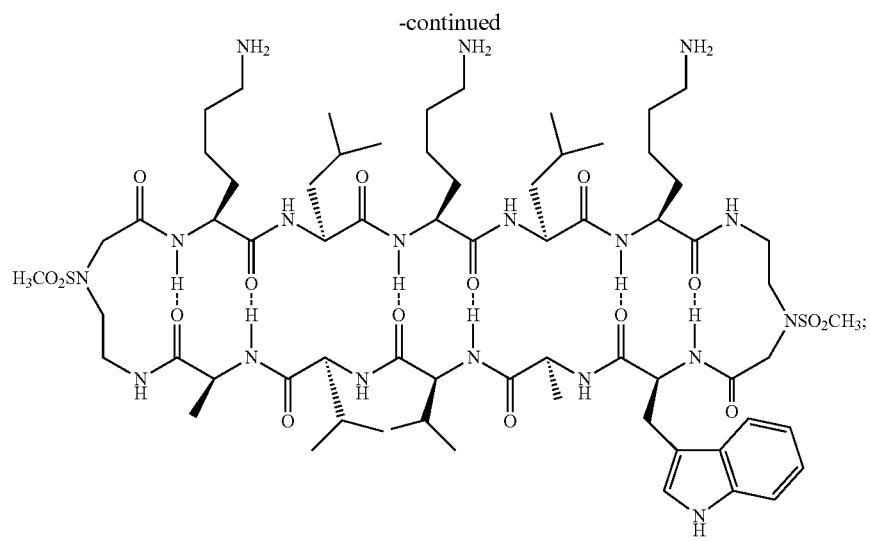
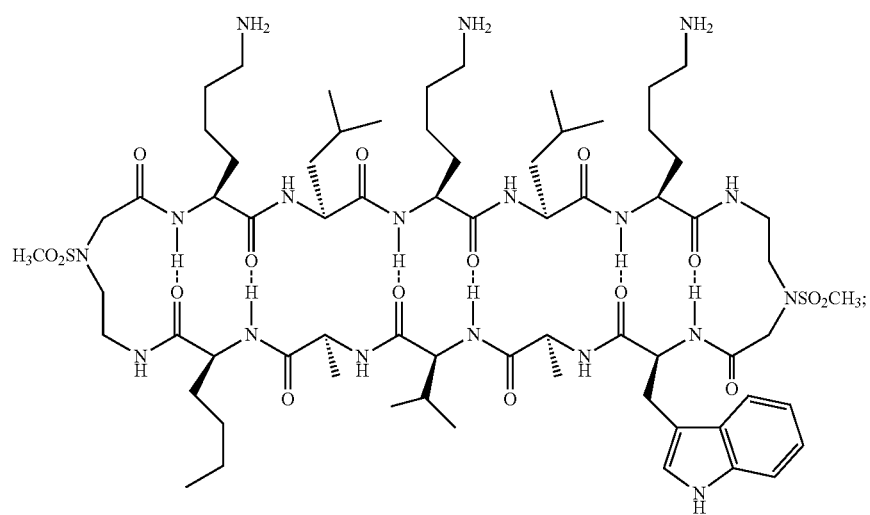
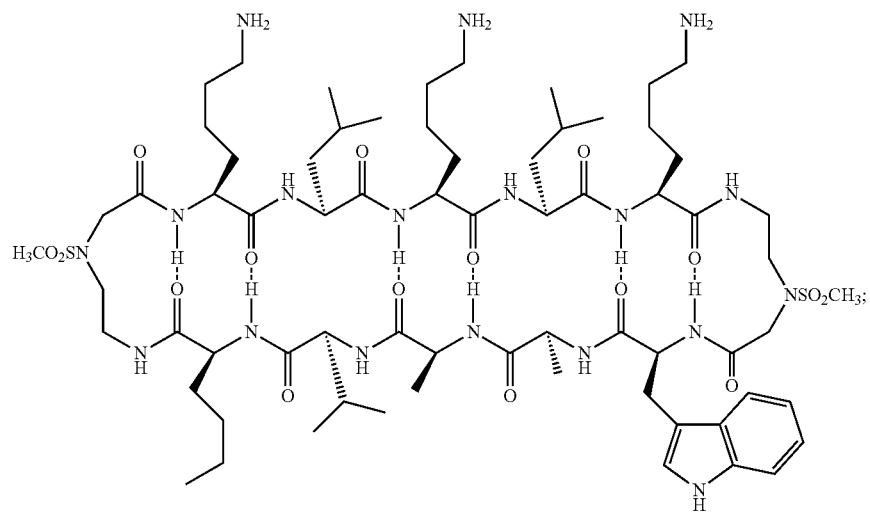

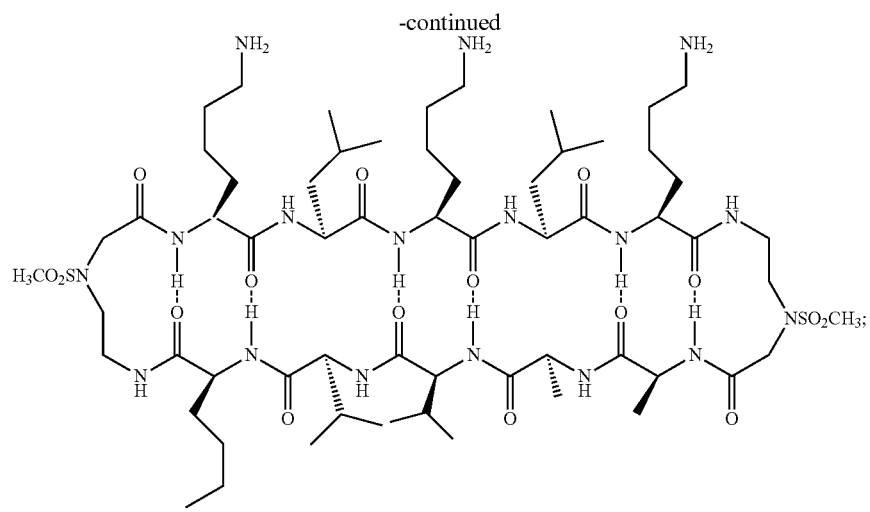
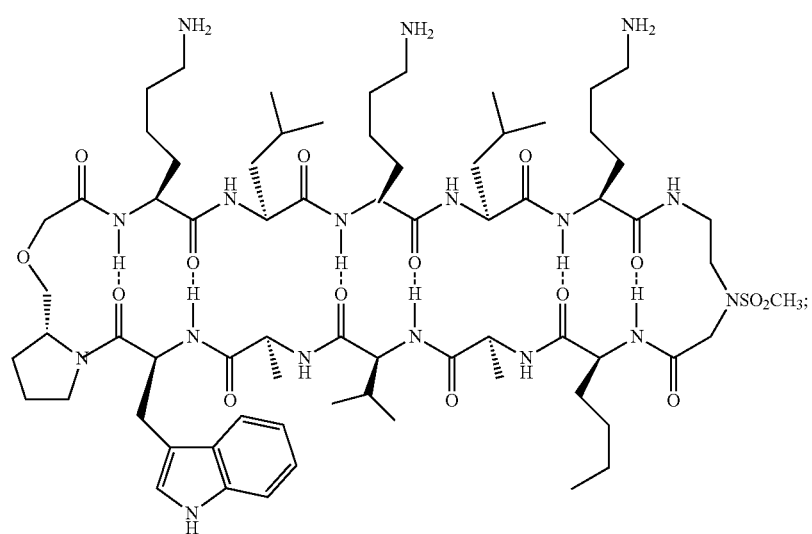
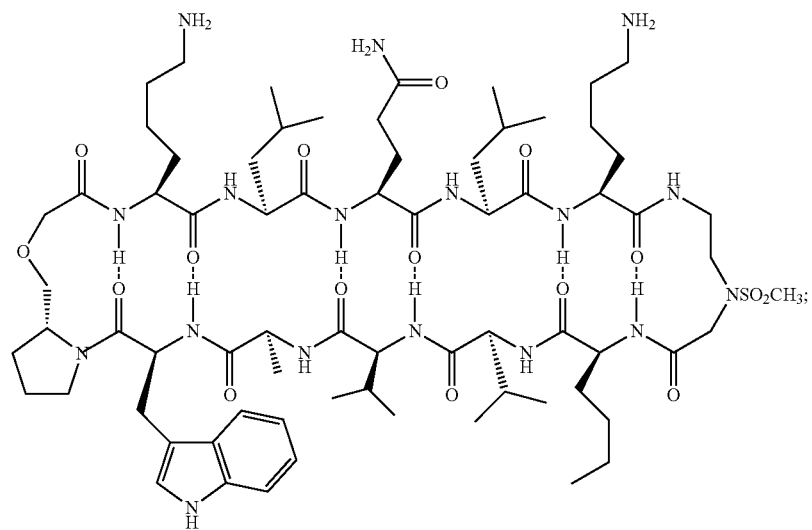

-continued
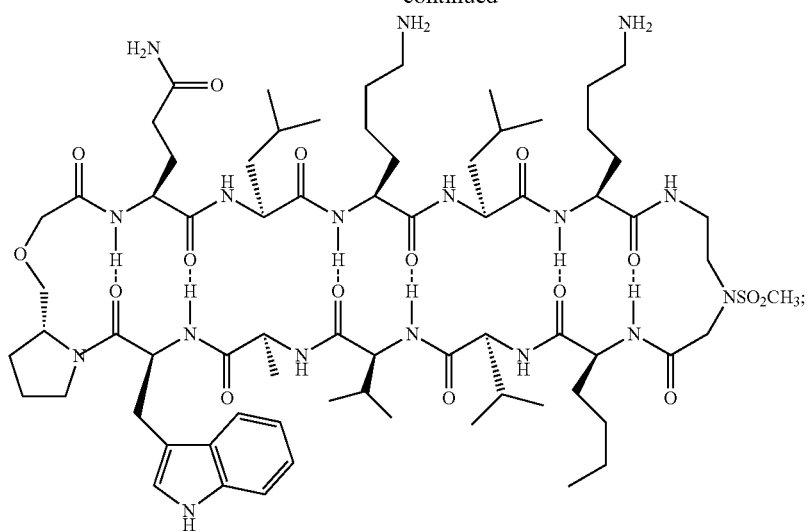
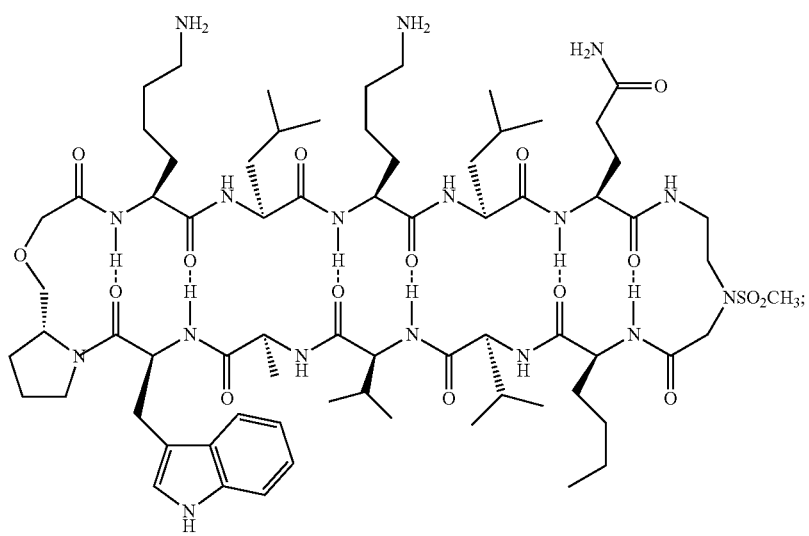
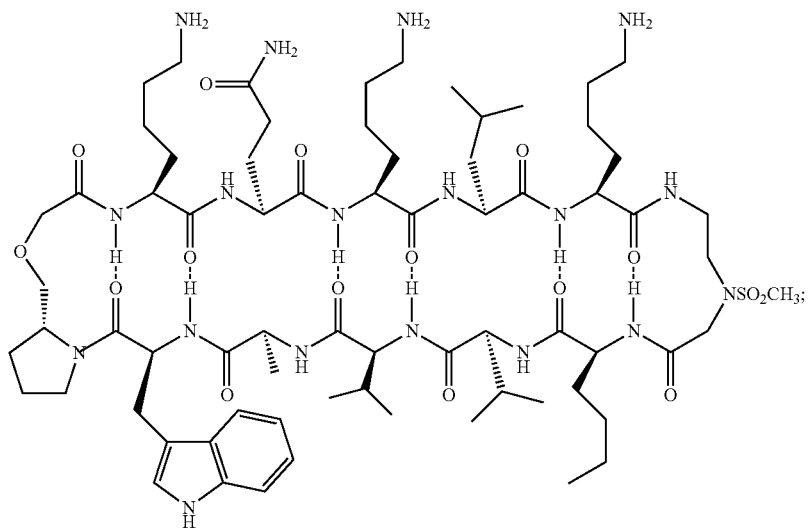

-continued
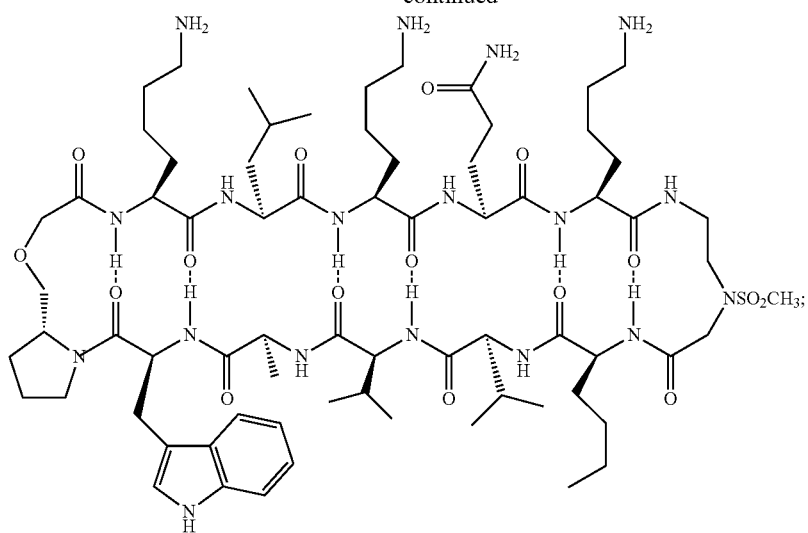
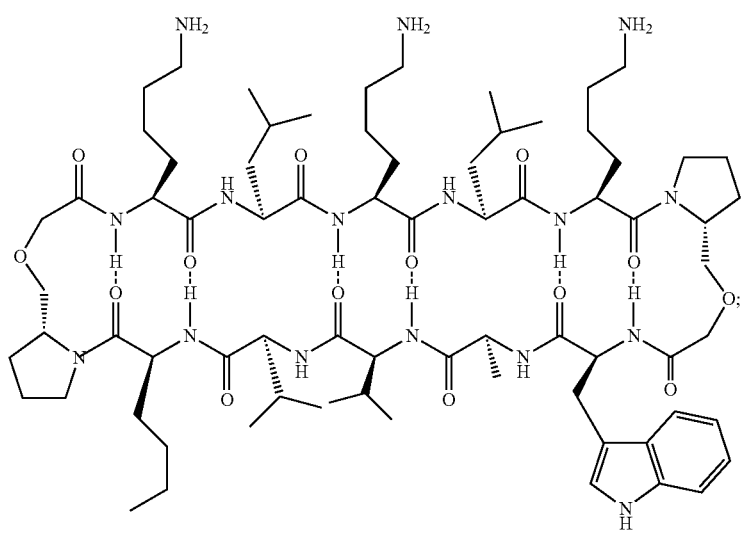
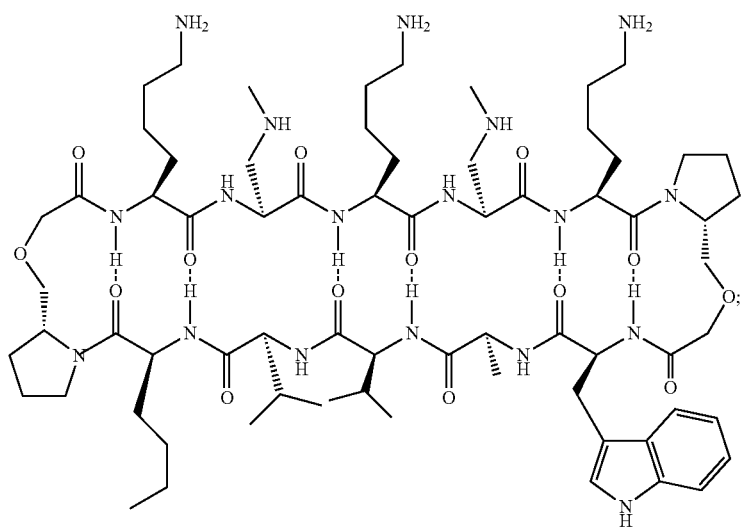

-continued
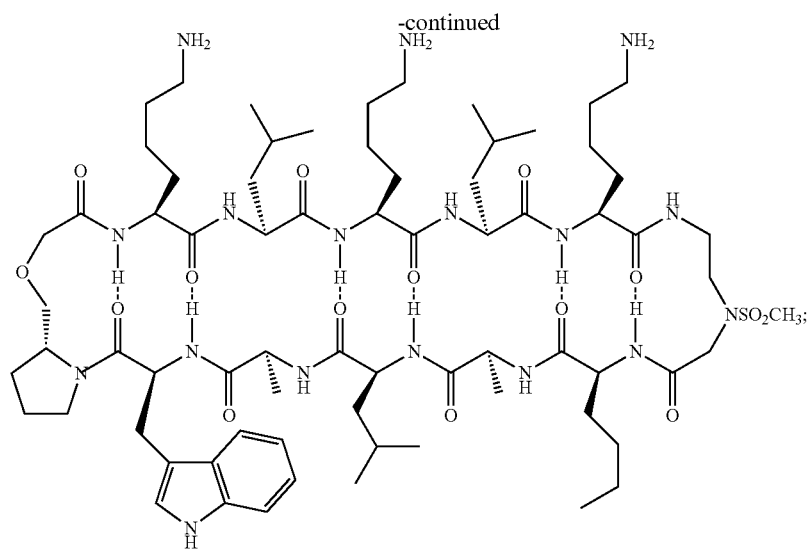
or a pharmaceutically acceptable salt of any of the foregoing.
5. The method of claim 3, wherein the cyclic compound has one of the following structures:
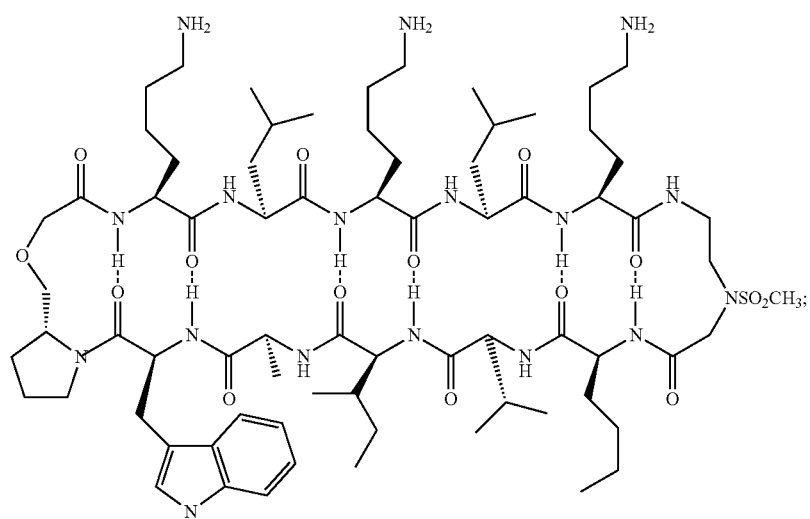
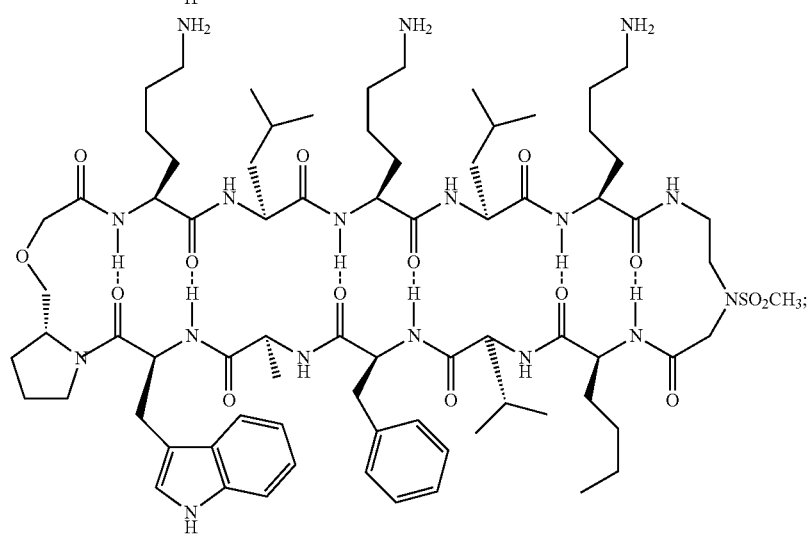

191
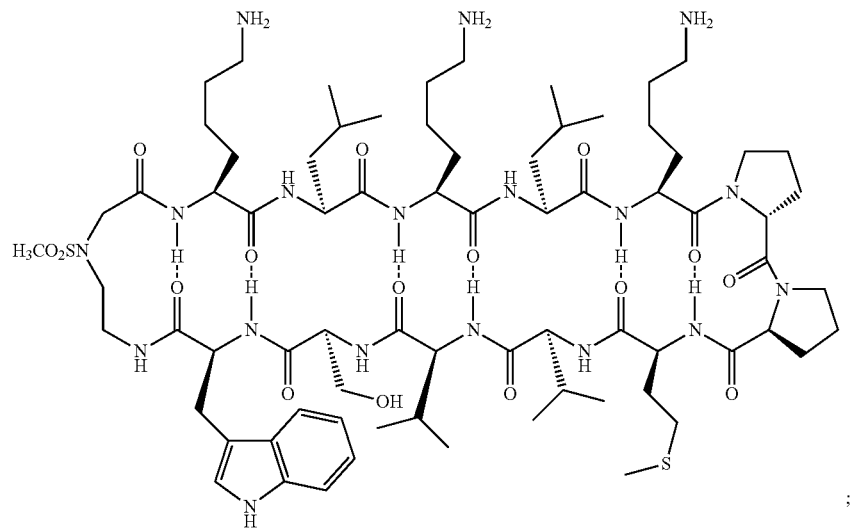
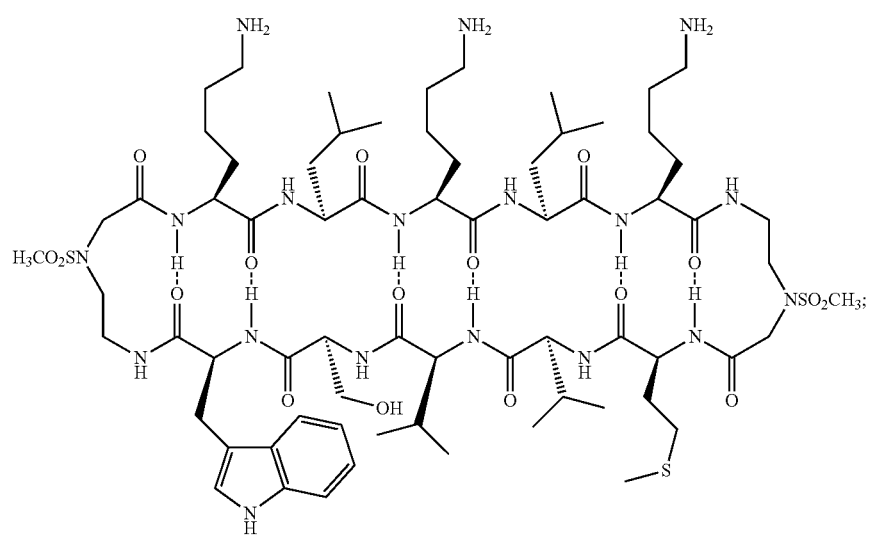
192
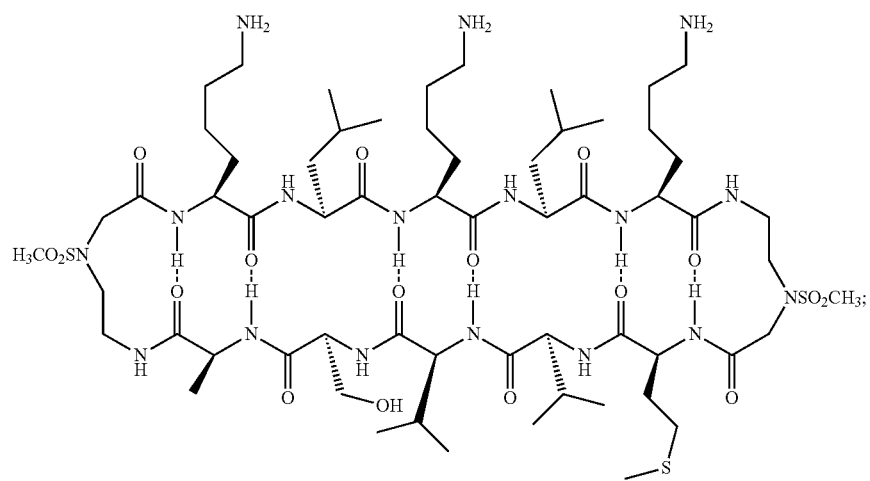

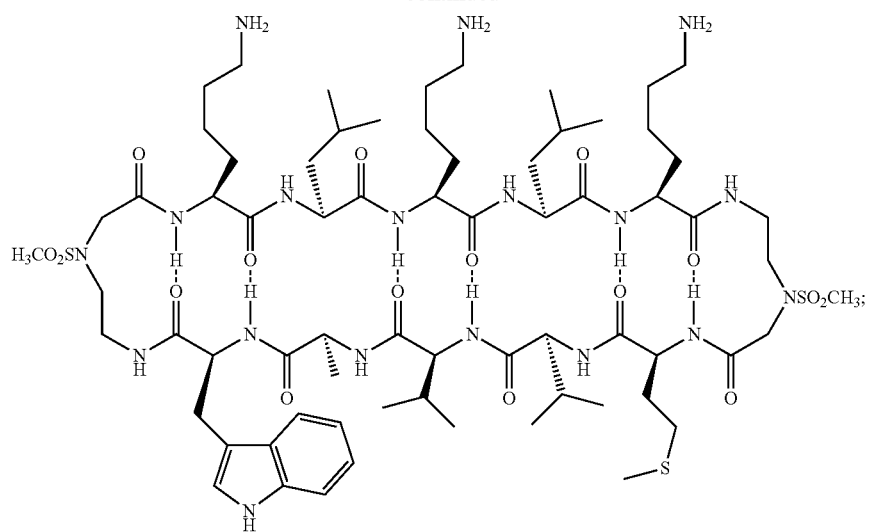
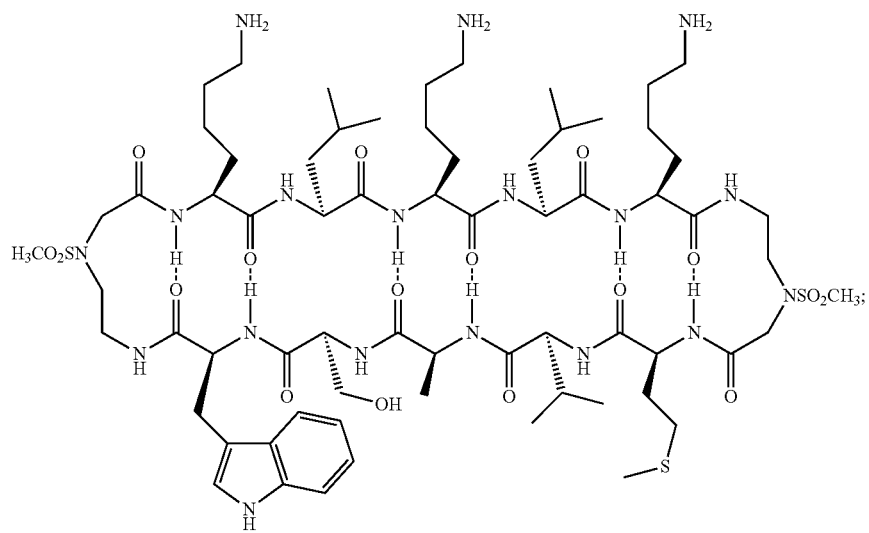
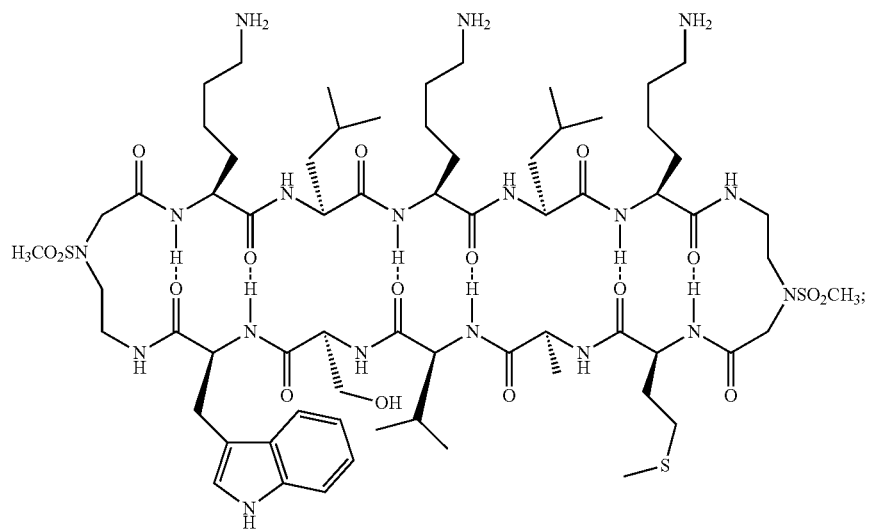

-continued
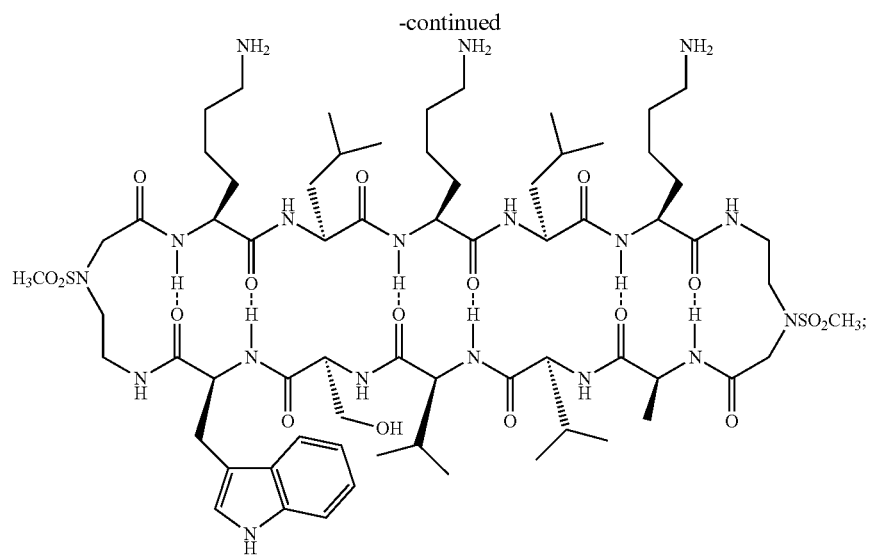
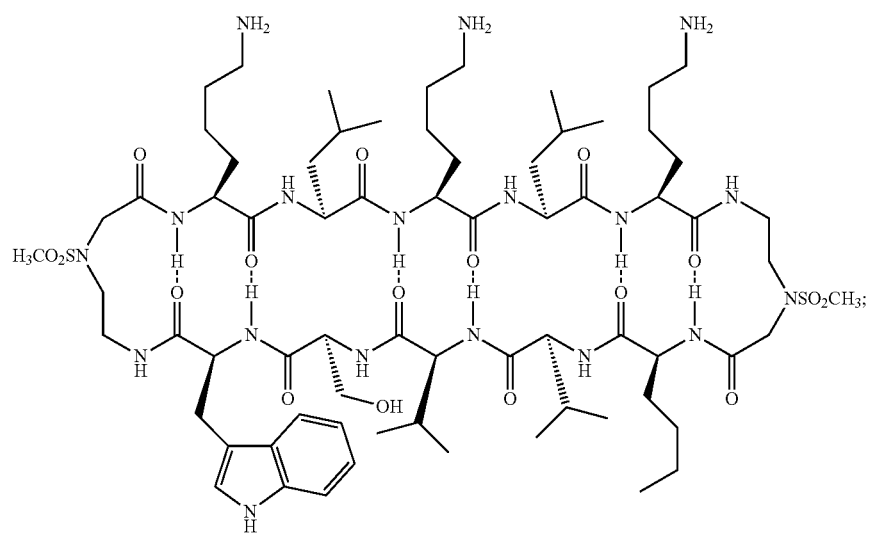
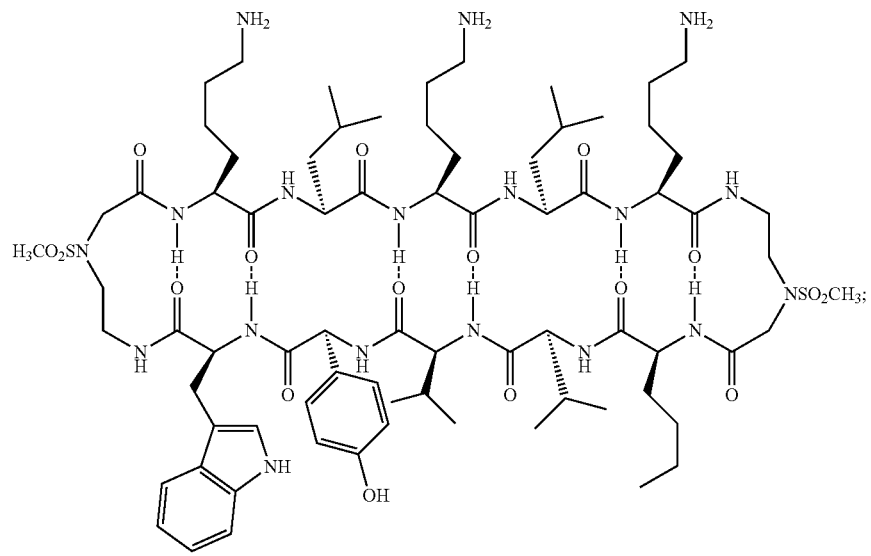

-continued
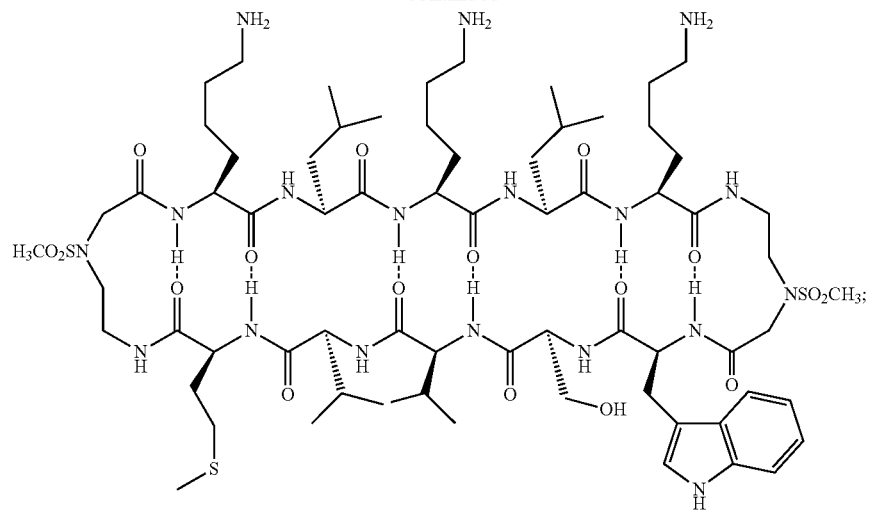
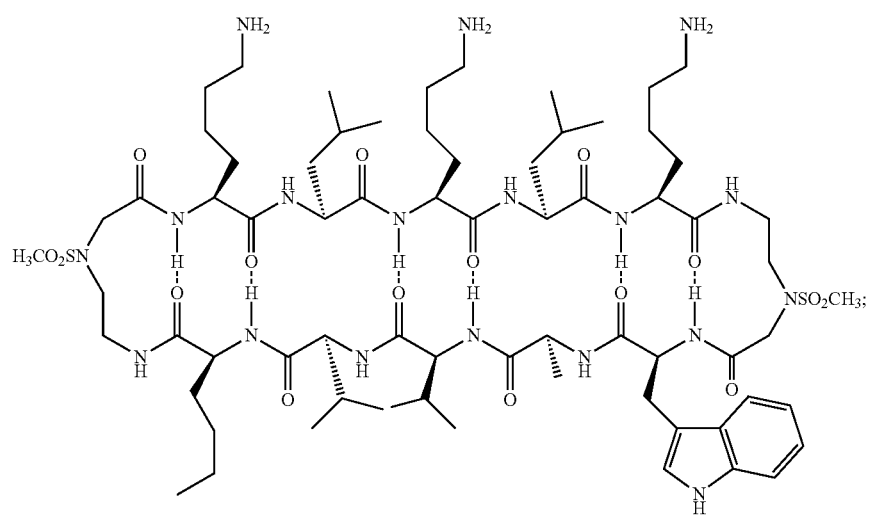
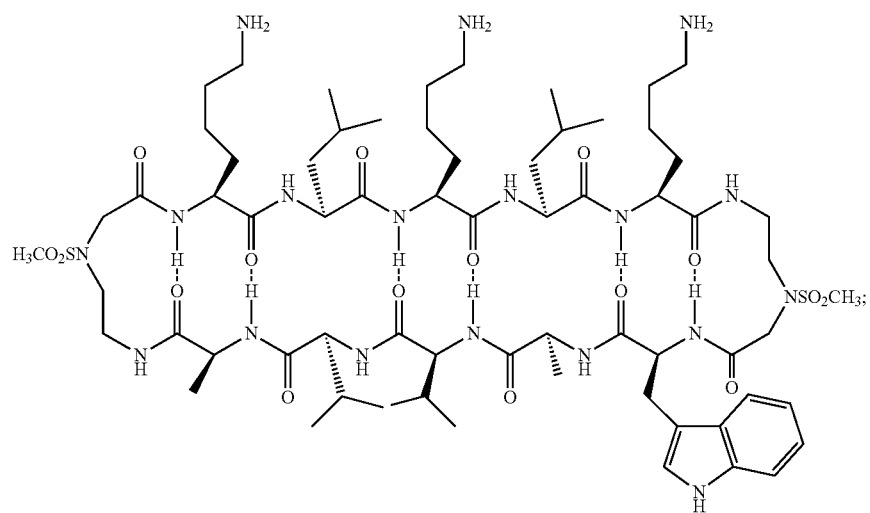

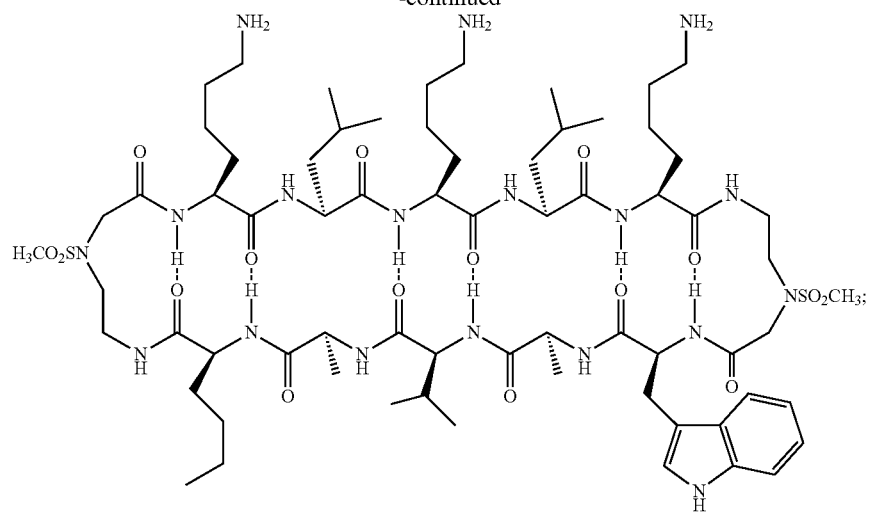
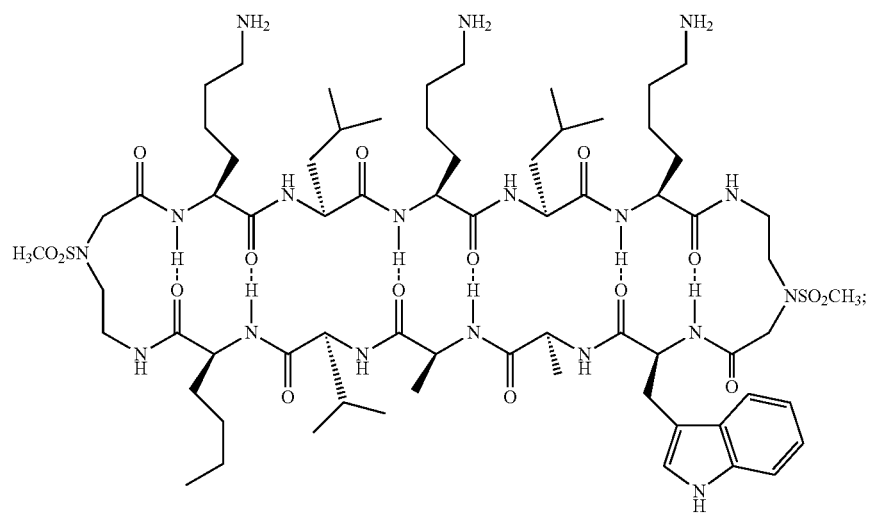
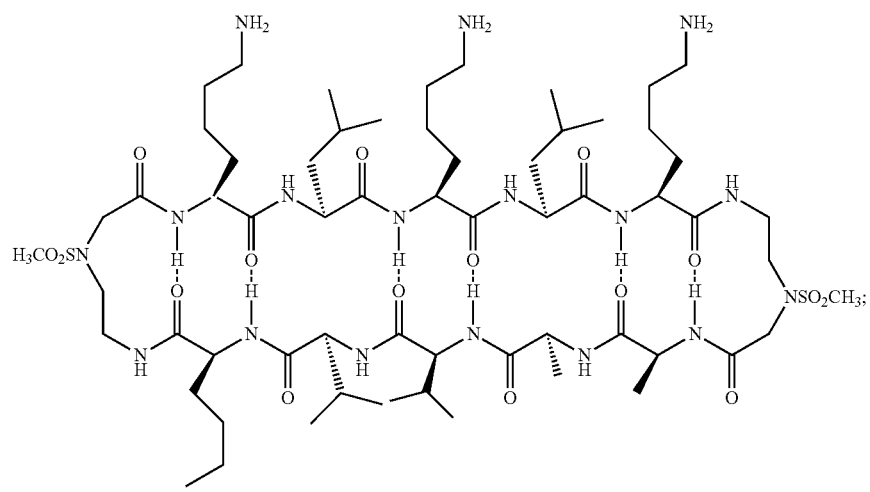

-continued
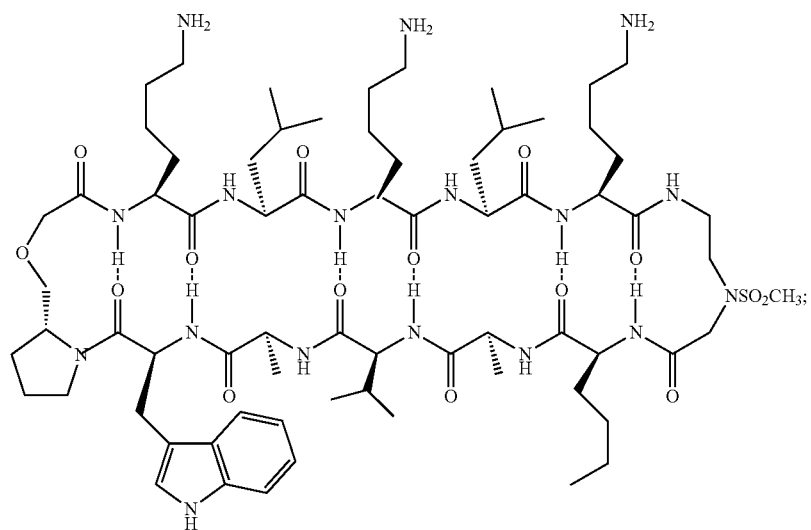
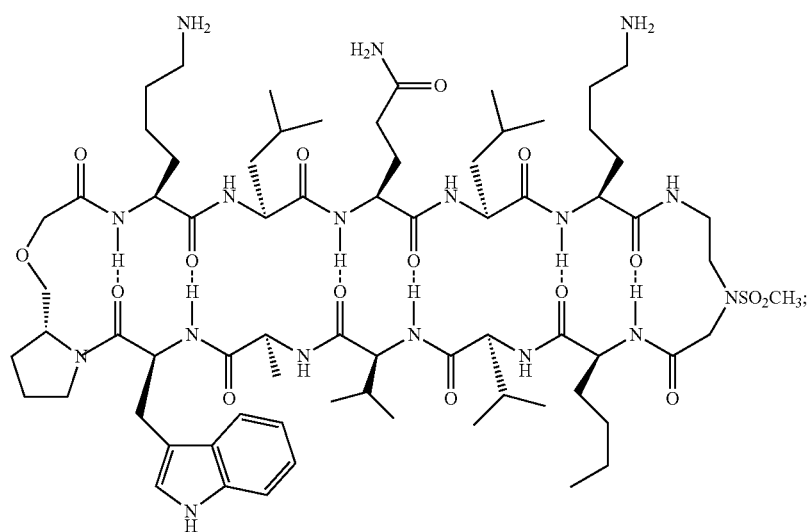
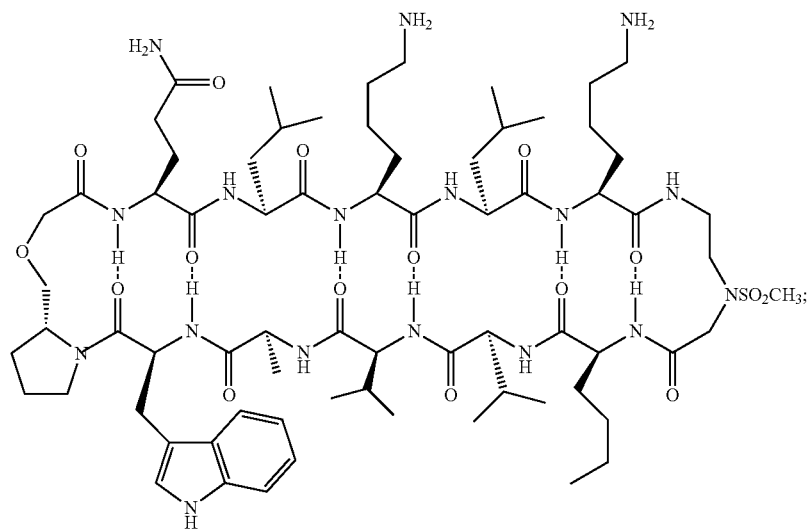

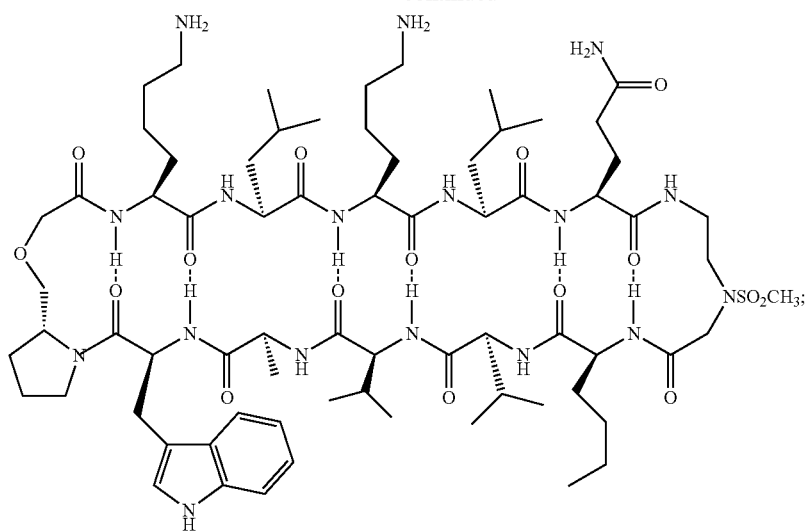
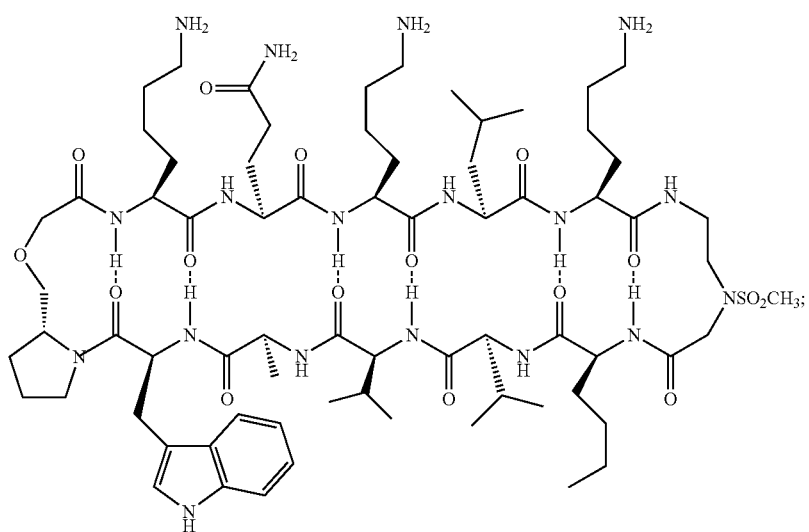
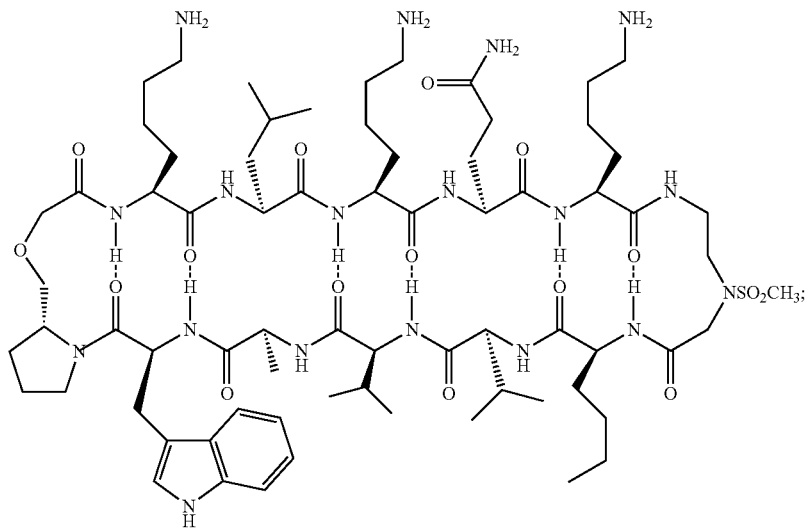

-continued
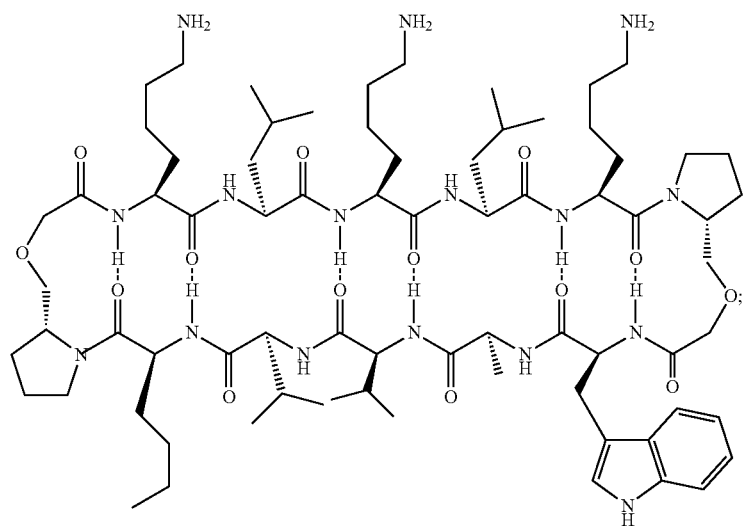
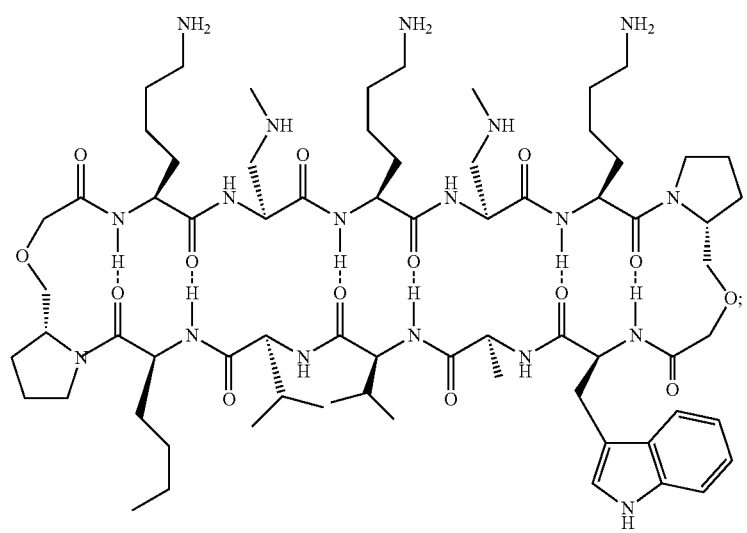
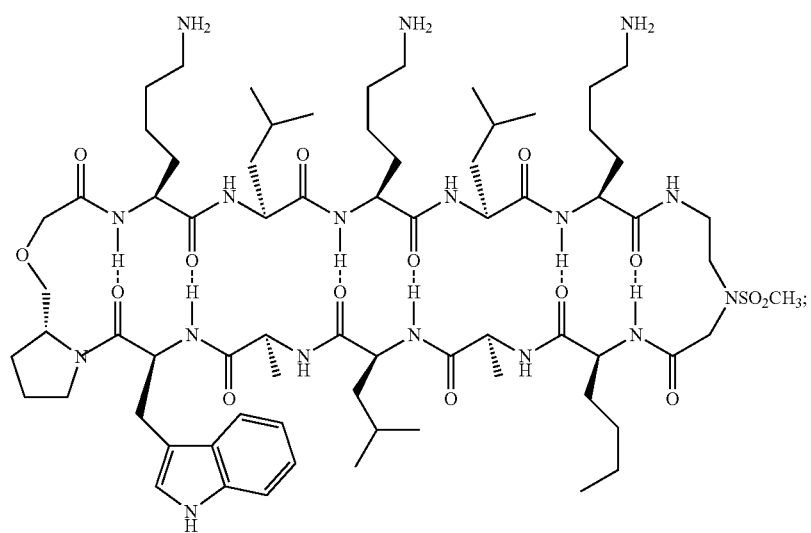

-continued
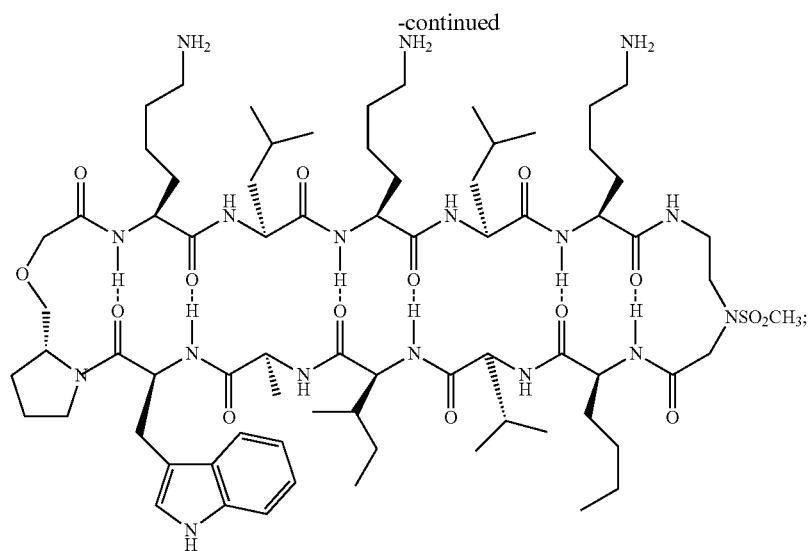
or a pharmaceutically acceptable salt of any of the foregoing.
6. The method of claim 1, wherein the cyclic compound has the structure:
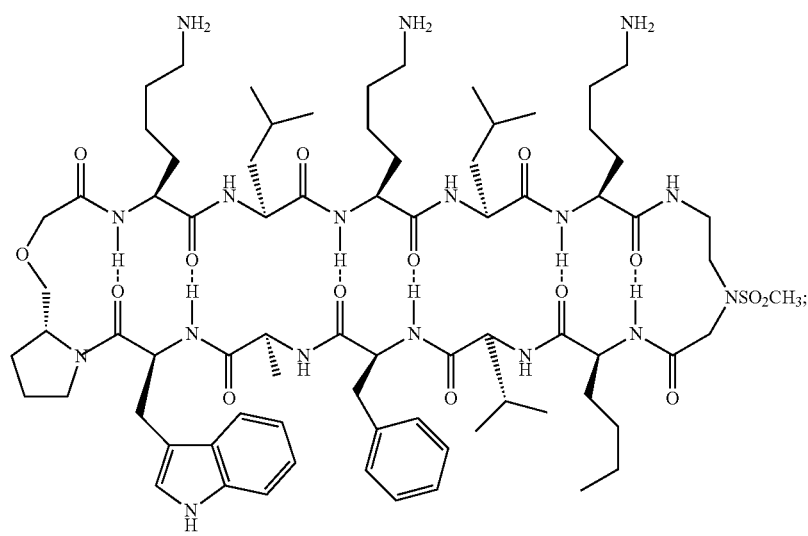

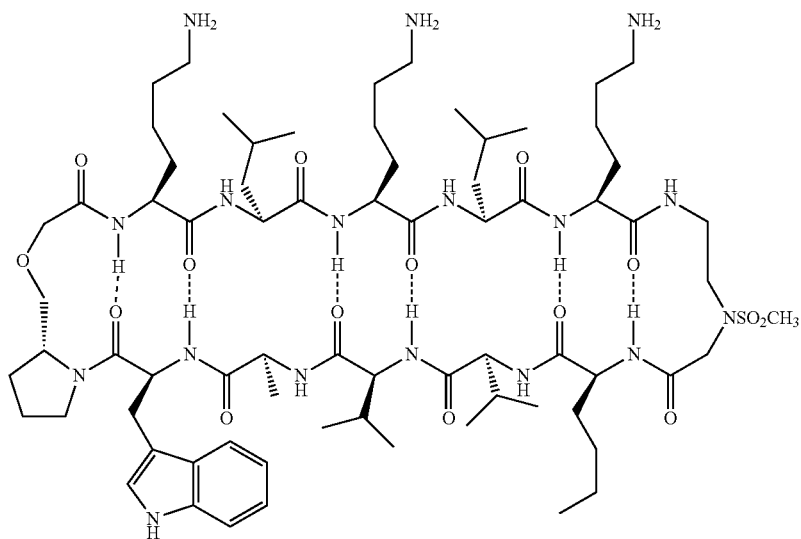

or a pharmaceutically acceptable salt thereof.

7. The method of claim 3, wherein the cyclic compound has the structure:

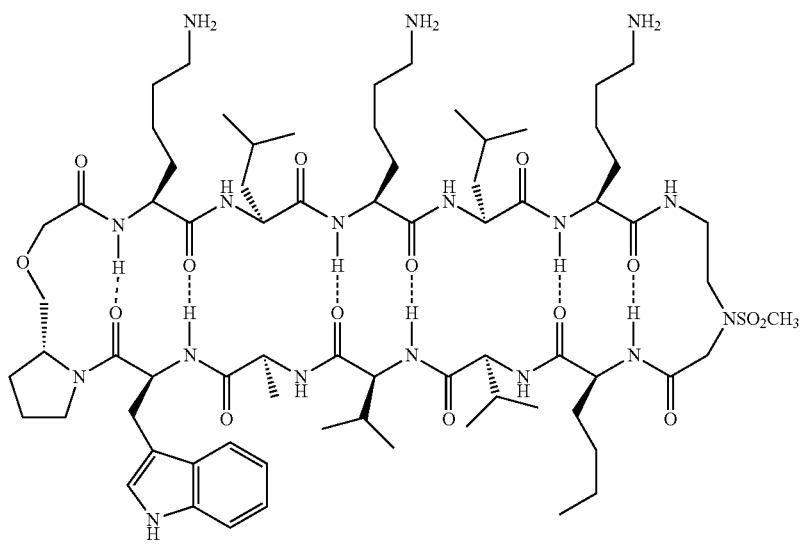

or a pharmaceutically acceptable salt thereof.

8. The method of claim 1, wherein the subject has multiple myeloma.

9. The method of claim 1, wherein the subject has lung cancer.

10. The method of claim 1, wherein the subject is human.

11. The method of claim 1, wherein the cyclic compound and the at least one other anti-cancer agent are administered concurrently.

12. The method of claim 1, wherein the cyclic compound and the at least one other anti-cancer agent are administered consecutively.

13. The method of claim 1, wherein the cyclic compound has the structure:

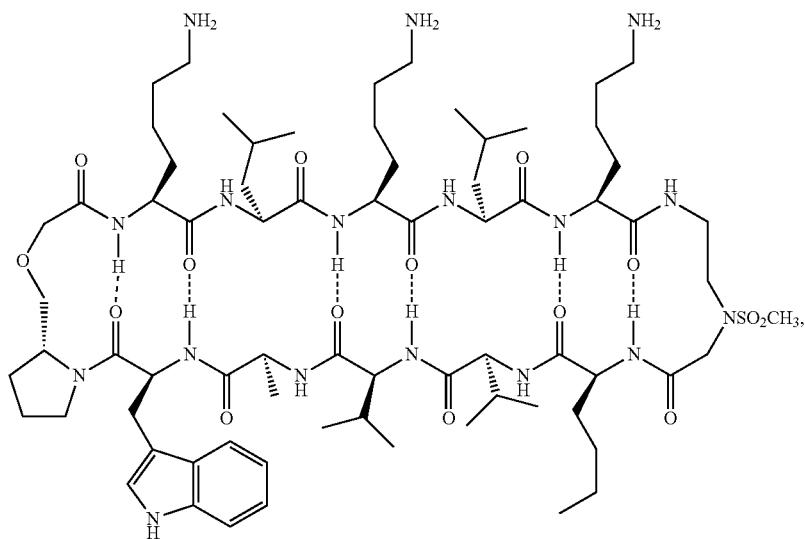
or a pharmaceutically acceptable salt thereof.
14. The method of claim 1, wherein the at least one other anti-cancer agent comprises a proteasome inhibitor.
15. The method of claim 1, wherein the subject is a mammal.
16. The method of claim 1, wherein the subject is a non-human mammal.
* * * * *

UNITED STATES PATENT AND TRADEMARK OFFICE
CERTIFICATE OF CORRECTION

PATENT NO. : 10,059,740 B2
APPLICATION NO. : 15/165687
DATED : August 28, 2018
INVENTOR(S) : Lori Hazlehurst et al.

It is certified that error appears in the above-identified patent and that said Letters Patent is hereby corrected as shown below:

In the Specification

Column 31
Line 2, "Examples of Chemotherapeutic" should read --Examples of Anti-Cancer--.
Line 38, "chloroethylnitrosourea (BCNU)" should read --bis-chloroethylnitrosourea (BCNU)--.
Line 42, "ROVERON-A" should read --ROFERON-A--.
Line 57, "diamminedichloroplatinum" should read --cis-diamminedichloroplatinum (CDDP)--.
Line 62, "THIOGUANINE TABLOID product" should read --Thioguanine (TABLOID product)--.

Column 32
Line 2, "Examples of Chemotherapeutic" should read --Examples of Anti-Cancer--.
Line 13, "Daunorubicin" should read --DAUNORUBICIN product--.

Column 33
Line 2, "Examples of Chemotherapeutic" should read --Examples of Anti-Cancer--.

Signed and Sealed this
Eighteenth Day of June, 2019

Andrei Iancu
*Director of the United States Patent and Trademark Office*

CERTIFICATE OF CORRECTION (continued)
U.S. Pat. No. 10,059,740 B2

In the Claims

Column 183

Lines 35-40, " 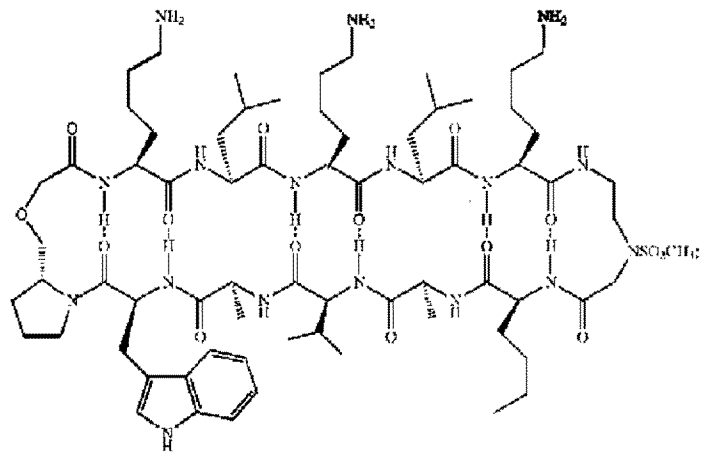 " should read

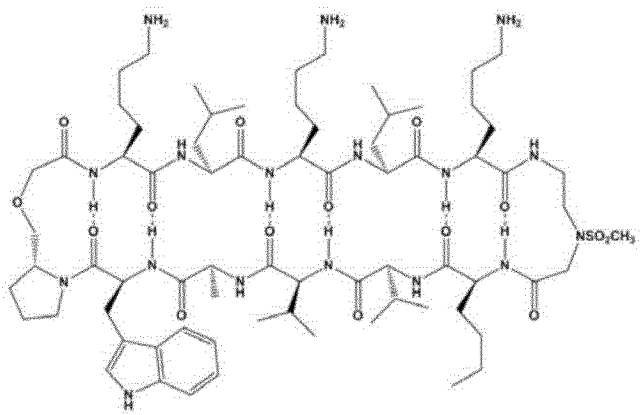

-- --.

Column 189

Lines 15-20, " 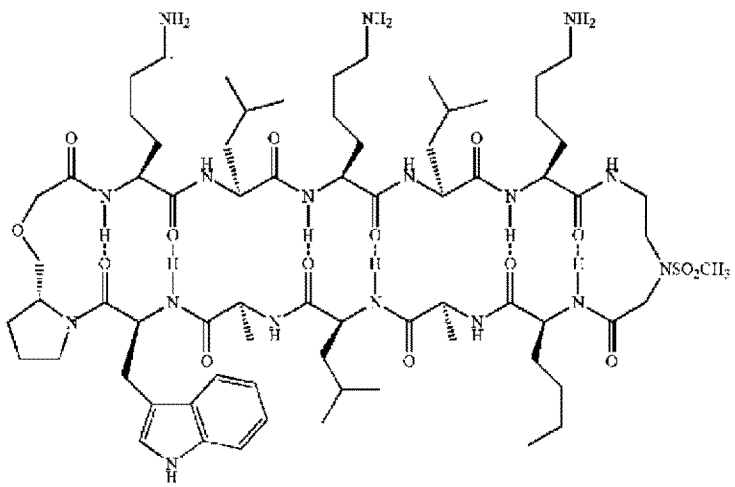 " should read

CERTIFICATE OF CORRECTION (continued)
U.S. Pat. No. 10,059,740 B2

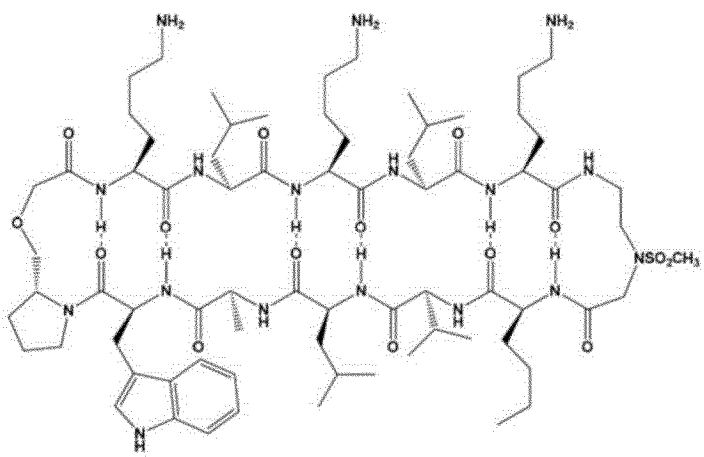

-- --.

Column 201

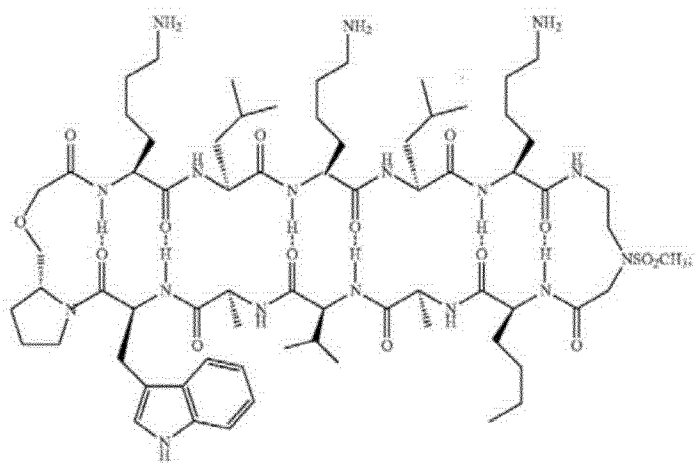

Line 15-20, " " should read

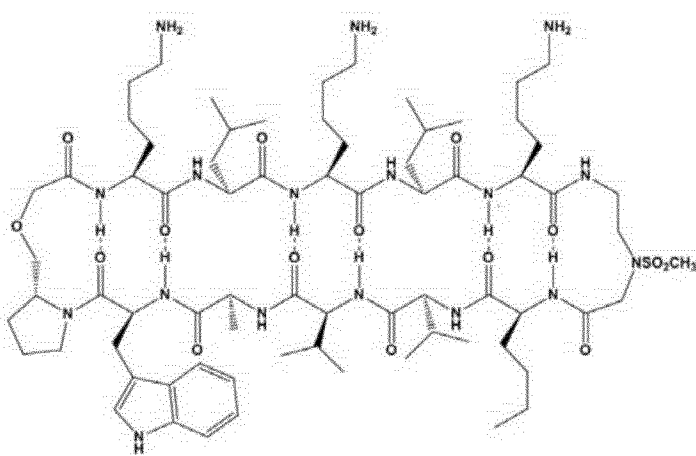

-- --.

CERTIFICATE OF CORRECTION (continued)
U.S. Pat. No. 10,059,740 B2

Page 4 of 4

Column 205

Lines 57-62, " 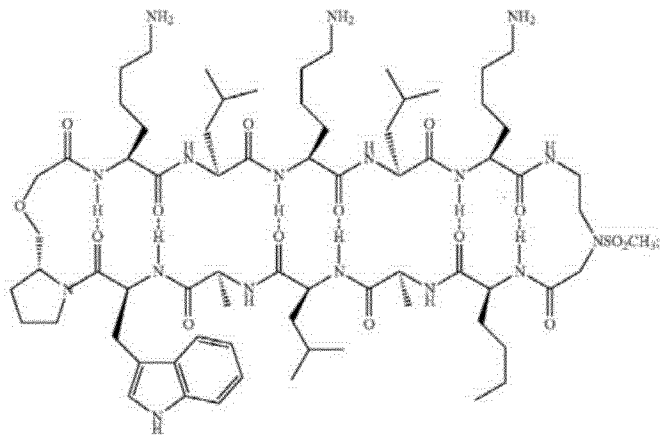 " should read

-- 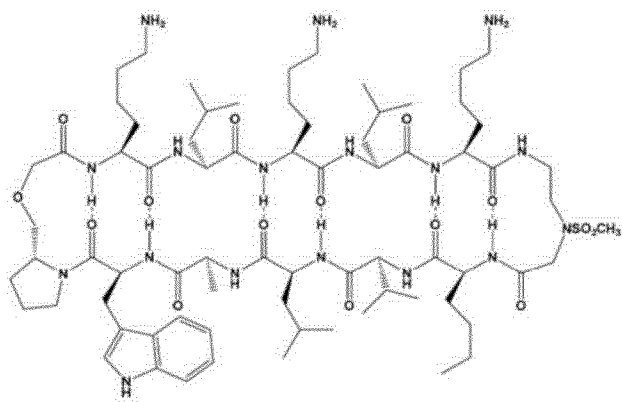 --.